US012495718B2

(12) United States Patent
Kim et al.

(10) Patent No.: US 12,495,718 B2
(45) Date of Patent: *Dec. 9, 2025

(54) COMPOUND AND ORGANIC LIGHT EMITTING DEVICE COMPRISING SAME

(71) Applicant: LG CHEM, LTD., Seoul (KR)

(72) Inventors: Minjun Kim, Daejeon (KR); Dong Hoon Lee, Daejeon (KR); Hyoung Seok Kim, Daejeon (KR); Sangwoo Lee, Daejeon (KR); Sang Duk Suh, Daejeon (KR); Donghee Kim, Daejeon (KR); Sunmin Kim, Daejeon (KR); Da Jung Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 657 days.

This patent is subject to a terminal disclaimer.

(21) Appl. No.: 17/293,896

(22) PCT Filed: Feb. 28, 2020

(86) PCT No.: PCT/KR2020/002906

§ 371 (c)(1),
(2) Date: May 13, 2021

(87) PCT Pub. No.: WO2020/175961

PCT Pub. Date: Sep. 3, 2020

(65) Prior Publication Data

US 2022/0029107 A1 Jan. 27, 2022

(30) Foreign Application Priority Data

Feb. 28, 2019 (KR) ........................ 10-2019-0024135

(51) Int. Cl.
*H10K 85/60* (2023.01)
*C07D 403/14* (2006.01)
(Continued)

(52) U.S. Cl.
CPC ....... *H10K 85/6572* (2023.02); *C07D 403/14* (2013.01); *C07D 405/14* (2013.01);
(Continued)

(58) Field of Classification Search
CPC .... C07D 403/04; H10K 50/11; H10K 85/342; H10K 85/615; H10K 85/654;
(Continued)

(56) References Cited

U.S. PATENT DOCUMENTS 9,190,618 B2 11/2015 Bae et al.
9,698,358 B2 * 7/2017 Hong ................ H10K 85/6574
(Continued)

FOREIGN PATENT DOCUMENTS

JP 2014522401 A 9/2014
JP 2015530732 A 10/2015
(Continued)

OTHER PUBLICATIONS

WO-2020175948-A1 machine translation (Year: 2020).*
WO 2020185059 A1 machine translation (Year: 2020).*

*Primary Examiner* — Elizabeth M. Dahlburg
(74) *Attorney, Agent, or Firm* — Bryan Cave Leighton Paisner LLP

(57) ABSTRACT

A compound of Chemical Formula 1:

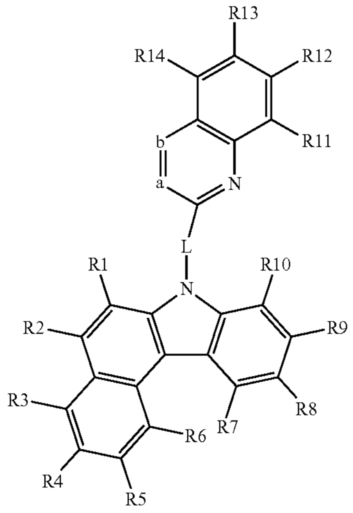

where at least one of R7 to R10 is Chemical Formula A, and the remaining R7 to R10 are hydrogen:

(Continued)

[Chemical Formula A]

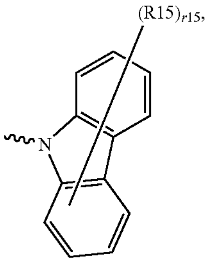

wherein in Chemical Formula A, 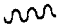 means a bond with R7 to R10; R15 is hydrogen, a nitrile group, a halogen group, a substituted or unsubstituted alkyl group, a substituted or unsubstituted silyl group, a substituted or unsubstituted aryl group, a substituted or unsubstituted heteroaryl group, or adjacent groups bond to each other to form a substituted or unsubstituted ring; and the other substituents are as defined in the specification, and an organic light emitting device including the same.

4 Claims, 1 Drawing Sheet

(51) Int. Cl.

| | |
|---|---|
| ***C07D 405/14*** | (2006.01) |
| ***C07D 409/14*** | (2006.01) |
| ***C09K 11/06*** | (2006.01) |
| ***H10K 50/11*** | (2023.01) |
| *H10K 101/10* | (2023.01) |

(52) U.S. Cl.

CPC ............ *C07D 409/14* (2013.01); *C09K 11/06* (2013.01); *H10K 85/615* (2023.02); *H10K 85/6574* (2023.02); *H10K 85/6576* (2023.02); *C09K 2211/1018* (2013.01); *H10K 50/11* (2023.02); *H10K 2101/10* (2023.02)

(58) Field of Classification Search

CPC ............ H10K 85/6572; H10K 85/6574; H01L 51/072; H01L 51/5012

See application file for complete search history.

(56) References Cited

U.S. PATENT DOCUMENTS

| | | | | |
|---|---|---|---|---|
| 9,768,393 | B2 | 9/2017 | Shin et al. | |
| 9,947,878 | B2 * | 4/2018 | Chun | H10K 85/615 |
| 10,186,669 | B2 | 1/2019 | Kang et al. | |
| 2014/0100367 | A1 | 4/2014 | Yoon et al. | |
| 2015/0060833 | A1 | 3/2015 | Kwon et al. | |
| 2015/0159084 | A1 | 6/2015 | Cho et al. | |
| 2016/0336518 | A1 | 11/2016 | Chun et al. | |
| 2017/0117485 | A1 | 4/2017 | Cho et al. | |
| 2017/0148998 | A1 * | 5/2017 | Kang | C07D 403/04 |
| 2021/0013411 | A1 | 1/2021 | Mo et al. | |
| 2021/0328155 | A1 | 10/2021 | Cho et al. | |

FOREIGN PATENT DOCUMENTS

| | | | | |
|---|---|---|---|---|
| JP | 2017510071 | A | 4/2017 | |
| JP | 2017518974 | A | 7/2017 | |
| JP | 2021521145 | A | 8/2021 | |
| KR | 10-2010-0023783 | A | 3/2010 | |
| KR | 10-2012-0021203 | A | 3/2012 | |
| KR | 10-2015-0027937 | A | 3/2015 | |
| KR | 10-2015-0108330 | A | 9/2015 | |
| KR | 10-2015-0135109 | A | 12/2015 | |
| KR | 10-2016-0022764 | A | 3/2016 | |
| KR | 10-2018-0053121 | A | 5/2018 | |
| KR | 10-2018-0125369 | A | 11/2018 | |
| WO | 2012165844 | A1 | 12/2012 | |
| WO | WO-2015093878 | A1 * | 6/2015 | C07D 409/14 |
| WO | 2019203550 | A1 | 10/2019 | |
| WO | WO-2020175948 | A1 * | 9/2020 | C07C 211/61 |
| WO | WO-2020185059 | A1 * | 9/2020 | H10K 50/11 |

* cited by examiner

COMPOUND AND ORGANIC LIGHT EMITTING DEVICE COMPRISING SAME

CROSS-REFERENCE TO RELATED APPLICATIONS

This application is a U.S. national stage of international Application No. PCT/KR2020/002906, filed Feb. 28, 2020, and claims priority to and the benefits of Korean Patent Application No. 10-2019-0024135, filed with the Korean Intellectual Property Office on Feb. 28, 2019, the entire contents of which are incorporated herein by reference.

TECHNICAL FIELD

The present specification relates to a compound, and an organic light emitting device including the same.

BACKGROUND

An organic light emission phenomenon generally refers to the conversion of electrical energy to light energy using an organic material. An organic light emitting device normally has a structure including an anode, a cathode, and an organic material layer therebetween. The organic material layer is often formed in a multilayer structure with different materials to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected into the organic material layer from the anode and the cathode, respectively. Excitons are formed when the injected holes and electrons meet, and light is emitted when these excitons fall back to the ground state.

Development of new materials for such an organic light emitting device has been continuously required.

SUMMARY

The present specification is directed to providing a compound, and an organic light emitting device including the same.

One exemplary embodiment of the present disclosure provides a compound represented by Chemical Formula 1:

[Chemical Formula 1]

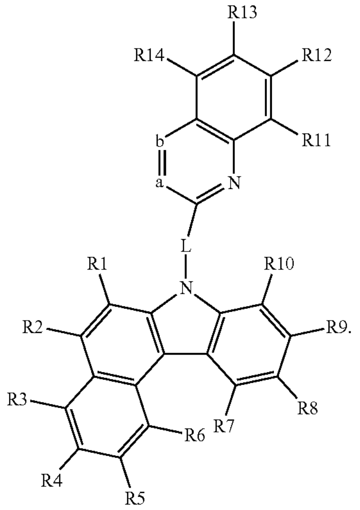

In Chemical Formula 1,

L is a direct bond, a substituted or unsubstituted arylene group, or a substituted or unsubstituted heteroarylene group, a and b are the same as or different from each other, and each independently is N or CR, R is a substituted or unsubstituted aryl group, or a substituted or unsubstituted heteroaryl group, R1 to R6 and R11 to R14 are the same as or different from each other, and each independently is hydrogen, a nitrile group, a halogen group, a substituted or unsubstituted alkyl group, a substituted or unsubstituted silyl group, a substituted or unsubstituted aryl group, or a substituted or unsubstituted heteroaryl group, and at least one of R7 to R10 is Chemical Formula A, and the rest are hydrogen:

[Chemical Formula A]

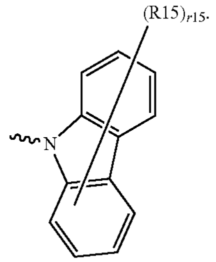

In Chemical Formula A,

 means a bond with R7 to R10,

R15 is hydrogen, a nitrile group, a halogen group, a substituted or unsubstituted alkyl group, a substituted or unsubstituted silyl group, a substituted or unsubstituted aryl group, or a substituted or unsubstituted heteroaryl group, or adjacent groups bond to each other to form a substituted or unsubstituted ring, and r15 is an integer of 0 to 8, and when r15 is 2 or greater, R15s are the same as or different from each other.

Another exemplary embodiment of the present disclosure provides an organic light emitting device including a first electrode; a second electrode provided opposite to the first electrode; and one or more organic material layers provided between the first electrode and the second electrode, wherein one or more of the one or more organic material layers include the compound.

A compound according to one exemplary embodiment of the present specification can be used as a material of an organic material layer of an organic light emitting device, and by using the same, high color purity and/or enhancement in lifetime properties of the organic light emitting device can be achieved.

REFERENCE NUMERALS USED HEREIN

Figure 1:
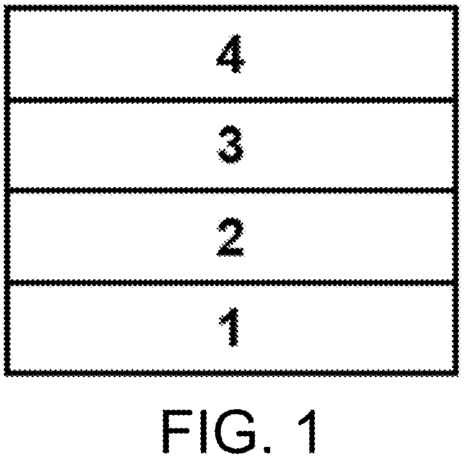
FIG. 1 and FIG. 2 are schematic illustrations of an organic light emitting device according to exemplary embodiments of the present specification.

1: Substrate
2: First Electrode
3: Light Emitting Layer
4: Second Electrode

5: Hole Injection Layer
6: Hole Transfer Layer
7: Hole Transfer Auxiliary Layer
8: Electron Blocking Layer
9: Hole Blocking Layer
10: Electron Injection and Transfer Layer

DETAILED DESCRIPTION

Hereinafter, the present specification will be described in more detail.

One exemplary embodiment of the present specification provides a compound represented by Chemical Formula 1.

In the compound of Chemical Formula 1, R is an aryl group or a heteroaryl group, at least one of R7 to R10 has the structure of Chemical Formula A as a substituent, and R1 to R6 and R11 to R14 do not form an additional ring.

Examples of the substituents in the present specification are described below, however, the substituents are not limited thereto.

The term "substitution" means a substituent replacing a hydrogen atom bonded to a carbon atom of a compound. The position of substitution is not limited as long as it is a position at which the hydrogen atom is substituted, and when there are two or more substituents substitute, the two or more substituents may be the same as or different from each other.

In the present specification, the term "substituted or unsubstituted" means being substituted with one or more substituents selected from the group consisting of deuterium; a nitrile group; a substituted or unsubstituted alkyl group; a substituted or unsubstituted cycloalkyl group; a substituted or unsubstituted silyl group; a substituted or unsubstituted alkoxy group; a substituted or unsubstituted arylamine group; a substituted or unsubstituted aryl group; and a substituted or unsubstituted heterocyclic group, or being substituted with a substituent linking two or more substituents among the substituents illustrated above, or having no substituents. For example, "a substituent linking two or more substituents" may include an aryl group substituted with an aryl group, an aryl group substituted with a heteroaryl group, a heterocyclic group substituted with an aryl group, an aryl group substituted with an alkyl group, and the like.

In the present specification, the alkyl group may be linear or branched, and although not particularly limited thereto, the number of carbon atoms is preferably from 1 to 30. Specifically, the number of carbon atoms is preferably from 1 to 20. More specifically, the number of carbon atoms is preferably from 1 to 10. Specific examples thereof may include a methyl group; an ethyl group; a propyl group; an n-propyl group; an isopropyl group; a butyl group; an n-butyl group; an isobutyl group; a tert-butyl group; a sec-butyl group; a 1-methylbutyl group; a 1-ethylbutyl group; a pentyl group; an n-pentyl group; an isopentyl group; a neopentyl group; a tert-pentyl group; a hexyl group; an n-hexyl group; a 1-methylpentyl group; a 2-methylpentyl group; a 4-methyl-2-pentyl group; a 3,3-dimethylbutyl group; a 2-ethylbutyl group; a heptyl group; an n-heptyl group; a 1-methylhexyl group; a cyclopentylmethyl group; a cyclohexylmethyl group; an octyl group; an n-octyl group; a tert-octyl group; a 1-methylheptyl group; a 2-ethylhexyl group; a 2-propylpentyl group; an n-nonyl group; a 2,2-dimethylheptyl group; a 1-ethylpropyl group; a 1,1-dimethylpropyl group; an isohexyl group; a 4-methylhexyl group; a 5-methylhexyl group and the like, but are not limited thereto.

In the present specification, the cycloalkyl group is not particularly limited, but preferably has 3 to 30 carbon atoms, and more preferably has 3 to 20 carbon atoms. Specific examples thereof may include a cyclopropyl group; a cyclobutyl group; a cyclopentyl group; a 3-methylcyclopentyl group; a 2,3-dimethylcyclopentyl group; a cyclohexyl group; a 3-methylcyclohexyl group; a 4-methylcyclohexyl group; a 2,3-dimethylcyclohexyl group; a 3,4,5-trimethylcyclohexyl group; a 4-tert-butylcyclohexyl group; a cycloheptyl group; a cyclooctyl group and the like, but are not limited thereto.

In the present specification, the alkoxy group may be linear, branched or cyclic. The number of carbon atoms of the alkoxy group is not particularly limited, but is preferably from 1 to 30. Specifically, the number of carbon atoms is preferably from 1 to 20. More specifically, the number of carbon atoms is preferably from 1 to 10. Specific examples thereof may include a methoxy group; an ethoxy group; an n-propoxy group; an isopropoxy group; an i-propyloxy group; an n-butoxy group; an isobutoxy group; a tert-butoxy group; a sec-butoxy group; an n-pentyloxy group; a neopentyloxy group; an isopentyloxy group; an n-hexyloxy group; a 3,3-dimethylbutyloxy group; a 2-ethylbutyloxy group; an n-octyloxy group; an n-nonyloxy group; an n-decyloxy group; a benzyloxy group; a p-methylbenzyloxy group and the like, but are not limited thereto.

In the present specification, the amine group may be selected from the group consisting of $—NH_2$; an alkylamine group; an N-alkylarylamine group; an arylamine group; an N-arylheteroarylamine group; an N-alkylheteroarylamine group and a heteroarylamine group, and although not particularly limited thereto, the number of carbon atoms is preferably from 1 to 30. Specific examples of the amine group may include a methylamine group; a dimethylamine group; an ethylamine group; a diethylamine group; a phenylanine group; a naphthylamine group; a biphenylamine group; an anthracenylamine group; a 9-methylanthracenylamine group; a diphenylamine group; an N-phenylnaphthylamine group; a ditolylamine group; an N-phenyltolylamine group; a triphenylamine group; an N-phenylbiphenylamine group; an N-phenylnaphthylamine group; an N-biphenylnaphthylamine group; an N-naphthylfluorenylamine group; an N-phenylphenanthrenylamine group; an N-biphenylphenanthrenylamine group; an N-phenylfluorenylamine group; an N-phenylterphenylamine group; an N-phenanthrenylfluorenylamine group; an N-biphenylfluorenylamine group and the like, but are not limited thereto.

In the present specification, the silyl group may be represented by —SiRaRbRc, and Ra, Rb and Rc are the same as or different from each other, and may be each independently hydrogen; a substituted or unsubstituted alkyl group; or a substituted or unsubstituted aryl group. Specific examples of the silyl group may include a trimethylsilyl group; a triethylsilyl group; a t-butyldimethylsilyl group; a vinyldimethylsilyl group; a propyldimethylsilyl group; a triphenylsilyl group; a diphenylsilyl group; a phenylsilyl group and the like, but are not limited thereto.

In the present specification, the aryl group is not particularly limited, but preferably has 6 to 30 carbon atoms, and more preferably has 6 to 20 carbon atoms. The aryl group may be monocyclic or polycyclic. When the aryl group is a monocyclic aryl group, the number of carbon atoms is not particularly limited, but is preferably from 6 to 30. More specifically, the number of carbon atoms is preferably from 6 to 20. Specific examples of the monocyclic aryl group may include a phenyl group; a biphenyl group; a terphenyl group and the like, but are not limited thereto. When the aryl group is a polycyclic aryl group, the number of carbon atoms is not particularly limited, but is preferably from 10 to 30. More specifically, the number of carbon atoms is preferably from 10 to 20. Specific examples of the polycyclic aryl group may include a naphthyl group; an anthracenyl group; a phenanthryl group; a triphenyl group; a pyrenyl group; a phenalenyl group; a perylenyl group; a chrysenyl group; a fluorenyl group and the like, but are not limited thereto.

In the present specification, an "adjacent" group may mean a substituent directly linked to an atom substituted by the corresponding substituent, a substituent sterically most closely positioned to the corresponding substituent, or another substituent of atom substituted by the corresponding substituent. For example, two substituents substituting ortho positions in a benzene ring, and two substituents substituting the same carbon in an aliphatic ring may be interpreted as groups "adjacent" to each other.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including two or more aryl groups may include monocyclic aryl groups, polycyclic aryl groups, or both monocyclic aryl groups and polycyclic aryl groups. For example, the aryl group in the arylamine group may be selected from among the examples of the aryl group described above.

In the present specification, the heteroaryl group is a group including one or more heteroatoms that are not carbon, and specifically, the heteroatom may include one or more atoms selected from the group consisting of O, N, Se, S and the like. The number of carbon atoms is not particularly limited, but is preferably from 2 to 30 and more preferably from 2 to 20, and the heteroaryl group may be monocyclic or polycyclic. Examples of the heteroaryl group may include a thiophene group; a furanyl group; a pyrrole group; an imidazolyl group; a thiazolyl group; an oxazolyl group; an oxadiazolyl group; a pyridyl group; a bipyridyl group; a pyrimidyl group; a triazinyl group; a triazolyl group; an acridyl group; a pyridazinyl group; a pyrazinyl group; a quinolinyl group; a quinazolinyl group; a quinoxalinyl group; a phthalazinyl group; a pyridopyrimidyl group; a pyridopyrazinyl group; a pyrazinopyrazinyl group; an isoquinolinyl group; an indolyl group; a carbazolyl group; a benzoxazolyl group; a benzimidazolyl group; a benzothiazolyl group; a benzocarbazolyl group; a benzothiophene group; a dibenzothiophene group; a benzofuranyl group; a phenanthrolinyl group; an isoxazolyl group; a thiadiazolyl group; a phenothiazinyl group; a dibenzofuranyl group and the like, but are not limited thereto.

In the present specification, the arylene group has the same definition as the aryl group except for being divalent.

In the present specification, the heteroarylene group has the same definition as the heteroaryl group except for being divalent.

In the present specification, when adjacent substituents bond to each other to form a ring, the ring may be a hydrocarbon ring, an aromatic ring or a heteroring. Herein, the hydrocarbon ring has the same definition as the cycloalkyl group except for those that are not monovalent, the aromatic ring has the same definition as the aryl group except for those that are not monovalent, and the heteroring has the same definition as the heteroaryl group except for those that are not monovalent.

In one exemplary embodiment of the present specification, R1 to R6 and R11 to R14 are hydrogen.

In one exemplary embodiment of the present specification, R15 is hydrogen, a nitrile group, a halogen group, an alkyl group, an aryl group or a heteroaryl group, or adjacent groups bond to each other to form a substituted or unsubstituted ring.

In one exemplary embodiment of the present specification, R15 is hydrogen, an aryl group having 6 to 30 carbon atoms or a heteroaryl group having 3 to 30 carbon atoms, or adjacent groups bond to each other to form a substituted or unsubstituted aromatic ring, or a substituted or unsubstituted heteroring.

In one exemplary embodiment of the present specification, R15 is hydrogen, or adjacent groups bond to each other to form an aromatic ring or a heteroring.

In one exemplary embodiment of the present specification, R15 is hydrogen, or adjacent groups bond to each other to form an aromatic ring.

In one exemplary embodiment of the present specification, R15 is hydrogen, or adjacent groups bond to each other to form a benzene ring.

In one exemplary embodiment of the present specification, one of R7 to R10 is Chemical Formula A, and the rest are hydrogen.

In one exemplary embodiment of the present specification, R7 of R7 to R10 is Chemical Formula A, and the rest are hydrogen.

In one exemplary embodiment of the present specification, R8 of R7 to R10 is Chemical Formula A, and the rest are hydrogen.

In one exemplary embodiment of the present specification, R9 of R7 to R10 is Chemical Formula A, and the rest are hydrogen.

In one exemplary embodiment of the present specification, R10 of R7 to R10 is Chemical Formula A, and the rest are hydrogen.

In one exemplary embodiment of the present specification, a and b are N.

In one exemplary embodiment of the present specification, a and b are CR.

In one exemplary embodiment of the present specification, a is N, and b is CR.

In one exemplary embodiment of the present specification, a is CR, and b is N.

In one exemplary embodiment of the present specification, R is a substituted or unsubstituted aryl group.

In one exemplary embodiment of the present specification, R is a substituted or unsubstituted heteroaryl group.

In one exemplary embodiment of the present specification, R is an aryl group having 6 to 30 carbon atoms unsubstituted or substituted with an aryl group; an aryl group having 6 to 30 carbon atoms unsubstituted or substituted with an alkyl group; or a heteroaryl group having 3 to 30 carbon atoms unsubstituted or substituted with an aryl group.

In one exemplary embodiment of the present specification, R is an aryl group having 6 to 30 carbon atoms unsubstituted or substituted with an aryl group having 6 to 20 carbon atoms; an aryl group having 6 to 30 carbon atoms unsubstituted or substituted with an alkyl group having 1 to 10 carbon atoms; or a heteroaryl group having 3 to 30 carbon atoms unsubstituted or substituted with an aryl group having 6 to 20 carbon atoms.

In one exemplary embodiment of the present specification, R is an aryl group having 6 to 30 carbon atoms unsubstituted or substituted with an aryl group having 6 to 20 carbon atoms.

In one exemplary embodiment of the present specification, R is an aryl group having 6 to 30 carbon atoms unsubstituted or substituted with an alkyl group having 1 to 10 carbon atoms.

In one exemplary embodiment of the present specification, R is a substituted or unsubstituted heteroaryl group having 3 to 30 carbon atoms.

In one exemplary embodiment of the present specification, R is an aryl group having 6 to 30 carbon atoms unsubstituted or substituted with a methyl group, an ethyl group, a propyl group, an isopropyl group, a butyl group or a tert-butyl group.

In one exemplary embodiment of the present specification, R is an aryl group having 6 to 30 carbon atoms unsubstituted or substituted with any one or more selected from among a phenyl group, a biphenyl group, a naphthyl group, an anthracene group, a phenanthrene group, a terphenyl group and a triphenyl group.

In one exemplary embodiment of the present specification, R is a phenyl group, a naphthyl group, a biphenyl group, a terphenyl group, an anthracene group, a phenanthrene group, a fluorene group, a triphenylene group or a pyrene group, and the phenyl group, the naphthyl group, the biphenyl group, the terphenyl group, the anthracene group, the phenanthrene group, the fluorene group, the triphenylene group or the pyrene group is unsubstituted or substituted with any one or more selected from among a methyl group, an ethyl group, a propyl group, an isopropyl group, a butyl group, a tert-butyl group, a phenyl group, a biphenyl group, a naphthyl group, an anthracene group, a phenanthrene group, a terphenyl group and a triphenyl group.

In one exemplary embodiment of the present specification, R is a phenyl group, a biphenyl group, a terphenyl group, a naphthyl group, a phenanthrene group or a fluorene group, and the phenyl group, the biphenyl group, the terphenyl group, the naphthyl group, the phenanthrene group or the fluorene group is unsubstituted or substituted with a phenyl group, a naphthyl group or a methyl group.

In one exemplary embodiment of the present specification, R is a phenyl group; a phenyl group substituted with a naphthyl group; a naphthyl group; a naphthyl group substituted with a phenyl group; a biphenyl group; a terphenyl group; a phenanthrene group; or a fluorene group substituted with a methyl group.

In one exemplary embodiment of the present specification, R is a heteroaryl group having 3 to 30 carbon atoms and including any one or more of N, O and S unsubstituted or substituted with an aryl group.

In one exemplary embodiment of the present specification, R is a heteroaryl group having 3 to 30 carbon atoms and including any one or more of N, O and S unsubstituted or substituted with an aryl group having 6 to 30 carbon atoms.

In one exemplary embodiment of the present specification, R is a pyridine group, a pyrimidine group, a triazine group, a dibenzofuran group, a dibenzothiophene group or a carbazole group, and the pyridine group, the pyrimidine group, the triazine group, the dibenzofuran group, the dibenzothiophene group or the carbazole group is unsubstituted or substituted with an aryl group having 6 to 30 carbon atoms.

In one exemplary embodiment of the present specification, R is a pyridine group, a pyrimidine group, a triazine group, a dibenzofuran group, a dibenzothiophene group or a carbazole group, and the pyridine group, the pyrimidine group, the triazine group, the dibenzofuran group, the dibenzothiophene group or the carbazole group is unsubstituted or substituted with a phenyl group, a biphenyl group, a terphenyl group, an anthracene group, a phenanthrene group or a naphthyl group.

In one exemplary embodiment of the present specification, R is a dibenzofuran group, a dibenzothiophene group, or a carbazole group unsubstituted or substituted with a phenyl group.

In one exemplary embodiment of the present specification, R is a phenyl group; a phenyl group substituted with a naphthyl group; a naphthyl group; a naphthyl group substituted with a phenyl group; a biphenyl group; a terphenyl group; a phenanthrene group; a fluorene group substituted with a methyl group, a dibenzofuran group, a dibenzothiophene group, or a carbazole group unsubstituted or substituted with a phenyl group.

In one exemplary embodiment of the present specification, L is a direct bond, a substituted or unsubstituted arylene group having 6 to 30 carbon atoms, or a substituted or unsubstituted heteroarylene group having 3 to 30 carbon atoms.

In one exemplary embodiment of the present specification, L is a direct bond, or an arylene group having 6 to 30 carbon atoms.

In one exemplary embodiment of the present specification, L is a direct bond, or an arylene group having 6 to 20 carbon atoms.

In one exemplary embodiment of the present specification, L is a direct bond, or an arylene group having 6 to 12 carbon atoms.

In one exemplary embodiment of the present specification, L is a direct bond, a phenylene group, a divalent biphenyl group or a divalent naphthyl group.

In one exemplary embodiment of the present specification, L is a direct bond.

In one exemplary embodiment of the present specification, Chemical Formula 1 is any one selected from:

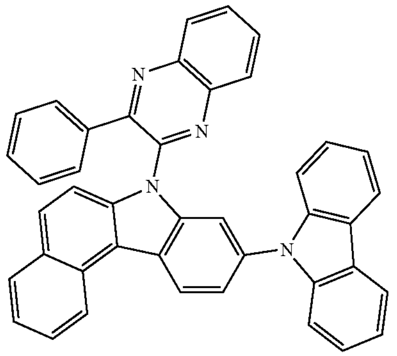

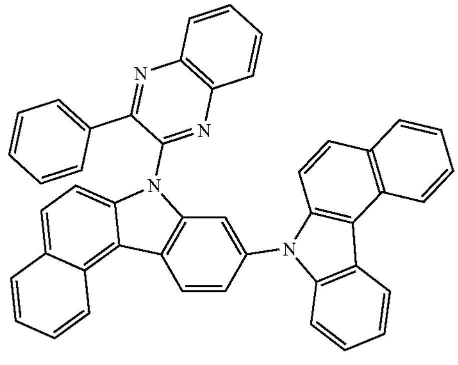

-continued
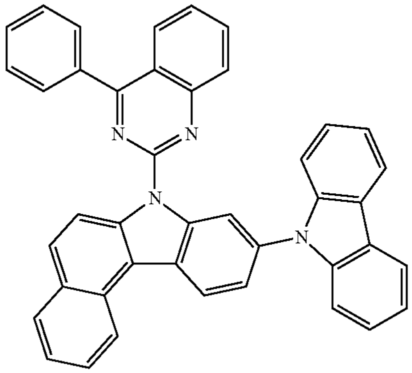
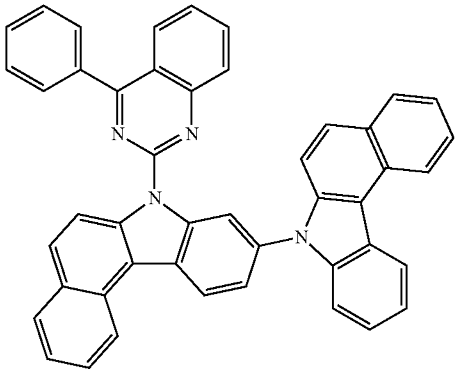
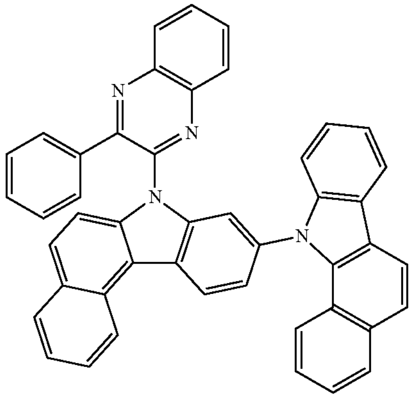
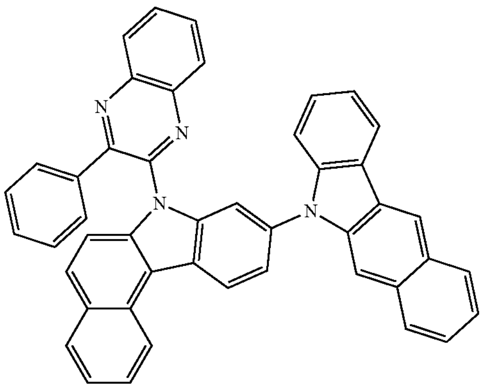
-continued
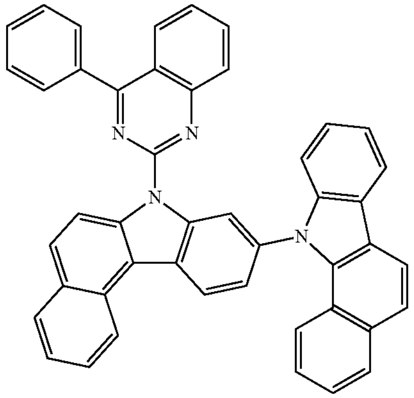
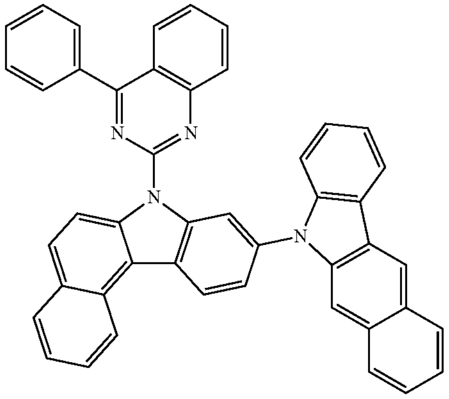
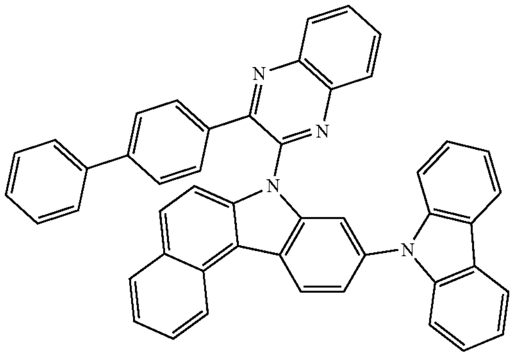
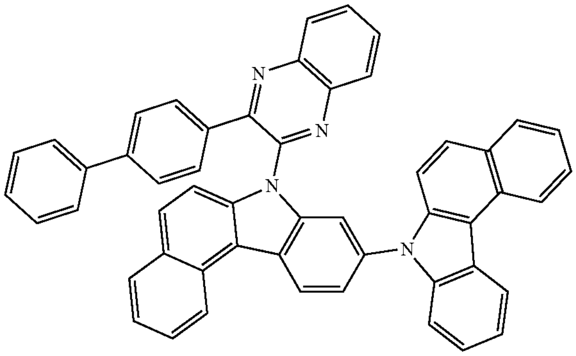

-continued
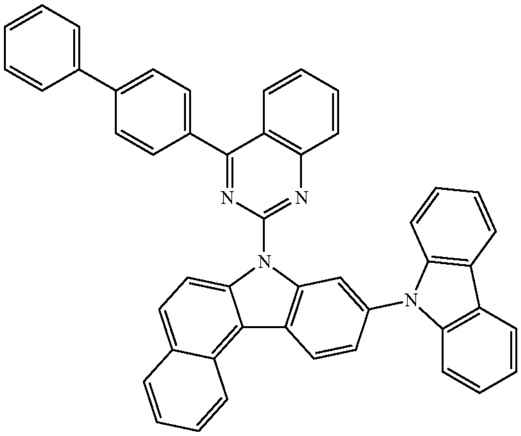
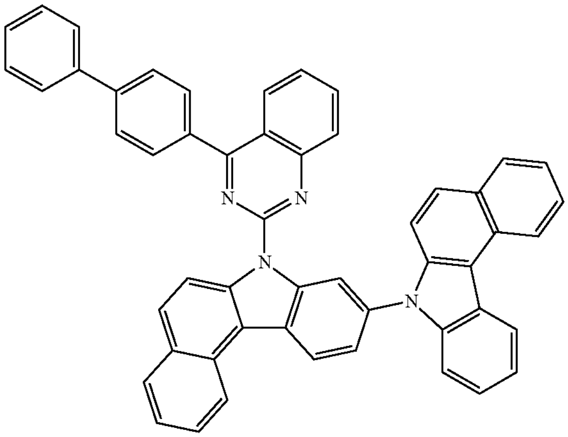
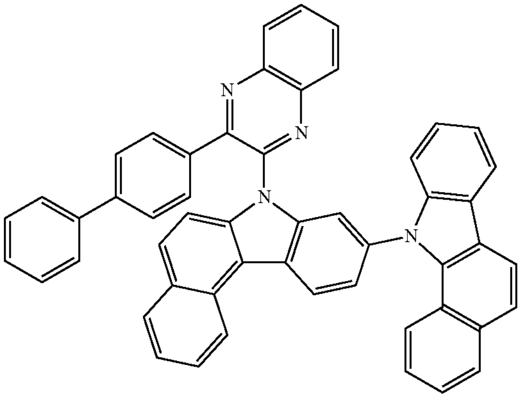
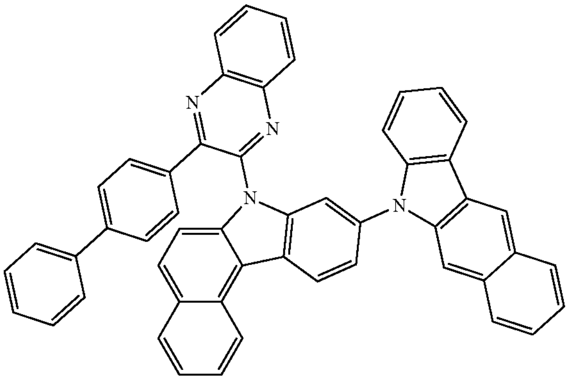
-continued
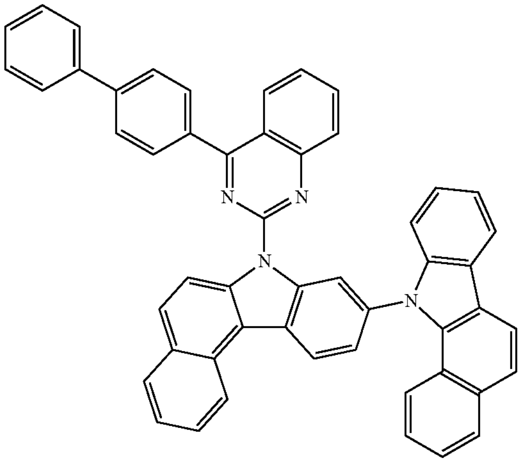
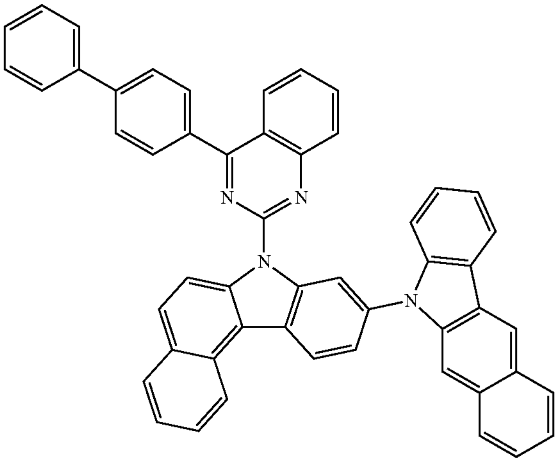
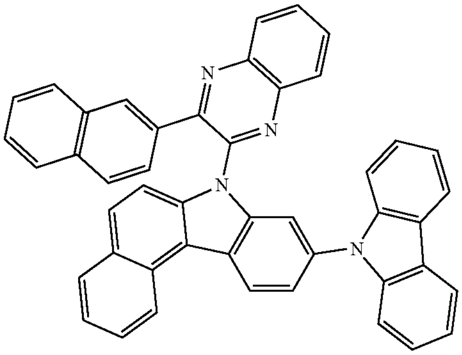
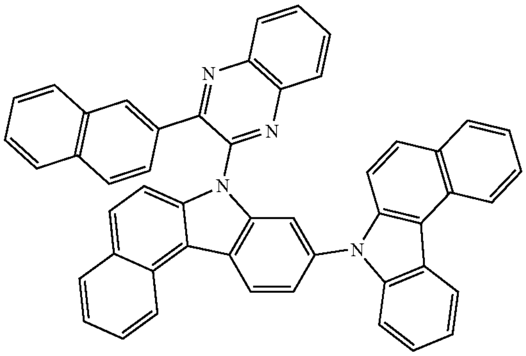

-continued
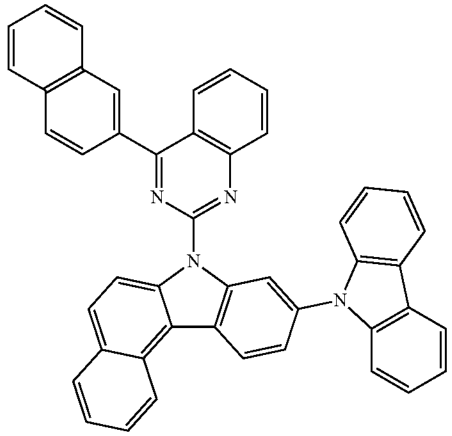
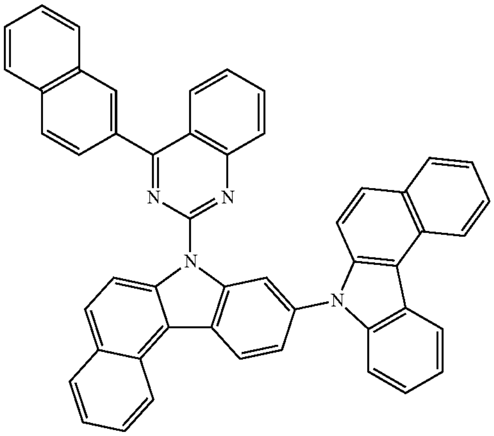
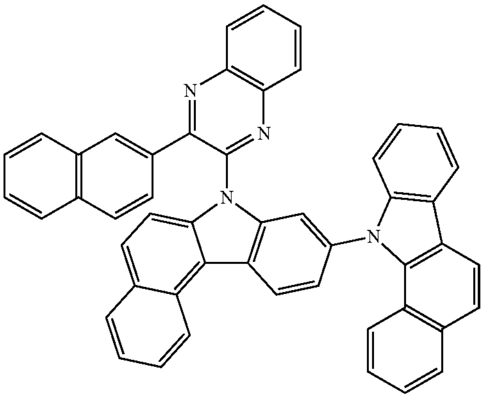
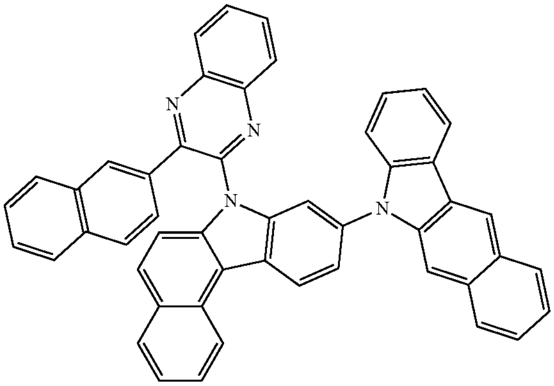
-continued
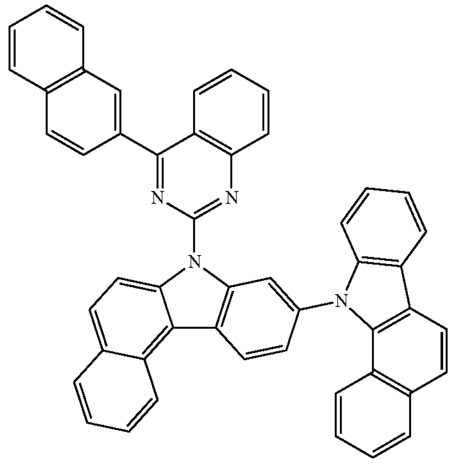
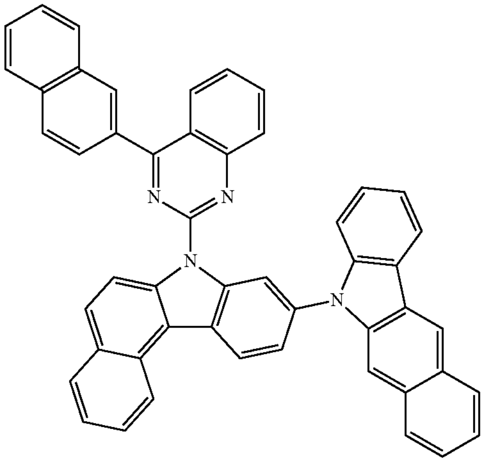
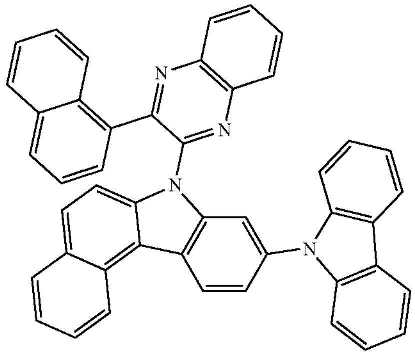
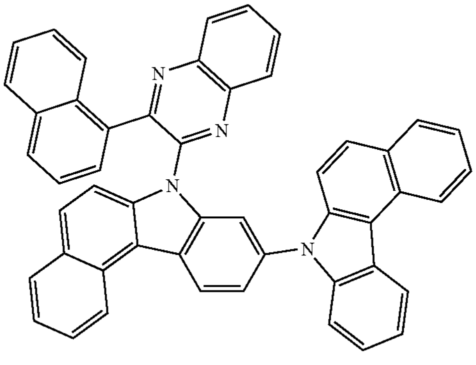

-continued
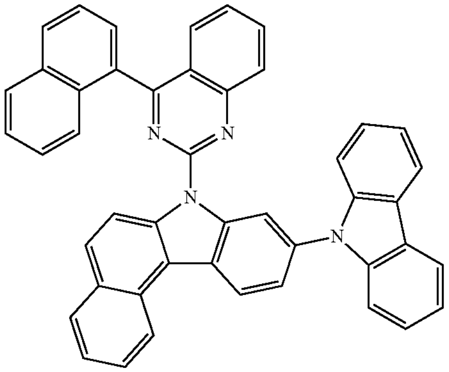
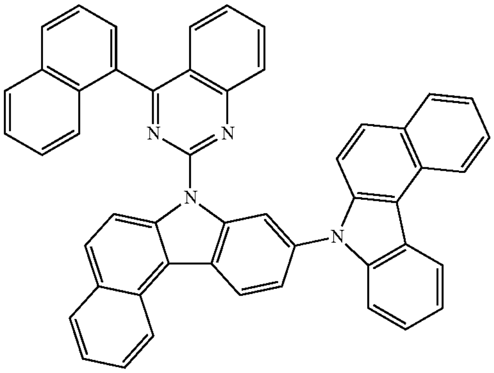
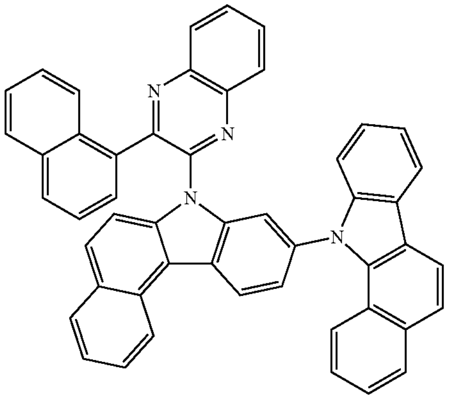
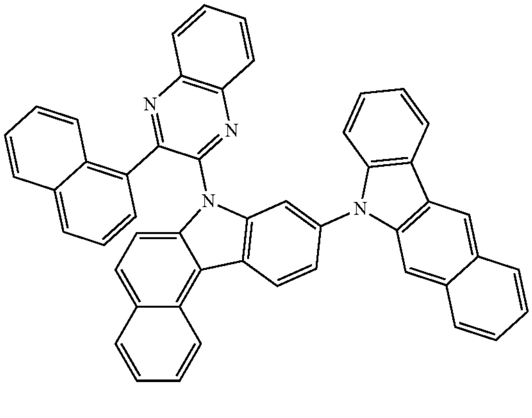
-continued
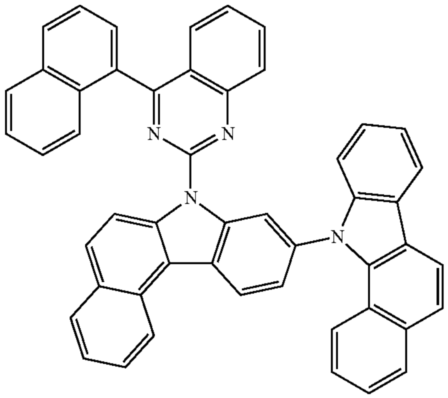
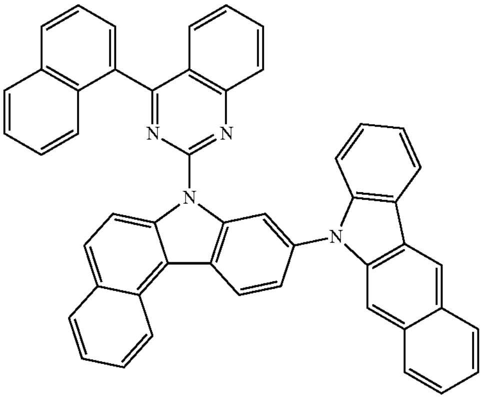
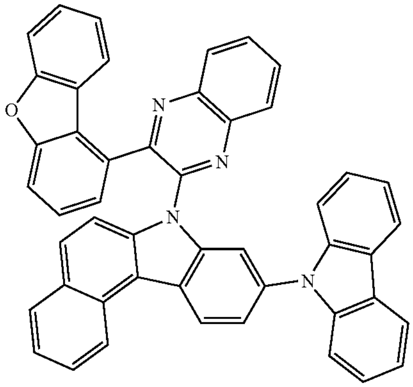
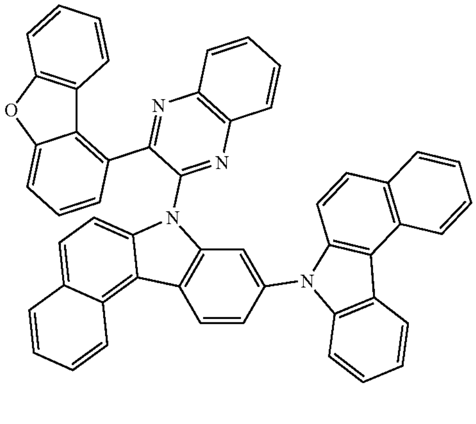

-continued
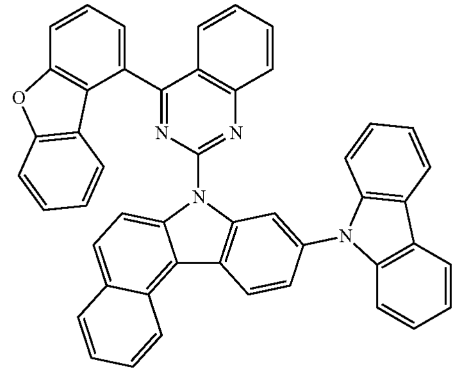
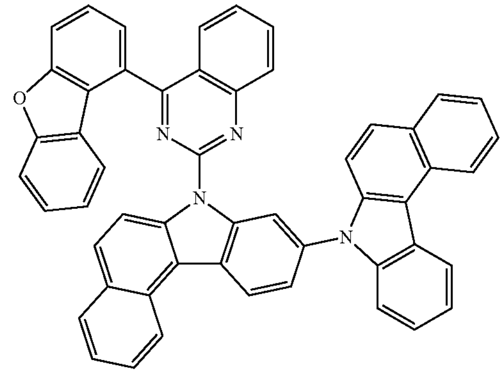
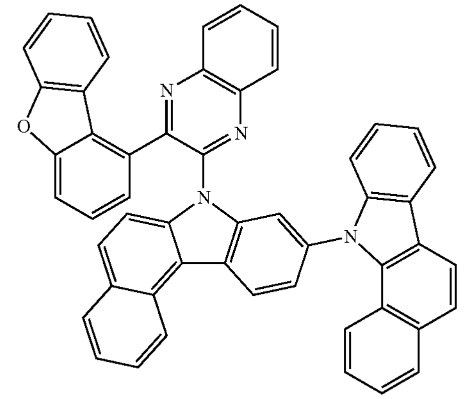
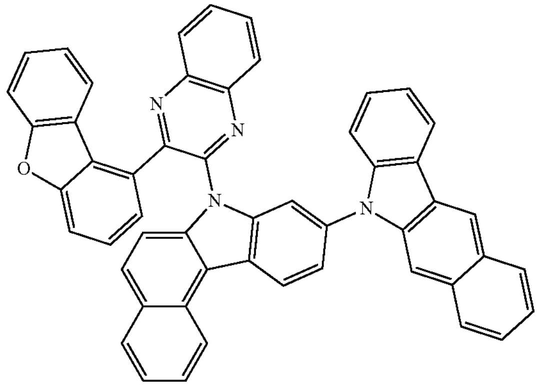
-continued
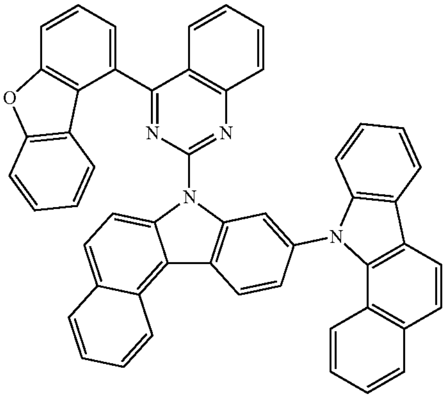
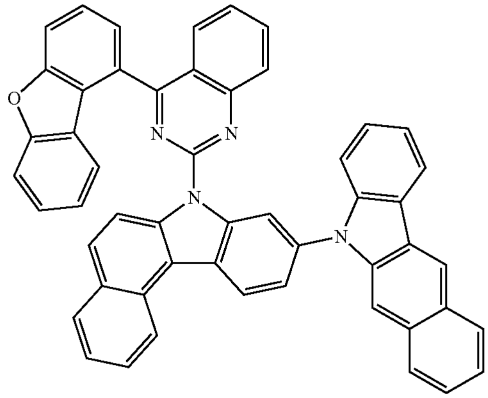
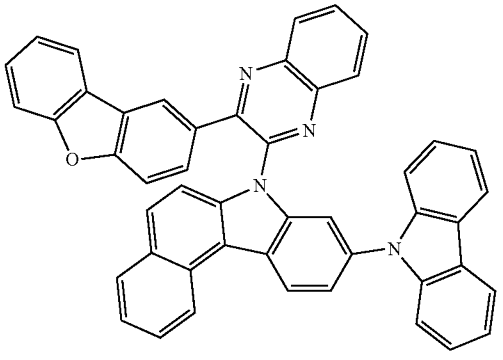
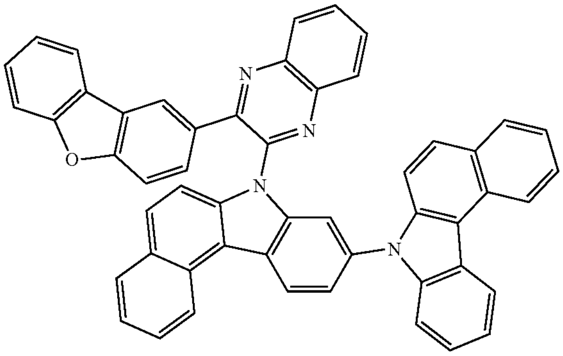

-continued
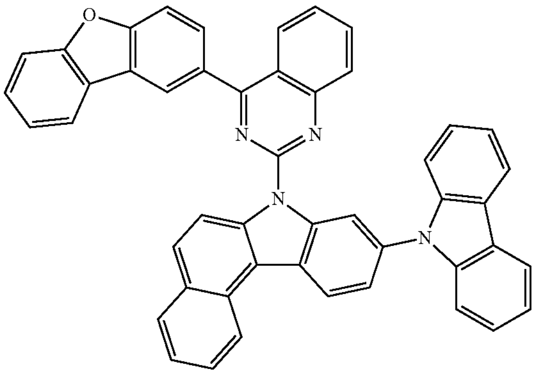
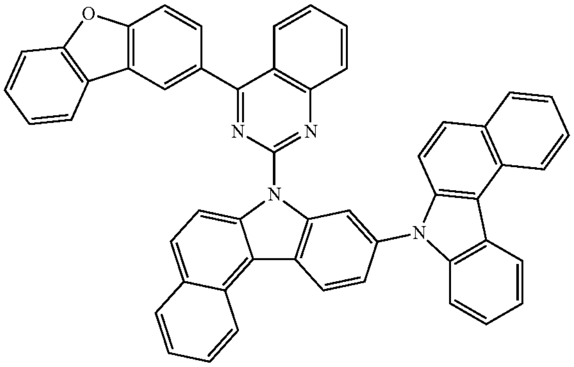
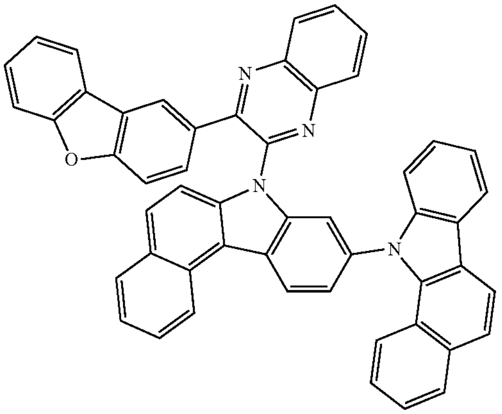
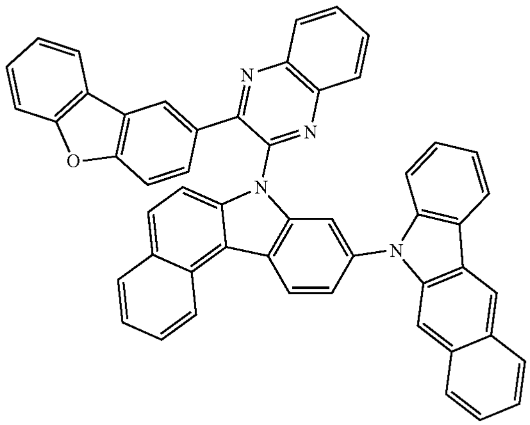
-continued
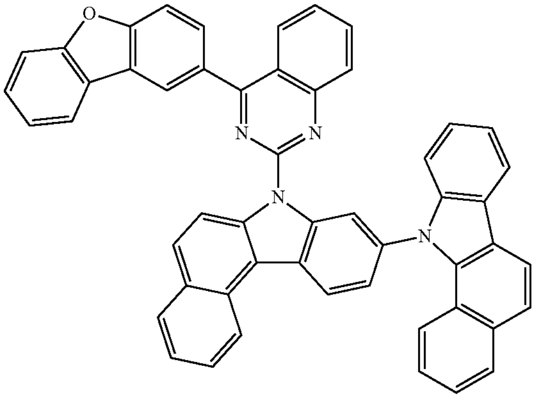
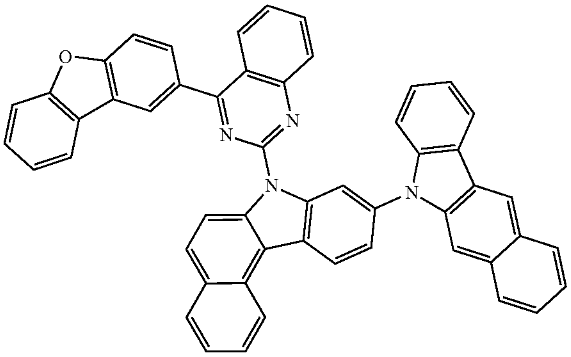
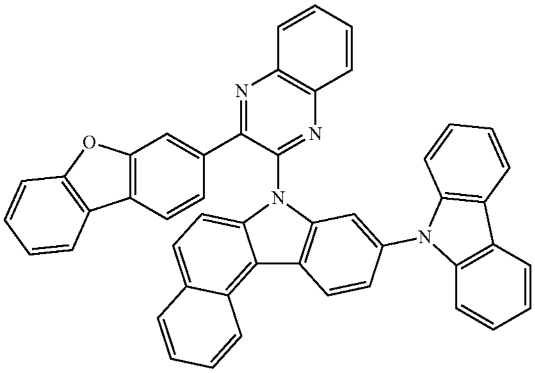
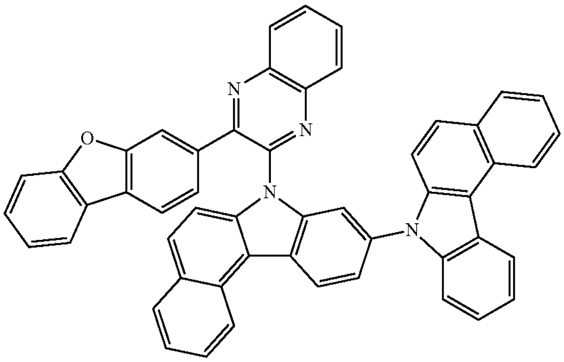

-continued
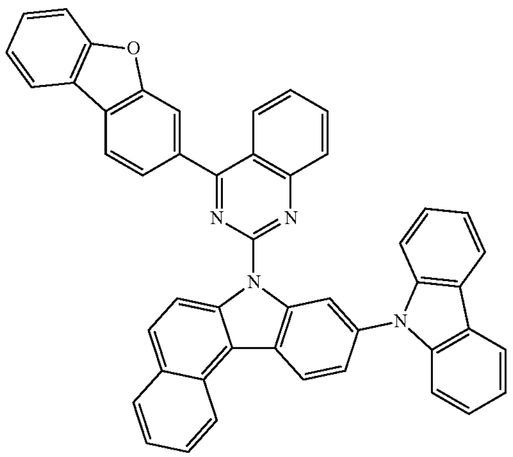
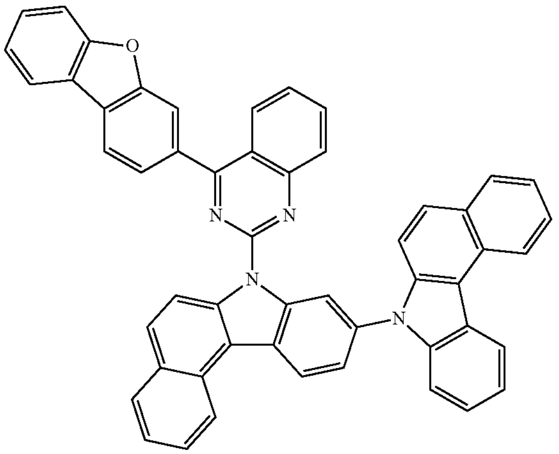
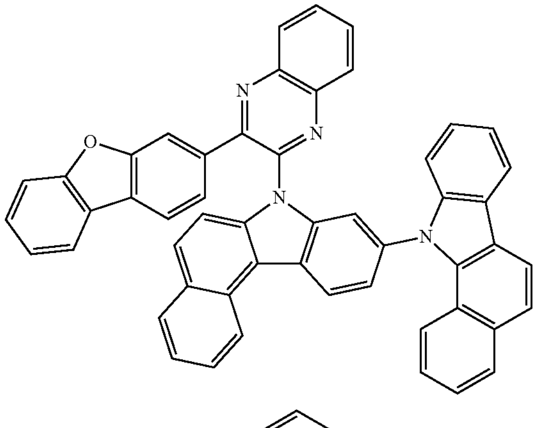
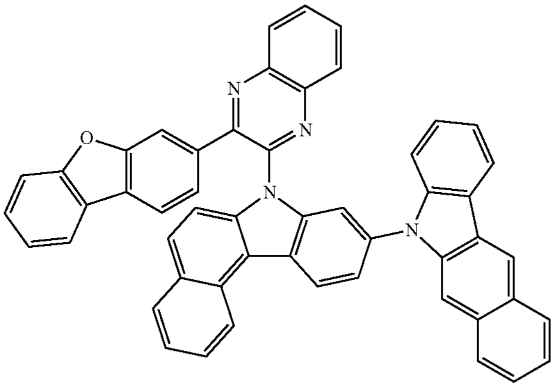
-continued
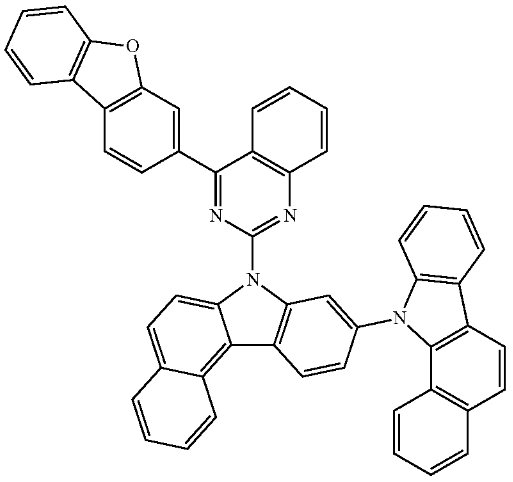
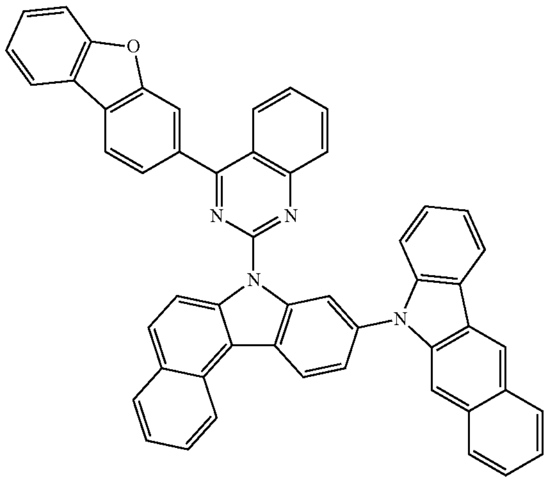
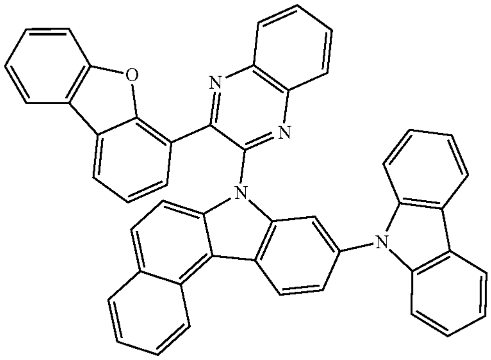
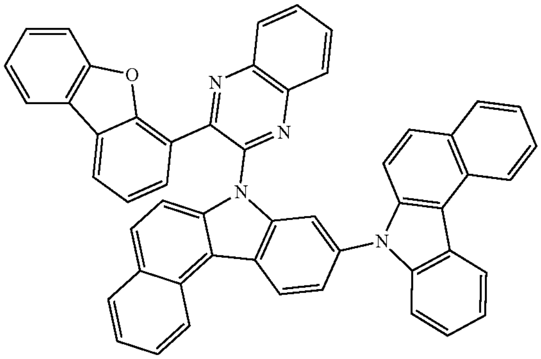

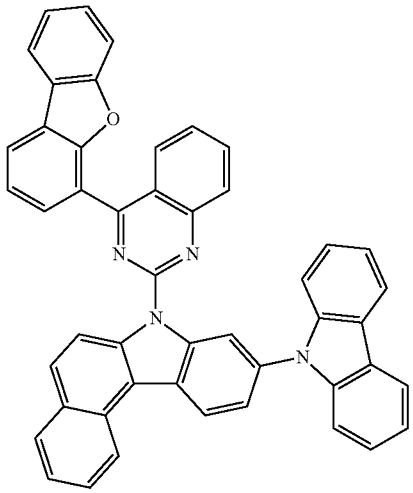
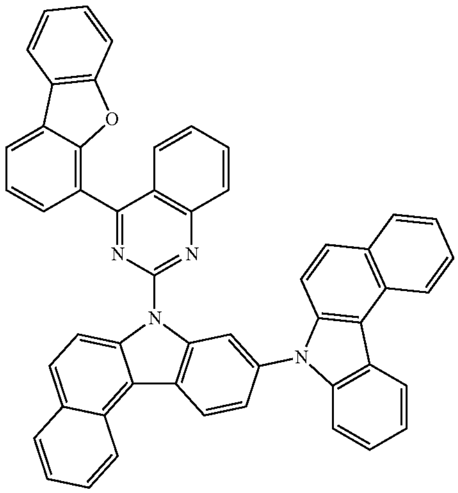
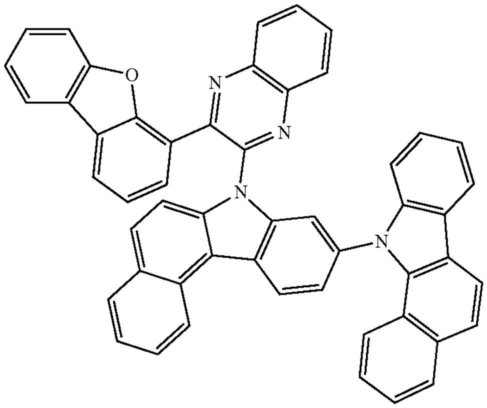
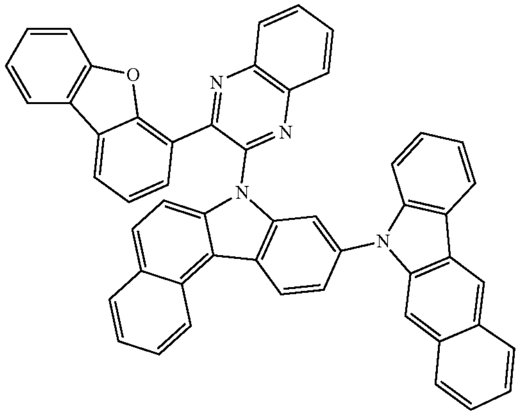
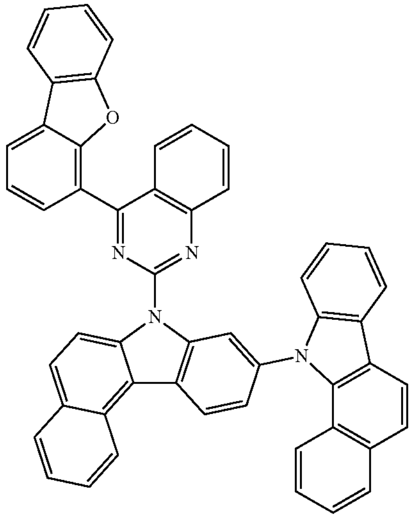
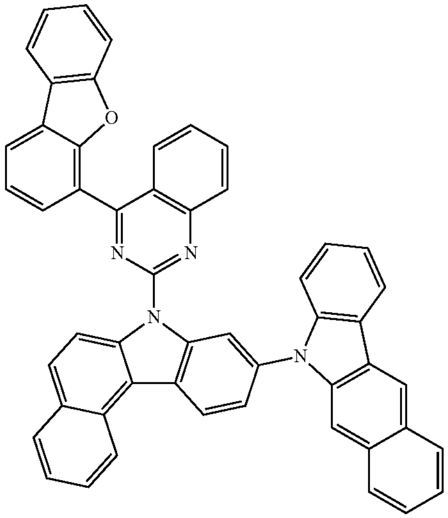

-continued
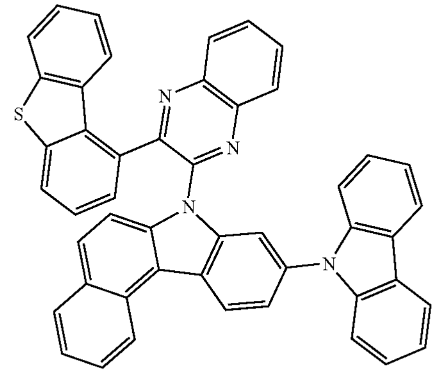
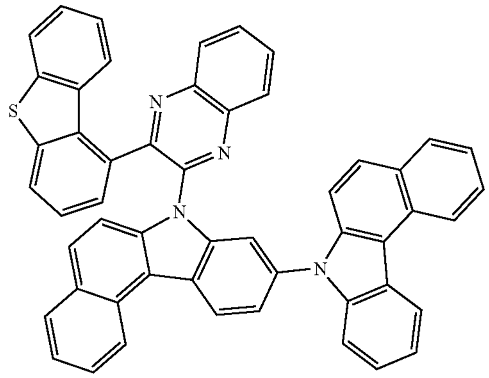
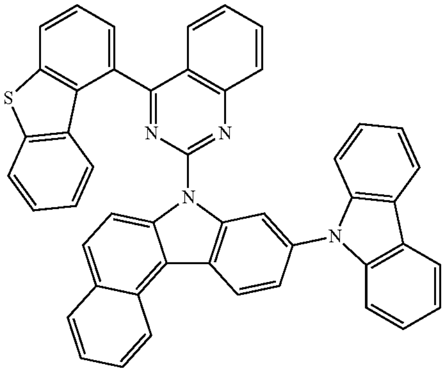
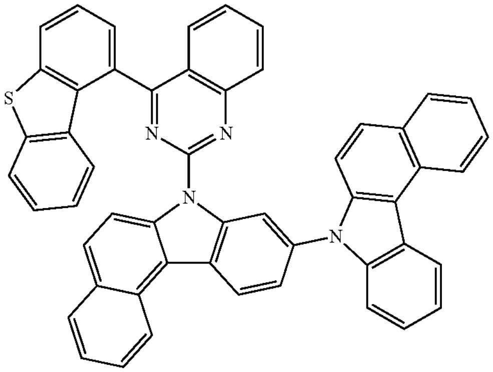
-continued
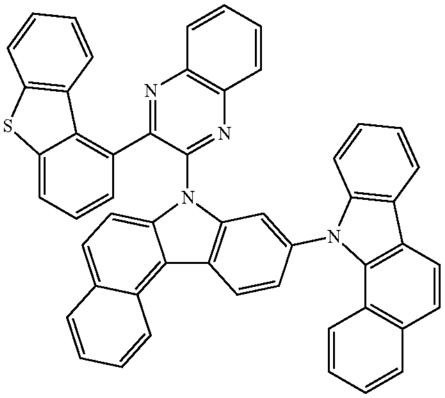
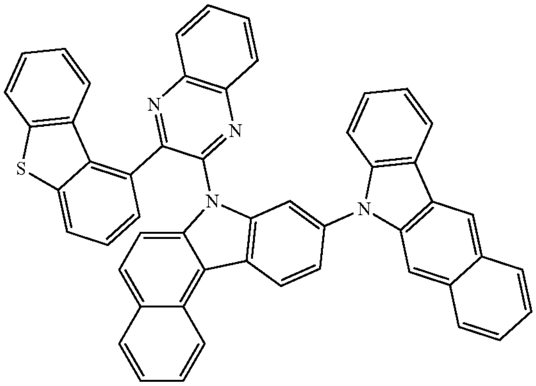
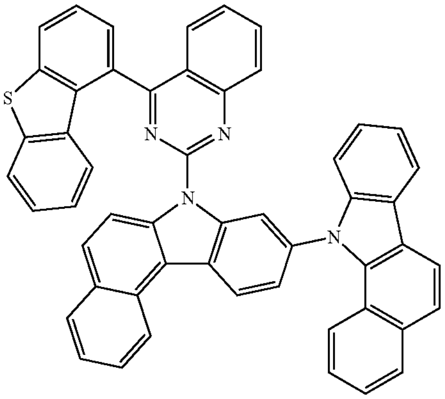
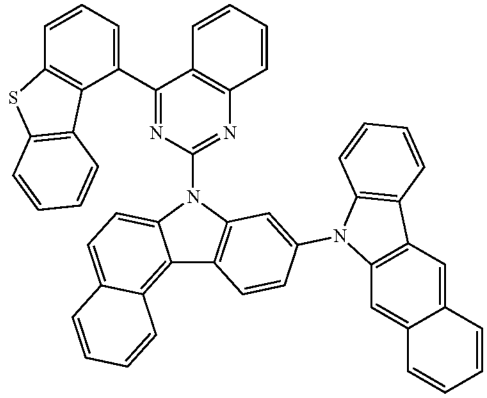

-continued
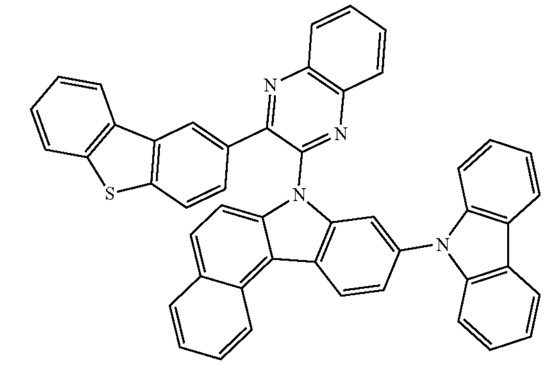
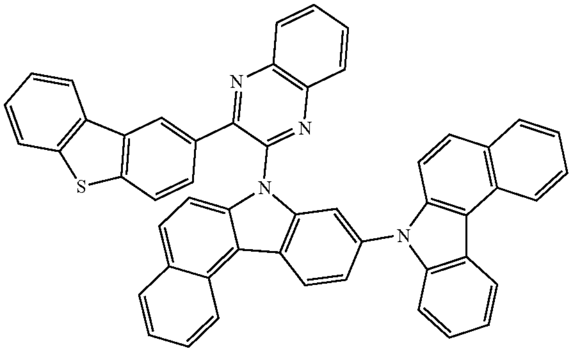
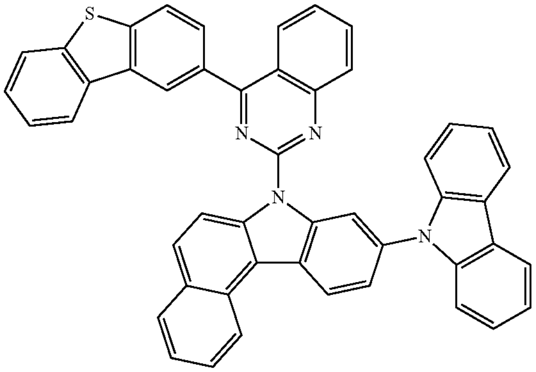
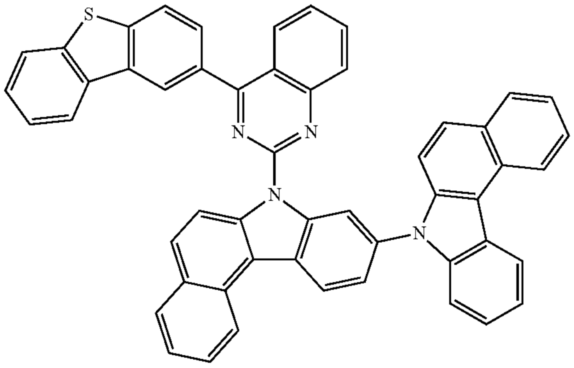
-continued
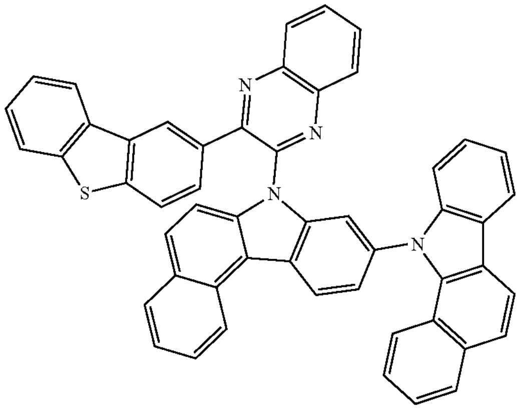
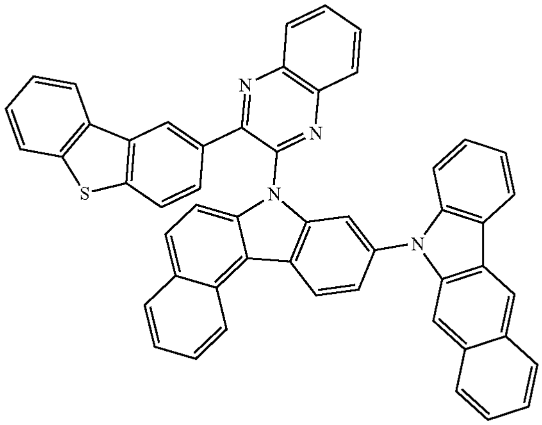
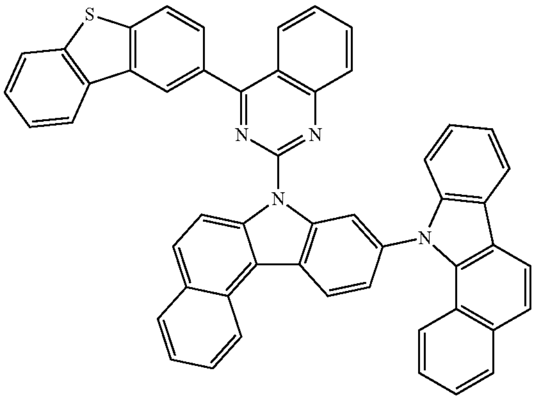
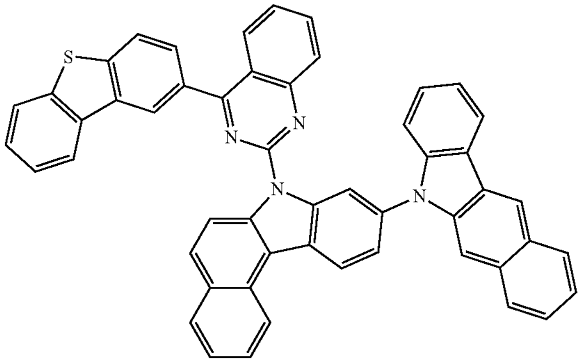

-continued
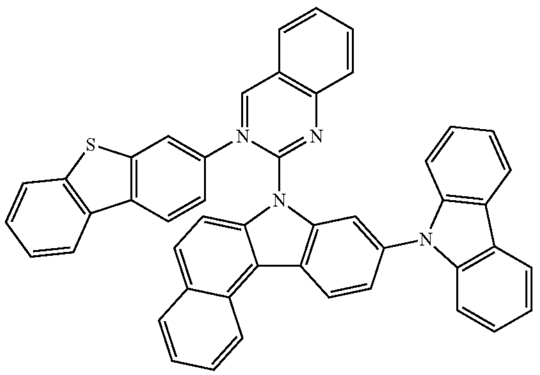
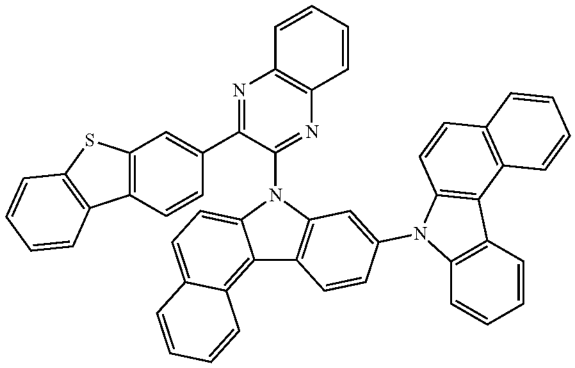
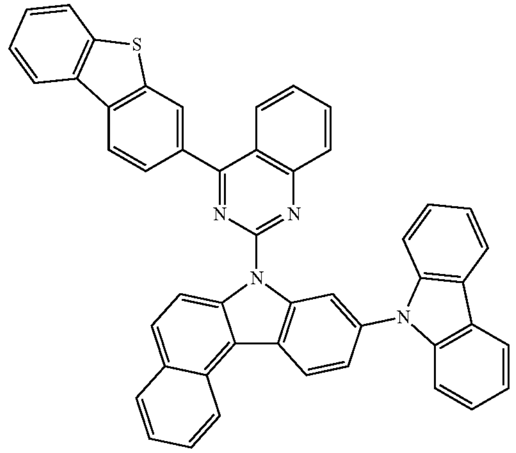
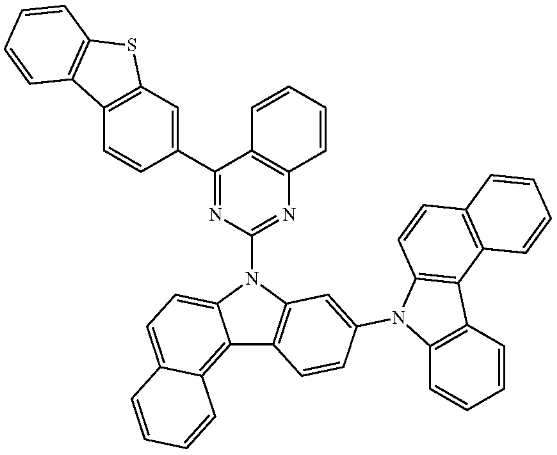
-continued
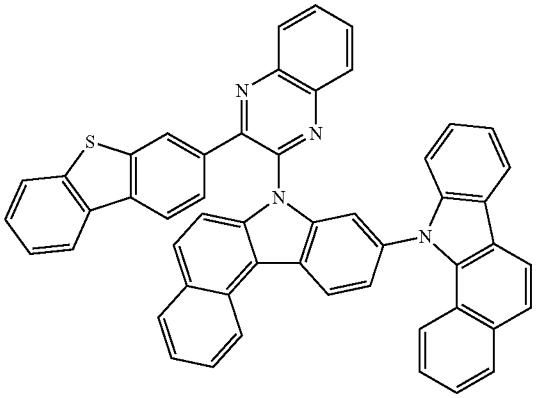
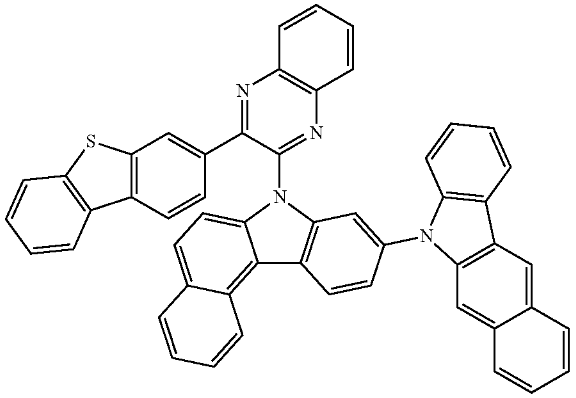
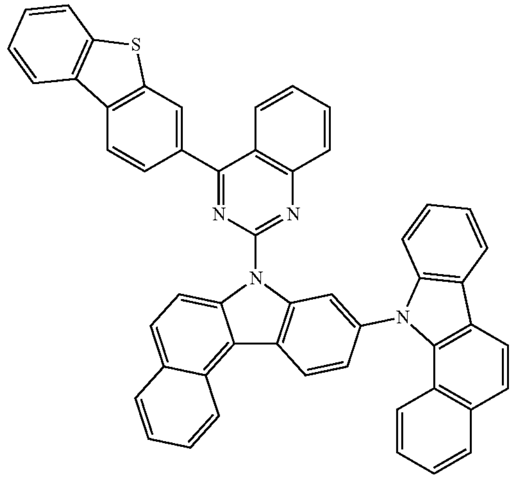

-continued
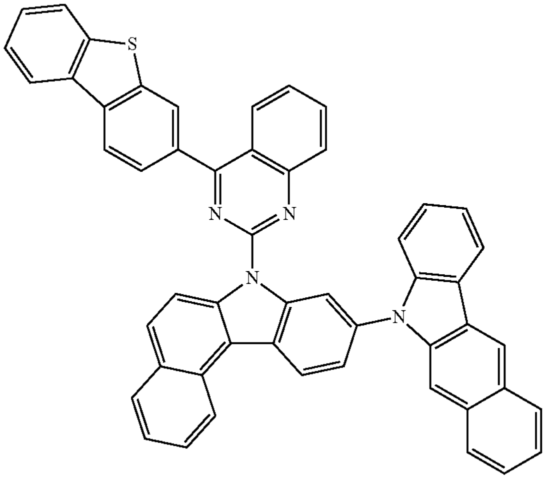
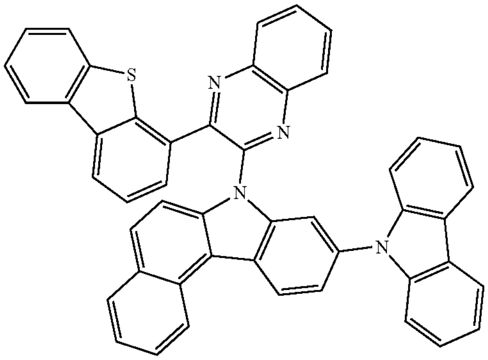
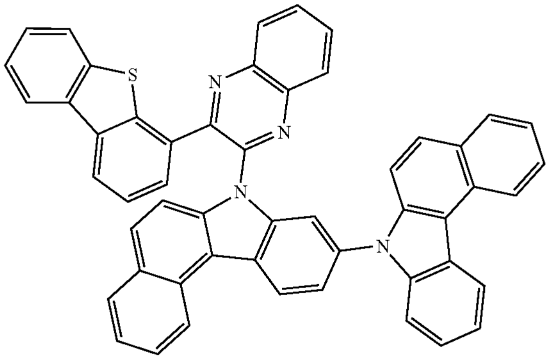
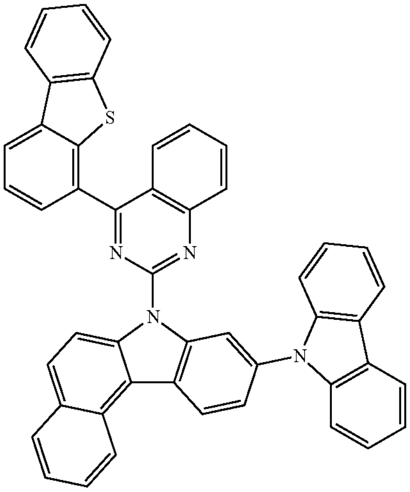
-continued
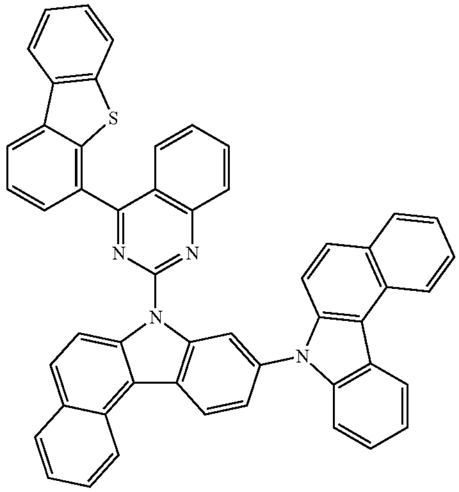
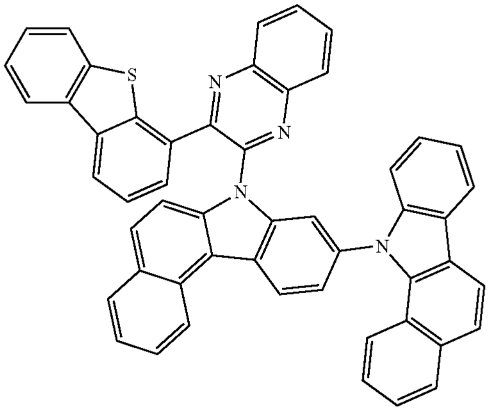
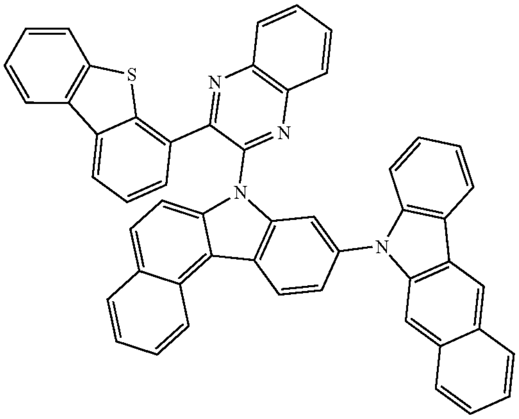

-continued
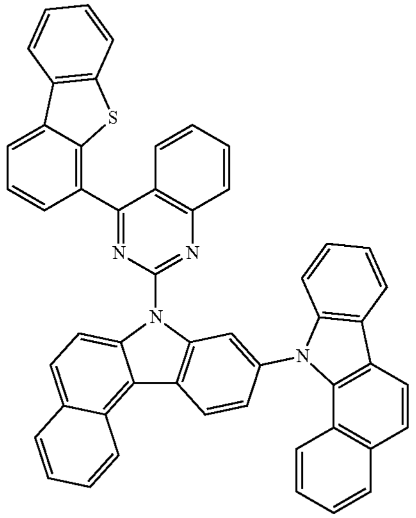
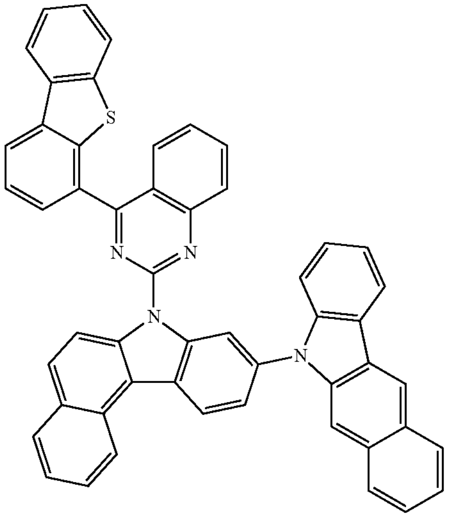
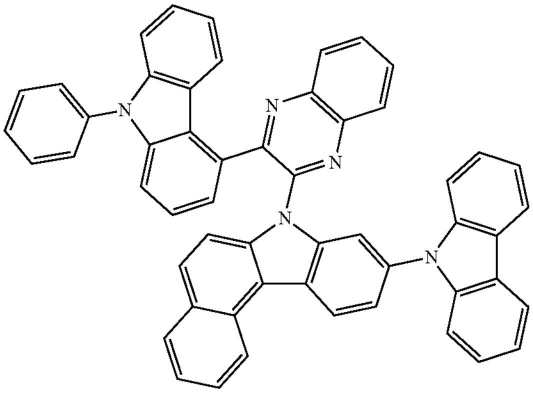
-continued
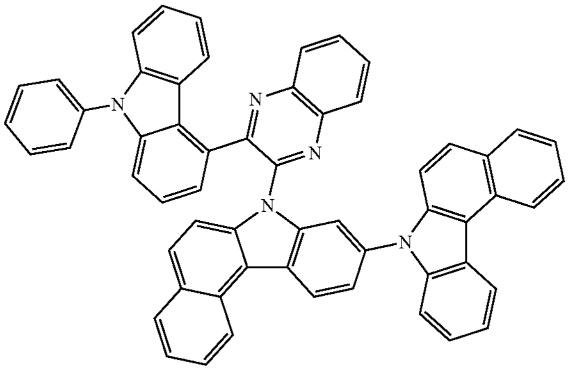
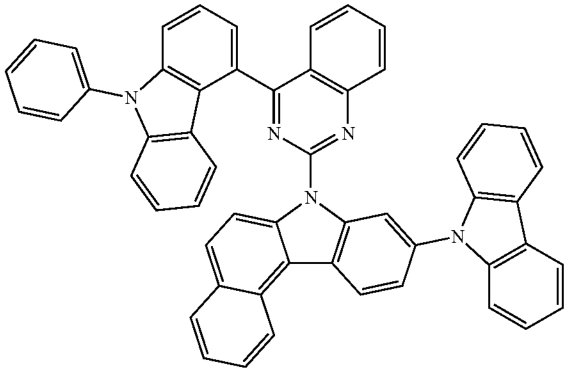
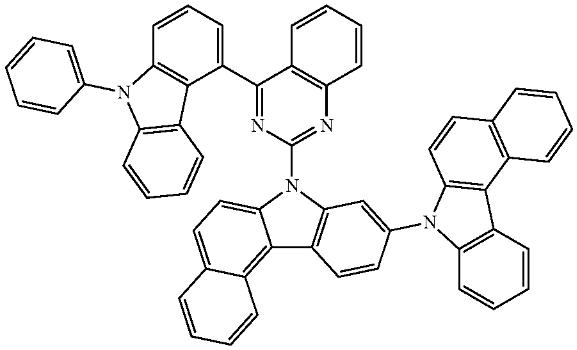
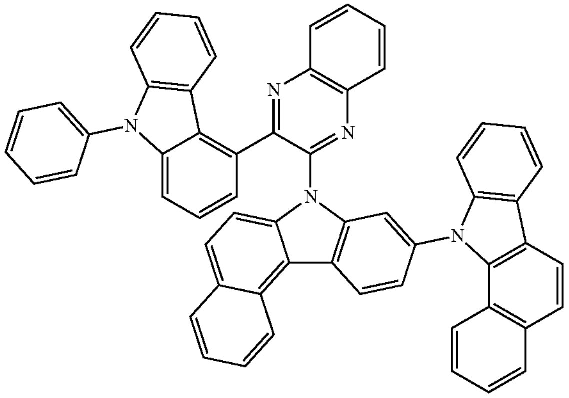

-continued
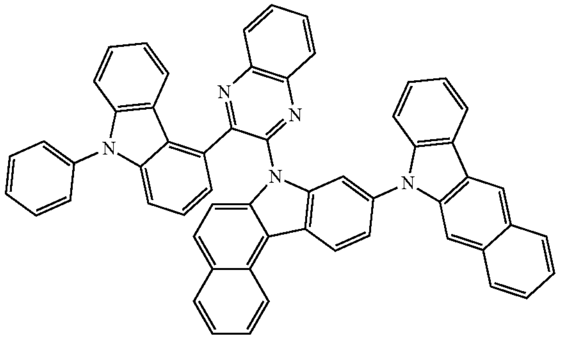
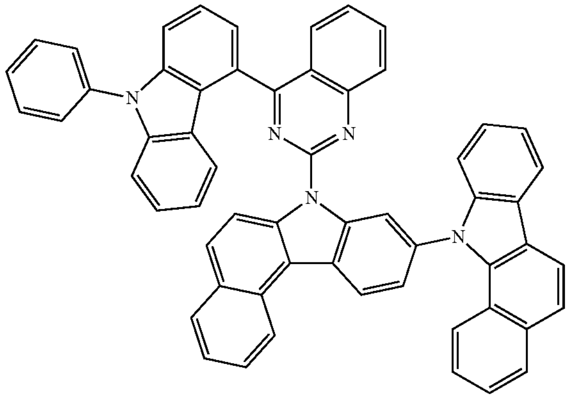
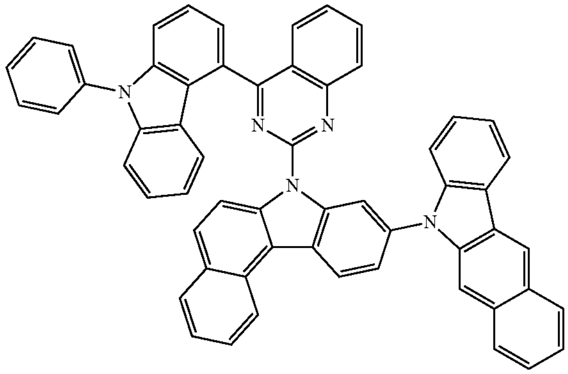
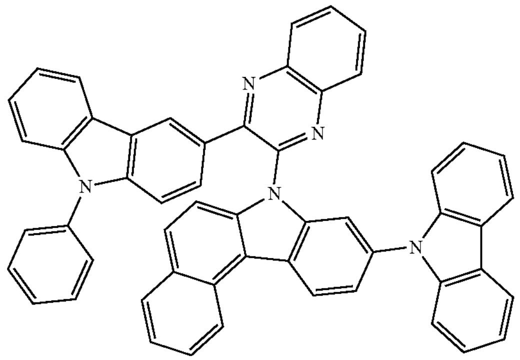
-continued
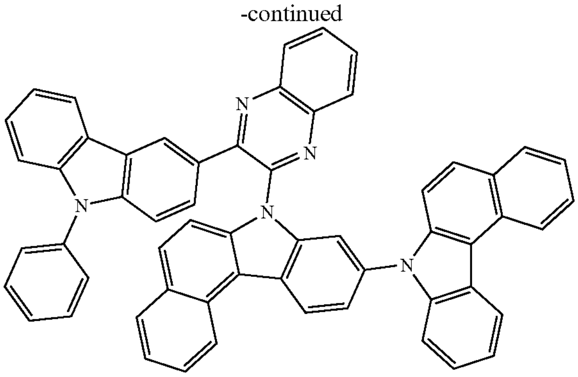
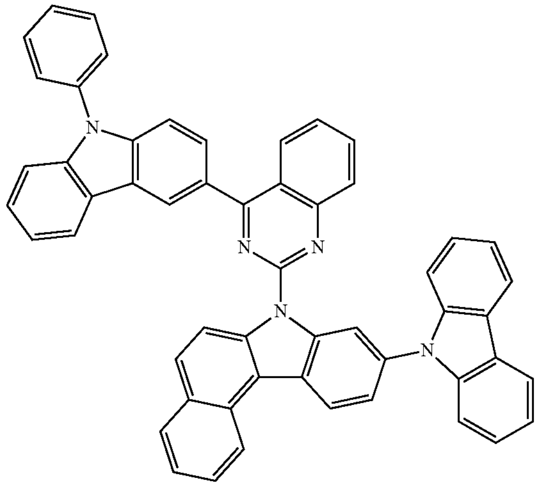
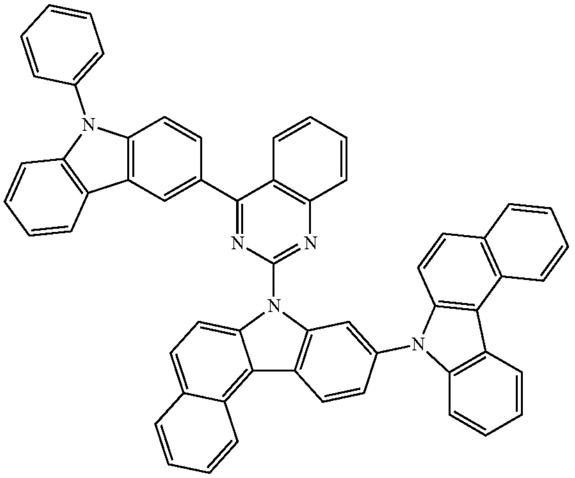
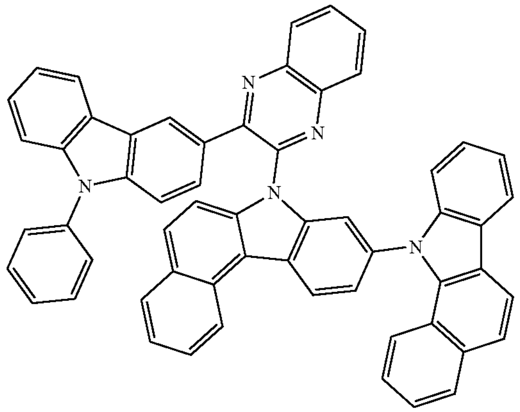

-continued
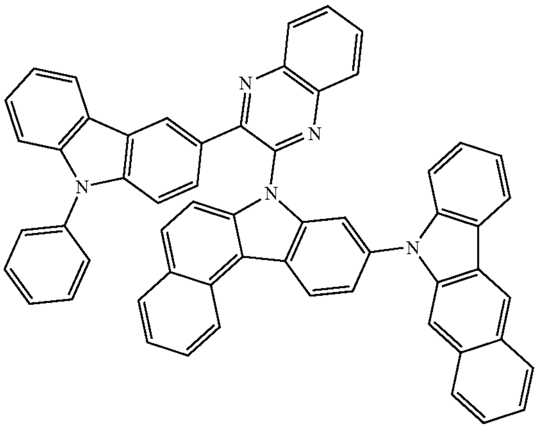
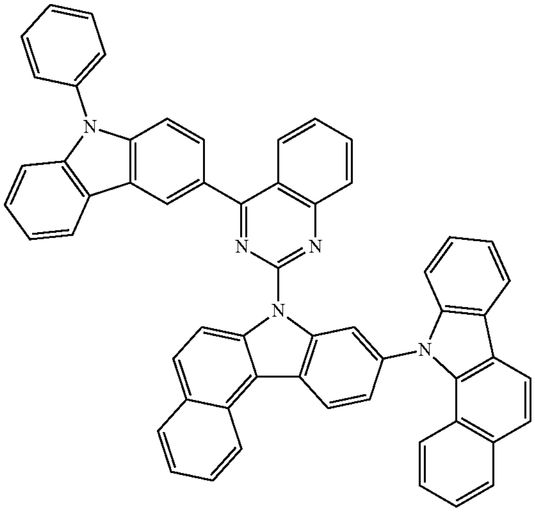
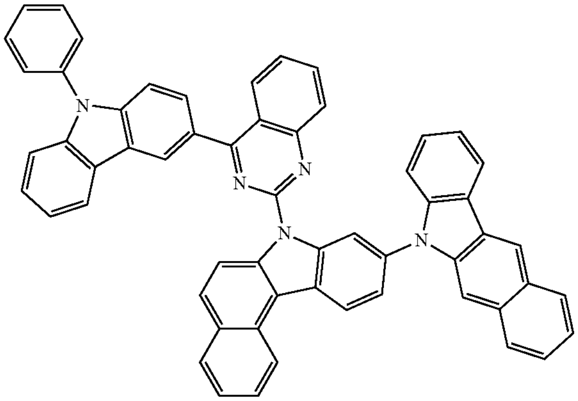
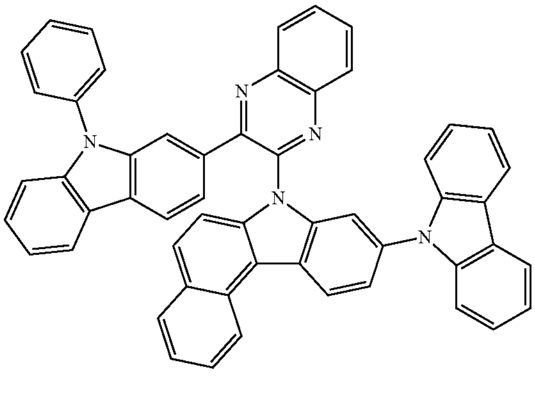
-continued
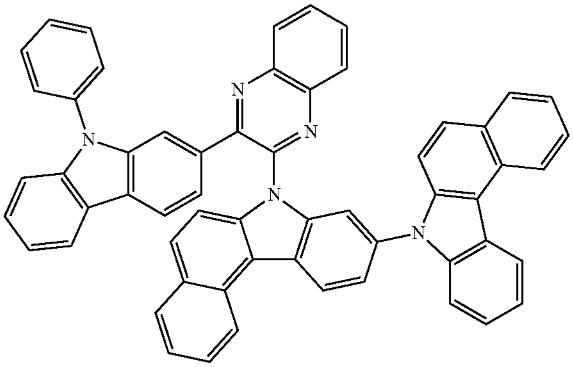
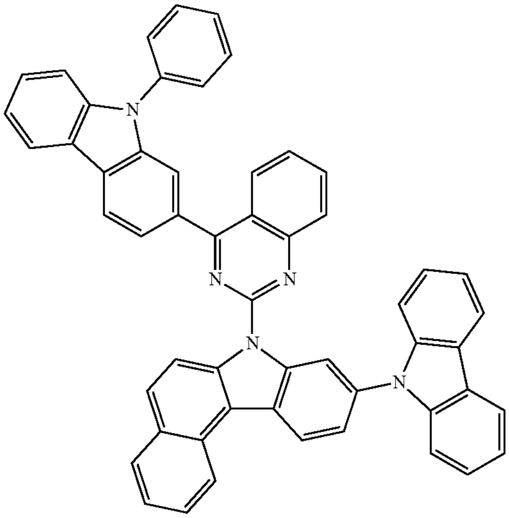
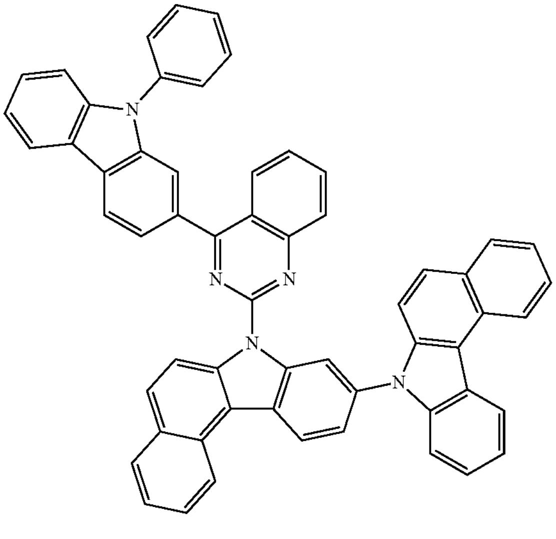

-continued
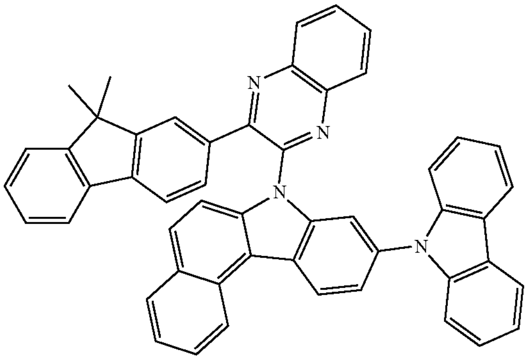
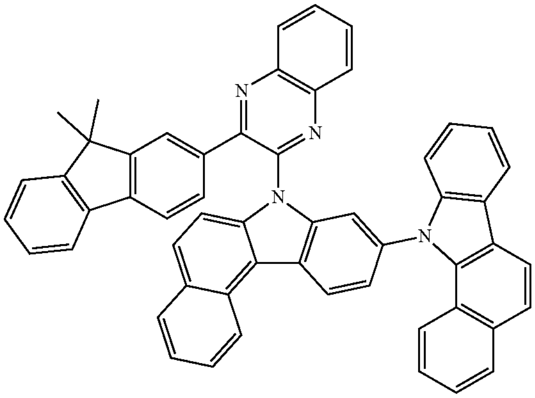
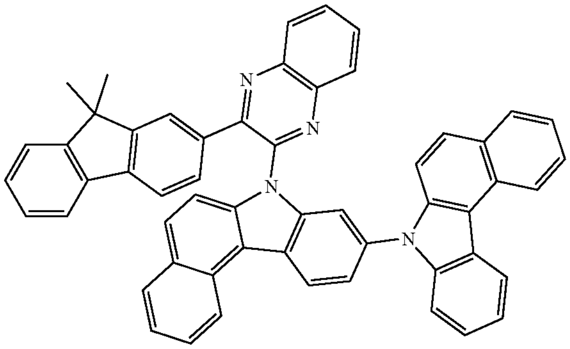
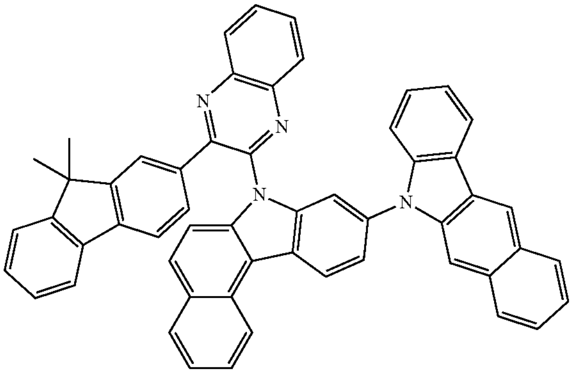
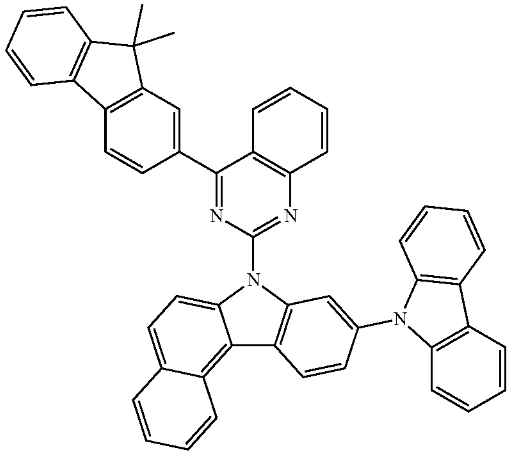
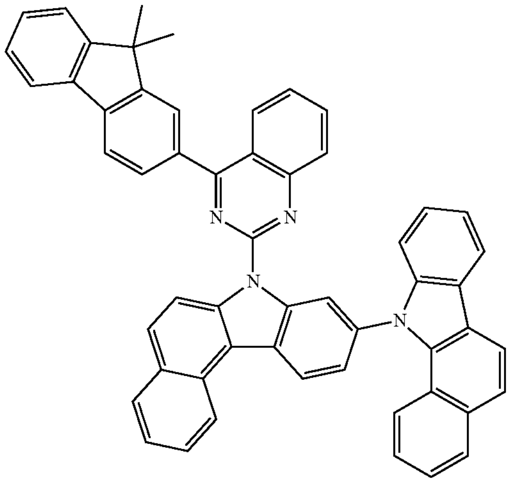
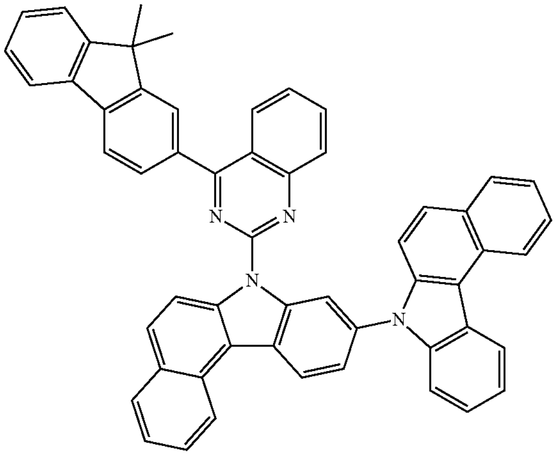
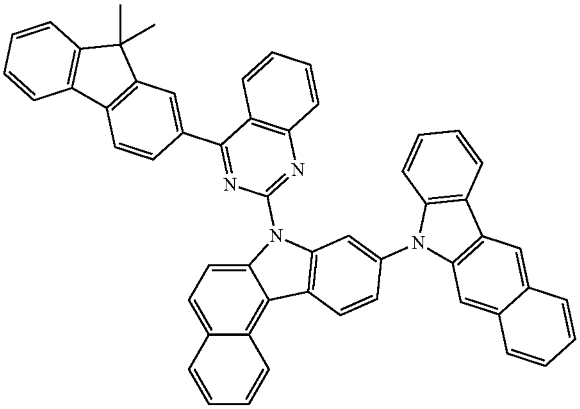

-continued
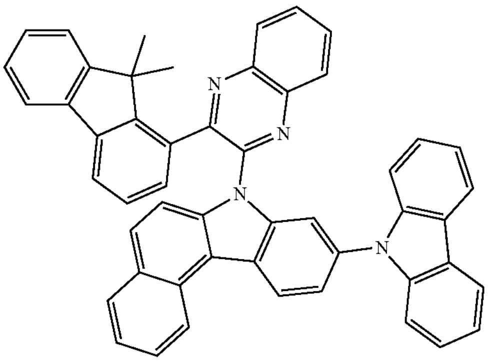
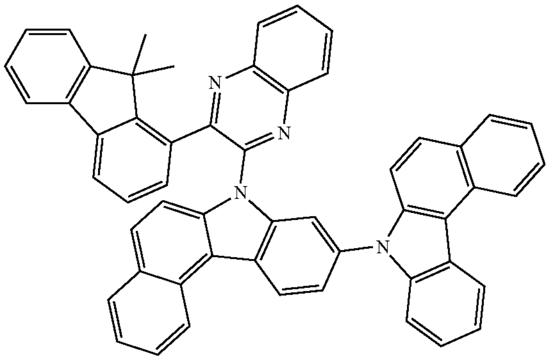
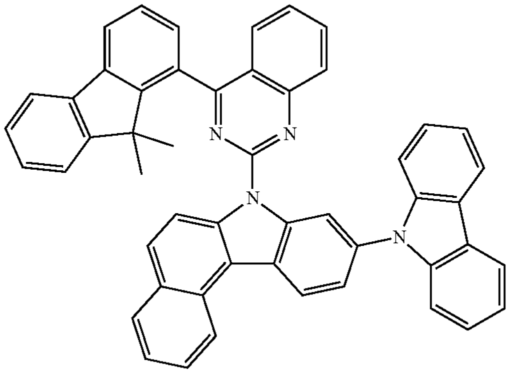
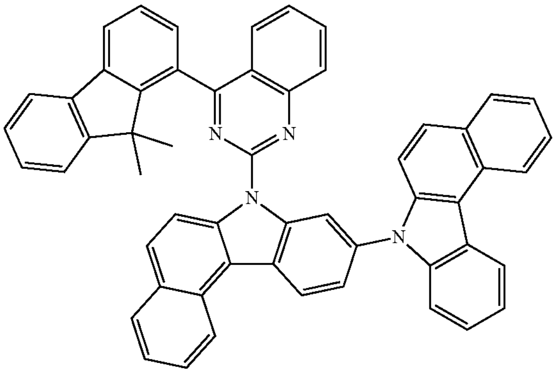
-continued
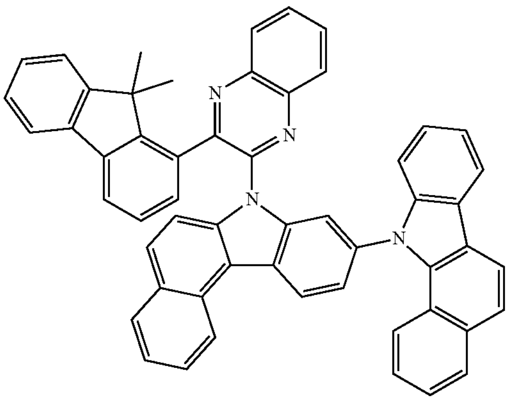
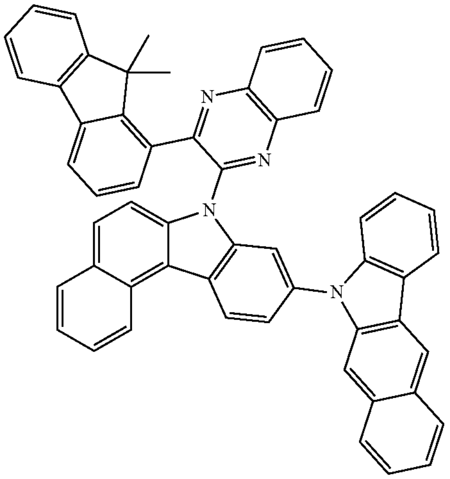
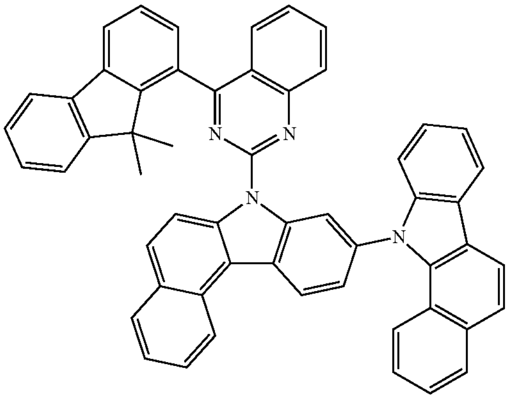
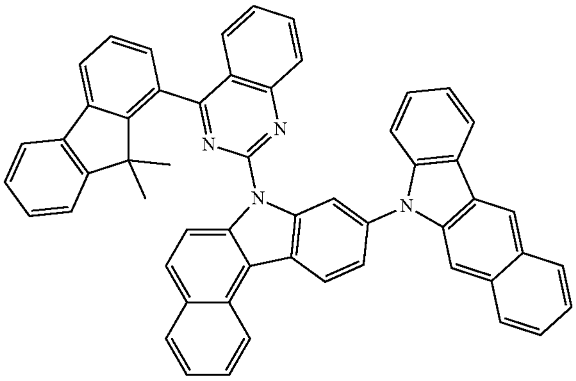

-continued
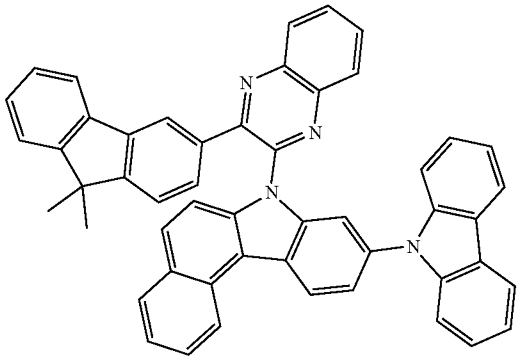
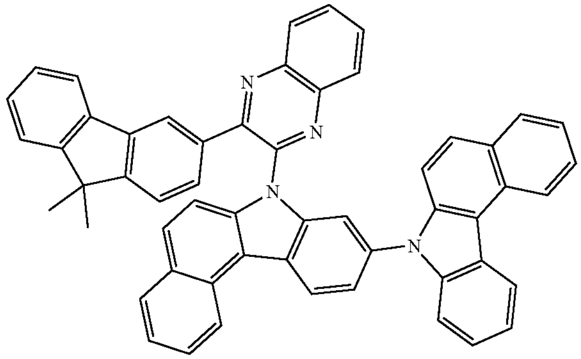
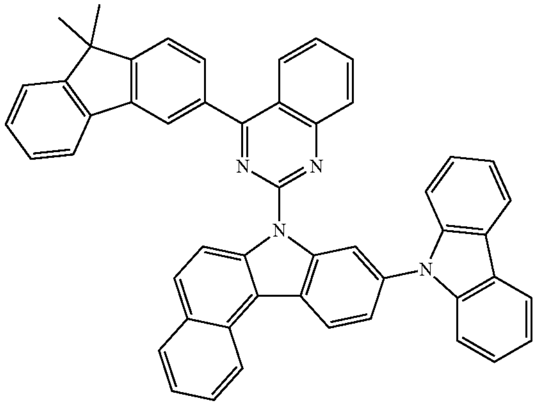
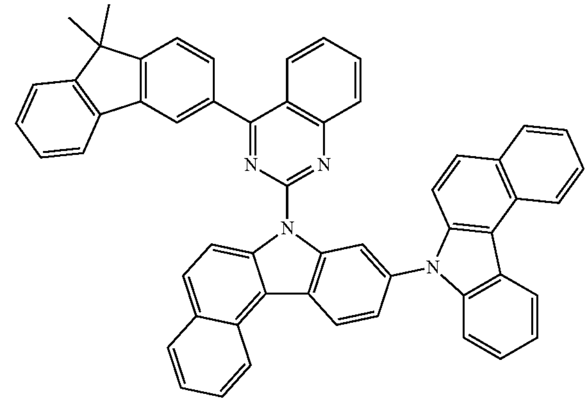
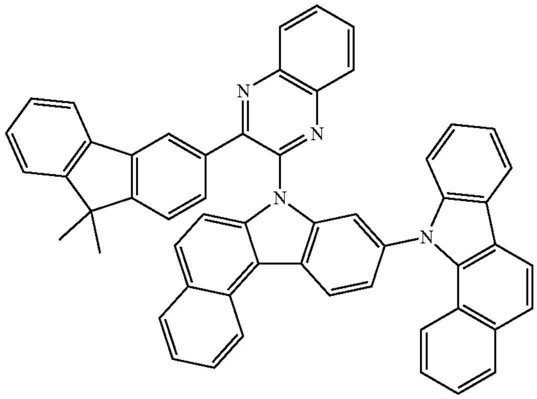
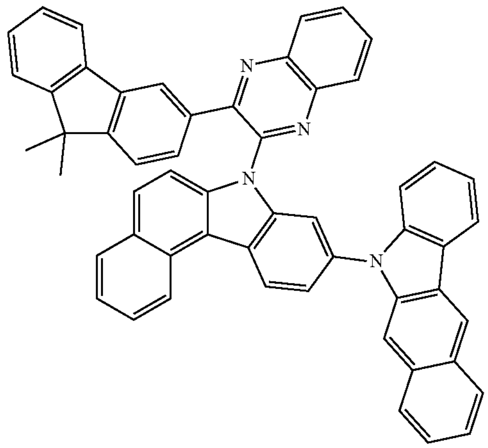
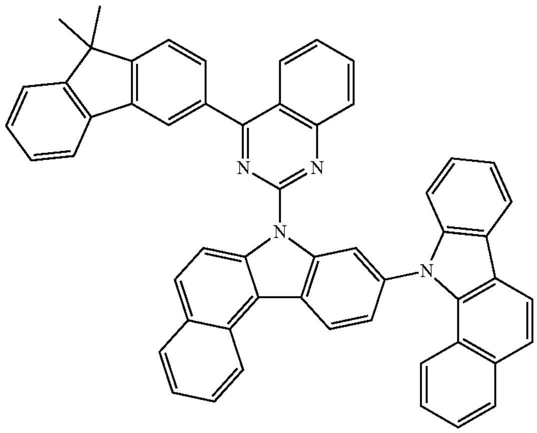
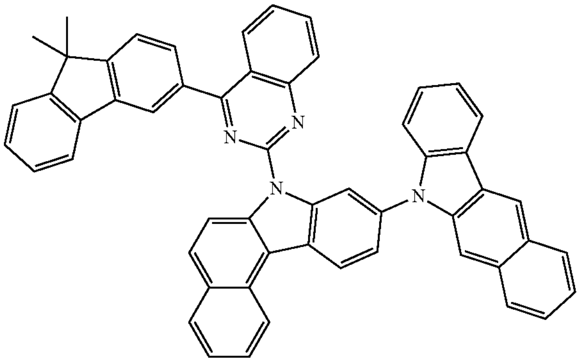
-continued -continued
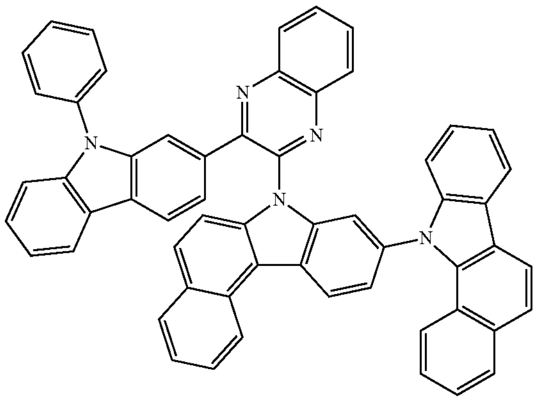
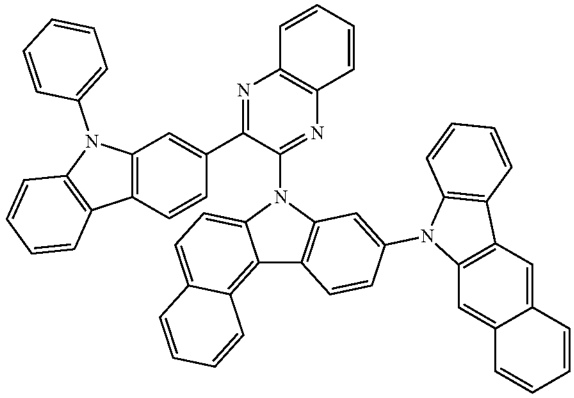
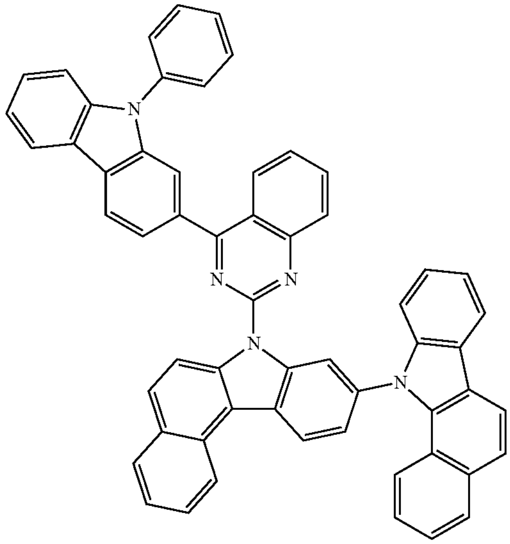
-continued
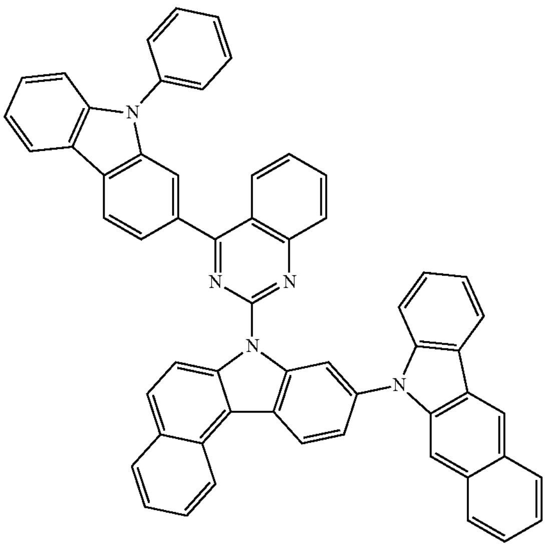
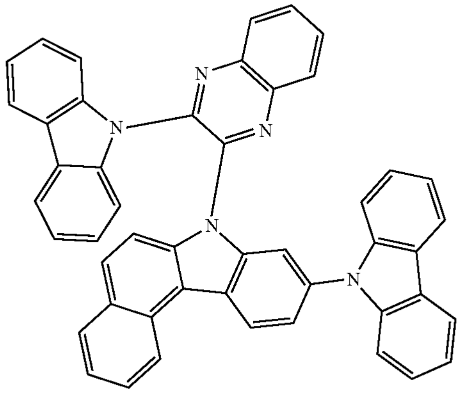
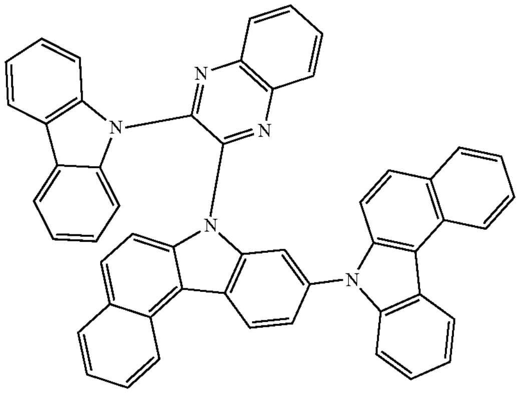

-continued
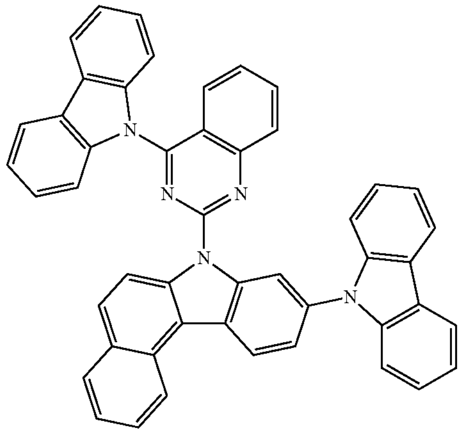
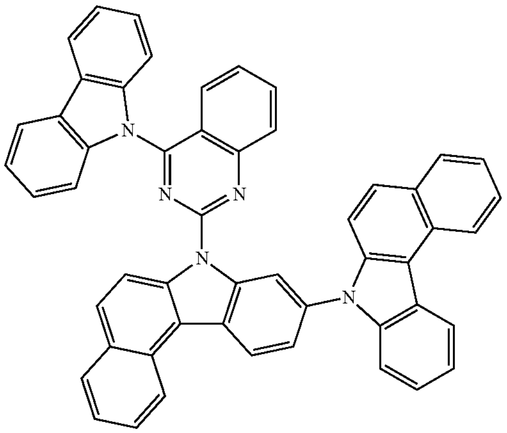
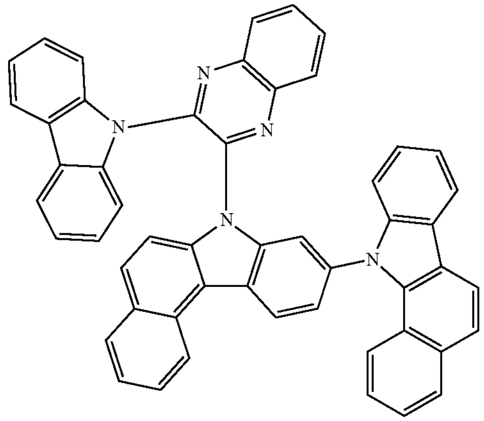
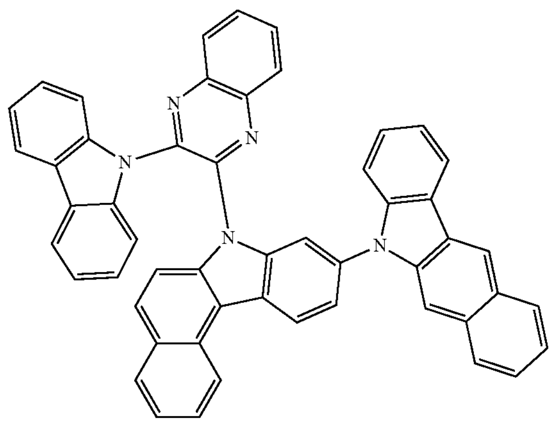
-continued
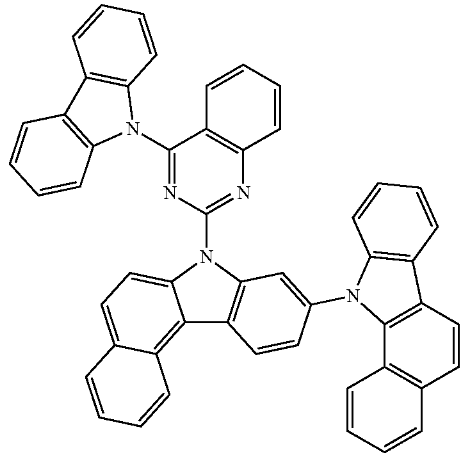
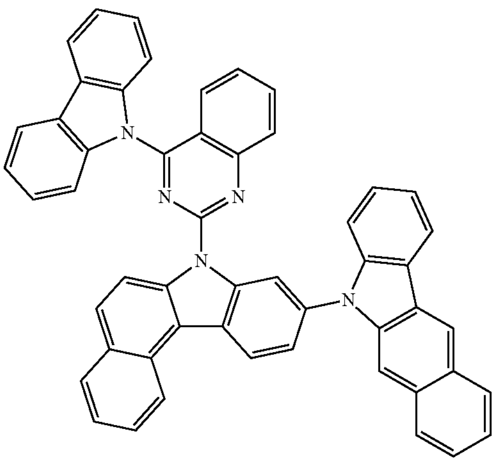
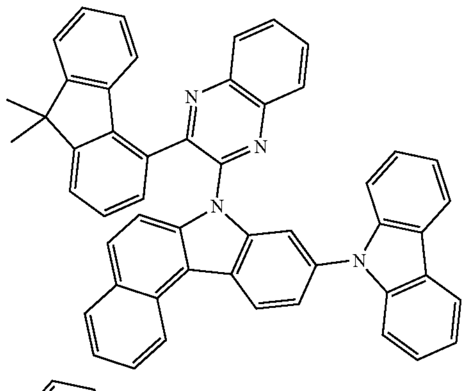
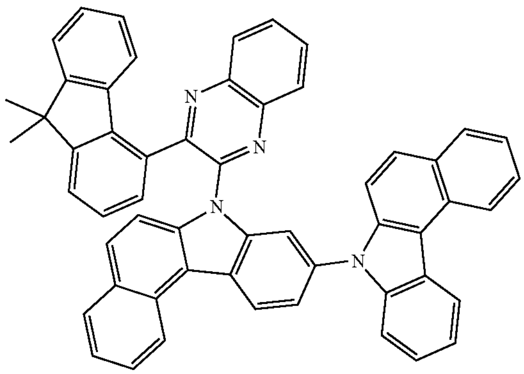

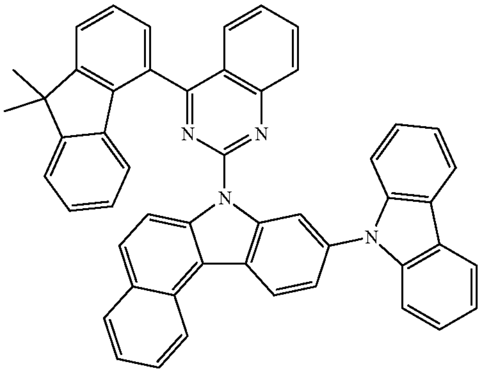
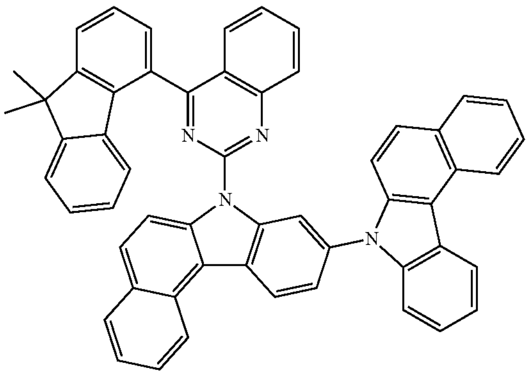
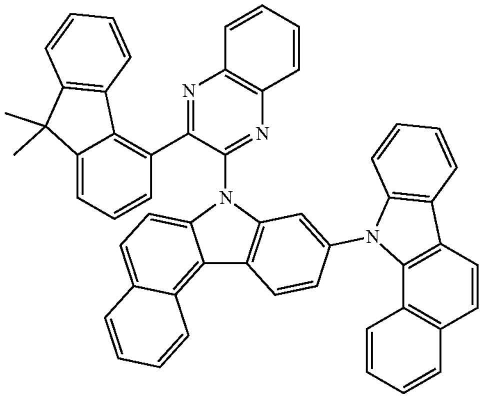
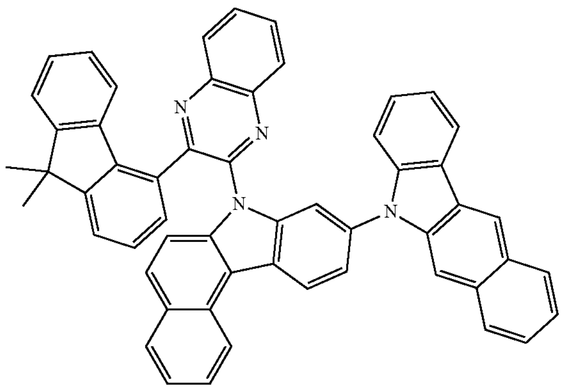
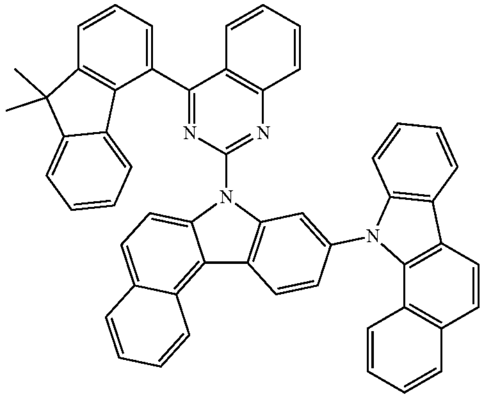
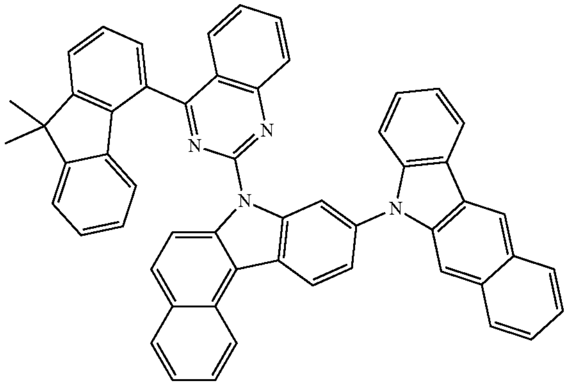
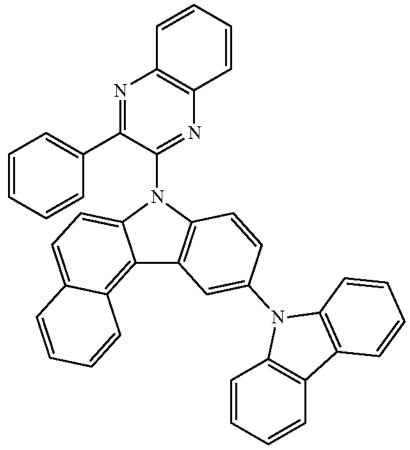
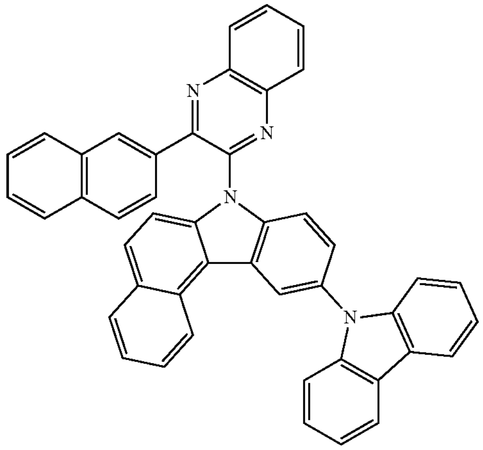

-continued
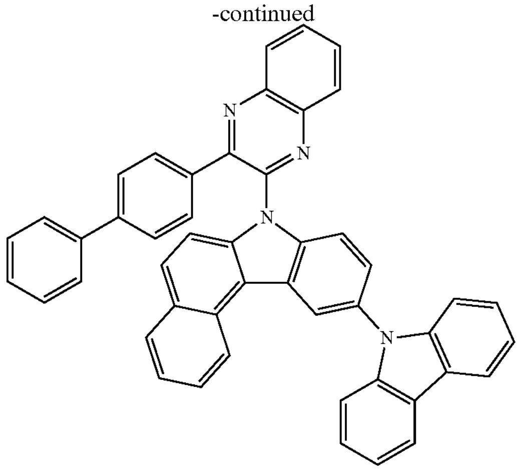
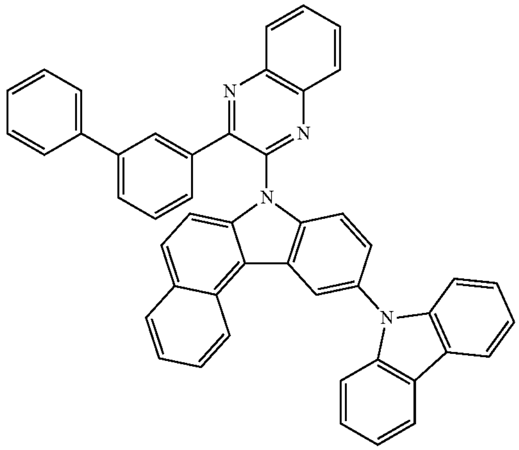
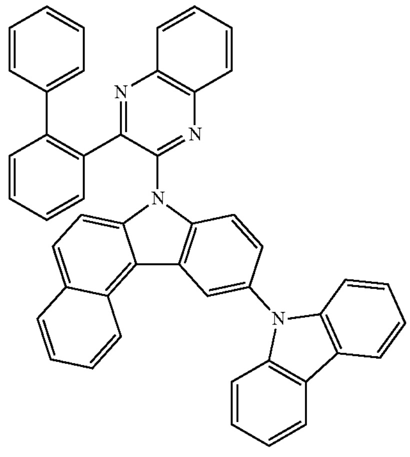
-continued
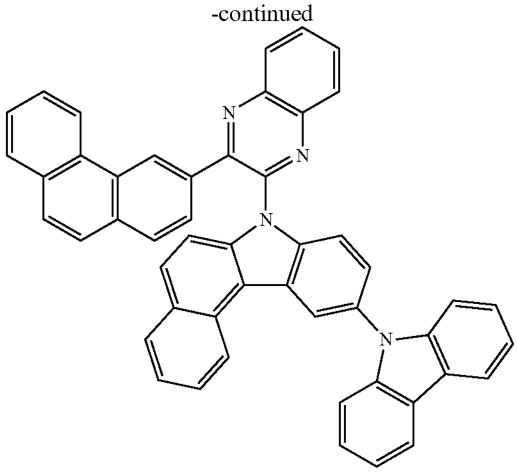
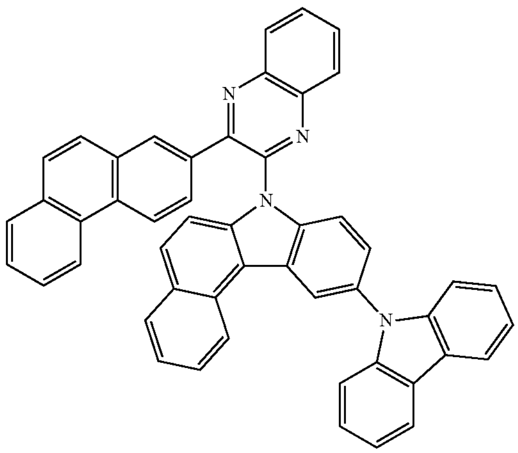
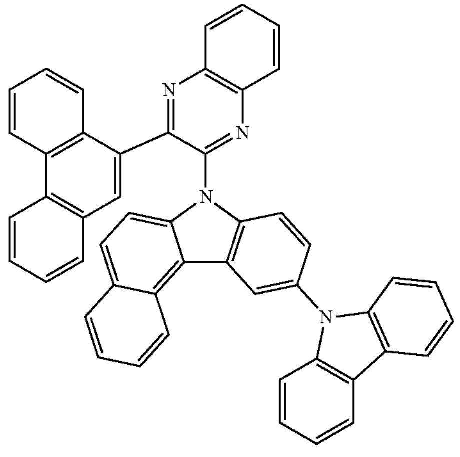

-continued
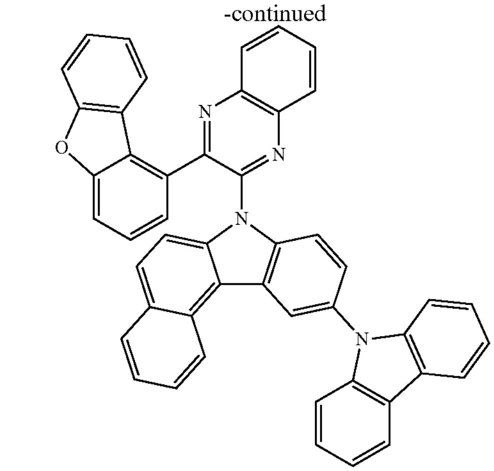
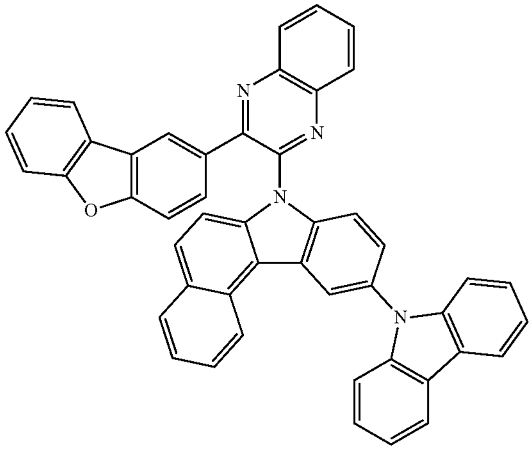
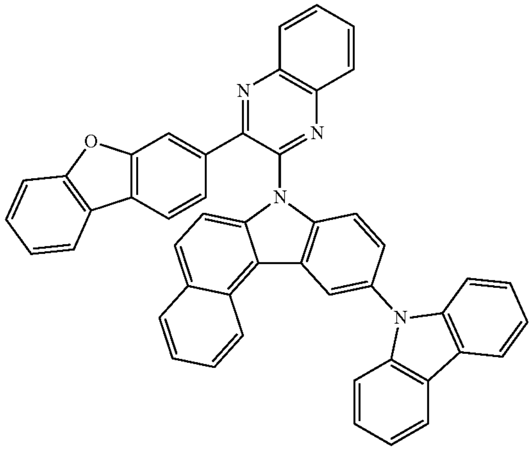
-continued
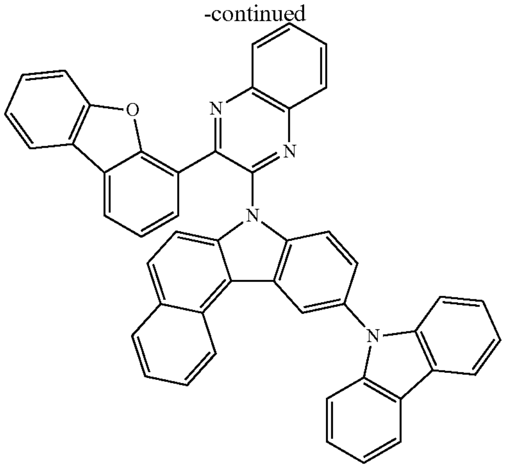
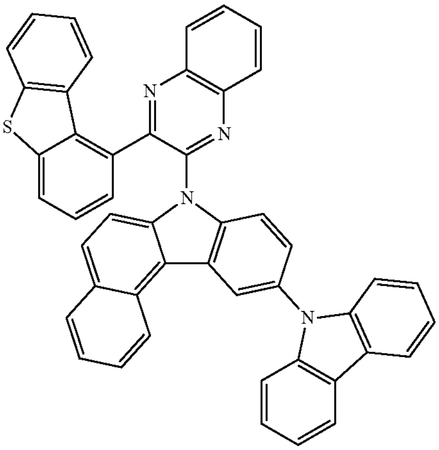
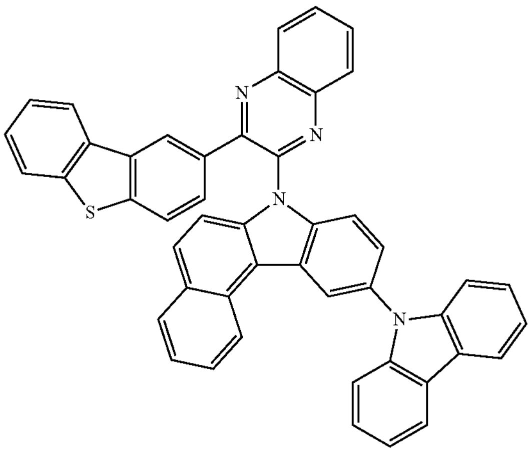

-continued
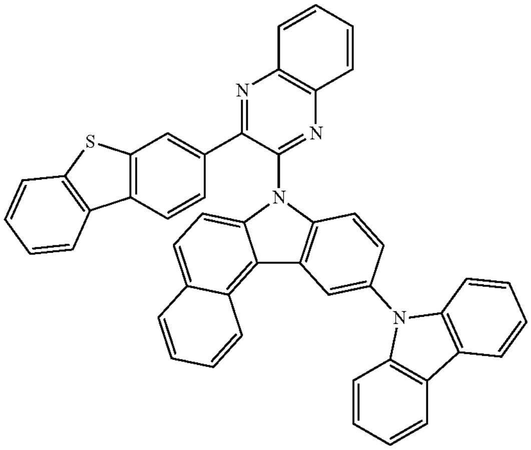
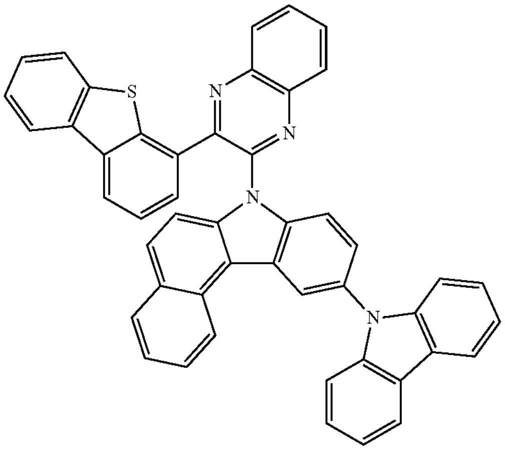
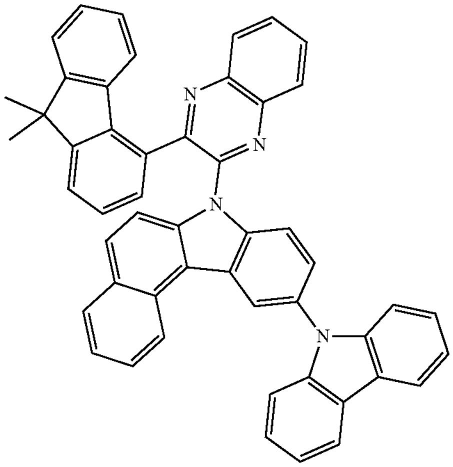
-continued
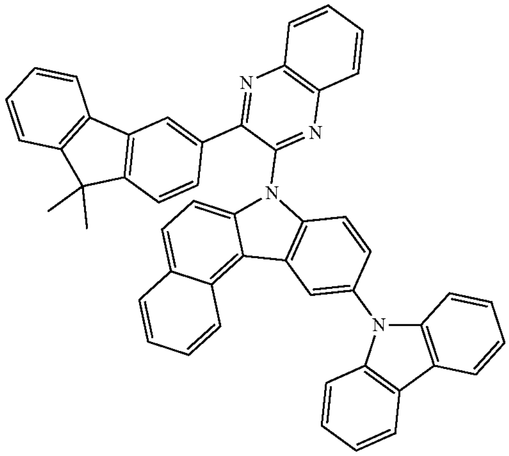
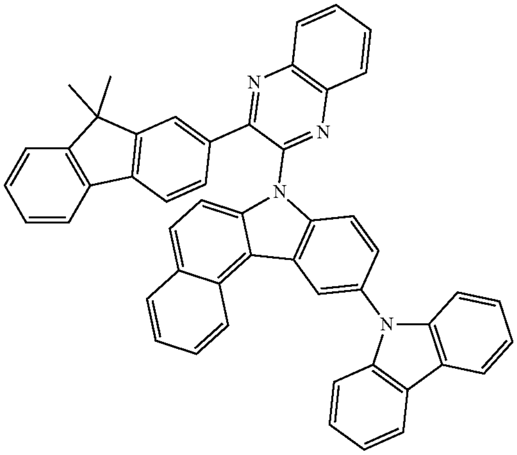
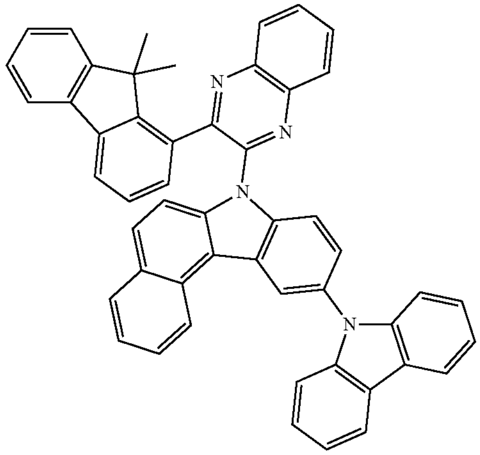

-continued
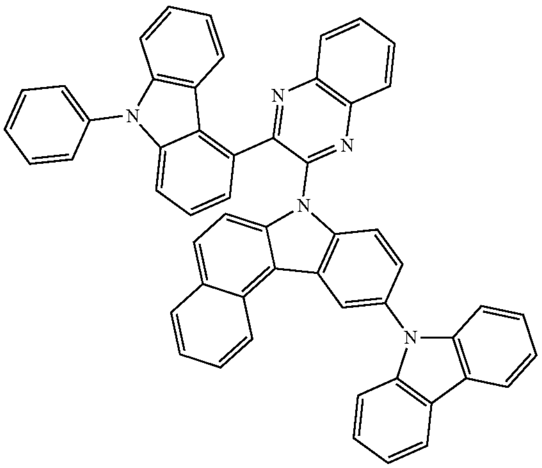
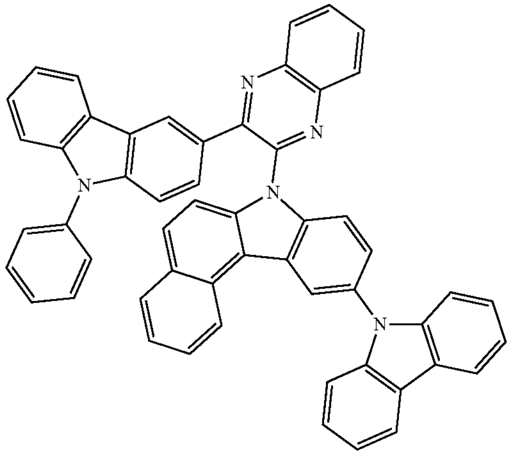
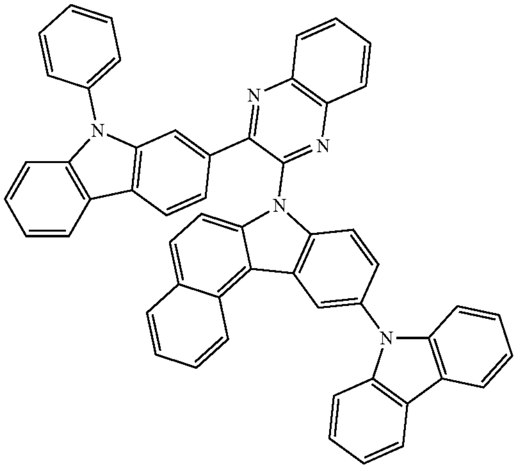
-continued
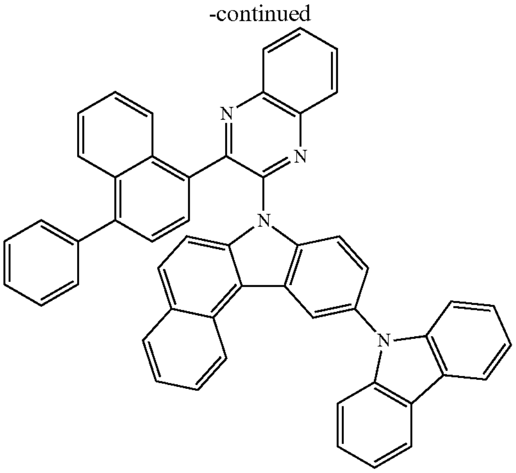
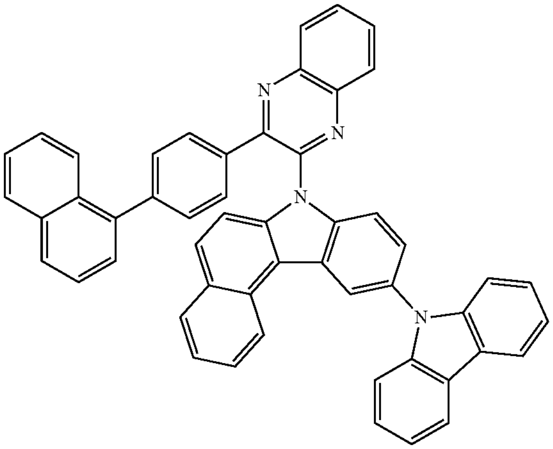
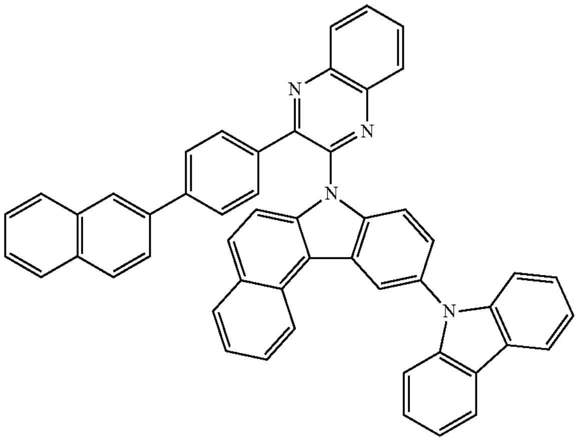

-continued
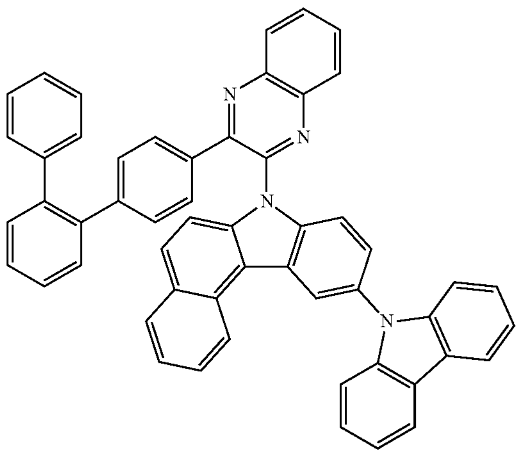
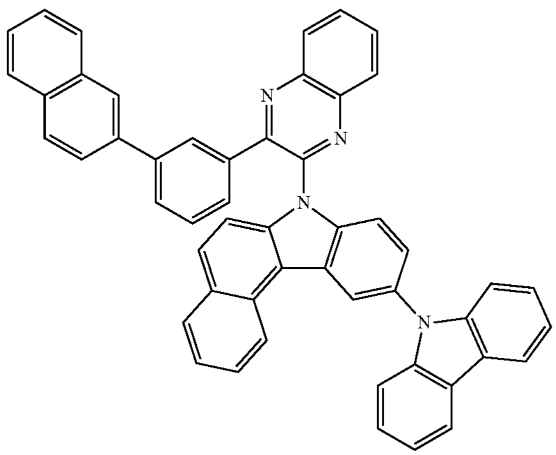
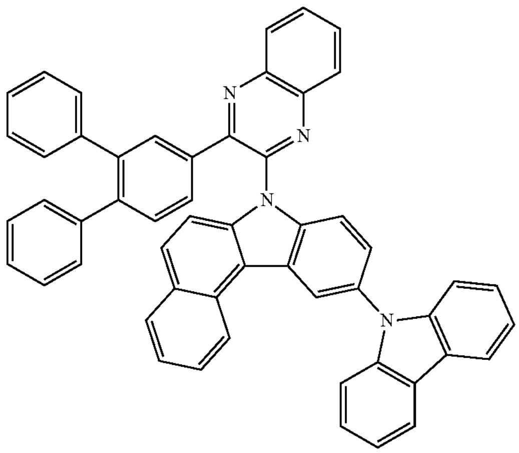
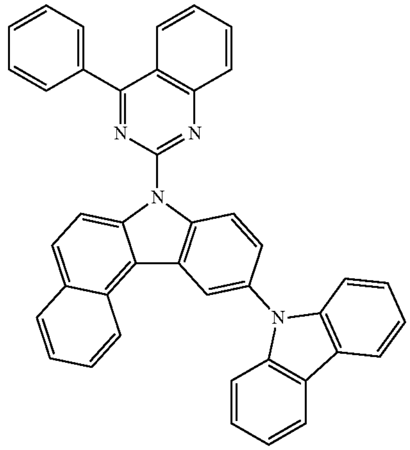
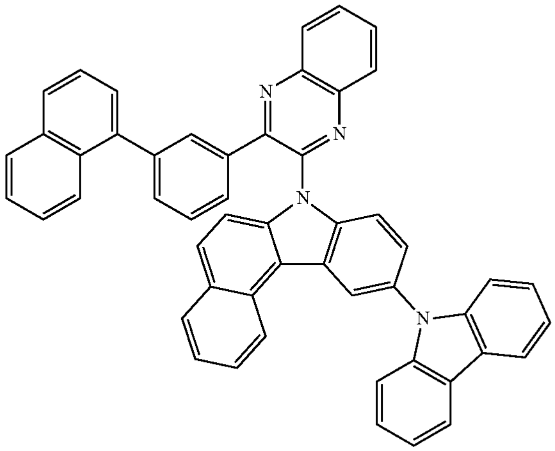
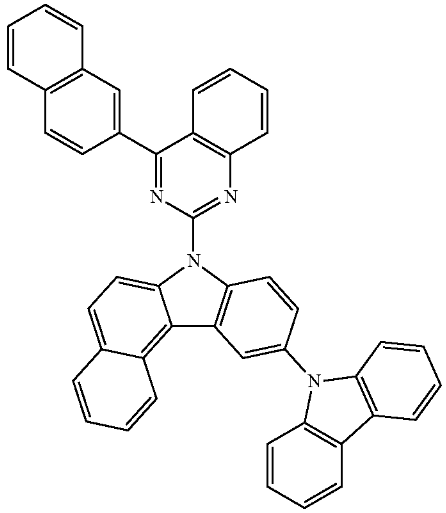
-continued -continued
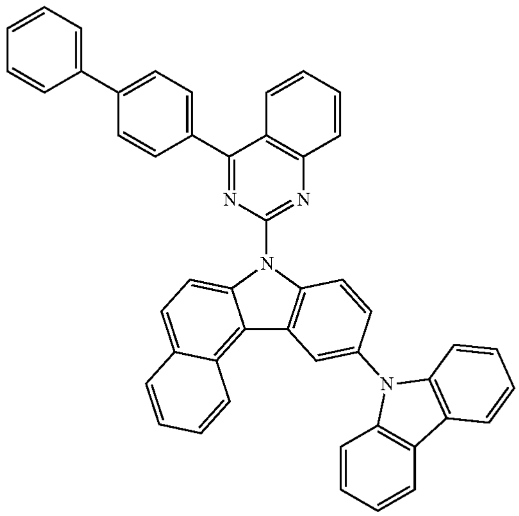
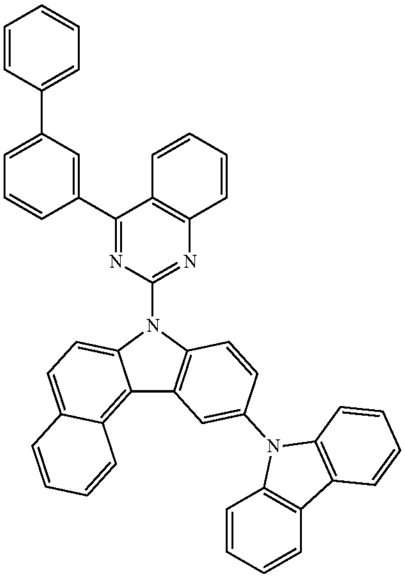
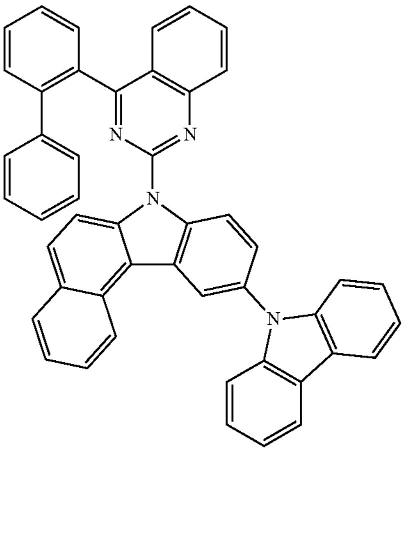
-continued
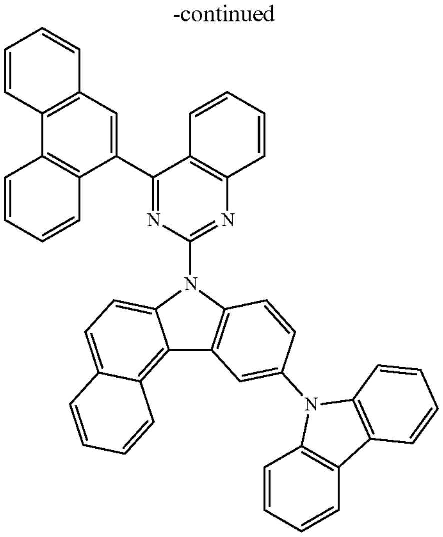
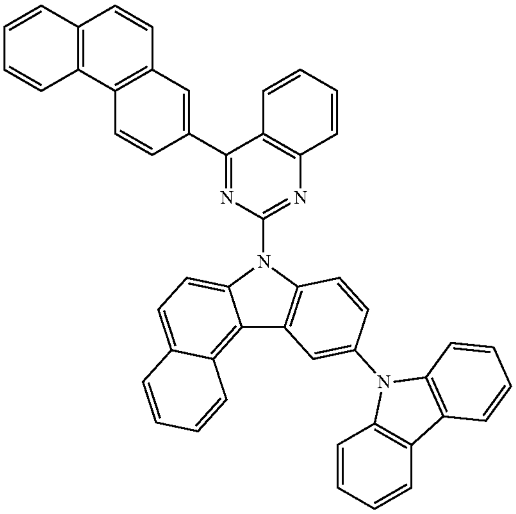
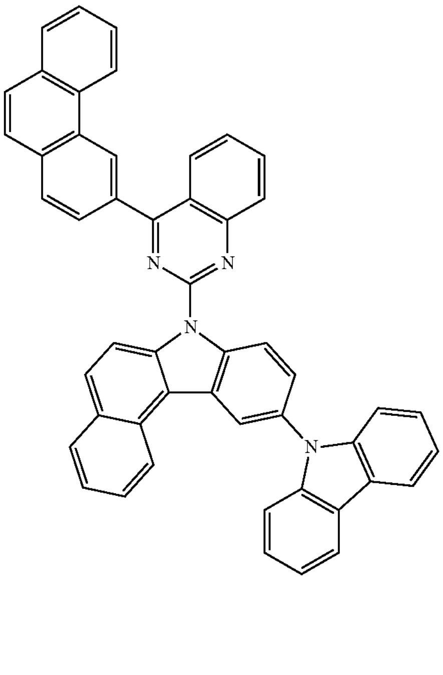

-continued
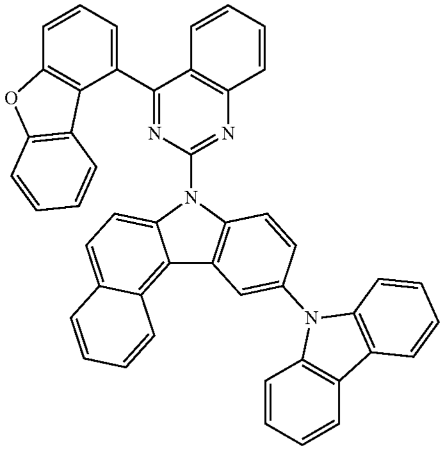
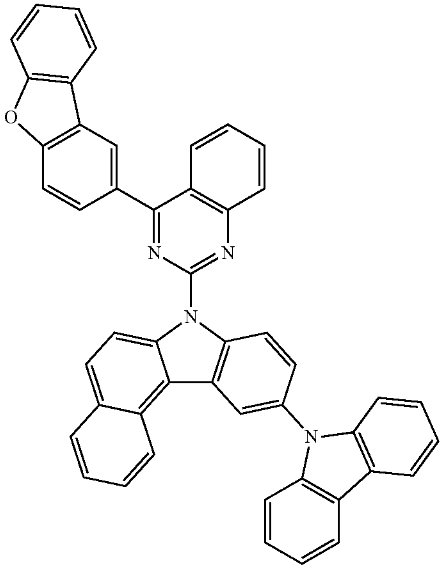
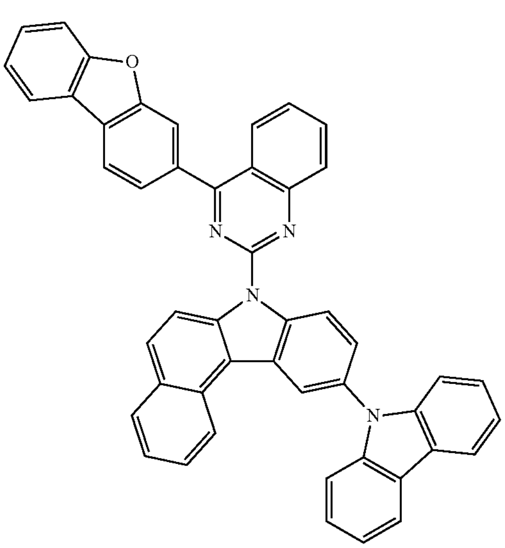
-continued
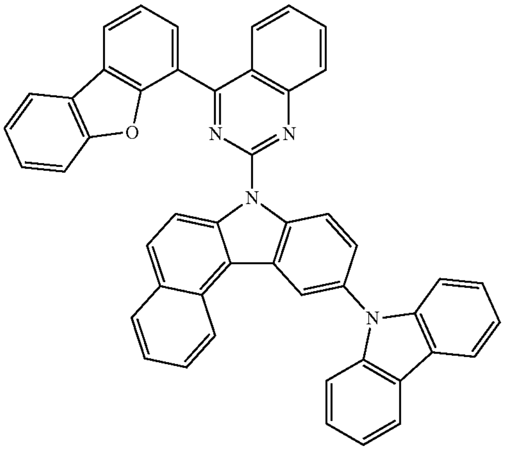
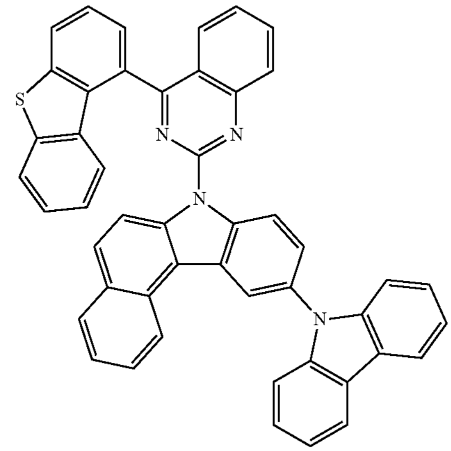
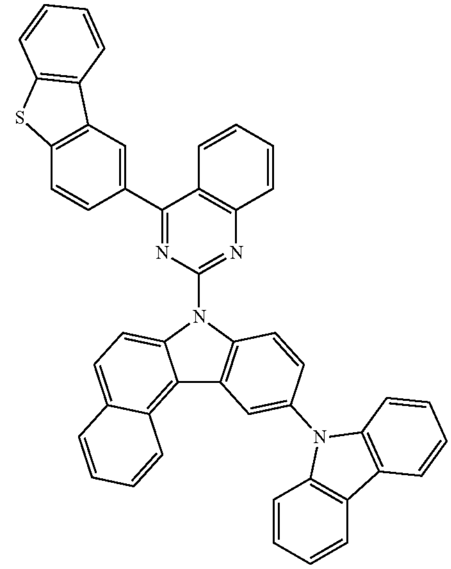

-continued
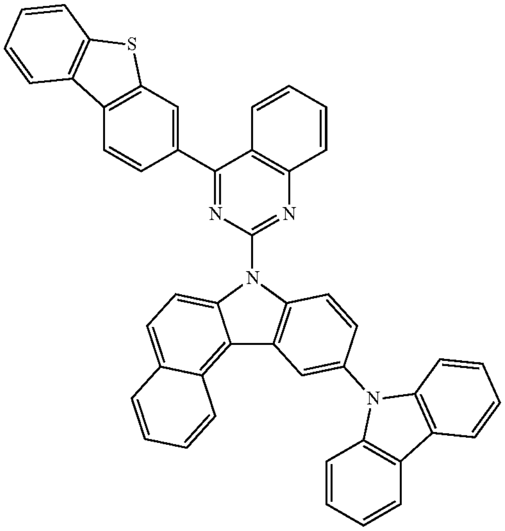
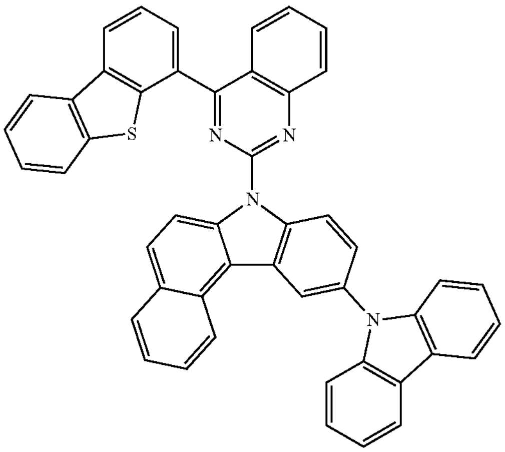
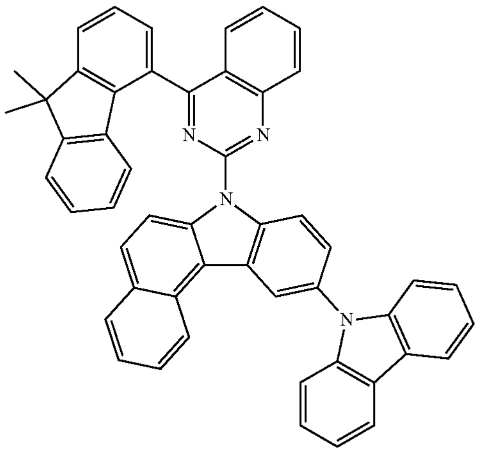
-continued
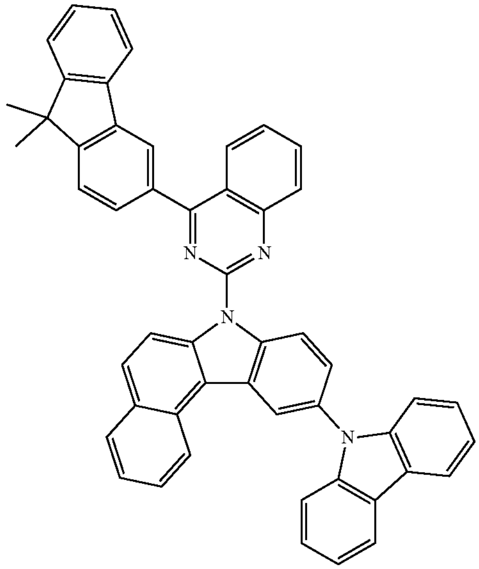
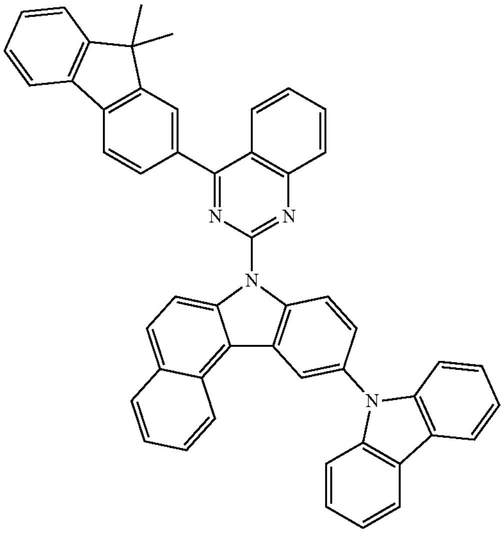
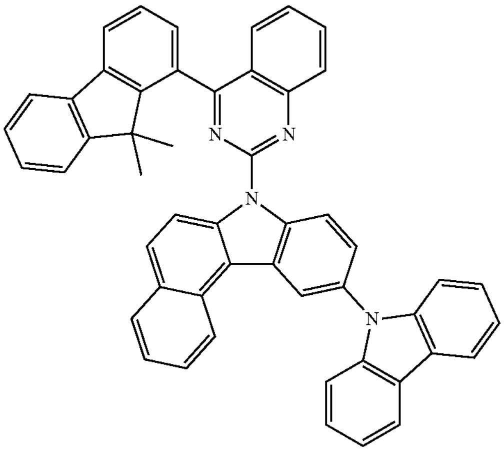

-continued
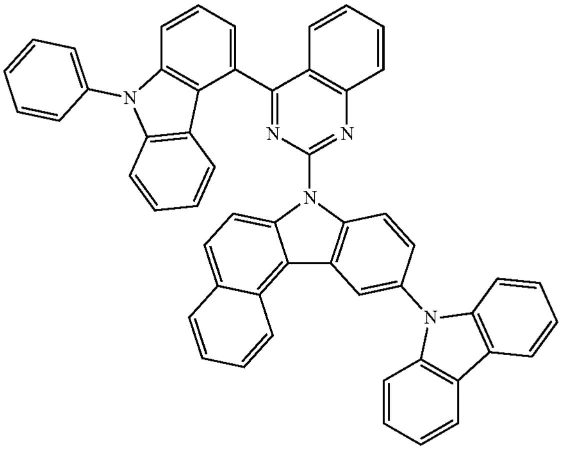
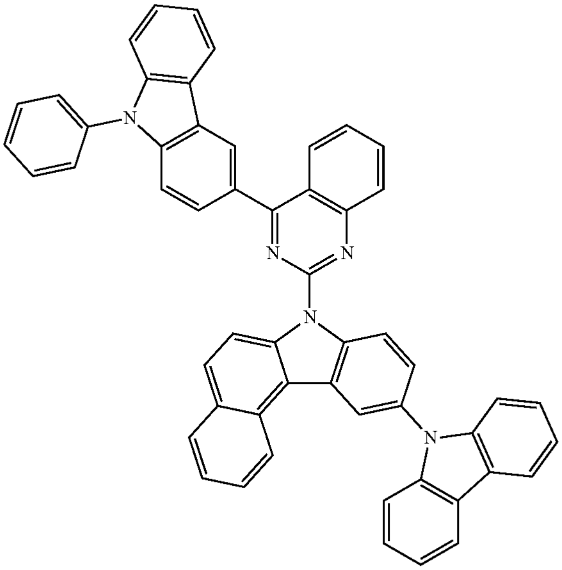
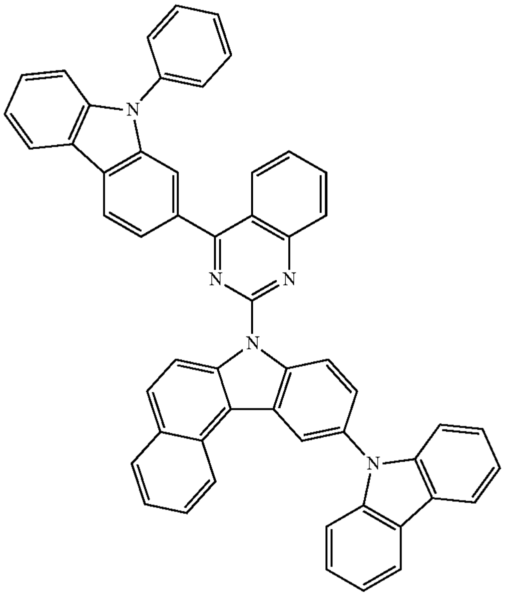
-continued
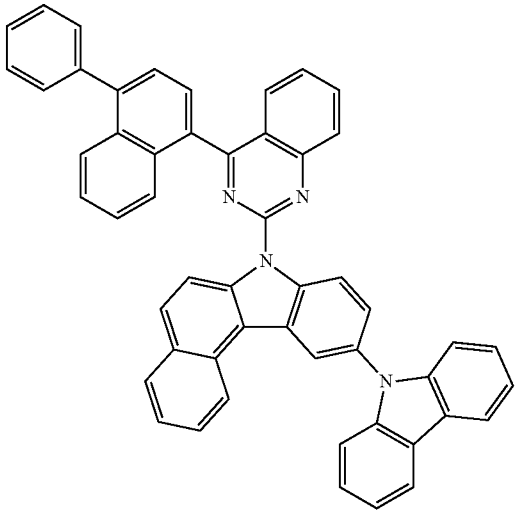
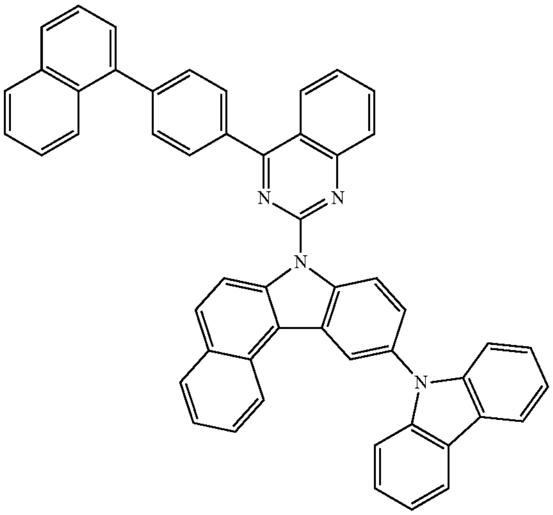
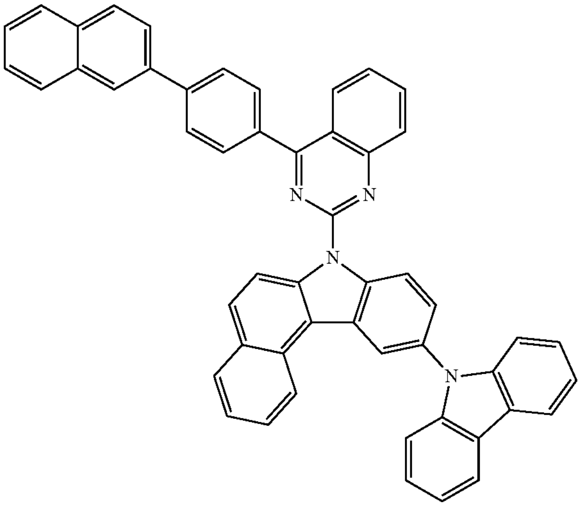

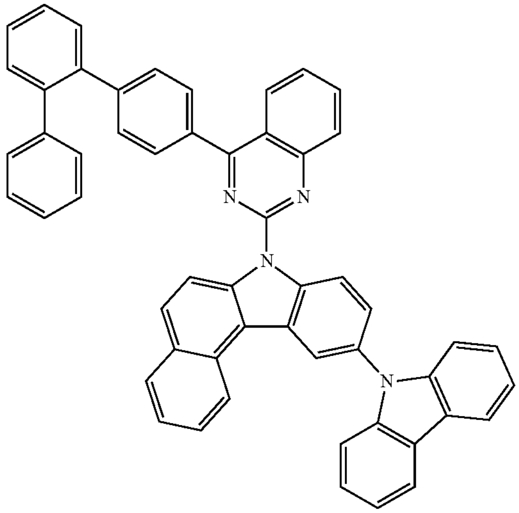
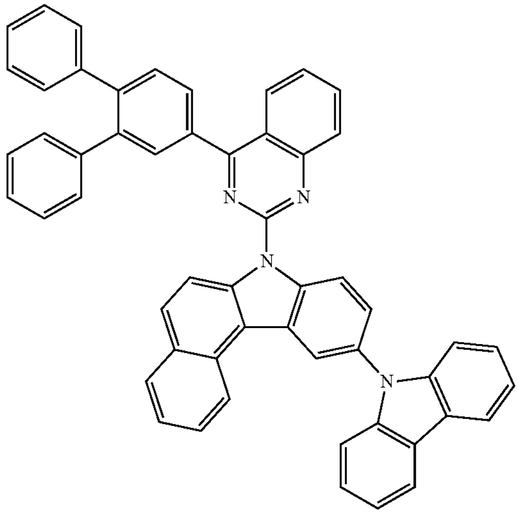
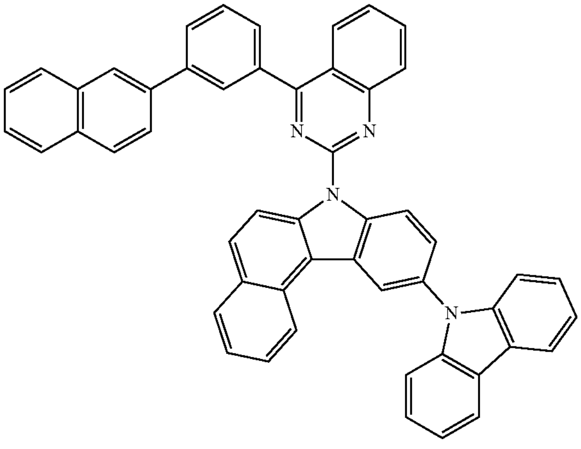
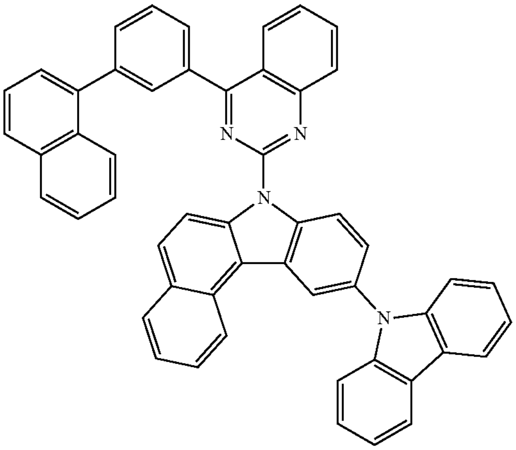
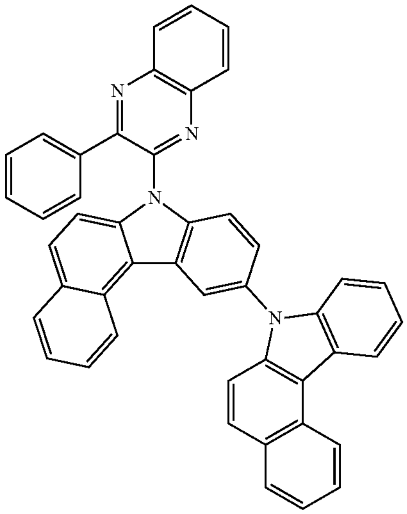
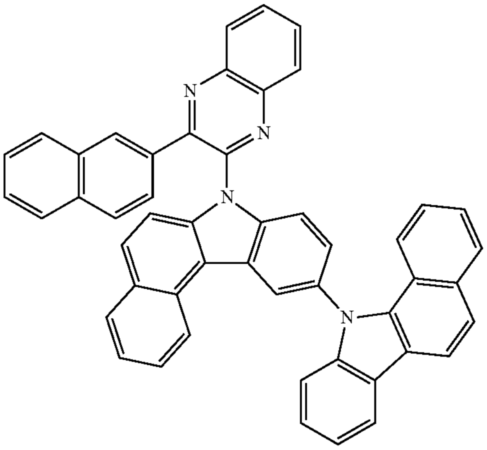

-continued
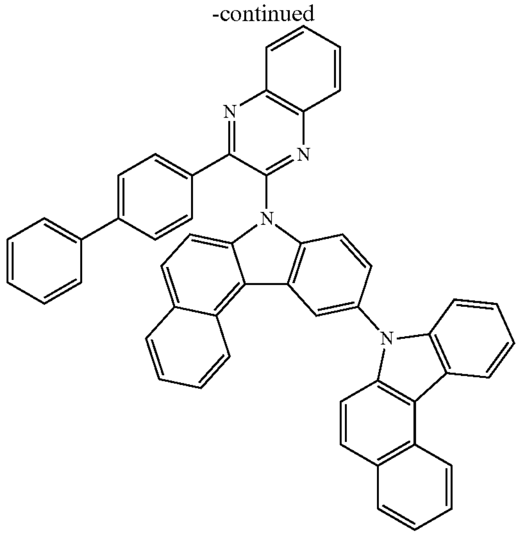
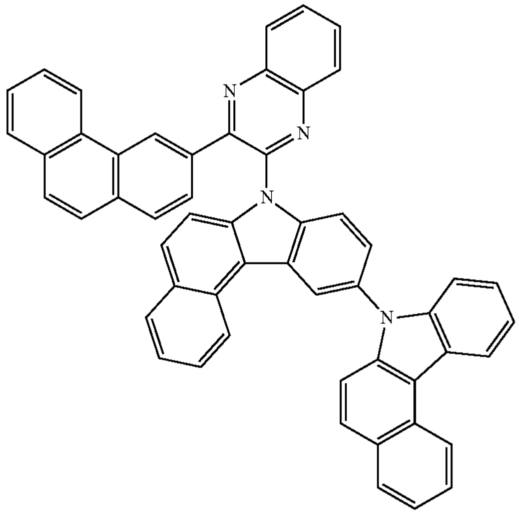
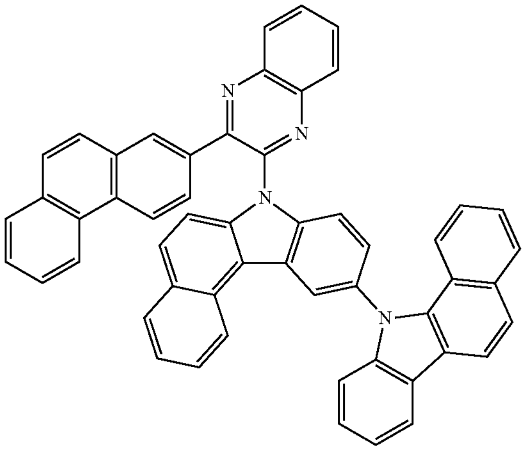
-continued
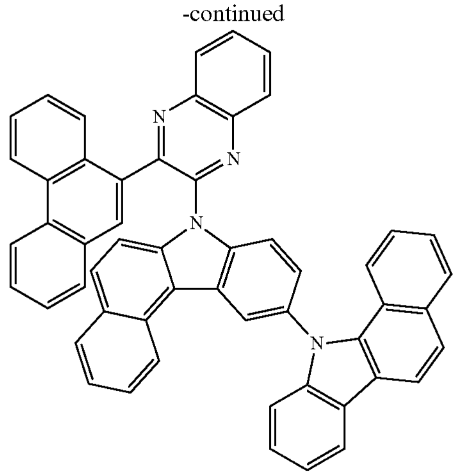
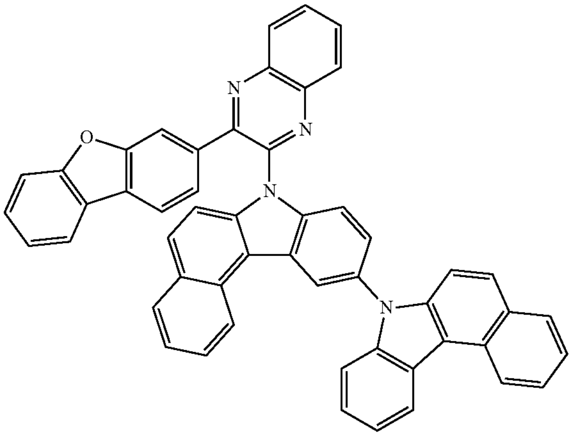
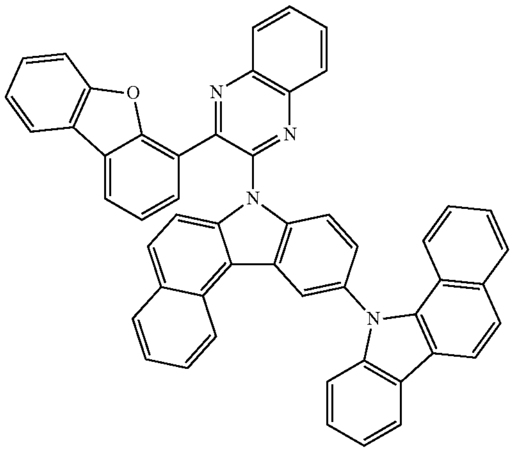

-continued
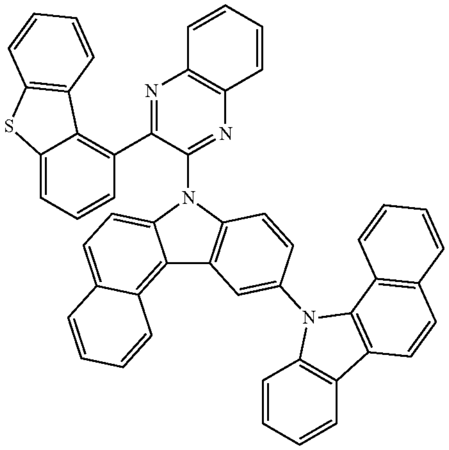
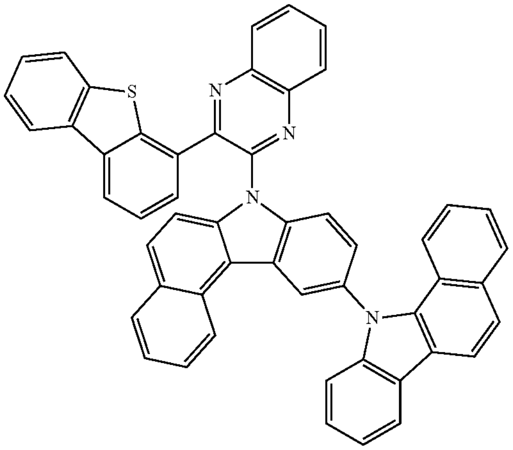
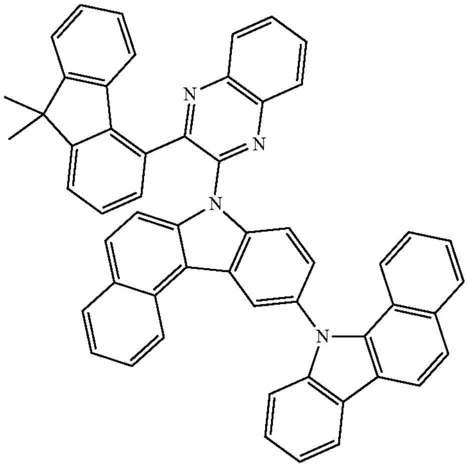
-continued
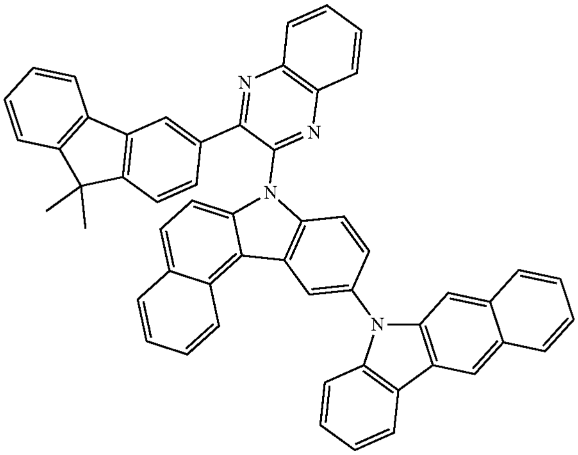
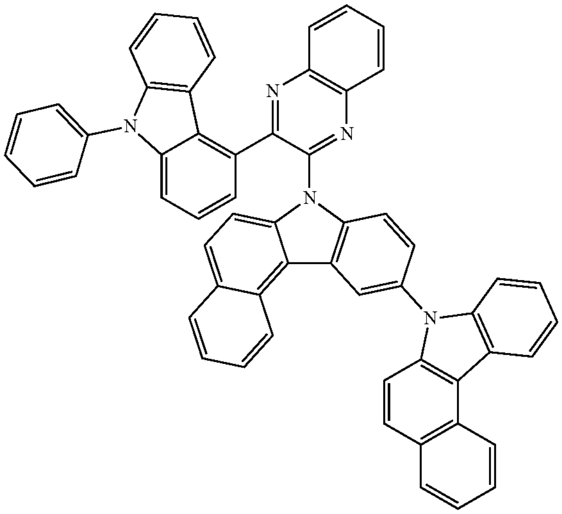
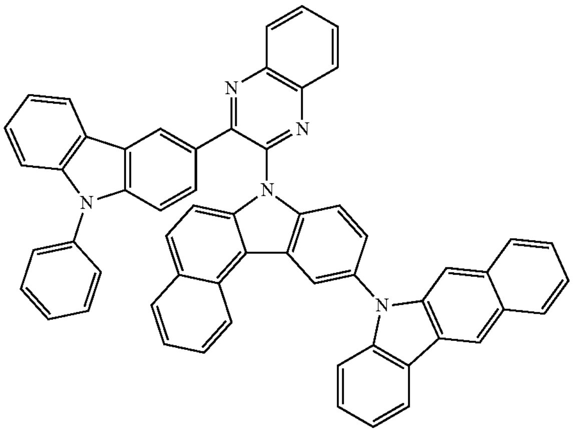

-continued
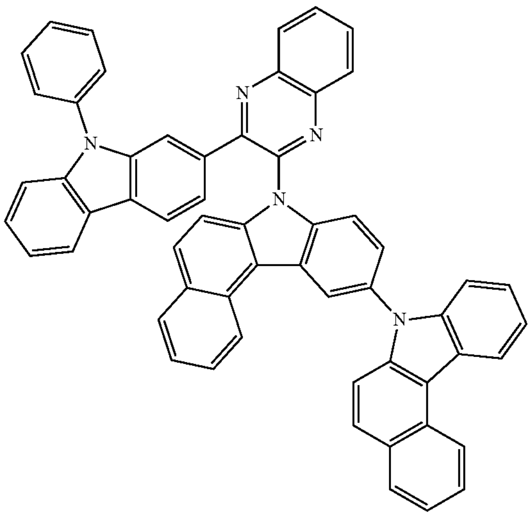
-continued
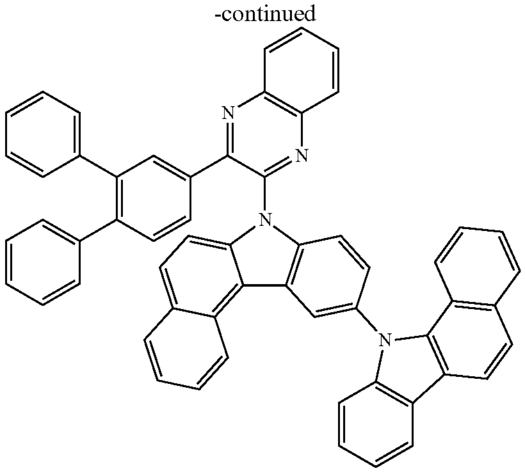
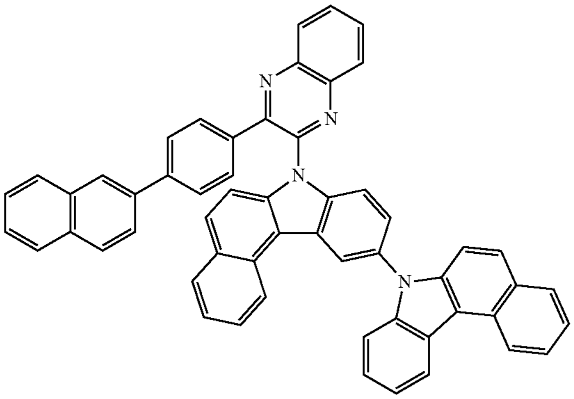
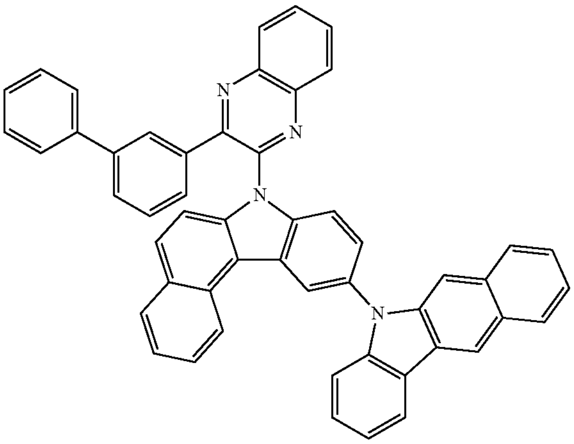
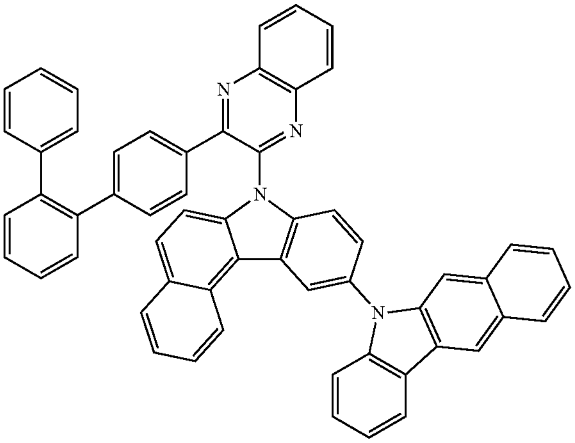
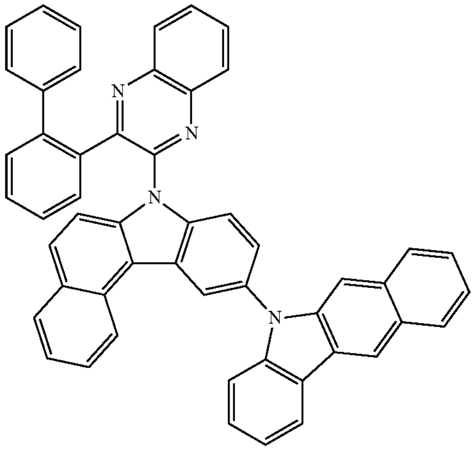

-continued
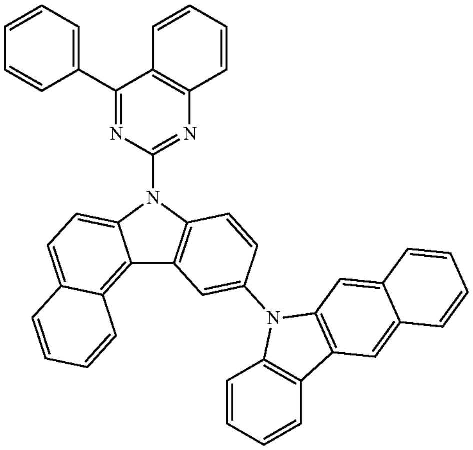
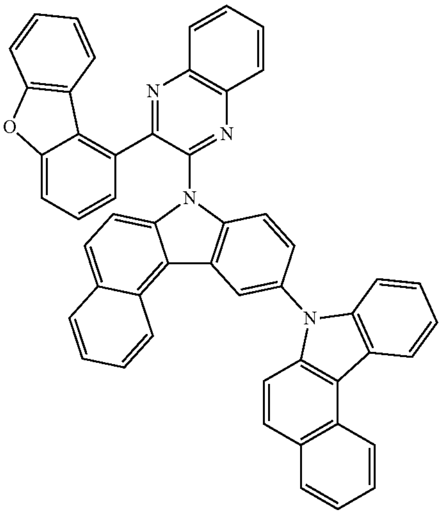
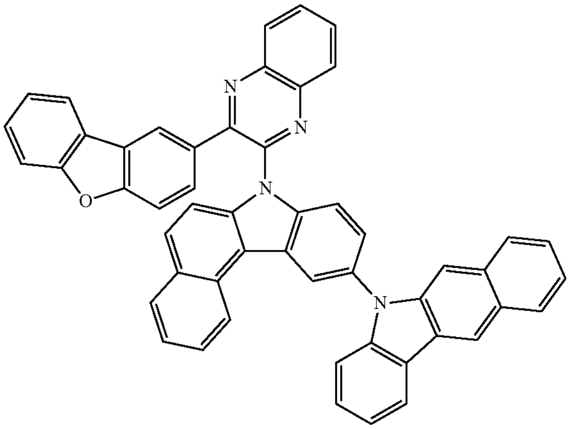
-continued
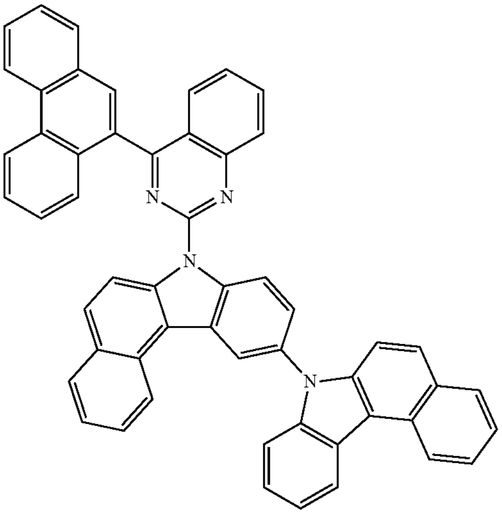
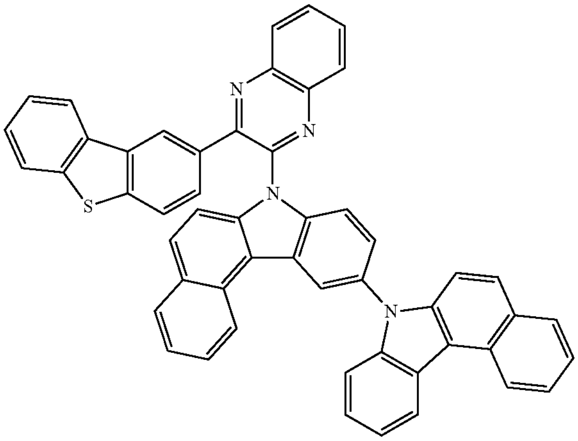
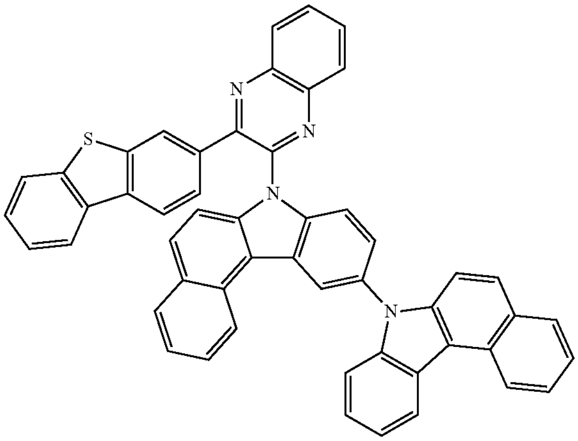

-continued
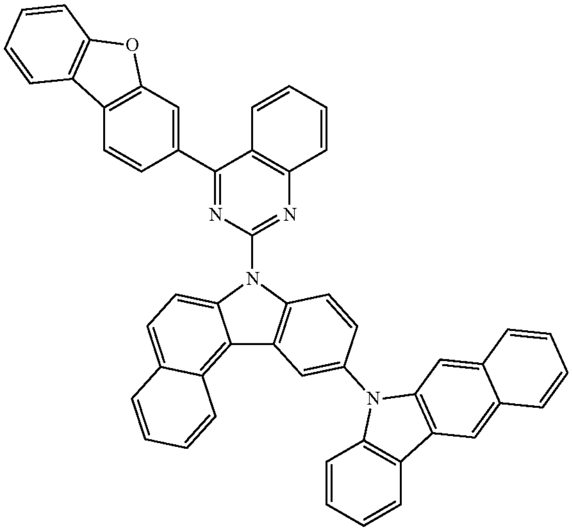
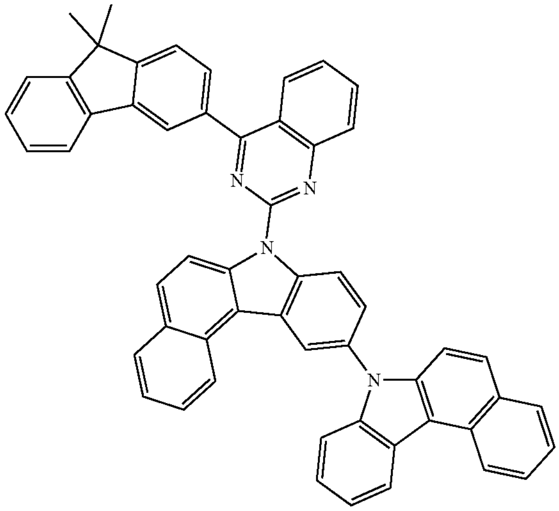
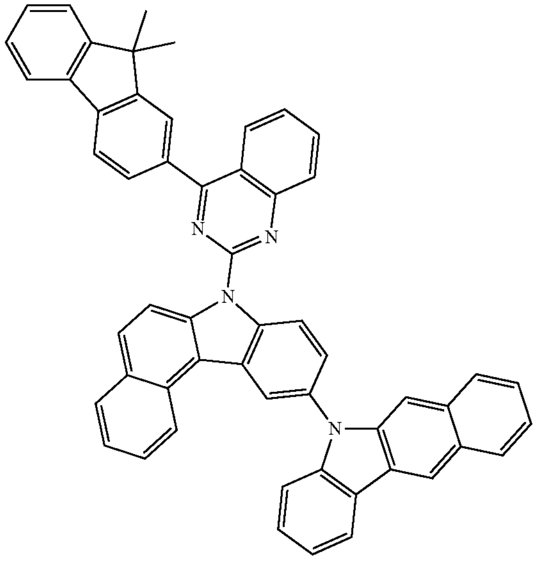
-continued
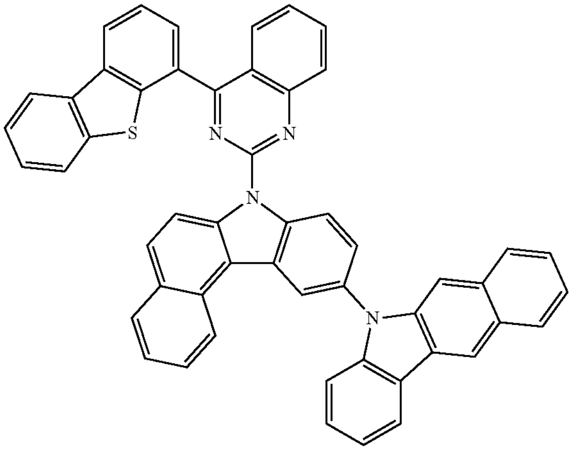
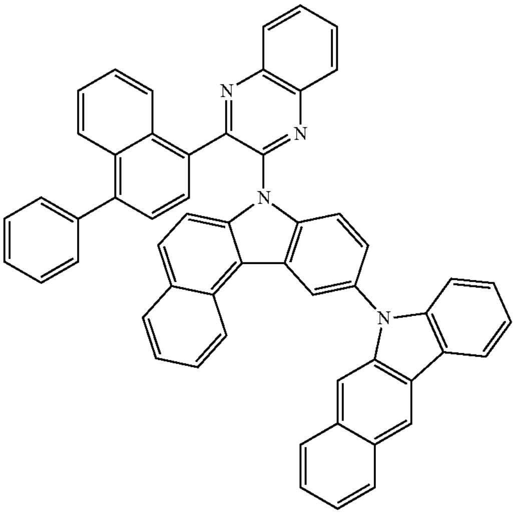
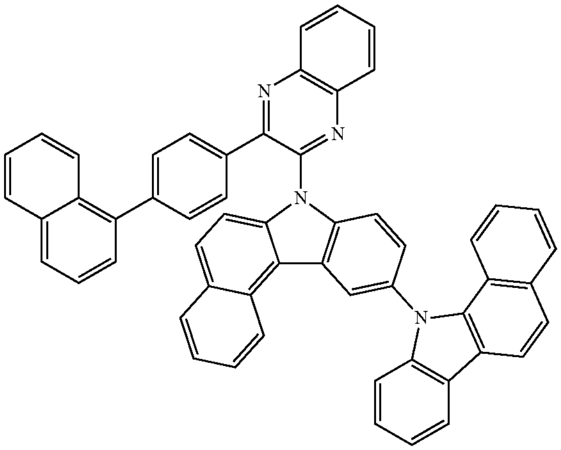

-continued
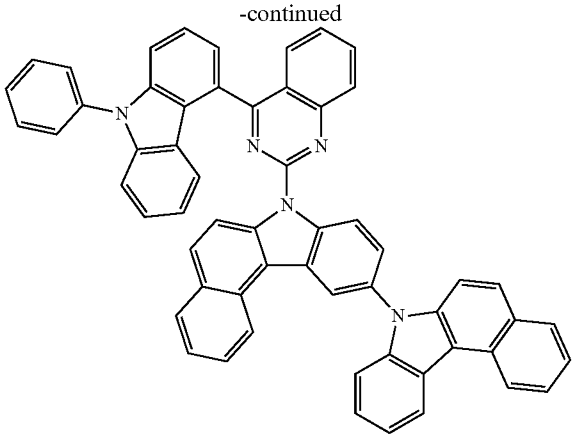
-continued
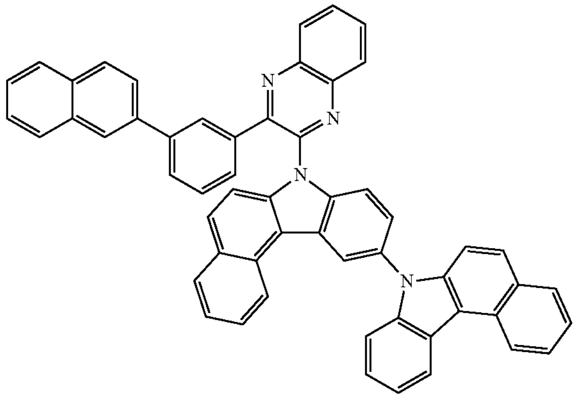
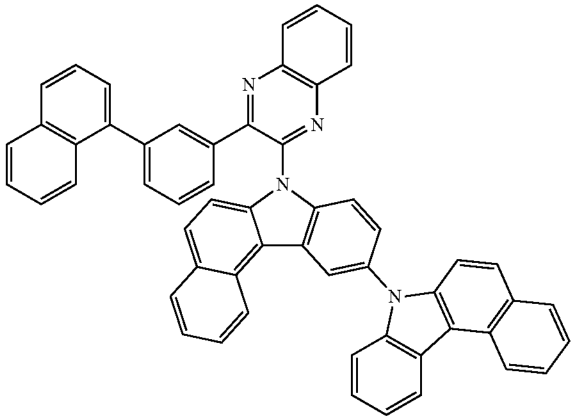
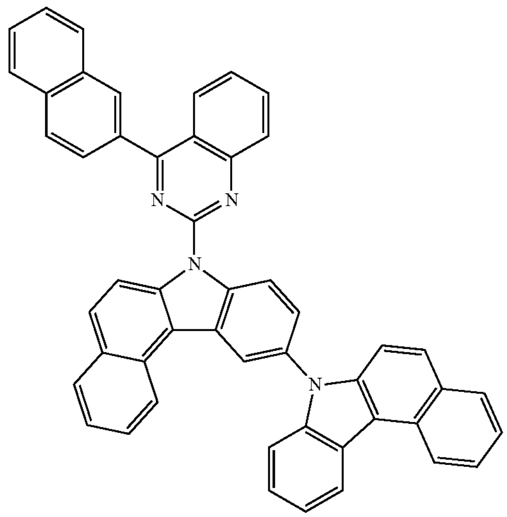
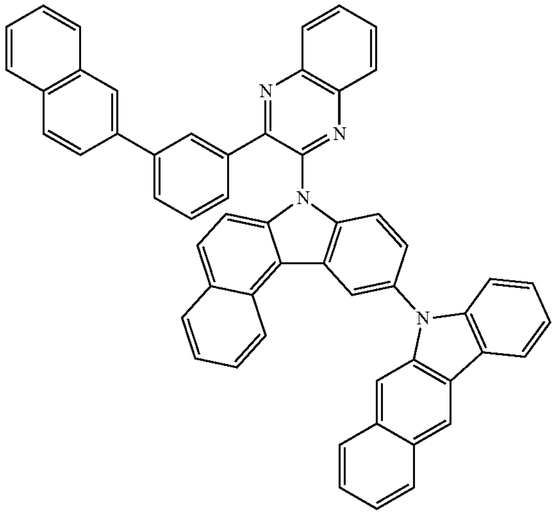
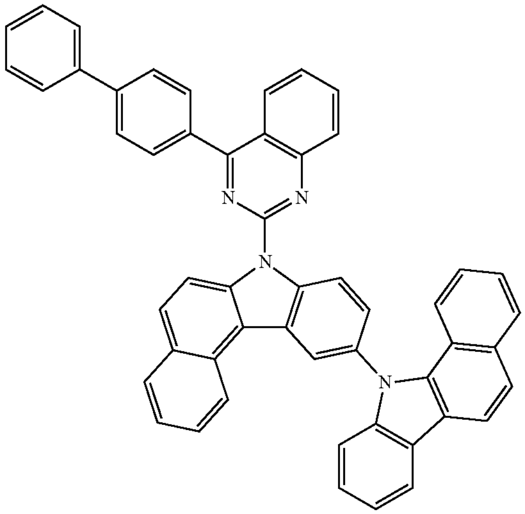

-continued
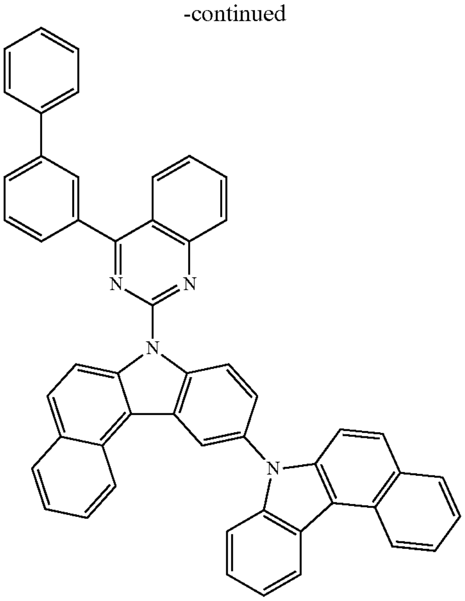
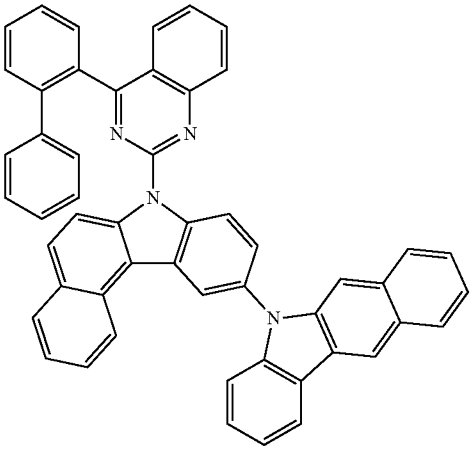
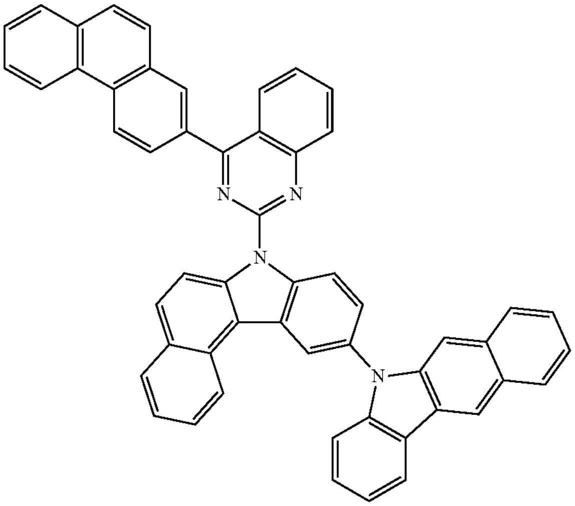
-continued
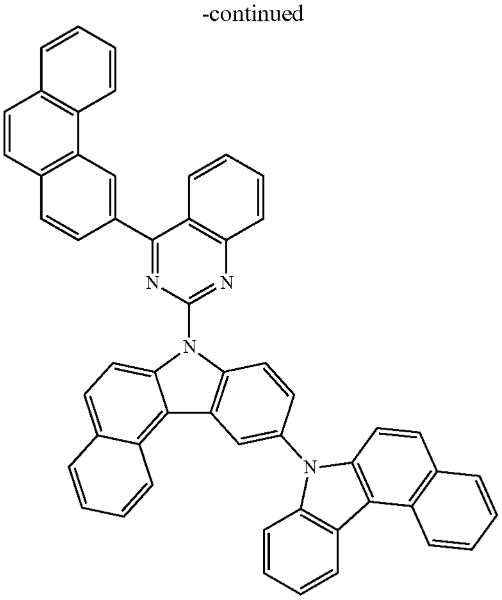
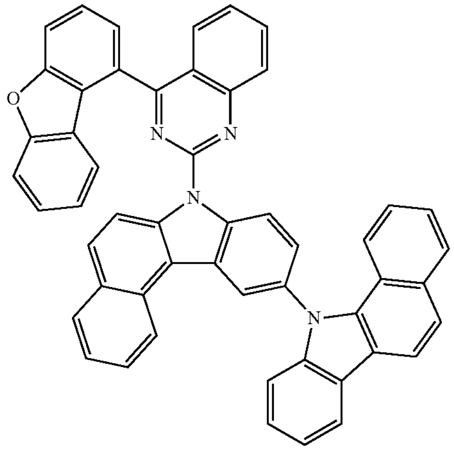
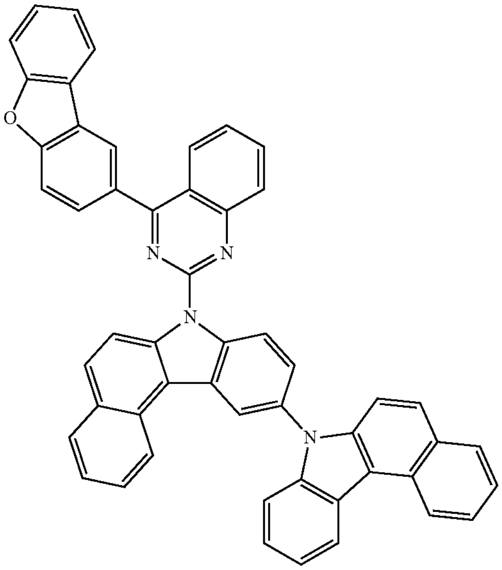

-continued
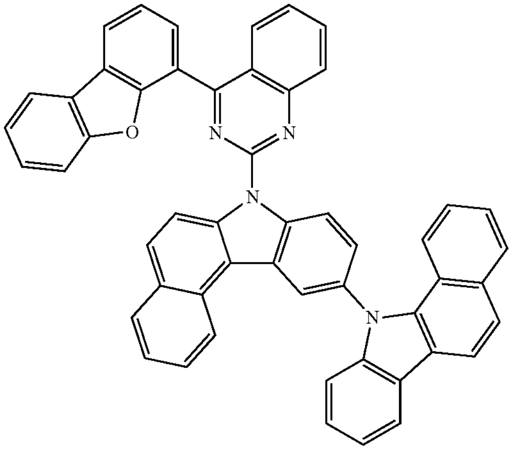
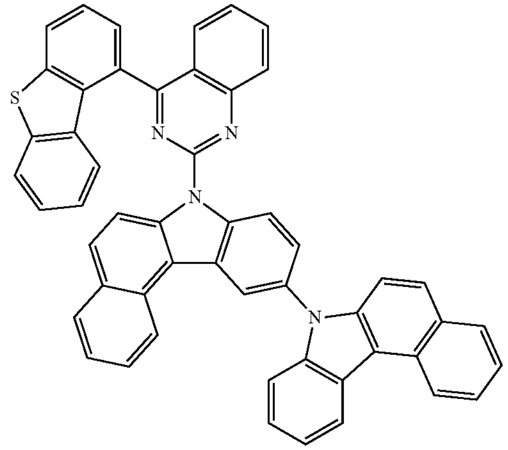
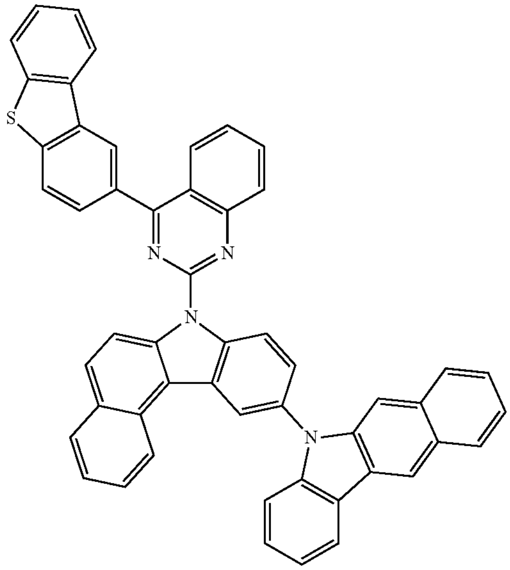
-continued
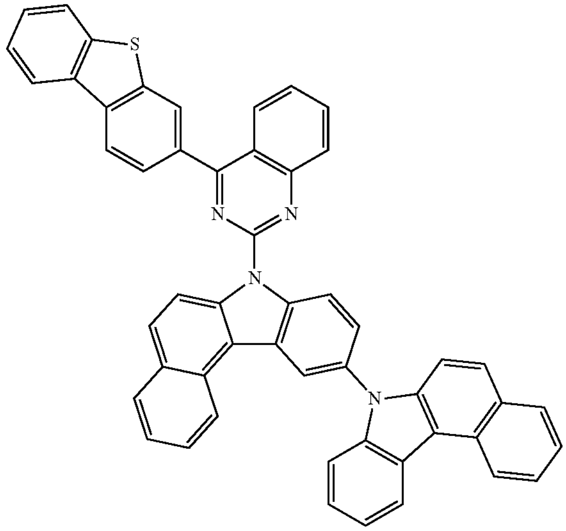
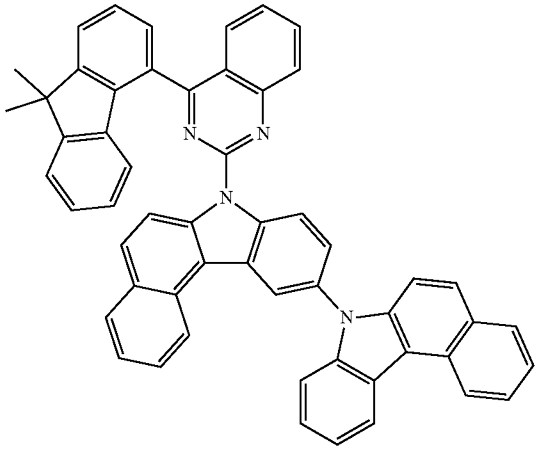
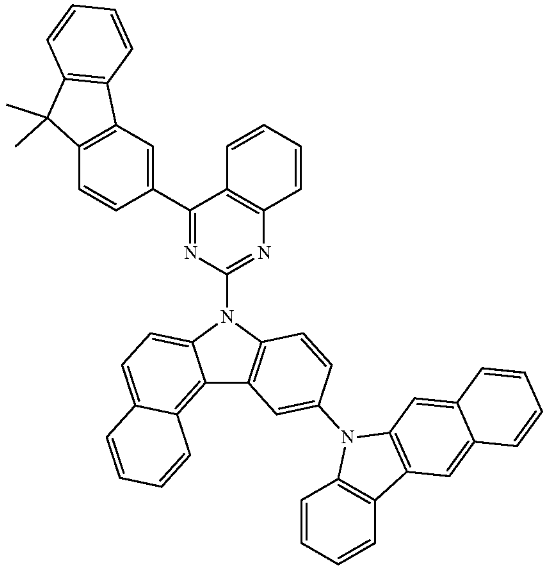

-continued
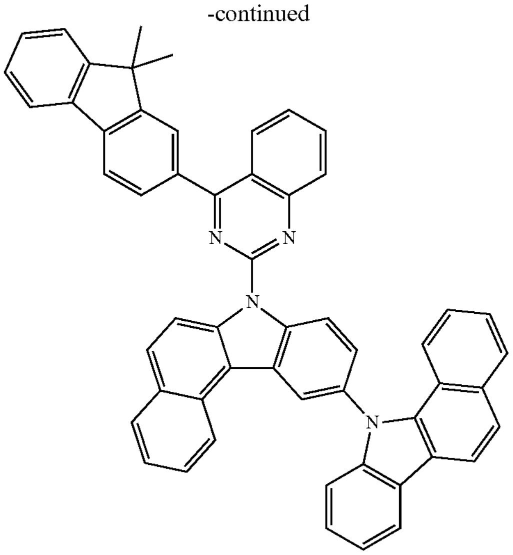
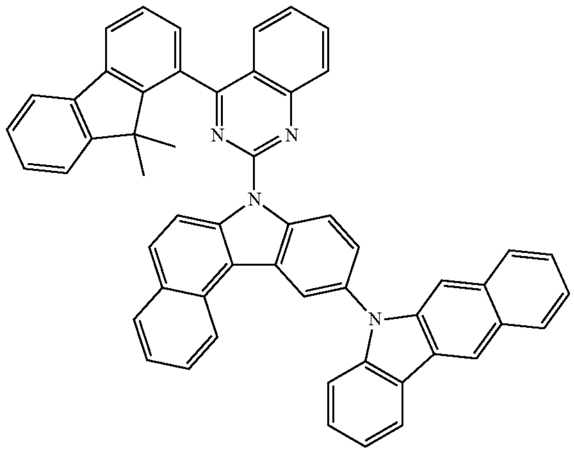
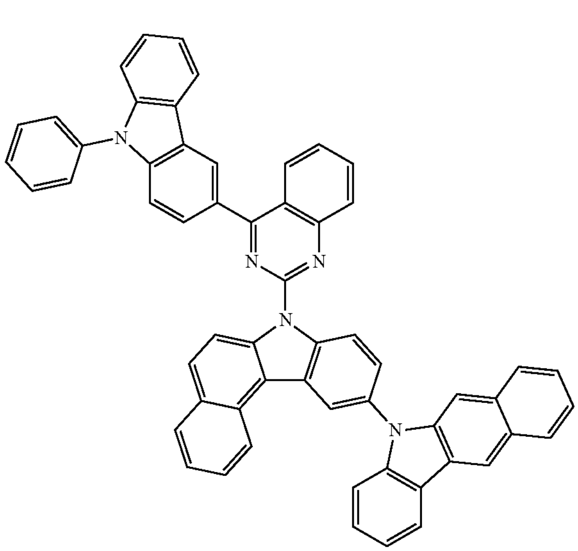
-continued
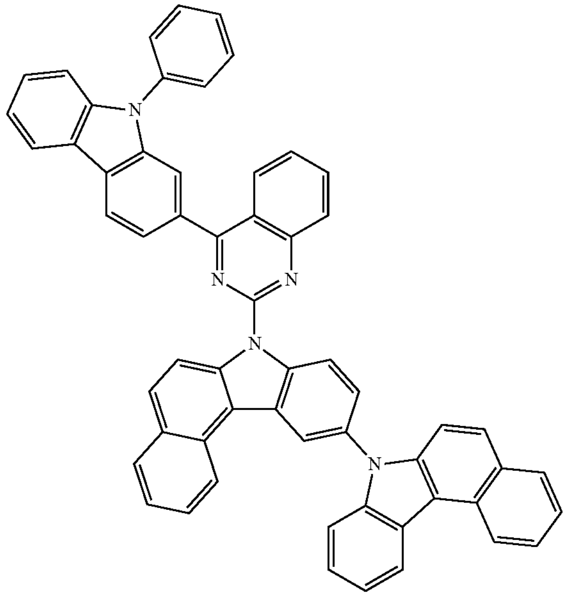
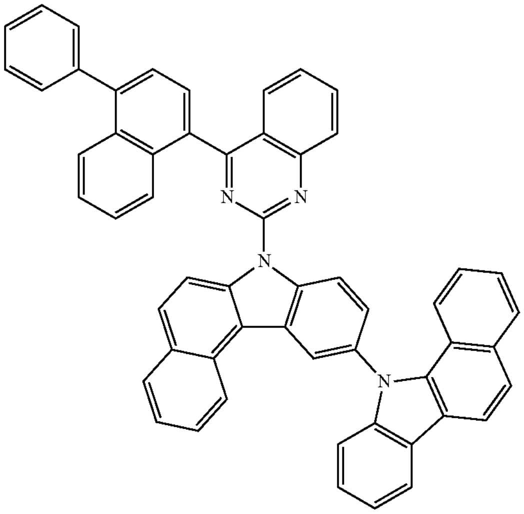
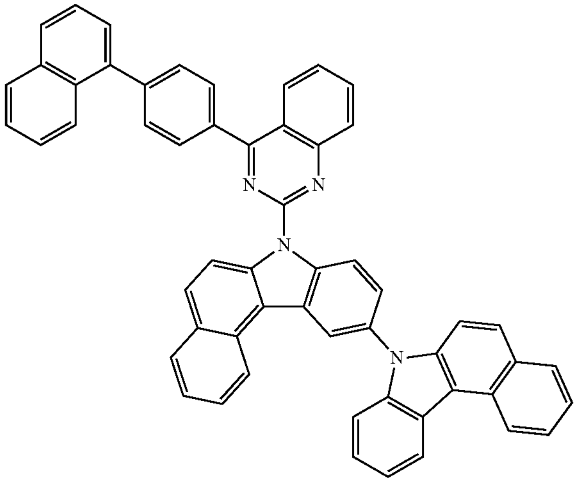

-continued

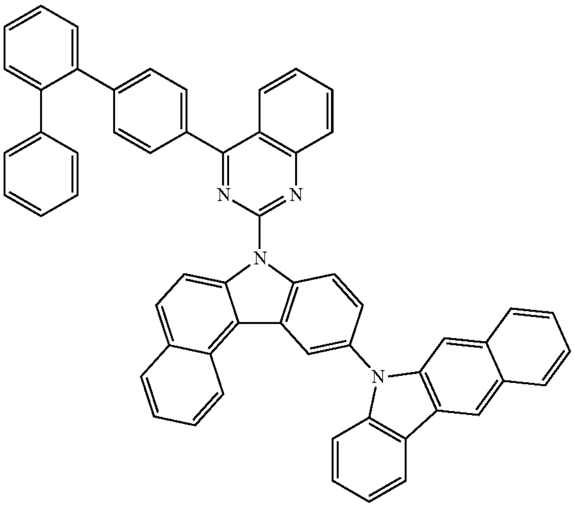

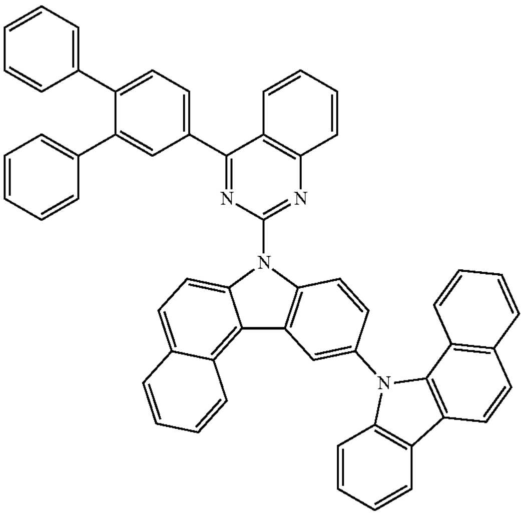

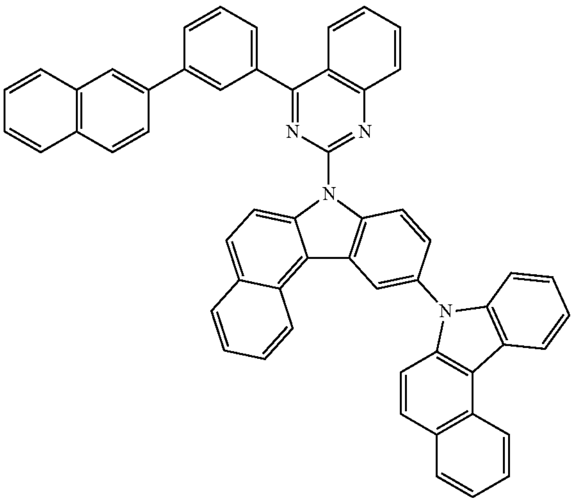

-continued

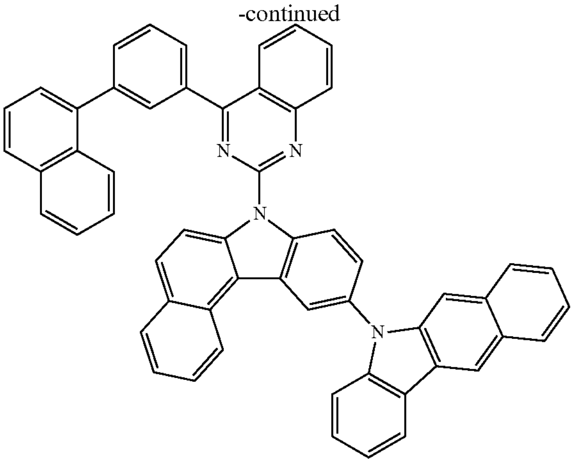

In the present specification, a description of a certain part "including" certain constituents means capable of further including other constituents, and does not exclude other constituents unless particularly stated to the contrary.

In the present specification, a description of a certain member being placed "on" another member includes not only a case of the one member in contact with the another member but a case of yet another member being present between the two members.

An organic light emitting device of the present disclosure includes a first electrode; a second electrode provided opposite to the first electrode; and one or more organic material layers provided between the first electrode and the second electrode, wherein one or more of the one or more organic material layers may include the compound described above.

Figure 2:
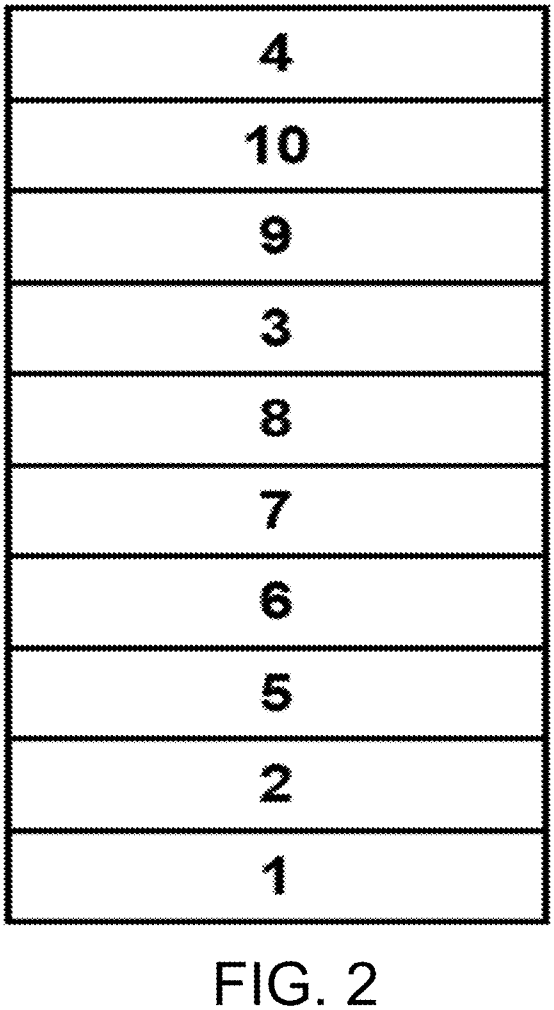

For example, the organic light emitting device of the present disclosure may have structures as illustrated in FIG. 1 and FIG. 2, however, the structure is not limited thereto.

FIG. 1 illustrates an organic light emitting device in which a first electrode (2), a light emitting layer (3) and a second electrode (4) are consecutively laminated on a substrate (1).

FIG. 2 illustrates an organic light emitting device in which a first electrode (2), a hole injection layer (5), a hole transfer layer (6), a hole transfer auxiliary layer (7), an electron blocking layer (8), a light emitting layer (3), a hole blocking layer (9), an electron injection and transfer layer (10) and a second electrode (4) are consecutively laminated on a substrate (1). The compound of the present disclosure may be preferably included in the light emitting layer (3), however, the structure is not limited thereto.

Additional layers may be further included in addition to the laminated structures used in FIG. 1 and FIG. 2, or some layers may be removed therefrom when used.

In one exemplary embodiment of the present disclosure, the first electrode is an anode, and the second electrode is a cathode.

In one exemplary embodiment of the present disclosure, the first electrode is a cathode, and the second electrode is an anode.

In one exemplary embodiment of the present disclosure, the organic material layer includes a light emitting layer, and the light emitting layer includes the compound of Chemical Formula 1.

In one exemplary embodiment of the present disclosure, the organic material layer includes a light emitting layer, and the light emitting layer includes a host and a dopant.

In one exemplary embodiment of the present disclosure, the organic material layer includes a light emitting layer, and the light emitting layer includes a host and a dopant in a mass ratio of 99:1 to 70:30.

In one exemplary embodiment of the present disclosure, the light emitting layer includes the compound of Chemical Formula 1 as a host.

In one exemplary embodiment of the present disclosure, the light emitting layer includes the compound of Chemical Formula 1 as a red host.

In one exemplary embodiment of the present disclosure, the light emitting layer further includes a dopant.

In one exemplary embodiment of the present disclosure, the light emitting layer includes a metal complex compound as a dopant material.

In one exemplary embodiment of the present disclosure, the light emitting layer includes an iridium-based complex compound as a dopant material.

In one exemplary embodiment of the present disclosure, the light emitting layer may include compounds selected from among the following compounds as a dopant material, however, the dopant material is not limited thereto:

Dp-1

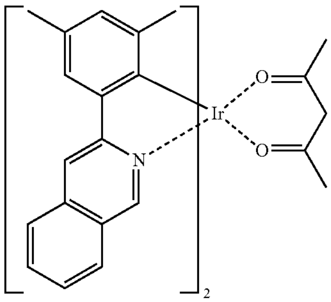

Dp-2

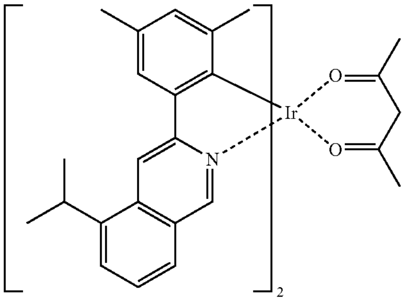

Dp-3

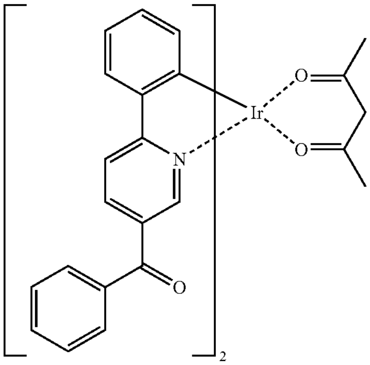

-continued

Dp-4

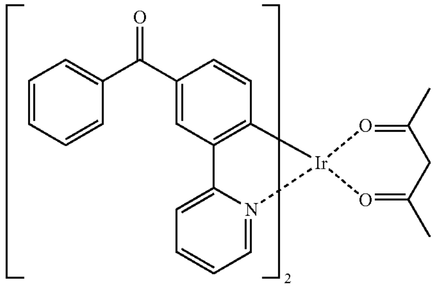

Dp-5

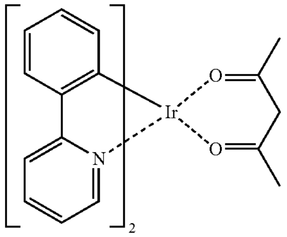

Dp-6

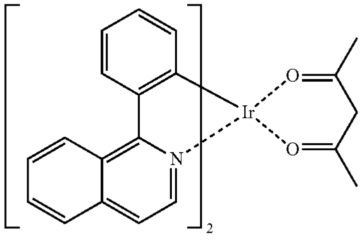

Dp-7

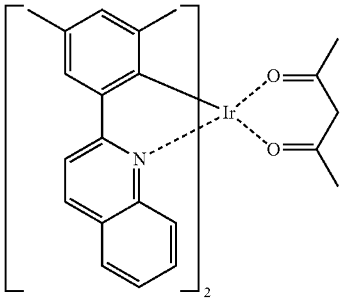

Dp-8

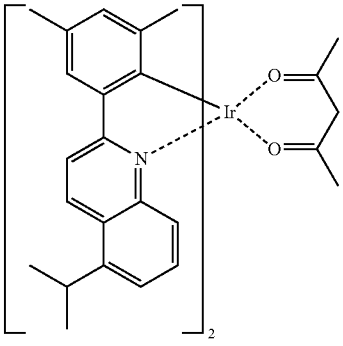

-continued
Dp-9
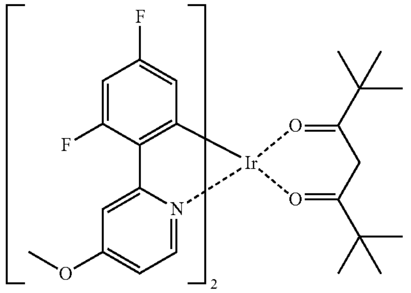
Dp-10
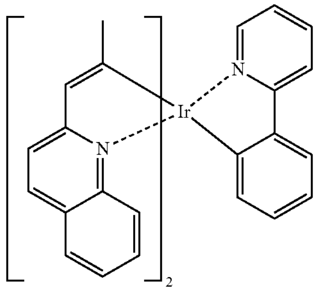
Dp-11
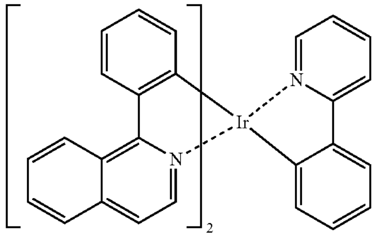
Dp-12
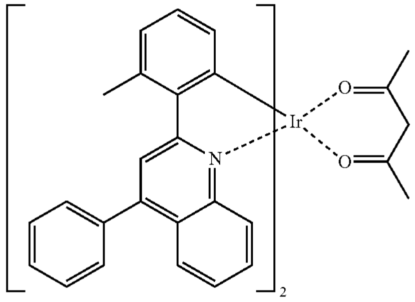
DP-13
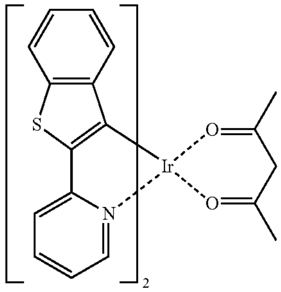
-continued
Dp-14
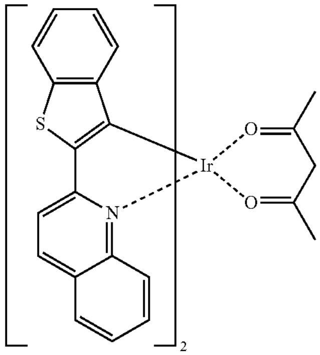
Dp15
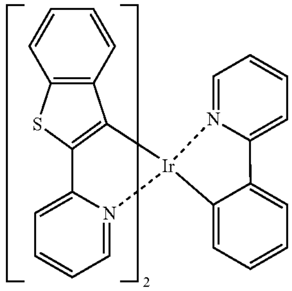
Dp-16
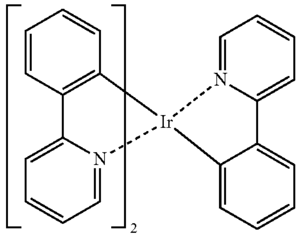
Dp-17
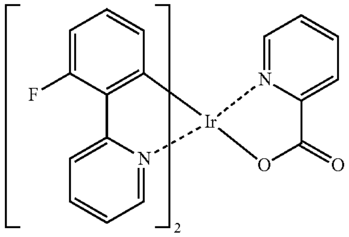
Dp-18
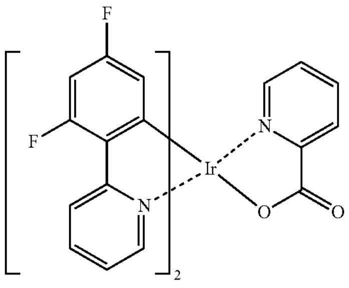

-continued
Dp-19
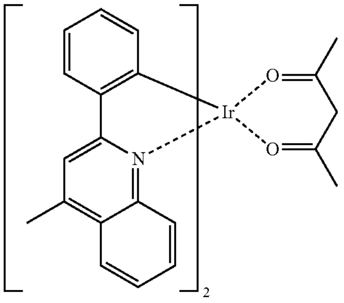
Dp-20
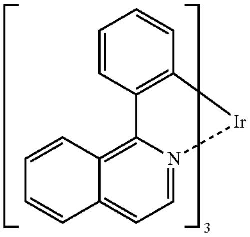
Dp-21
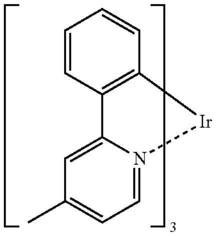
Dp-22
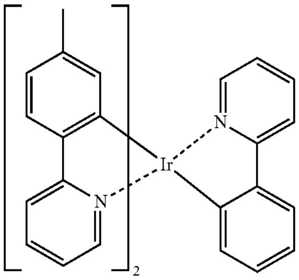
Dp-23
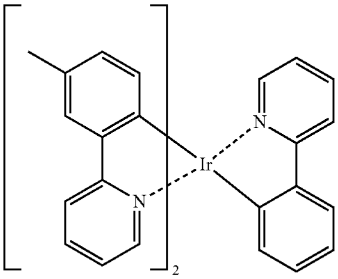
-continued
Dp-24
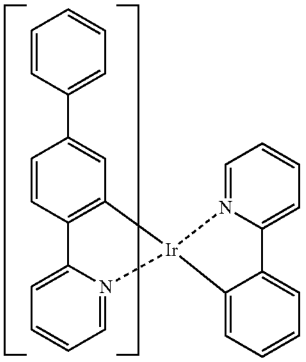
Dp-25
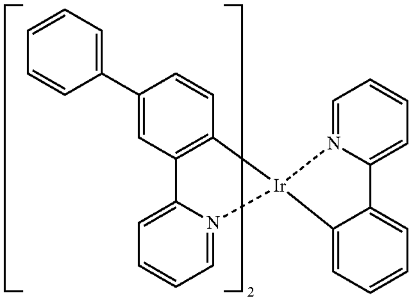
Dp-26
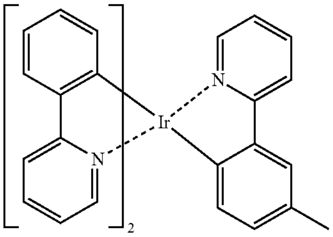
Dp-27
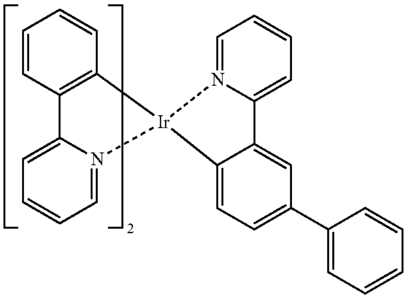
Dp-28
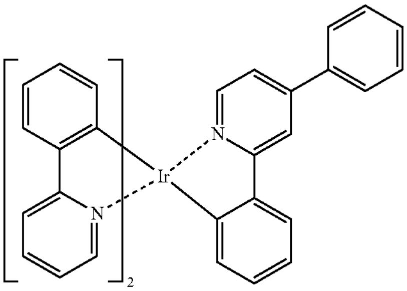

-continued
Dp-29
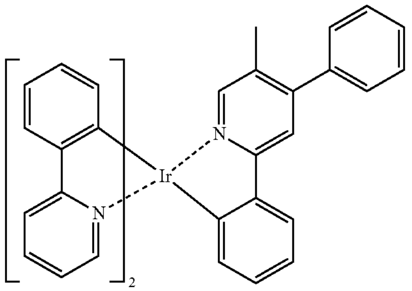
Dp-30
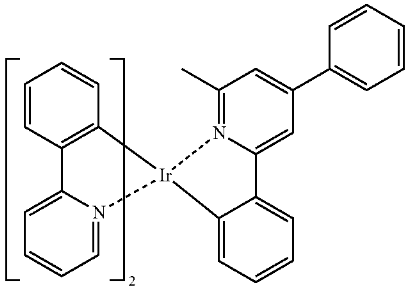
Dp-31
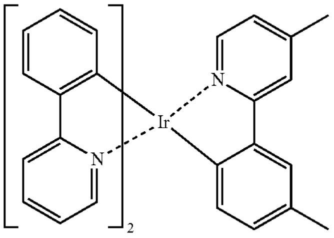
Dp-32
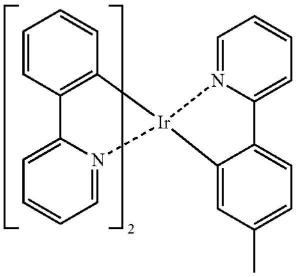
Dp-33
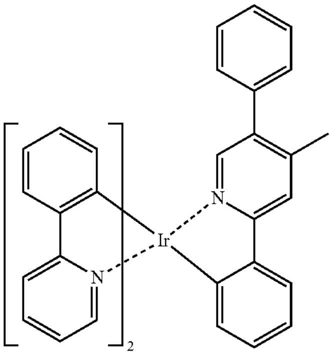
-continued
Dp-34
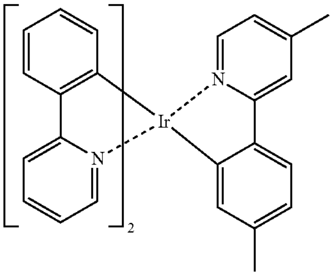
Dp-35
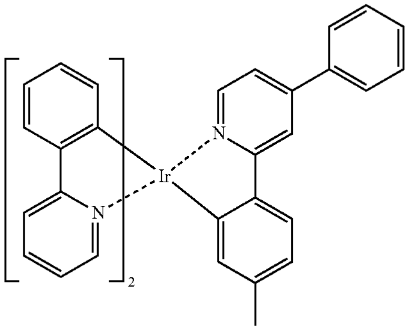
Dp-36
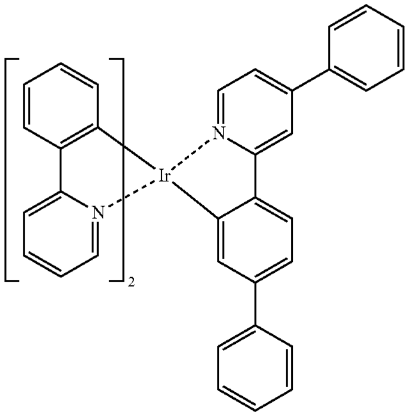
Dp-37
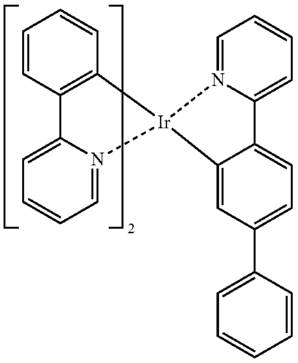

-continued

Dp-38

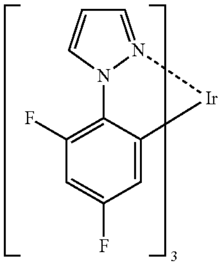

In one exemplary embodiment of the present disclosure, the organic material layer includes a hole injection layer, a hole transfer layer, or a hole injection and transfer layer, and the hole injection layer, the hole transfer layer, or the hole injection and transfer layer may include the compound of Chemical Formula 1.

In one exemplary embodiment of the present disclosure, the organic material layer includes an electron injection layer, an electron transfer layer, or an electron injection and transfer layer, and the electron injection layer, the electron transfer layer, or the electron injection and transfer layer may include the compound of Chemical Formula 1.

In one exemplary embodiment of the present disclosure, the organic material layer includes an electron blocking layer or a hole blocking layer, and the electron blocking layer or the hole blocking layer may include the compound of Chemical Formula 1.

For example, the organic light emitting device according to the present disclosure may be manufactured by forming an anode on a substrate by depositing a metal, a metal oxide having conductivity, or an alloy thereof using a physical vapor deposition (PVD) method such as sputtering or e-beam evaporation, forming an organic material layer including a hole injection layer, a hole transfer layer, a light emitting layer and an electron transfer layer, and an organic material layer including the compound of Chemical Formula 1 thereon, and then depositing a material capable of being used as a cathode thereon. In addition to such a method, the organic light emitting device may also be manufactured by consecutively depositing a cathode material, an organic material layer and an anode material on a substrate.

As the anode material, materials having a large work function are normally preferred so that hole injection into an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDT), polypyrrole and polyaniline, but are not limited thereto.

As the cathode material, materials having a small work function are normally preferred so that electron injection into an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection material is a material that may favorably receive holes from an anode at a low voltage, and the highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

As the hole transfer material, materials capable of receiving holes from an anode or a hole injection layer, moving the holes to a light emitting layer, and having high mobility for the holes are suited. Specific examples thereof include arylamine-based organic materials, conductive polymers, block copolymers having conjugated parts and non-conjugated parts together, and the like, but are not limited thereto.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxy-quinoline aluminum complexes ($Alq_3$); carbazole-based compounds; dimerized styryl compounds; BAlq; 10-hydroxybenzoquinoline-metal compounds; benzoxazole, benzothiazole and benzimidazole-based compounds; poly(p-phenylenevinylene) (PPV)-based polymers; spiro compounds; polyfluorene; rubrene, and the like, but are not limited thereto.

When the organic light emitting device includes a plurality of organic material layers, the organic material layers may be formed with the same materials or different materials.

The organic light emitting device of the present specification may be manufactured using materials and methods known in the art except that one or more layers of the organic material layers are formed using the compound.

Another embodiment of the present specification provides a method for manufacturing an organic light emitting device formed using the compound.

The dopant material may include aromatic compounds, styrylamine compounds, boron complexes, fluoranthene compounds, metal complexes and the like. Specifically, the aromatic compound is a fused aromatic ring derivative having a substituted or unsubstituted arylamino group, and arylamino group-including pyrene, anthracene, chrysene, peryflanthene and the like may be included. As the styrylamine compound, compounds in which substituted or unsubstituted arylamine is substituted with at least one arylvinyl group may be used, and one or more substituents selected from the group consisting of an aryl group, a silyl group, an alkyl group, a cycloalkyl group and an arylamino group, which may be substituted or unsubstituted. Specifically, styrylamine, styryldiamine, styryltriamine, styryltetraamine and the like may be included, however, the styrylamine compound is not limited thereto. In addition, as the metal complex, iridium complexes, platinum complexes and the like may be included, however, the metal complex is not limited thereto.

The electron transfer layer is a layer receiving electrons from an electron injection layer and transferring the electrons to a light emitting layer, and as the electron transfer material, materials capable of favorably receiving electrons from a cathode, moving the electrons to a light emitting layer, and having high mobility for the electrons are suited. Specific examples thereof include Al complexes of 8-hydroxyquinoline; complexes including $Alq_3$; organic radical compounds; hydroxyflavon-metal complexes, and the like, but are not limited thereto. The electron transfer layer may be used together with any desired cathode material known in the art. Particularly, examples of a suitable cathode material may include common materials having low work function and including an additional aluminum layer or a silver layer. Specifically, cesium, barium, calcium, ytterbium and samarium are included, and in each case, an additional aluminum layer or a silver layer is included.

The electron injection layer is a layer injecting electrons from an electrode, and compounds having an electron transferring ability, having the ability to inject electrons from a cathode into a light emitting layer or light emitting material, and preventing excitons generated in the light emitting layer from moving to a hole injection layer, and in addition thereto, having an excellent thin film forming ability are preferred. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound includes 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)beryllium, bis(10-hydroxybenzo[h]quinolinato)zinc, bis(2-methyl-8-quinolinato) chlorogallium, bis(2-methyl-8-quinolinato)(o-cresolato) gallium, bis(2-methyl-8-quinolinato)(1-naphtholato)aluminum, bis(2-methyl-8-quinolinato)(2-naphtholato)gallium and the like, but is not limited thereto.

The hole blocking layer is a layer blocking holes from reaching a cathode, and may be generally formed under the same condition as the hole injection layer. Specific examples thereof may include oxadiazole derivatives, triazole derivatives, phenanthroline derivatives, BCP, aluminum complexes and the like, but are not limited thereto.

The organic light emitting device according to the present specification may be a top-emission type, a bottom-emission type or a dual-emission type depending on the materials used.

The organic light emitting device of the present disclosure may be manufactured using common organic light emitting device manufacturing methods and materials except that one or more organic material layers including the compound of Chemical Formula 1 are formed.

Preparation of the compounds of the present disclosure and manufacturing of the organic light emitting device using the same will be described below. These are for helping those skilled in the art understand the present disclosure, and the present disclosure is not limited thereto. All the compounds described in the present disclosure may be prepared by varying types of starting materials, substituents and positions of substitutions.

Synthesis Example and Example

Compounds of the present disclosure were prepared using a Buchwald-Hartwig coupling reaction, a Heck coupling reaction, a Suzuki coupling reaction or the like as a representative reaction.

Preparation Example 1

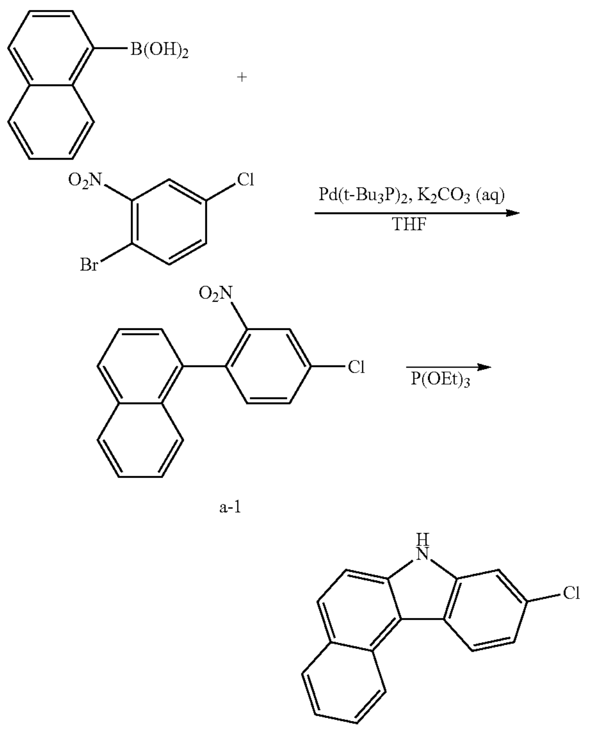

a-1 a

1) Preparation of Chemical Formula a-1

Naphthalen-1-ylboronic acid (100 g, 581.2 mmol) and 1-bromo-4-chloro-2-nitrobenzene (150.2 g, 639.3 mmol) were introduced to THE (2000 ml) under the nitrogen atmosphere, and the result was stirred and refluxed. After that, potassium carbonate (321.3 g, 2324.6 mmol) dissolved in water (964 ml) was introduced thereto, and after sufficiently stirring the result, bis(tri-tert-butylphosphine)palladium(0) (3 g, 5.8 mmol) was introduced thereto. After reacting for 2 hours, the result was cooled to room temperature, and after separating the organic layer and the water layer, the organic layer was distilled. This was dissolved in chloroform again, washed twice with water, and then the organic layer was separated, stirred after introducing anhydrous magnesium sulfate thereto and filtered, and the filtrate was vacuum distilled. The concentrated compound was purified using silica gel column chromatography to prepare Chemical Formula a-1 (111.9 g). (Yield 68%, MS: $[M+H]^+=$ 284)

2) Preparation of Chemical Formula a

Chemical Formula a-1 (111.9 g, 1.0 eq.) was introduced to $P(OEt)_3$ (500 mL), and the result was stirred under reflux. After 3 hours, the reaction material was poured into water to drop crystals, and filtered. The filtered solids were completely dissolved in chloroform, and then washed with water. The solution in which a product was dissolved was vacuum concentrated to drop crystals, and cooled and then filtered. The result was purified using column chromatography to obtain Chemical Formula a (50.6 g). (Yield 51%, $[M+H]^+=$ 252)

Preparation Example 2

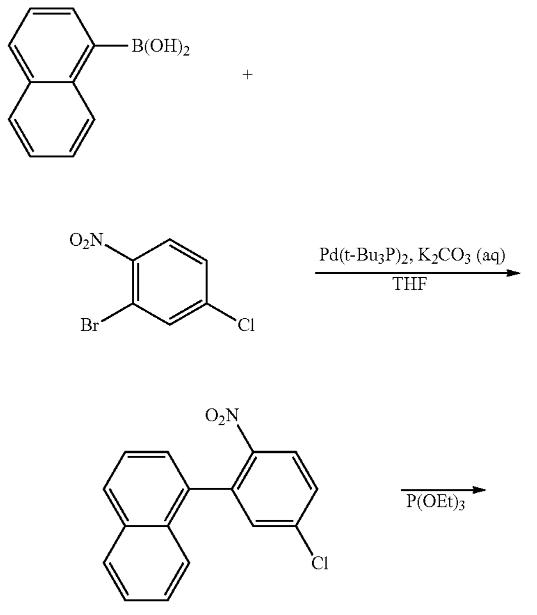

b-1

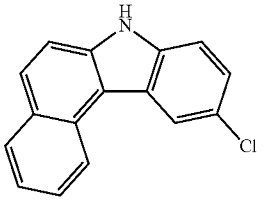

b

Chemical Formula b-1 was synthesized using 2-bromo-4-chloro-1-nitrobenzene instead of 1-bromo-4-chloro-2-nitrobenzene used in Preparation Example 1, and Chemical Formula b was subsequently synthesized.

Synthesis Example 1

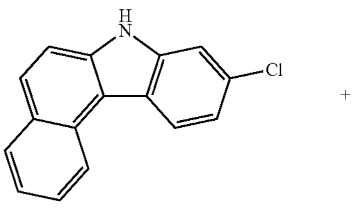

A

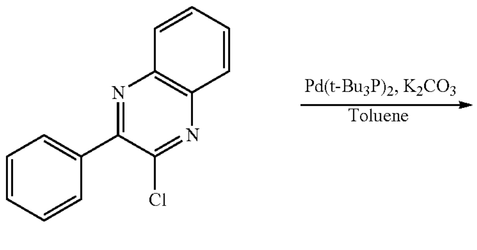

-continued

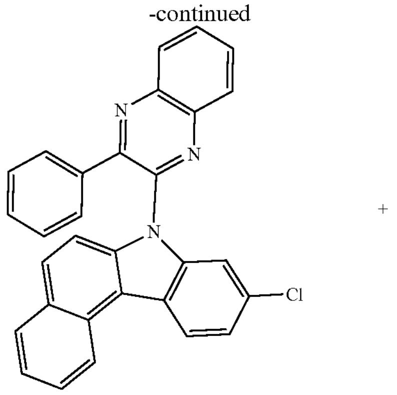

[Intermediate 1]

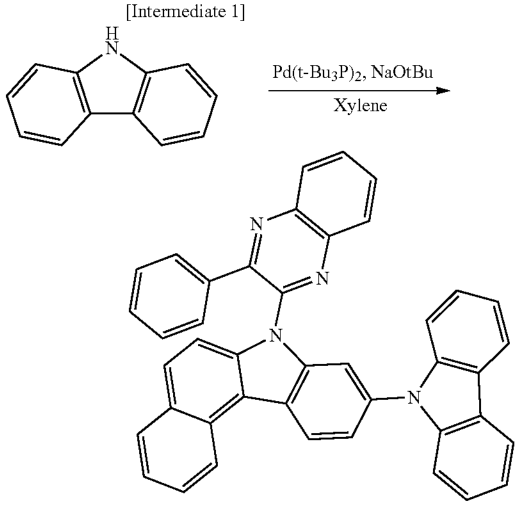

[Compound 1]

Synthesis of Intermediate 1

Chemical Formula a (20 g, 79.7 mmol), 2-chloro-3-phenylquinoxaline (19.1 g, 79.7 mmol) and tripotassium phosphate (15.3 g, 159.3 mmol) were introduced to toluene (400 ml) under the nitrogen atmosphere, and the result was stirred and refluxed. After that, bis(tri-tert-butylphosphine) palladium(0) (0.8 g, 1.6 mmol) was introduced thereto. The reaction was terminated after 2 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Intermediate 1 (21.8 g). (Yield 60%, MS: $[M+H]^+=456$)

Synthesis of Compound 1

Intermediate 1 (20 g, 43.9 mmol), 9H-carbazole (7.3 g, 43.9 mmol) and sodium tert-butoxide (8.4 g, 87.9 mmol) were introduced to xylene (400 ml) under the nitrogen atmosphere, and the result was stirred and refluxed. After that, bis(tri-tert-butylphosphine)palladium(0) (0.4 g, 0.9 mmol) was introduced thereto. The reaction was terminated after 2 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 1 (15.2 g). (Yield 59%, MS: [M+H]$^+$=587) In the following Synthesis Examples 2 to 18, Intermediates 2 to 18 were prepared by varying starting materials and substituents in Synthesis of Intermediate 1.

Synthesis Example 2

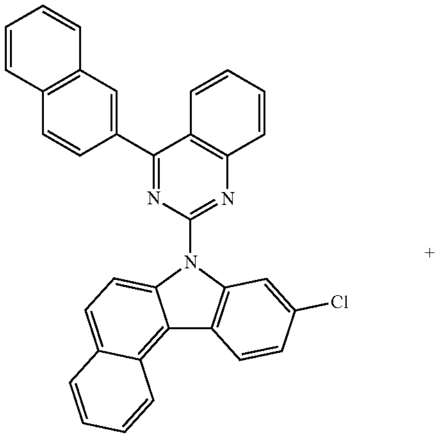

[Intermediate 2]

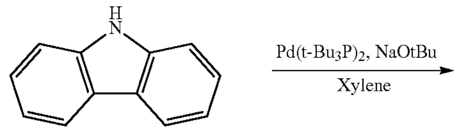

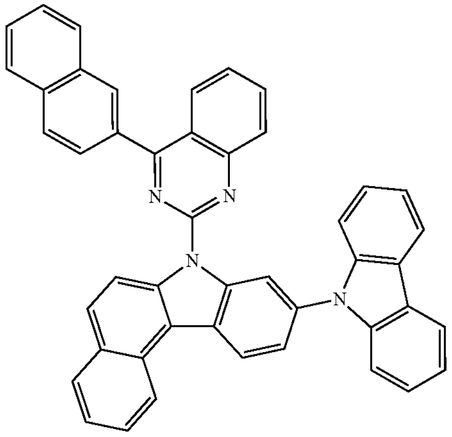

[Compound 2]

Intermediate 2 (10 g, 19.8 mmol), 9H-carbazole (3.5 g, 20.8 mmol) and sodium tert-butoxide (3.8 g, 39.6 mmol) were introduced to xylene (200 ml) under the nitrogen atmosphere, and the result was stirred and refluxed. After that, bis(tri-tert-butylphosphine)palladium(0) (0.2 g, 0.4 mmol) was introduced thereto. The reaction was terminated after 2 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 2 (8.2 g). (Yield 65%, MS: [M+H]$^+$=637)

Synthesis Example 3

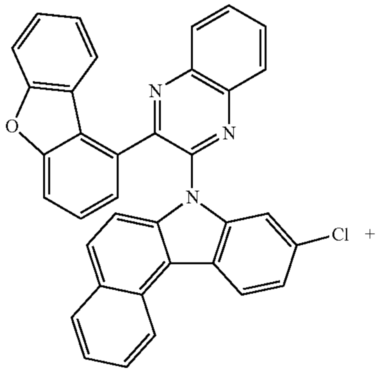

[Intermediate 3]

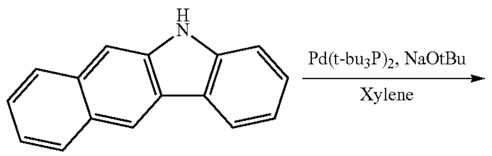

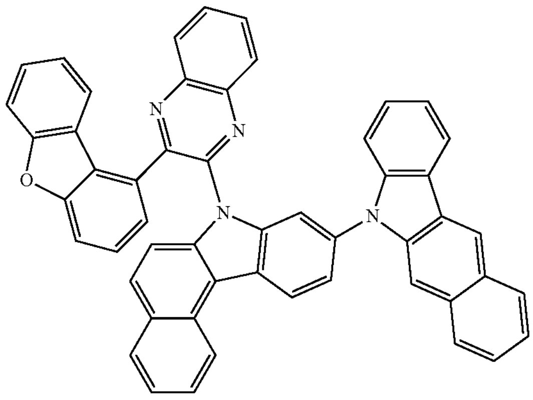

[Compound 3]

Intermediate 3 (10 g, 18.3 mmol), 5H-benzo[b]carbazole (4.2 g, 19.3 mmol) and sodium tert-butoxide (3.5 g, 36.7 mmol) were introduced to xylene (200 ml) under the nitrogen atmosphere, and the result was stirred and refluxed. After that, bis(tri-tert-butylphosphine)palladium(0) (0.2 g, 0.4 mmol) was introduced thereto. The reaction was terminated after 2 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 3 (7.3 g). (Yield 55%, MS: [M+H]$^+$=727)

Synthesis Example 4

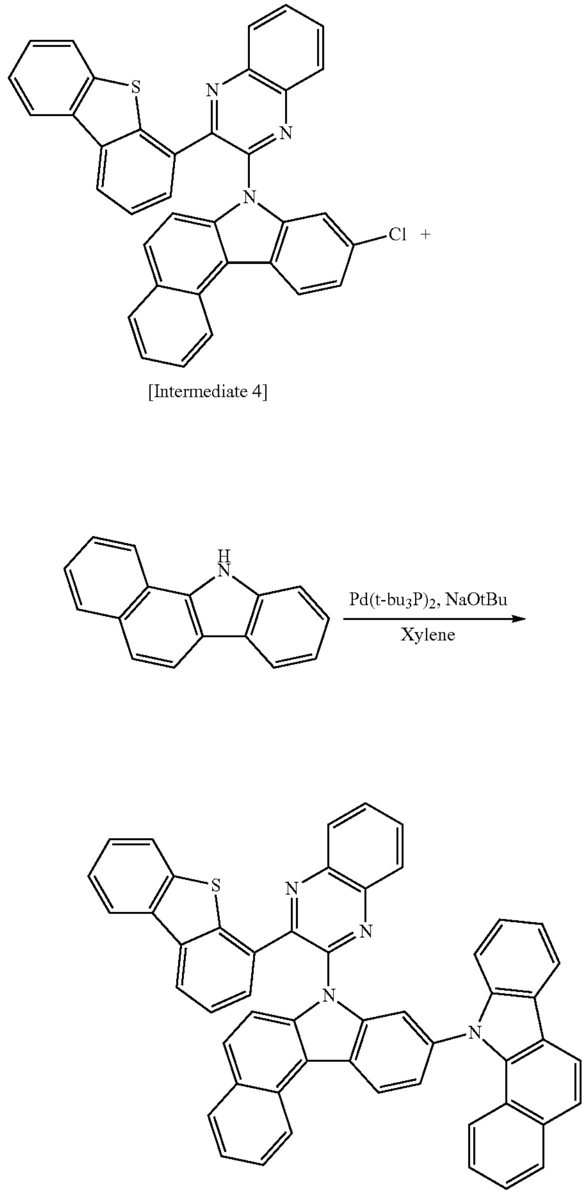

[Intermediate 4]

[Compound 4]

Intermediate 4 (10 g, 17.8 mmol), 11H-benzo[a]carbazole (4.1 g, 18.7 mmol) and sodium tert-butoxide (3.4 g, 35.6 mmol) were introduced to xylene (200 ml) under the nitrogen atmosphere, and the result was stirred and refluxed. After that, bis(tri-tert-butylphosphine)palladium(0) (0.2 g, 0.4 mmol) was introduced thereto. The reaction was terminated after 3 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 4 (8.9 g). (Yield 67%, MS: $[M+H]^+=743$)

Synthesis Example 5

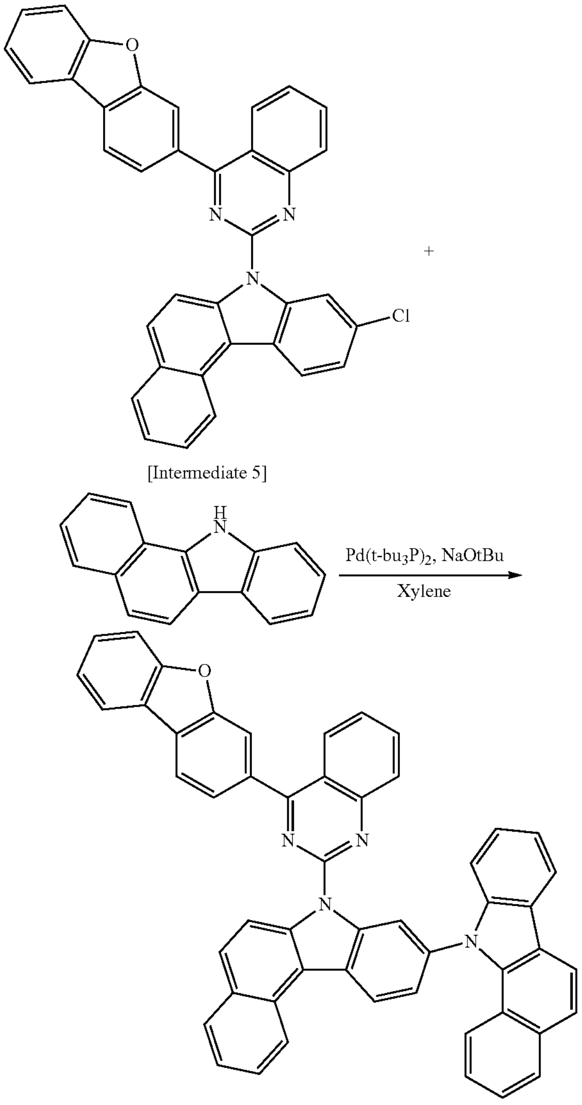

[Intermediate 5]

[Compound 5]

Intermediate 5 (10 g, 18.3 mmol), 11H-benzo[a]carbazole (4.2 g, 19.3 mmol) and sodium tert-butoxide (3.5 g, 36.7 mmol) were introduced to xylene (200 ml) under the nitrogen atmosphere, and the result was stirred and refluxed. After that, bis(tri-tert-butylphosphine)palladium(0) (0.2 g, 0.4 mmol) was introduced thereto. The reaction was terminated after 3 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 5 (9.3 g). (Yield 70%, MS: $[M+H]^+=727$)

Synthesis Example 6

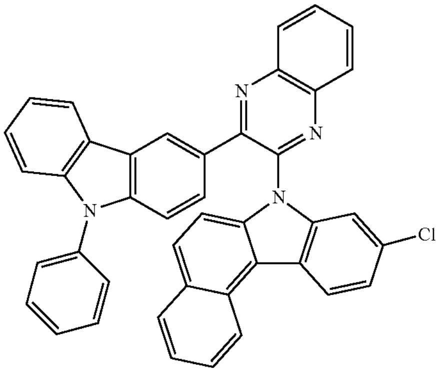

+

[Intermediate 6]

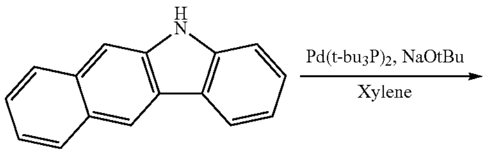

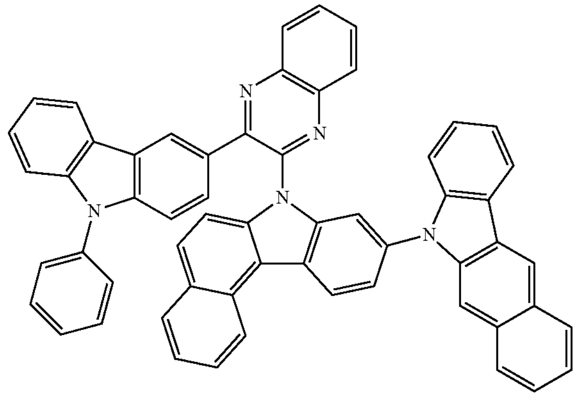

[Compound 6]

Intermediate 6 (10 g, 16.1 mmol), 5H-benzo[b]carbazole (3.7 g, 16.9 mmol) and sodium tert-butoxide (3.1 g, 32.2 mmol) were introduced to xylene (200 ml) under the nitrogen atmosphere, and the result was stirred and refluxed. After that, bis(tri-tert-butylphosphine)palladium(0) (0.2 g, 0.3 mmol) was introduced thereto. The reaction was terminated after 3 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 6 (8.1 g). (Yield 63%, MS: $[M+H]^+=802$)

Synthesis Example 7

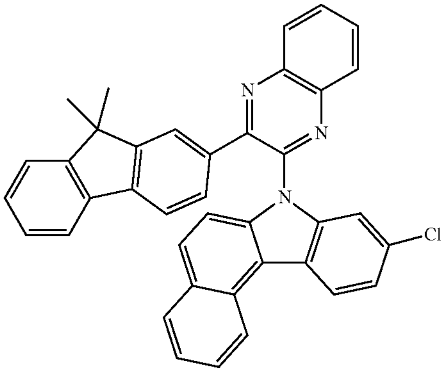

+

[Intermediate 7]

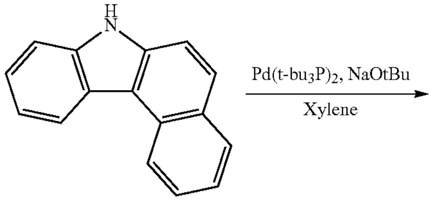

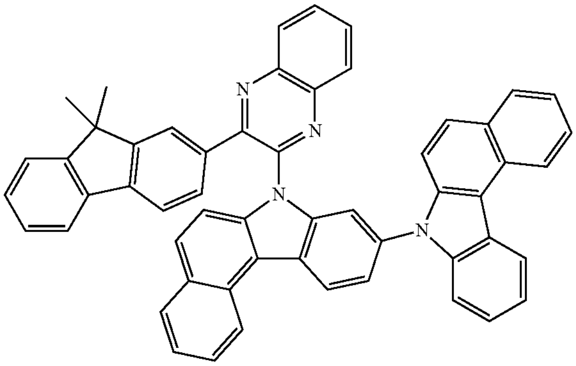

[Compound 7]

Intermediate 7 (10 g, 17.5 mmol), 7H-benzo[c]carbazole (4 g, 18.4 mmol) and sodium tert-butoxide (3.4 g, 35 mmol) were introduced to xylene (200 ml) under the nitrogen atmosphere, and the result was stirred and refluxed. After that, bis(tri-tert-butylphosphine)palladium(0) (0.2 g, 0.4 mmol) was introduced thereto. The reaction was terminated after 2 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 7 (7.6 g). (Yield 58%, MS: $[M+H]^+=753$)

Synthesis Example 8

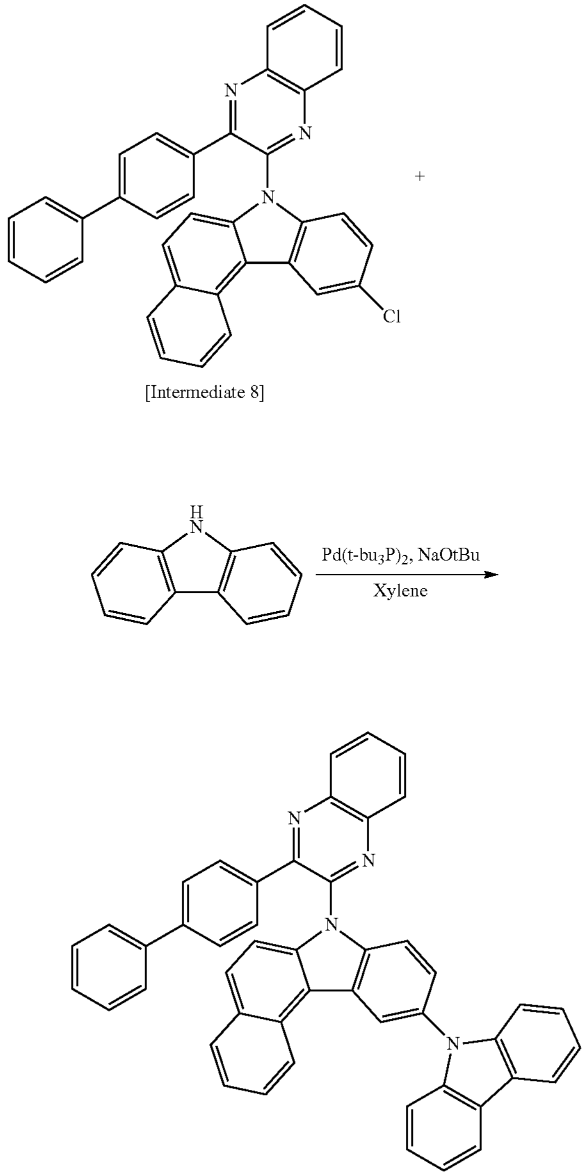

[Intermediate 8]

[Compound 8]

Intermediate 8 (10 g, 18.8 mmol), 9H-carbazole (3.3 g, 19.8 mmol) and sodium tert-butoxide (3.6 g, 37.7 mmol) were introduced to xylene (200 ml) under the nitrogen atmosphere, and the result was stirred and refluxed. After that, bis(tri-tert-butylphosphine)palladium(0) (0.2 g, 0.4 mmol) was introduced thereto. The reaction was terminated after 3 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 8 (6.5 g). (Yield 52%, MS: $[M+H]^+=663$)

Synthesis Example 9

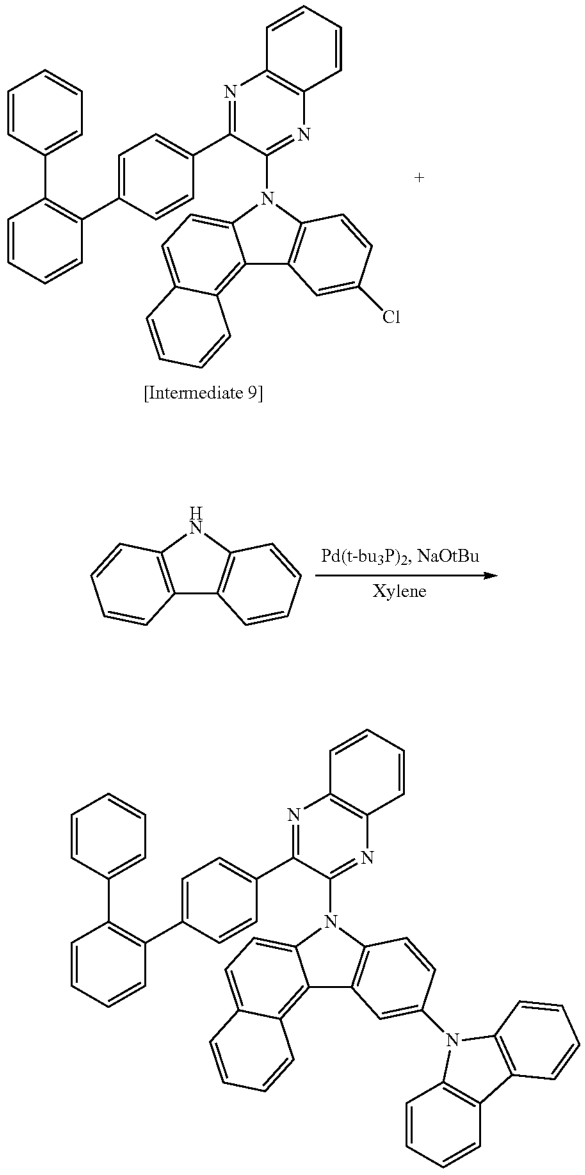

[Intermediate 9]

[Compound 9]

Intermediate 9 (10 g, 16.5 mmol), 9H-carbazole (2.9 g, 17.3 mmol) and sodium tert-butoxide (3.2 g, 32.9 mmol) were introduced to xylene (200 ml) under the nitrogen atmosphere, and the result was stirred and refluxed. After that, bis(tri-tert-butylphosphine)palladium(0) (0.2 g, 0.3 mmol) was introduced thereto. The reaction was terminated after 3 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 9 (6.9 g). (Yield 57%, MS: $[M+H]^+=739$)

Synthesis Example 10

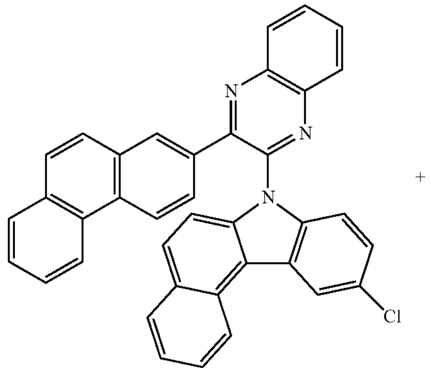

[Intermediate 10]

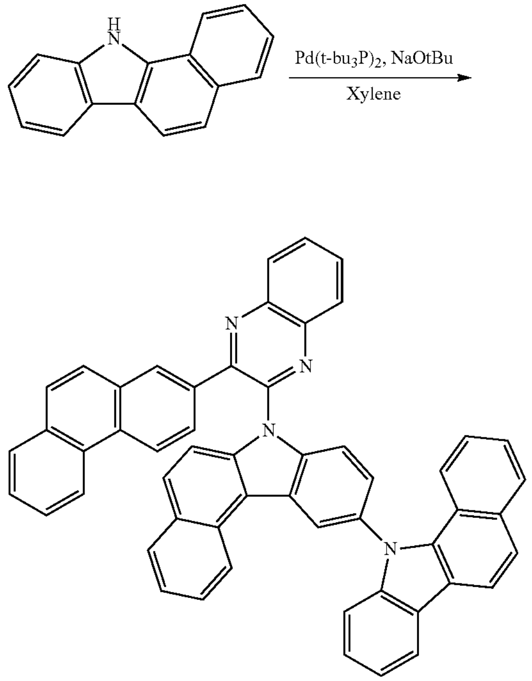

[Compound 10]

Intermediate 10 (10 g, 18 mmol), 11H-benzo[a]carbazole (4.1 g, 18.9 mmol) and sodium tert-butoxide (3.5 g, 36 mmol) were introduced to xylene (200 ml) under the nitrogen atmosphere, and the result was stirred and refluxed. After that, bis(tri-tert-butylphosphine)palladium(0) (0.2 g, 0.4 mmol) was introduced thereto. The reaction was terminated after 3 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 10 (8.2 g). (Yield 62%, MS: $[M+H]^+=737$)

Synthesis Example 11

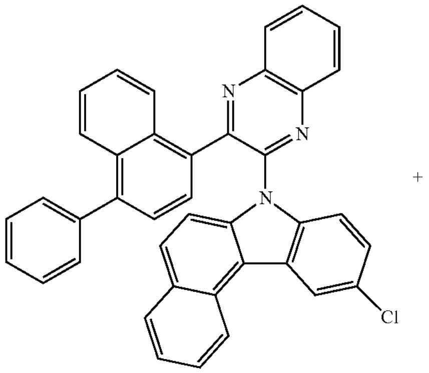

[Intermediate 11]

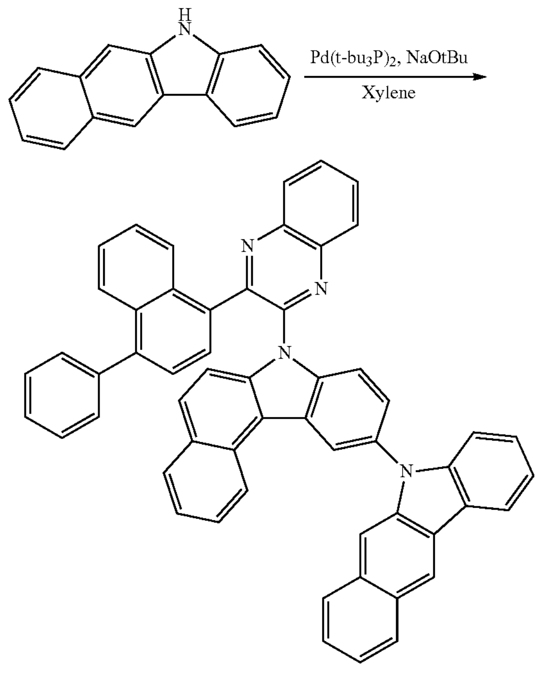

[Compound 11]

Intermediate 11 (10 g, 17.2 mmol), 5H-benzo[b]carbazole (3.9 g, 18.1 mmol) and sodium tert-butoxide (3.3 g, 34.4 mmol) were introduced to xylene (200 ml) under the nitrogen atmosphere, and the result was stirred and refluxed. After that, bis(tri-tert-butylphosphine)palladium(0) (0.2 g, 0.3 mmol) was introduced thereto. The reaction was terminated after 3 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 11 (8.3 g). (Yield 63%, MS: $[M+H]^+=763$)

Synthesis Example 12

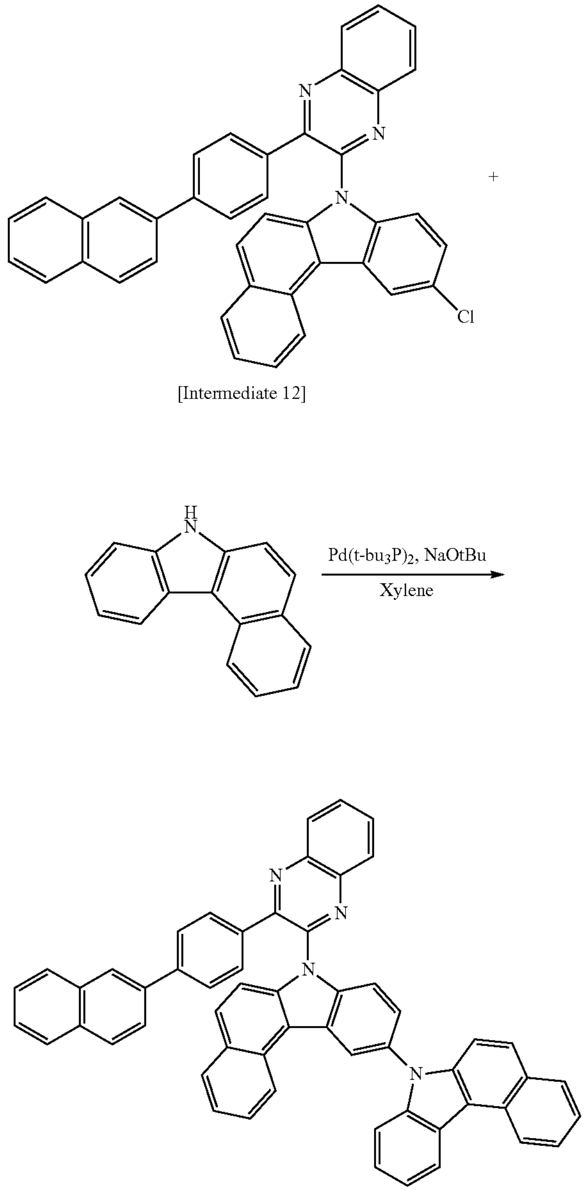

[Intermediate 12]
[Compound 12]

Intermediate 12 (10 g, 17.2 mmol), 7H-benzo[c]carbazole (3.9 g, 18.1 mmol) and sodium tert-butoxide (3.3 g, 34.4 mmol) were introduced to xylene (200 ml) under the nitrogen atmosphere, and the result was stirred and refluxed. After that, bis(tri-tert-butylphosphine)palladium(0) (0.2 g, 0.3 mmol) was introduced thereto. The reaction was terminated after 2 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 12 (8 g). (Yield 61%, MS: $[M+H]^+=763$)

Synthesis Example 13

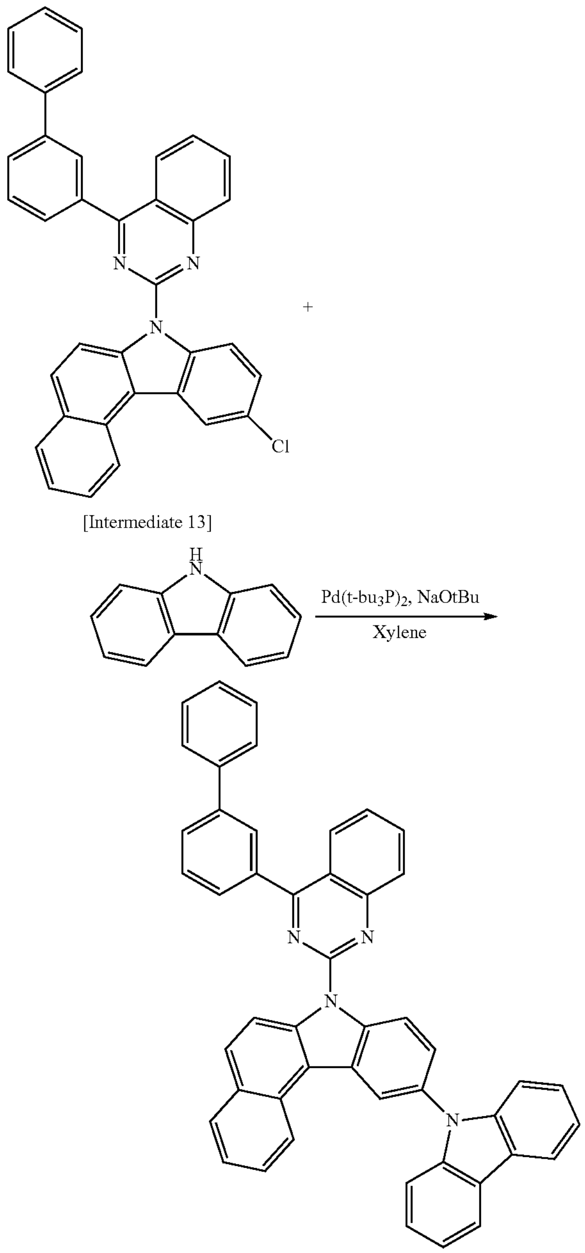

[Intermediate 13]
[Compound 13]

Intermediate 13 (10 g, 18.8 mmol), 9H-carbazole (3.3 g, 19.8 mmol) and sodium tert-butoxide (3.6 g, 37.7 mmol) were introduced to xylene (200 ml) under the nitrogen atmosphere, and the result was stirred and refluxed. After that, bis(tri-tert-butylphosphine)palladium(0) (0.2 g, 0.4 mmol) was introduced thereto. The reaction was terminated after 3 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 13 (7.9 g). (Yield 63%, MS: $[M+H]^+$=663)

Synthesis Example 14

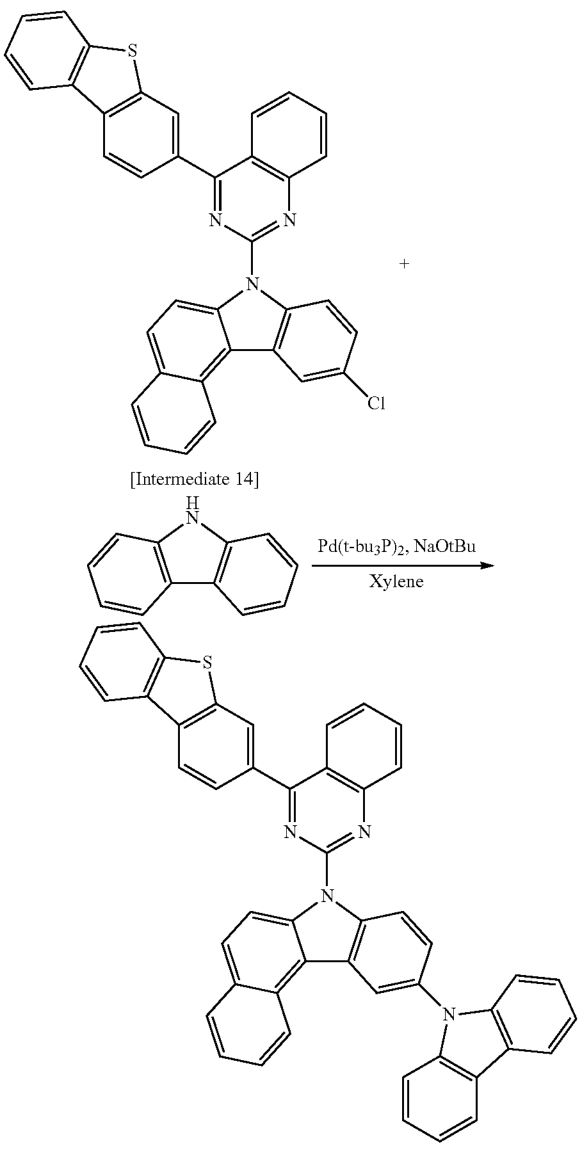

[Intermediate 14]

[Compound 14]

Intermediate 14 (10 g, 17.8 mmol), 9H-carbazole (3.1 g, 18.7 mmol) and sodium tert-butoxide (3.4 g, 35.6 mmol) were introduced to xylene (200 ml) under the nitrogen atmosphere, and the result was stirred and refluxed. After that, bis(tri-tert-butylphosphine)palladium(0) (0.2 g, 0.4 mmol) was introduced thereto. The reaction was terminated after 3 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 14 (7.3 g). (Yield 59%, MS: $[M+H]^+$=693)

Synthesis Example 15

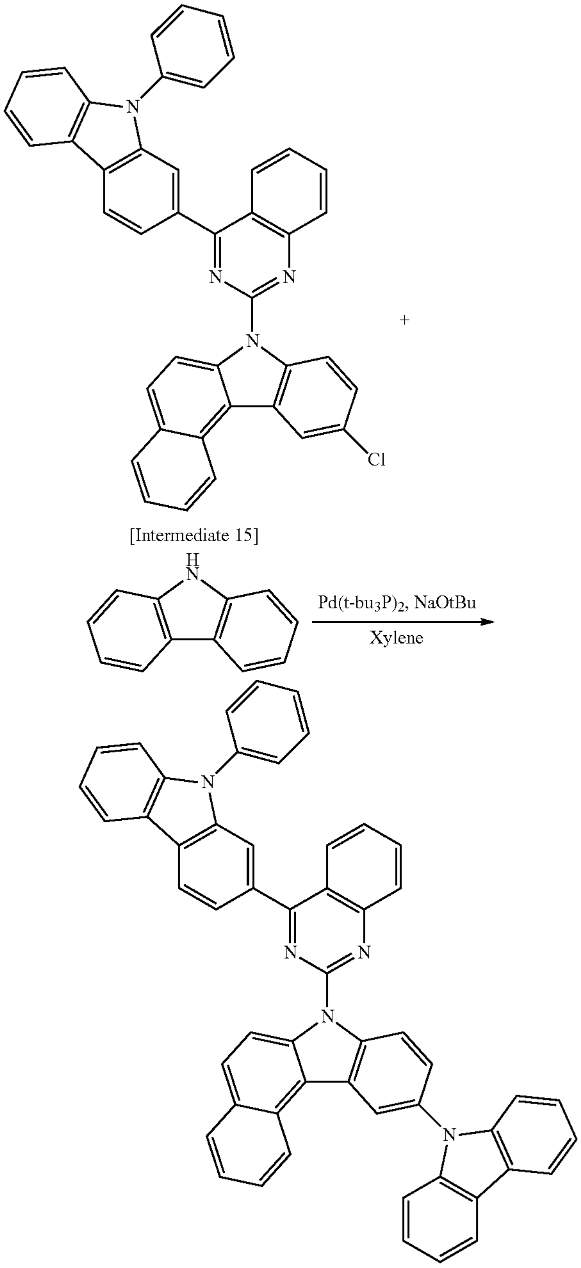

[Intermediate 15]

[Compound 15]

Intermediate 15 (10 g, 16.1 mmol), 9H-carbazole (2.8 g, 16.9 mmol) and sodium tert-butoxide (3.1 g, 32.2 mmol) were introduced to xylene (200 ml) under the nitrogen atmosphere, and the result was stirred and refluxed. After that, bis(tri-tert-butylphosphine)palladium(0) (0.2 g, 0.3 mmol) was introduced thereto. The reaction was terminated after 3 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 15 (7.1 g). (Yield 59%, MS: $[M+H]^+$=752)

Synthesis Example 16

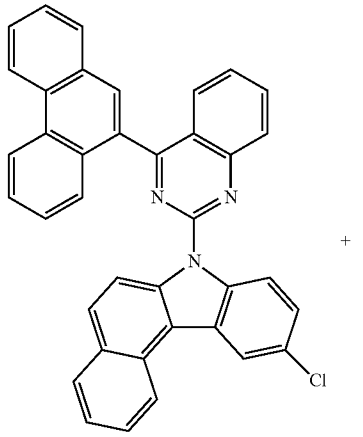

[Intermediate 16]

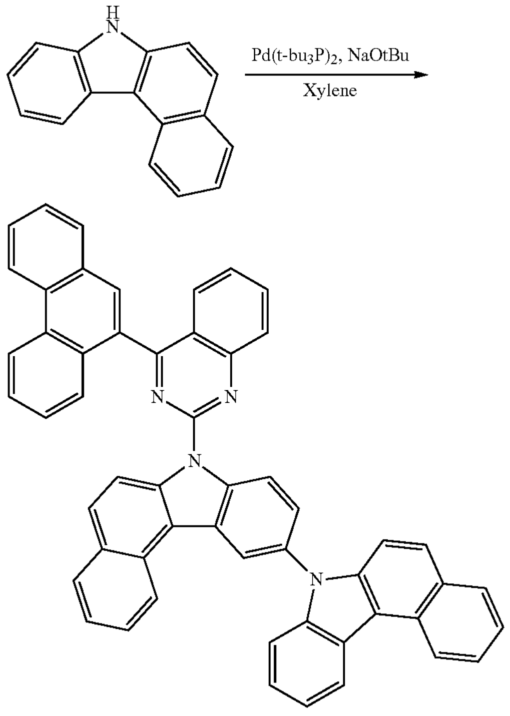

[Compound 16]

Intermediate 16 (10 g, 18 mmol), 7H-benzo[c]carbazole (4.1 g, 18.9 mmol) and sodium tert-butoxide (3.5 g, 36 mmol) were introduced to xylene (200 ml) under the nitrogen atmosphere, and the result was stirred and refluxed. After that, bis(tri-tert-butylphosphine)palladium(0) (0.2 g, 0.4 mmol) was introduced thereto. The reaction was terminated after 2 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 16 (8.9 g). (Yield 67%, MS: $[M+H]^+$=737)

Synthesis Example 17

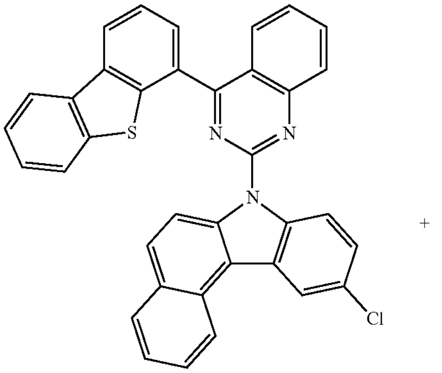

[Intermediate 17]

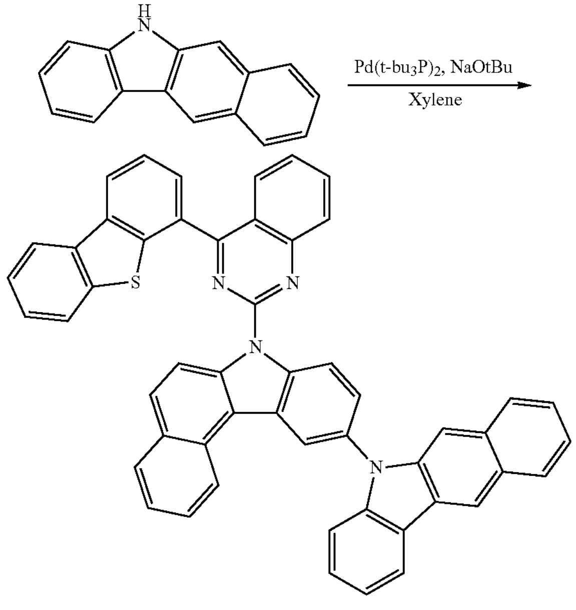

[Compound 17]

Intermediate 17 (10 g, 17.8 mmol), 5H-benzo[b]carbazole (4.1 g, 18.7 mmol) and sodium tert-butoxide (3.4 g, 35.6 mmol) were introduced to xylene (200 ml) under the nitrogen atmosphere, and the result was stirred and refluxed. After that, bis(tri-tert-butylphosphine)palladium(0) (0.2 g, 0.4 mmol) was introduced thereto. The reaction was terminated after 3 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 17 (7 g). (Yield 53%, MS: $[M+H]^+$=743)

Synthesis Example 18

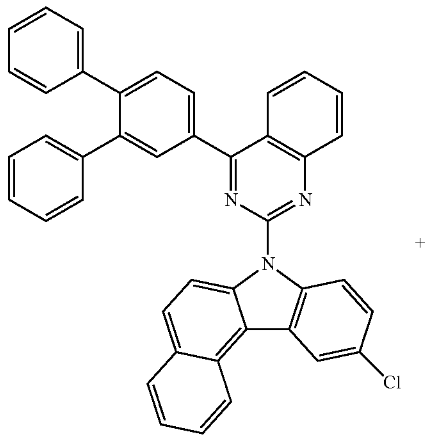

[Intermediate 18]

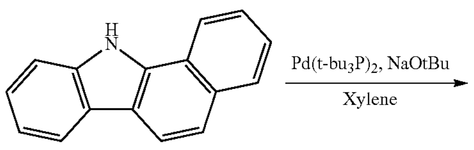

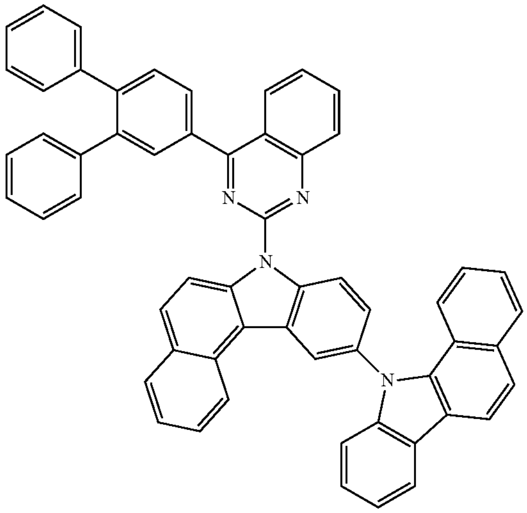

[Compound 18]

Intermediate 18 (10 g, 16.5 mmol), 11H-benzo[a]carbazole (3.8 g, 17.3 mmol) and sodium tert-butoxide (3.2 g, 32.9 mmol) were introduced to xylene (200 ml) under the nitrogen atmosphere, and the result was stirred and refluxed. After that, bis(tri-tert-butylphosphine)palladium(0) (0.2 g, 0.3 mmol) was introduced thereto. The reaction was terminated after 2 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 18 (7.5 g). (Yield 58%, MS: $[M+H]^+=789$)

Comparative Example 1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, the following HI-1 compound was formed to a thickness of 1150 Å as a hole injection layer while p-doping the following A-1 compound thereto in a concentration of 1.5%. On the hole injection layer, the following HT-1 compound was vacuum deposited to form a hole transfer layer having a film thickness of 1000 Å. Subsequently, the HT-2 Compound was vacuum deposited to a film thickness of 500 Å on the hole transfer layer to form a hole transfer auxiliary layer. On the hole transfer auxiliary layer, the following EB-1 compound was vacuum deposited to a film thickness of 150 Å to form an electron blocking layer. Then, on the EB-1 deposited film, the following RH-1 compound and the following Dp-8 compound were vacuum deposited in a weight ratio of 98:2 to form a red light emitting layer having a thickness of 400 Å. On the light emitting layer, a hole blocking layer was formed by vacuum depositing the following HB-1 compound to a film thickness of 30 Å. Subsequently, an electron injection and transfer layer was formed on the hole blocking layer to a thickness of 300 Å by vacuum depositing the following ET-1 Compound and the following LiQ compound in a weight ratio of 2:1. On the electron injection and transfer layer, a cathode was formed by consecutively depositing lithium fluoride (LiF) and aluminum to a thickness of 12 Å and a thickness of 1,000 Å, respectively.

In the above-mentioned process, the deposition rates of the organic materials were maintained at 0.4 Å/sec to 0.7 Å/sec, the deposition rates of the lithium fluoride and the aluminum of the cathode were maintained at 0.3 Å/sec and 2 Å/sec, respectively, and the degree of vacuum during the deposition was maintained at $2\times10^{-7}$ torr to $5\times10^{-8}$ torr, and as a result, an organic light emitting device was manufactured.

HI-1
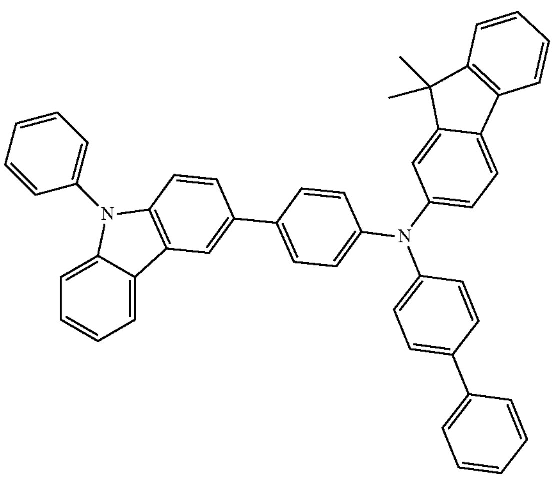
A-1
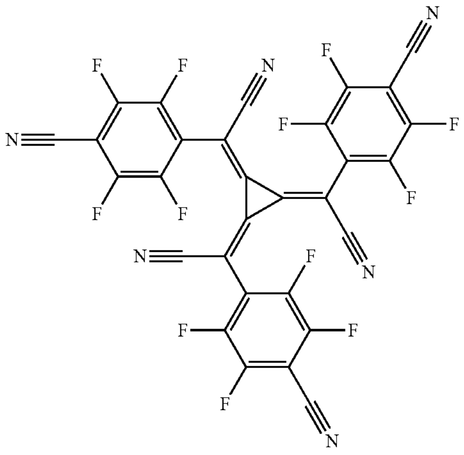
AT-1
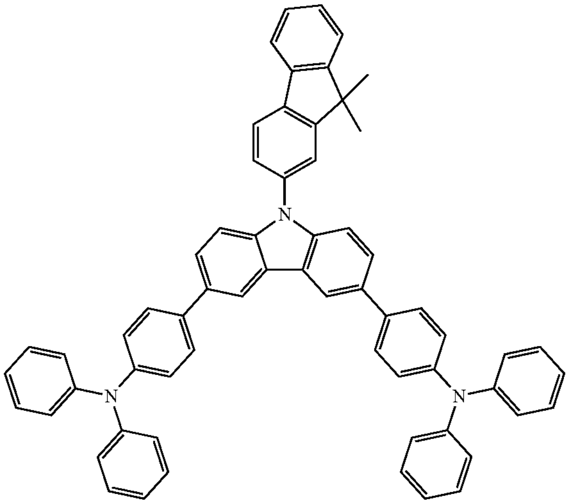
HT-2
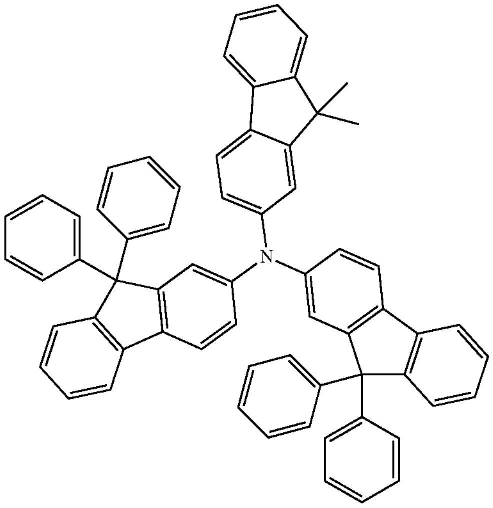
EB-1
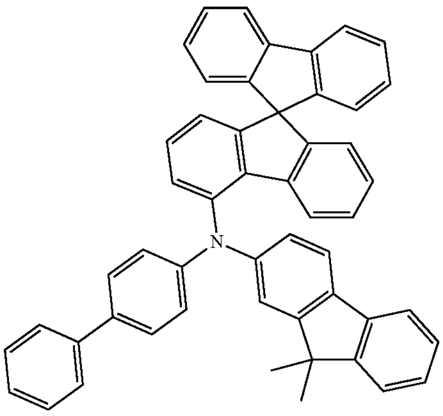
RH-1
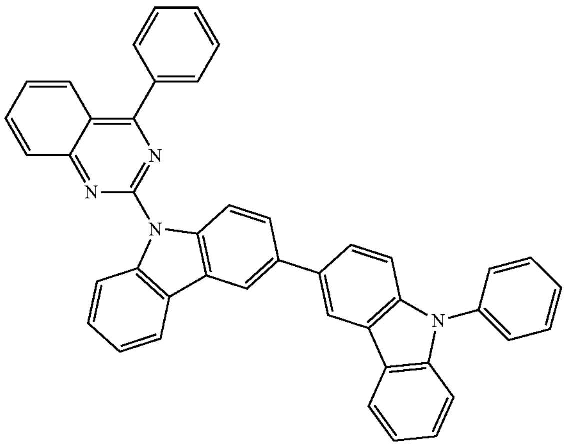

-continued
Dp-8
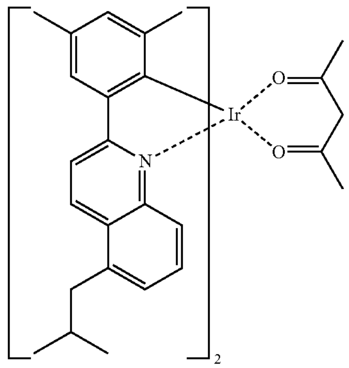
HB-1
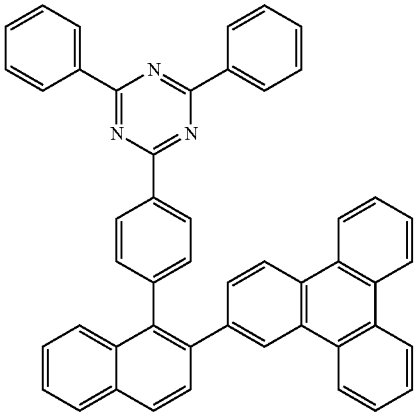
ET-1
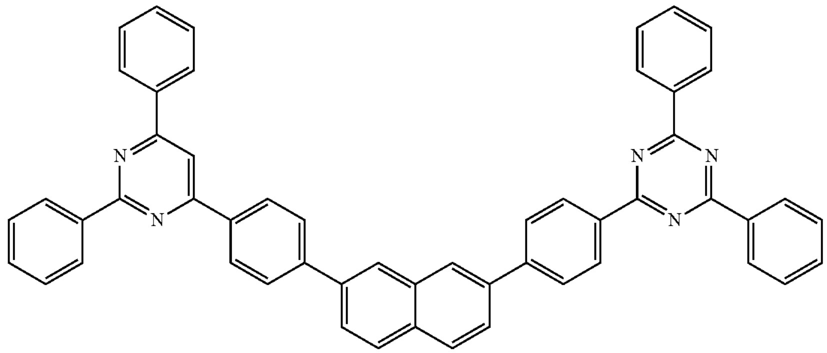
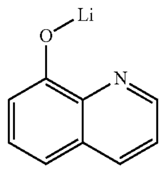
LiQ
RH-2
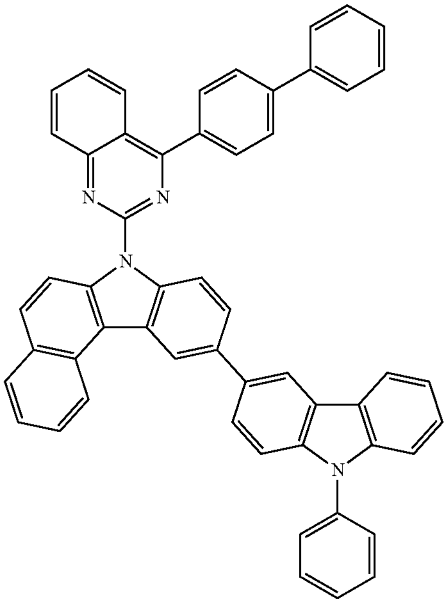

-continued
RH-3
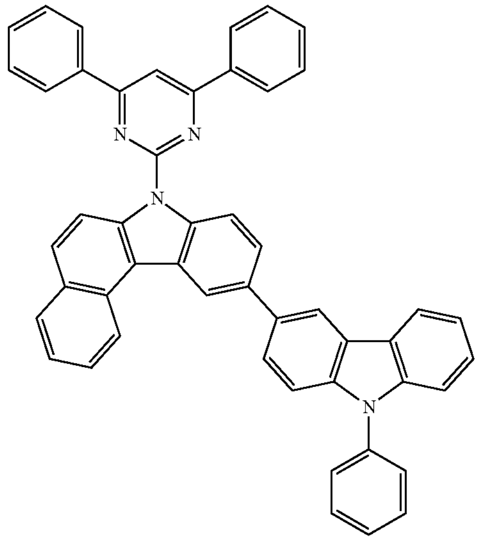
RH-4
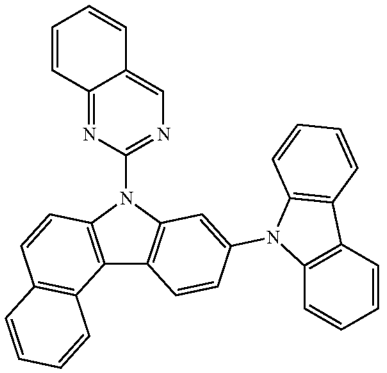
RH-5
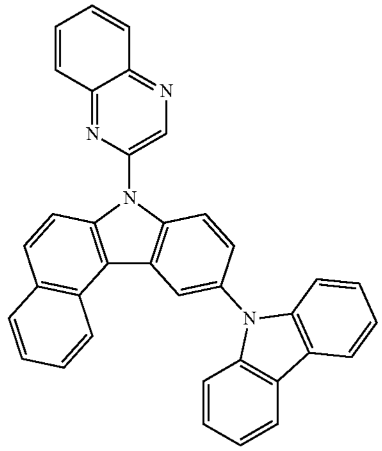
RH-6
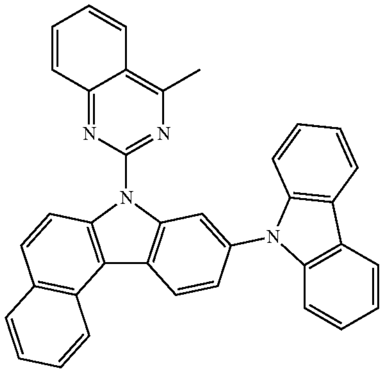
RH-7
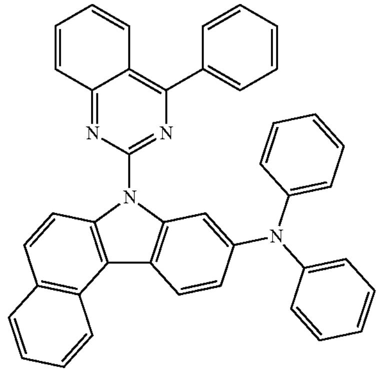
RH-8
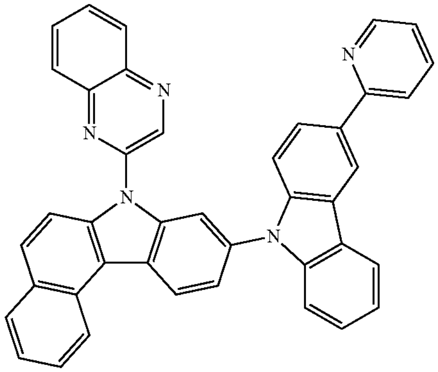

-continued

RH-9

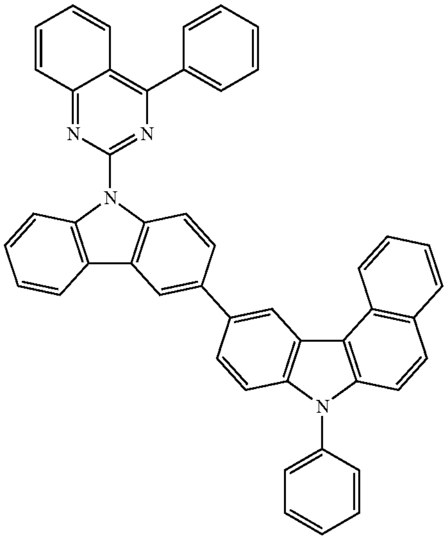

RH-10

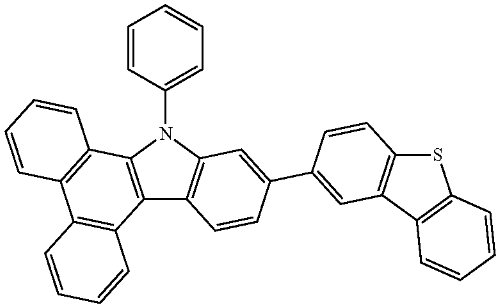

RH-11

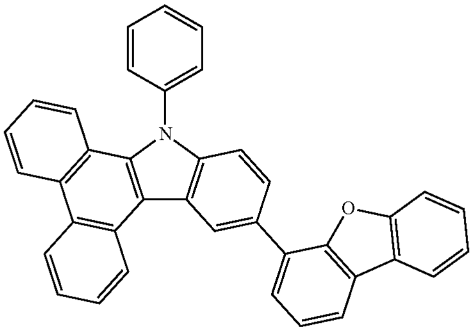

RH-12

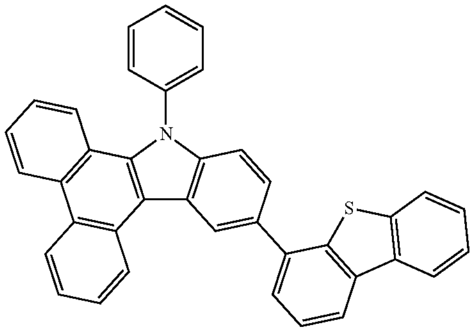

RH-13

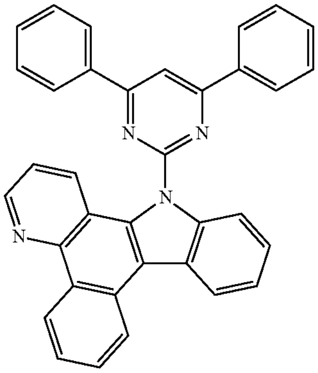

RH-14

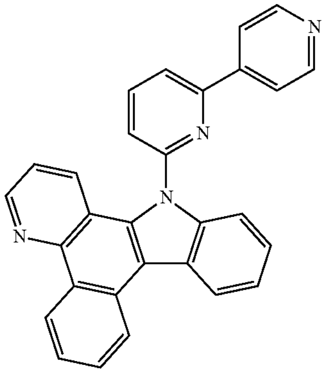

Example 1 to Example 18

Organic light emitting devices were manufactured in the same manner as the organic light emitting device of Comparative Example 1 except that compounds described in the following Table 1 were used instead of RH-1.

Comparative Example 2 to Comparative Example 14

Organic light emitting devices were manufactured in the same manner as the organic light emitting device of Comparative Example 1 except that compounds described in the following Table 1 were used instead of RH-1.

When applying a current of 10 mA/$cm^2$ to each of the organic light emitting devices manufactured in Example 1 to Example 18 and Comparative Example 1 to Comparative Example 14, voltage, efficiency and lifetime were measured, and the results are shown in the following Table 1. T95 means time taken for luminance decreasing to 95% from initial luminance (5000 nit).

TABLE 1

| | Light Emitting Layer | Driving Voltage (V) | Efficiency (cd/A) | Lifetime (T95) |
|---|---|---|---|---|
| Comparative Example1 | RH-1 | 4.8 | 33 | 221 |

TABLE 1-continued

| | Light Emitting Layer | Driving Voltage (V) | Efficiency (cd/A) | Lifetime (T95) |
|---|---|---|---|---|
| Example 1 | Compound 1 | 4.1 | 43 | 292 |
| Example 2 | Compound 2 | 4.4 | 40 | 347 |
| Example 3 | Compound 3 | 4.0 | 44 | 271 |
| Example 4 | Compound 4 | 4.1 | 42 | 283 |
| Example 5 | Compound 5 | 4.3 | 39 | 301 |
| Example 6 | Compound 6 | 4.1 | 43 | 284 |
| Example 7 | Compound 7 | 4.1 | 44 | 257 |
| Example 8 | Compound 8 | 4.2 | 41 | 291 |
| Example 9 | Compound 9 | 4.1 | 45 | 278 |
| Example 10 | Compound 10 | 4.0 | 40 | 283 |
| Example 11 | Compound 11 | 4.2 | 44 | 261 |
| Example 12 | Compound 12 | 4.1 | 42 | 252 |
| Example 13 | Compound 13 | 4.3 | 38 | 310 |
| Example 14 | Compound 14 | 4.4 | 36 | 297 |
| Example 15 | Compound 15 | 4.2 | 39 | 307 |
| Example 16 | Compound 16 | 4.3 | 36 | 311 |
| Example 17 | Compound 17 | 4.2 | 37 | 302 |
| Example 18 | Compound 18 | 4.4 | 38 | 291 |
| Comparative Example 2 | RH-2 | 4.7 | 34 | 231 |
| Comparative Example 3 | RH-3 | 4.4 | 37 | 173 |
| Comparative Example 4 | RH-4 | 4.9 | 28 | 78 |
| Comparative Example 5 | RH-5 | 4.9 | 30 | 31 |
| Comparative Example 6 | RH-6 | 5.0 | 24 | 57 |
| Comparative Example 7 | RH-7 | 5.4 | 31 | 56 |
| Comparative Example 8 | RH-8 | 4.9 | 29 | 34 |
| Comparative Example 9 | RH-9 | 4.8 | 33 | 208 |
| Comparative Example 10 | RH-10 | 5.2 | 14 | 31 |
| Comparative Example 11 | RH-11 | 5.1 | 17 | 38 |
| Comparative Example 12 | RH-12 | 5.1 | 19 | 34 |
| Comparative Example 13 | RH-13 | 4.9 | 28 | 135 |
| Comparative Example 14 | RH-14 | 5.2 | 13 | 11 |

When examining Table 1 presenting the results of the experiments, it was identified that the compound of the present disclosure was capable of improving light emission efficiency, driving voltage and lifetime properties in driving a red light emitting device.

Specifically, in Comparative Examples 2, 3 and 9, the substituent that is not hydrogen among the substituents corresponding to substituents R7 to R10 of the present disclosure is carbazole, however, bonding types of the carbazole are different. While Chemical Formula A of the present disclosure has N of the carbazole directly bonding to the core, Compounds RH-2, RH-3 and RH-9 have benzene of the carbazole bonding to the core structure. In Comparative Example 7, the substituent that is not hydrogen among the substituents corresponding to substituents R7 to R10 is an amine group.

It was seen that Examples 1 to 18 had properties of low voltage, high efficiency and long lifetime compared to Comparative Examples 2, 3, 7 and 9.

In RH-4, RH-5, RH-6 and RH-8 used in Comparative Examples 4, 5, 6 and 8, respectively, the substituent corresponding to R of Chemical Formula 1 of the present disclosure is hydrogen or an alkyl group. Meanwhile, in the present disclosure, R is an aryl group or a heteroaryl group. It was seen that Examples 1 to 18 had properties of low voltage, high efficiency and long lifetime compared to Comparative Examples 4, 5, 6 and 8.

Comparative Examples 10 to 14 used Compounds RH-10 to RH-14 in which R1 to R6 form an additional aromatic or heteroring. In the present disclosure, R1 to R6 did not form an additional ring. It was seen that Examples 1 to 18 had properties of low voltage, high efficiency and long lifetime compared to Comparative Examples to 14.

When comparing the experimental results between the compounds of the present disclosure and the compounds of the comparative examples, it was seen that, in the compounds of the present disclosure, electrons and holes were well-balanced in the red device structure, which was advantageous for exciton formation and allowed favorable energy transfer to the dopant, and as a result, driving voltage, efficiency and lifetime properties were all improved.

The invention claimed is:

1. A compound of Chemical Formula 1:

[Chemical Formula 1]

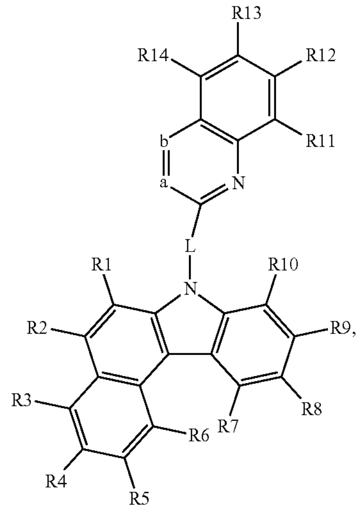

wherein, in Chemical Formula 1:

L is a direct bond;

a is CR and b is N;

R is an aryl group selected from among a phenyl group, a naphthyl group, a biphenyl group, a terphenyl group, an anthracene group, a phenanthrene group, a fluorene group, a triphenylene group or a pyrene group, and the phenyl group, the naphthyl group, the biphenyl group, the terphenyl group, the anthracene group, the phenanthrene group, the fluorene group, the triphenylene group or the pyrene group is unsubstituted or substituted with any one or more selected from among a methyl group, an ethyl group, a propyl group, an isopropyl group, a butyl group, a tert-butyl group, a phenyl group, a biphenyl group, a naphthyl group, an anthracene group, a phenanthrene group, a terphenyl group, and a triphenyl group, or a heteroaryl group selected from among a pyridine group, a pyrimidine group, a triazine group, a dibenzofuran group, a dibenzothiophene group or a carbazole group, and the pyridine group, the pyrimidine group, the triazine group, the dibenzofuran group, the dibenzothiophene group or the carbazole group is unsubstituted or substituted with a phenyl group, a biphenyl group, a terphenyl group, an anthracene group, a phenanthrene group, or a naphthyl group;

R1 to R6 and R11 to R14 are hydrogen; and at least one of R7 to R10 is Chemical Formula A, and the remaining R7 to R10 are hydrogen:

[Chemical Formula A]

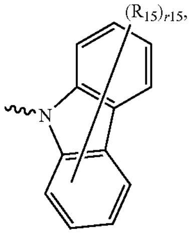

wherein in Chemical Formula A:

 means a bond with R7 to R10;

R15 is hydrogen, or adjacent groups bond to each other to form a benzene ring, provided that Chemical Formula A is not a dibenzocarbazole group; and r15 is an integer of 0 to 8.

2. The compound of claim 1, wherein the compound of Chemical Formula 1 is any one compound selected from among the following compounds:

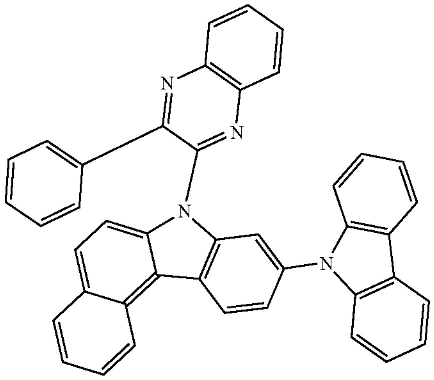

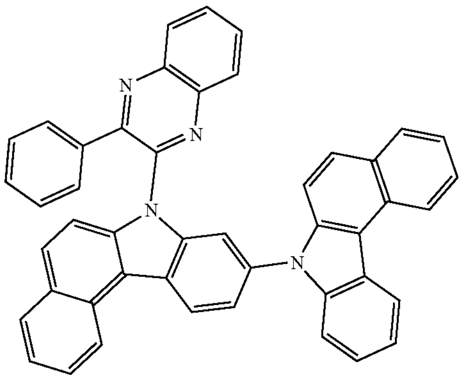

-continued

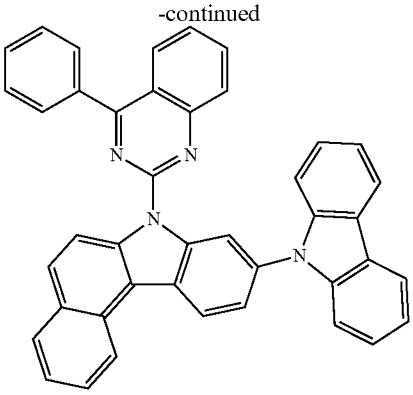

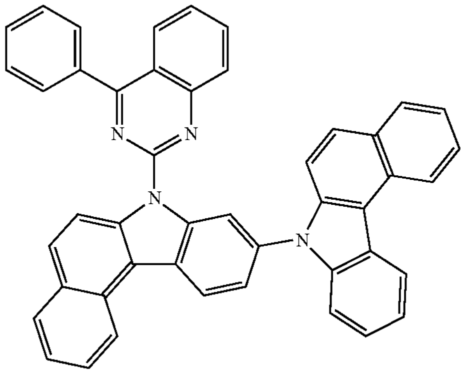

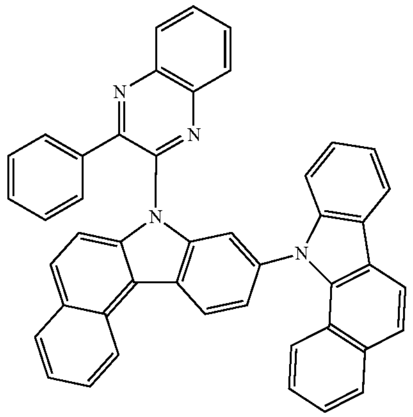

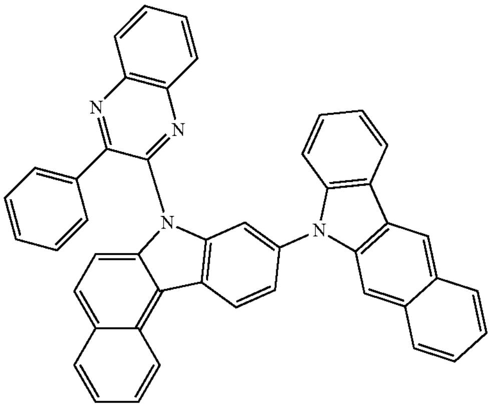

-continued
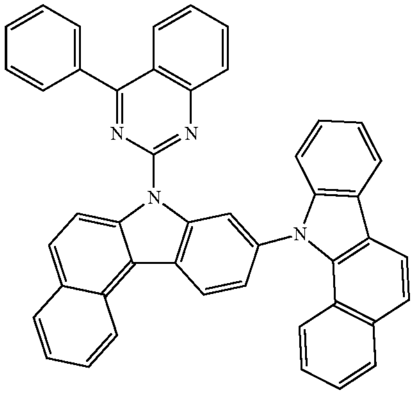
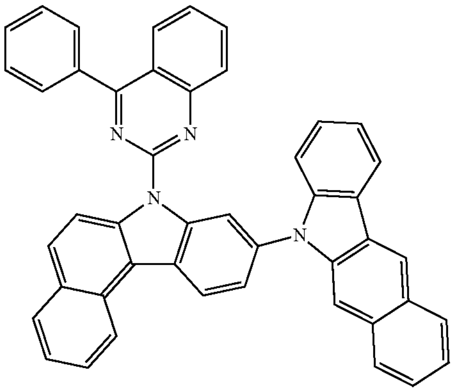
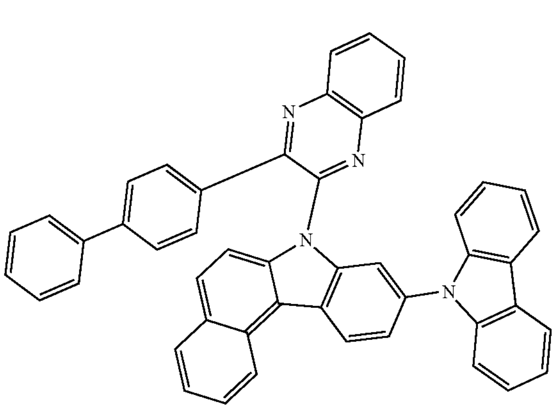
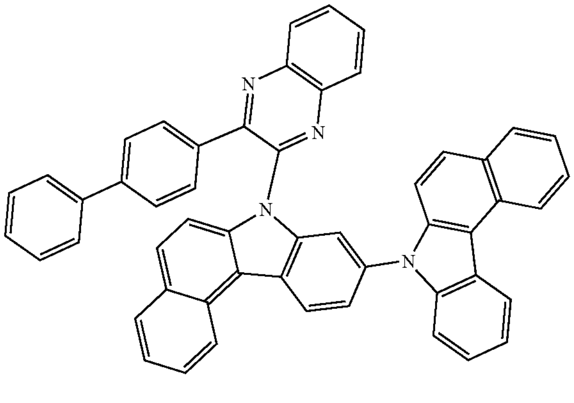
-continued
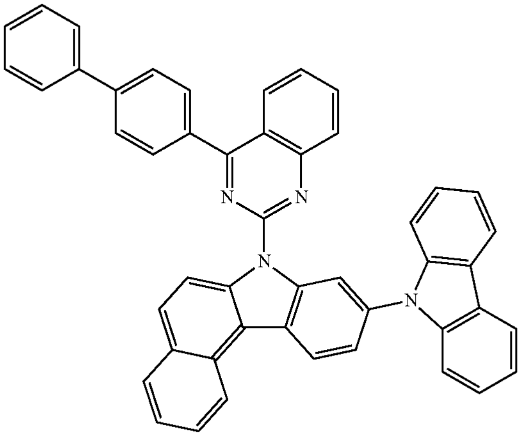
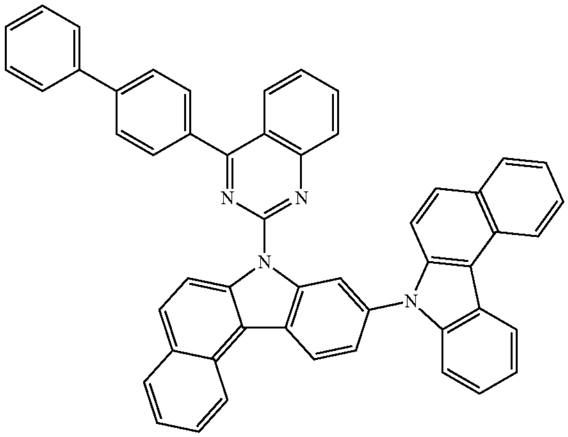
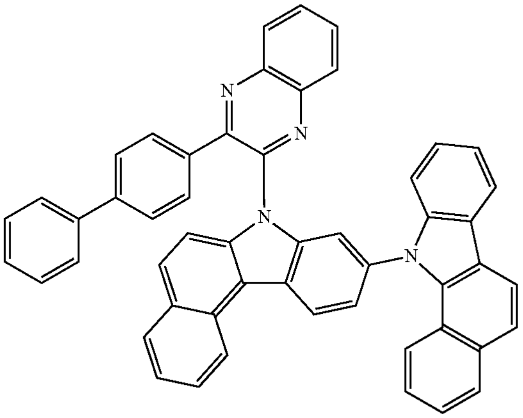
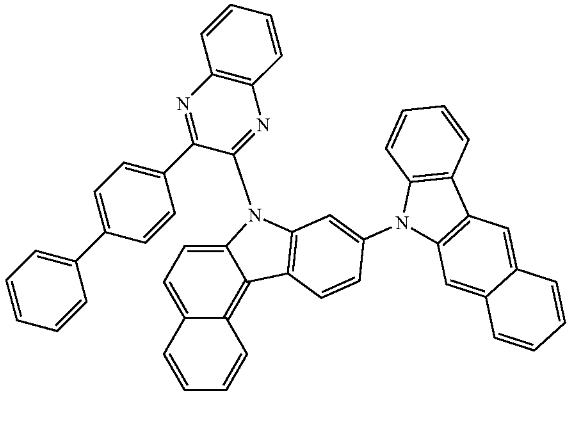

-continued
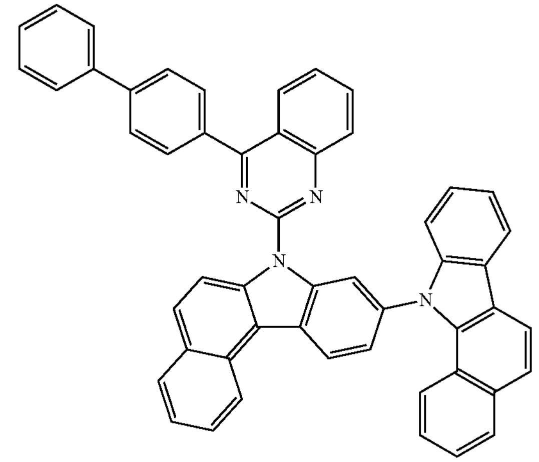
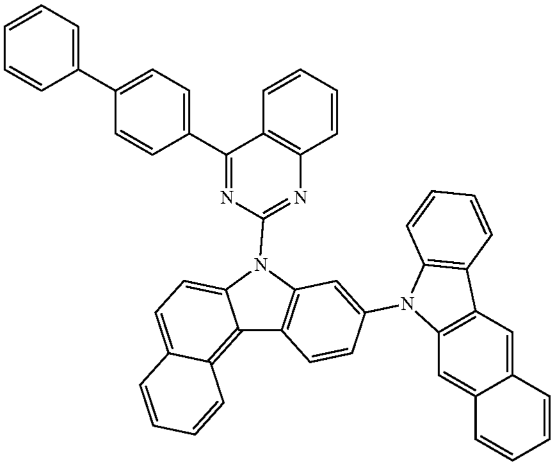
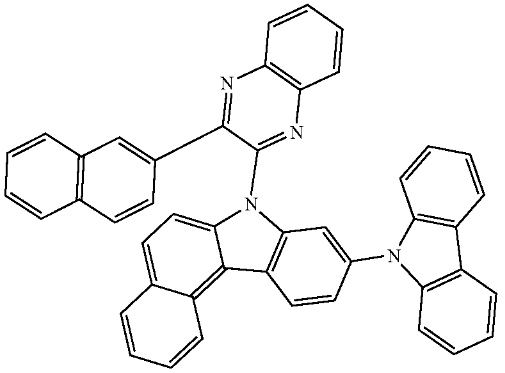
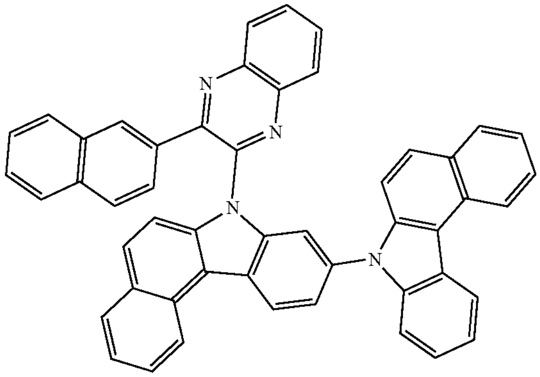
-continued
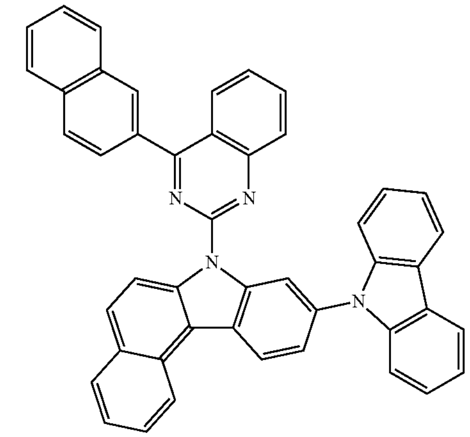
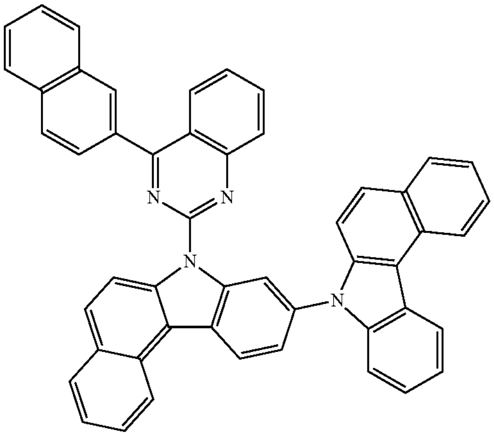
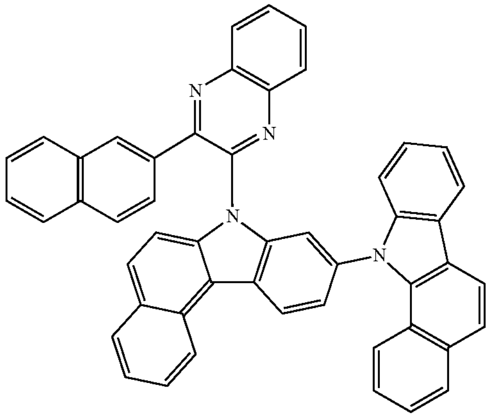
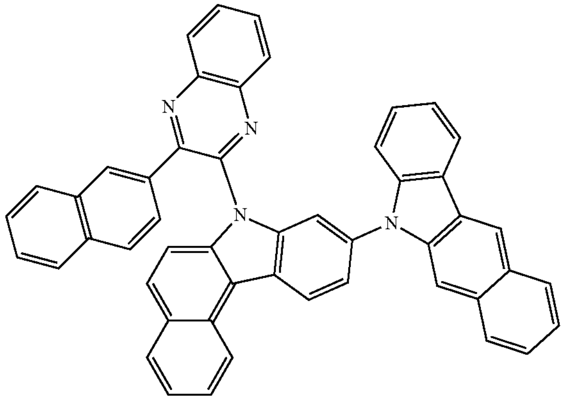

-continued
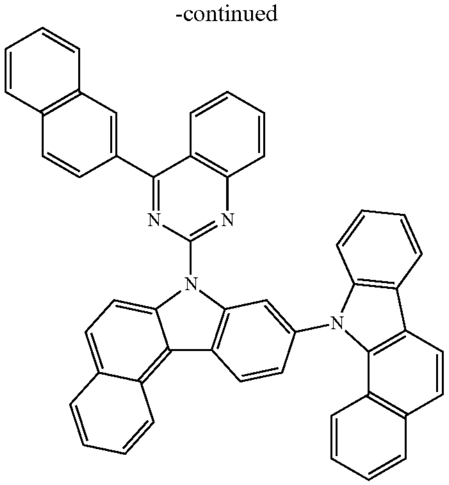
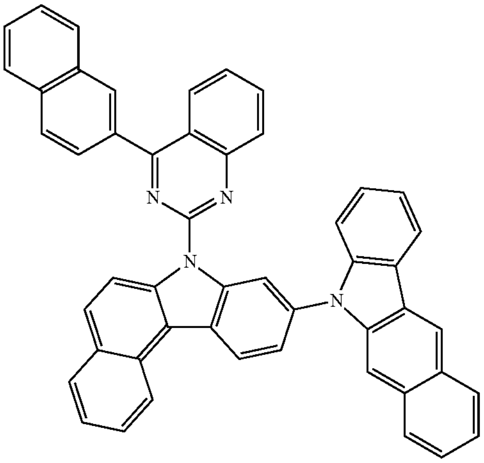
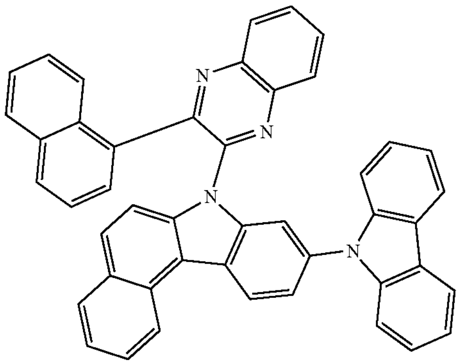
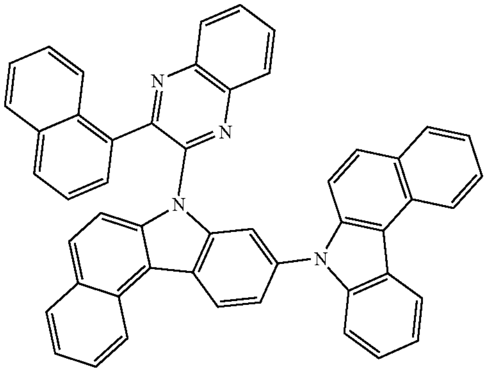
-continued
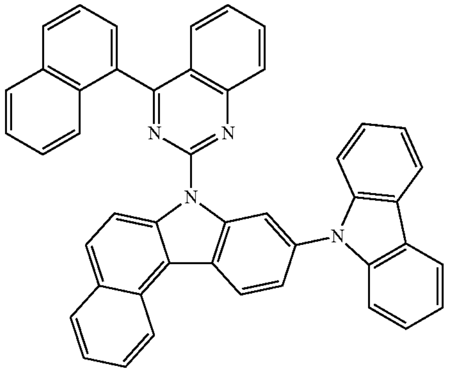
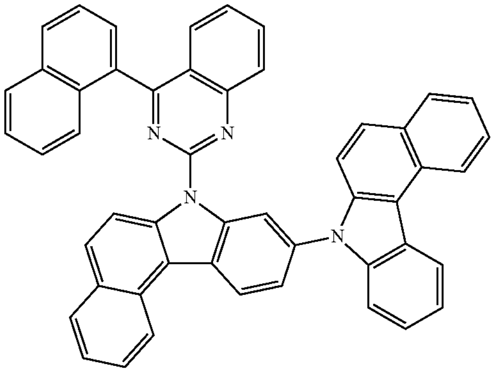
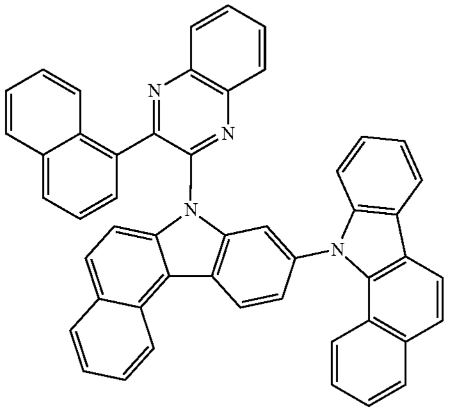
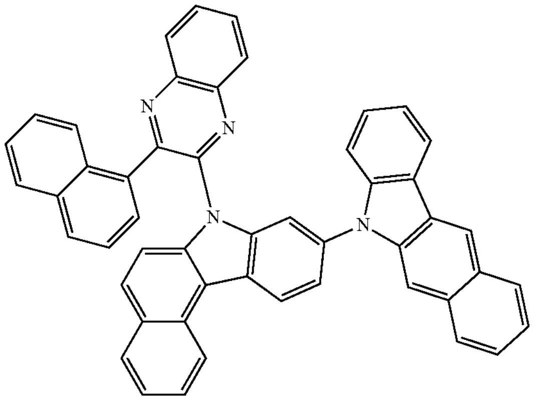

-continued
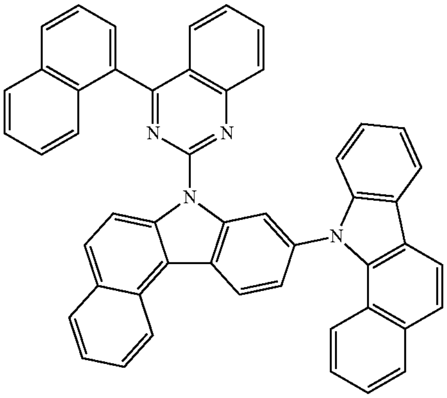
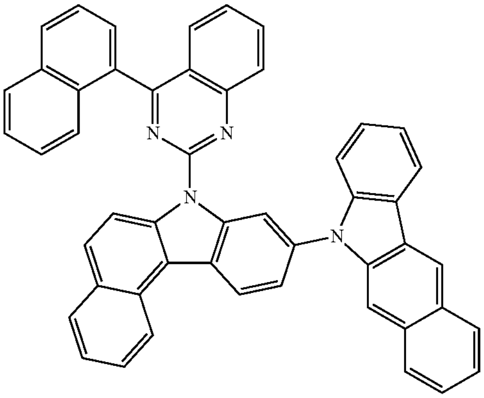
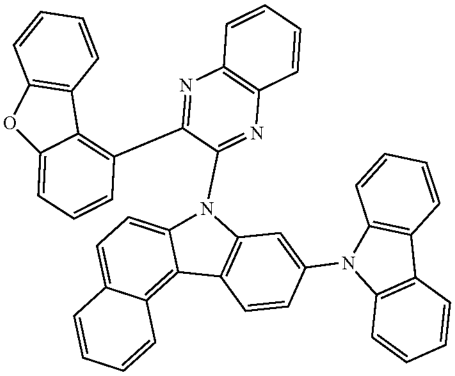
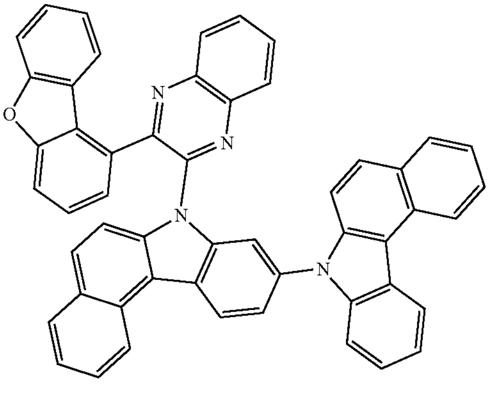
-continued
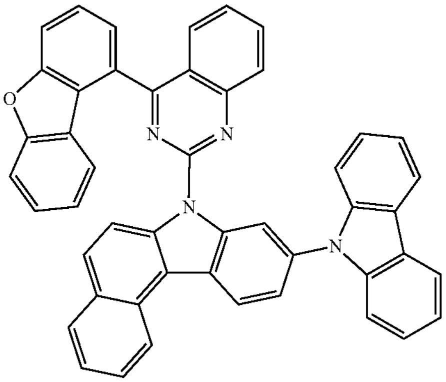
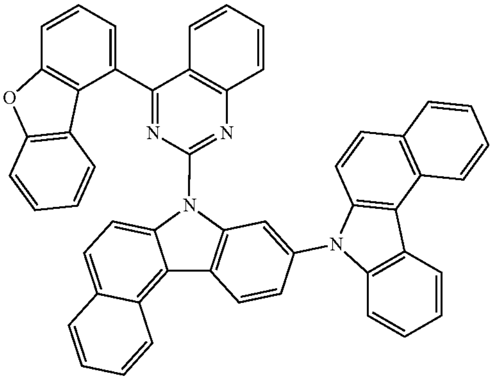
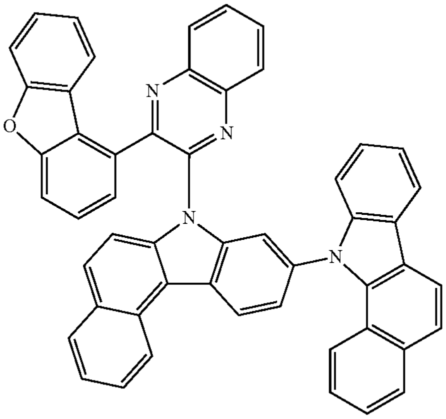
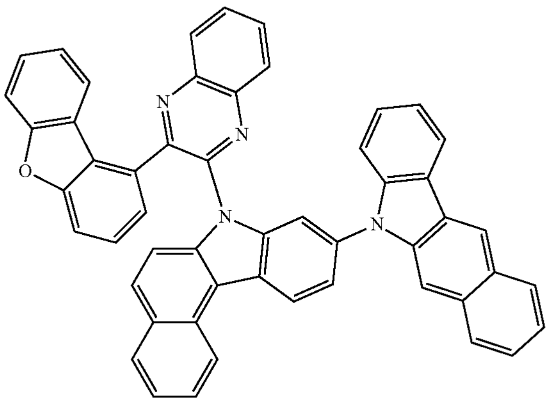

-continued
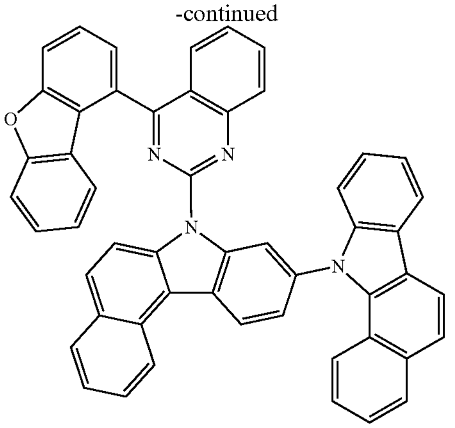
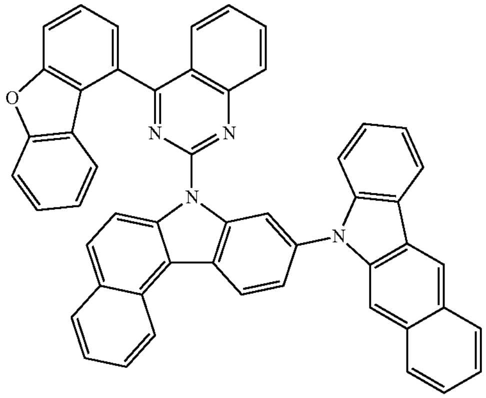
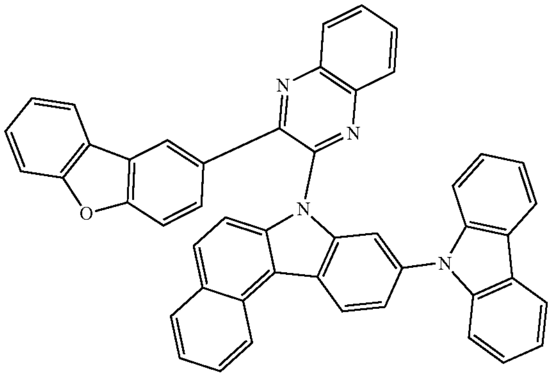
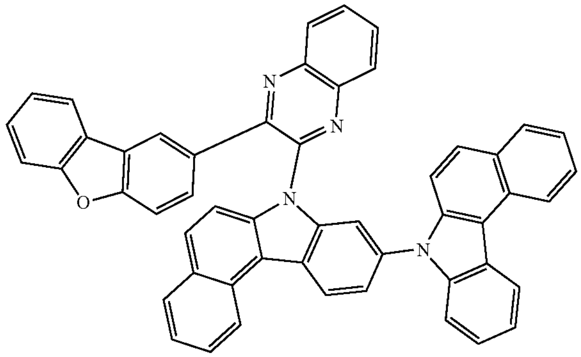
-continued
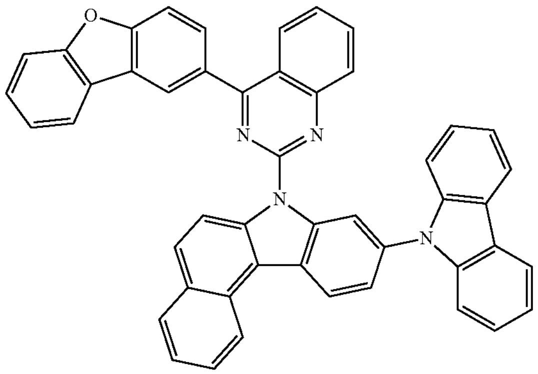
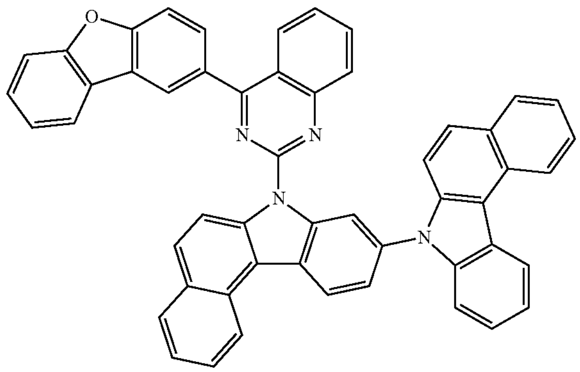
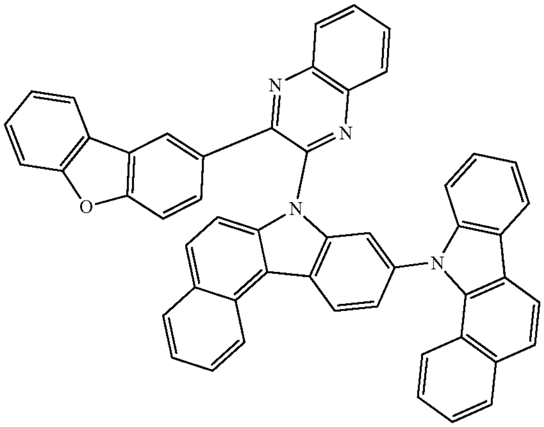
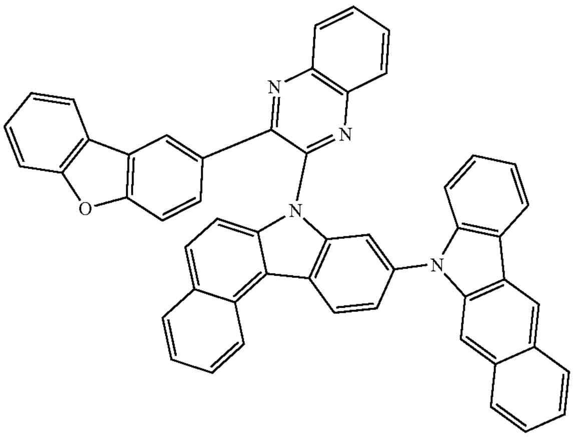

-continued
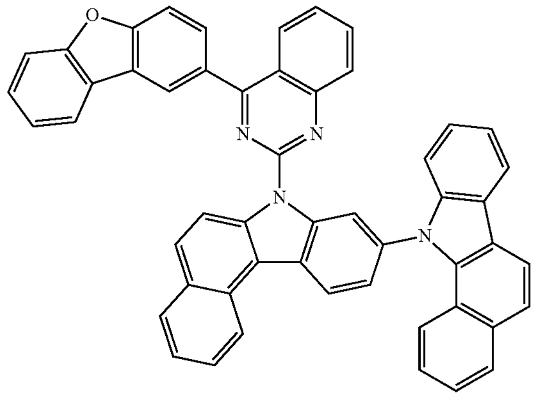
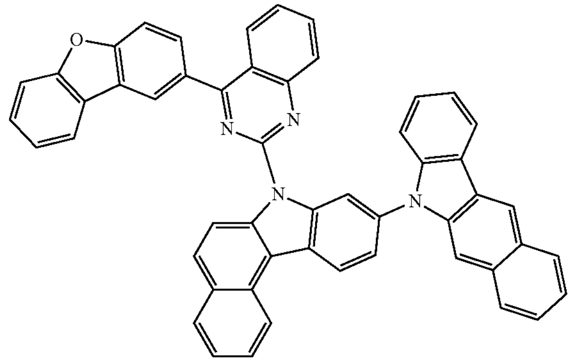
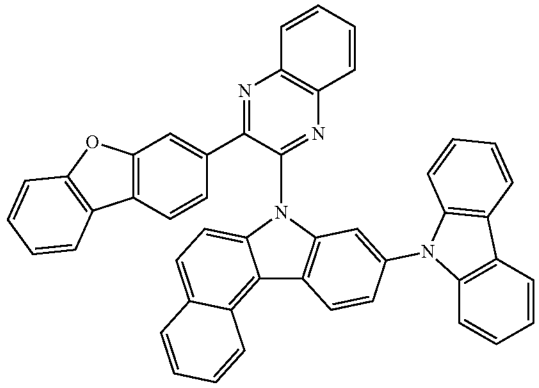
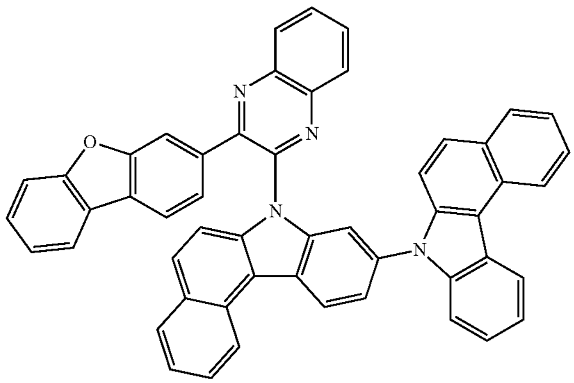
-continued
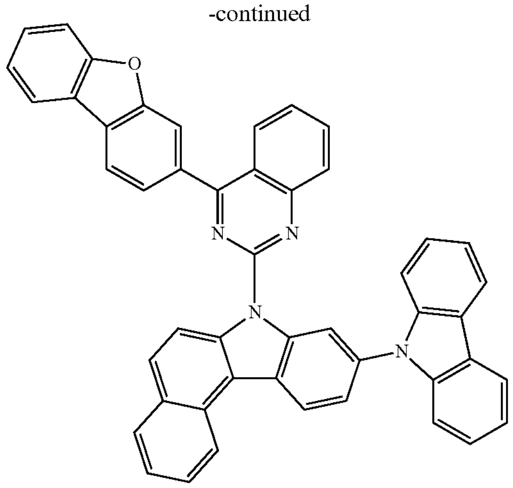
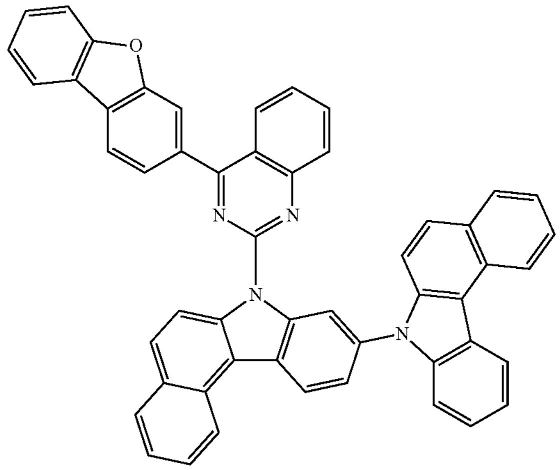
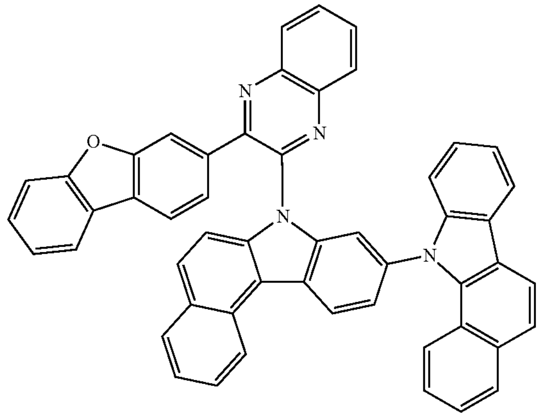

-continued
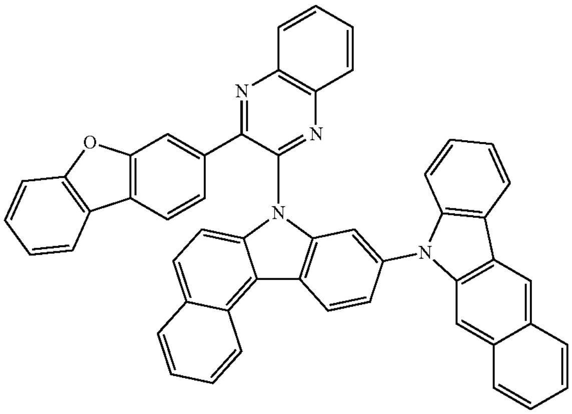
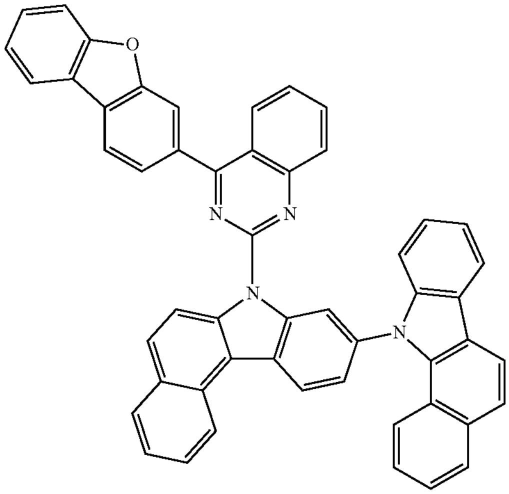
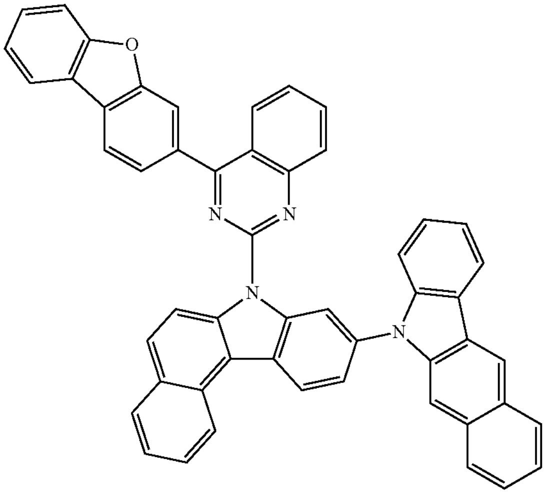
-continued
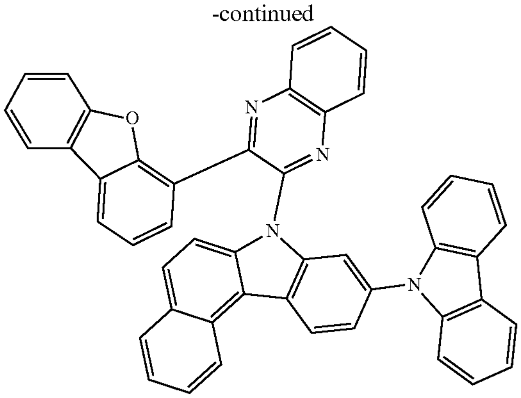
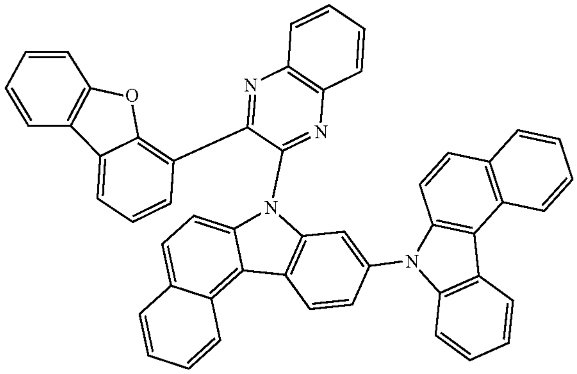
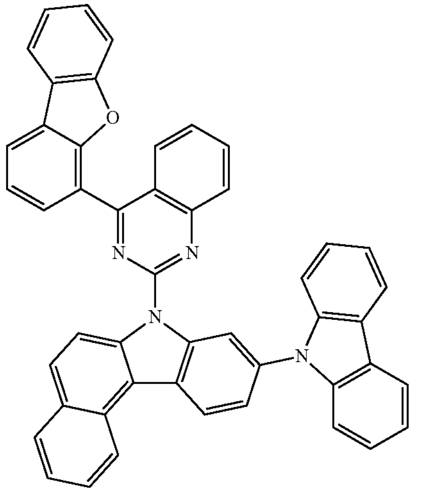
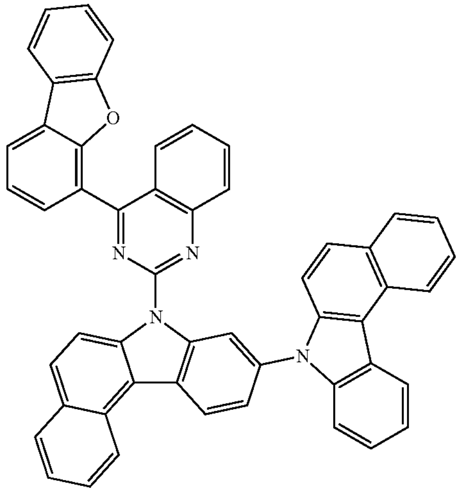

-continued
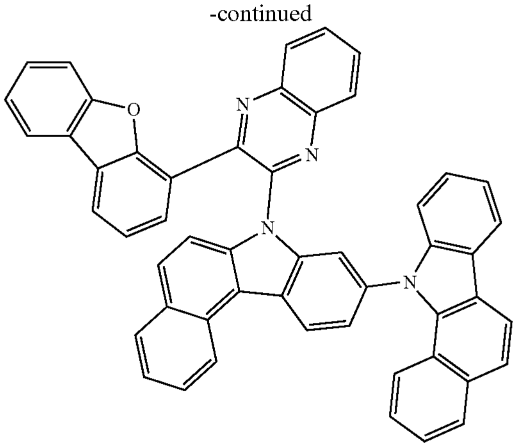
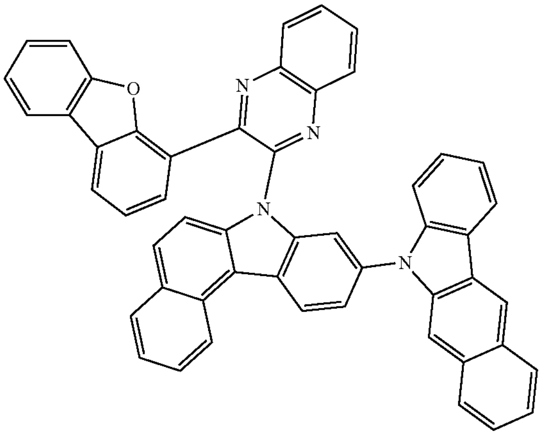
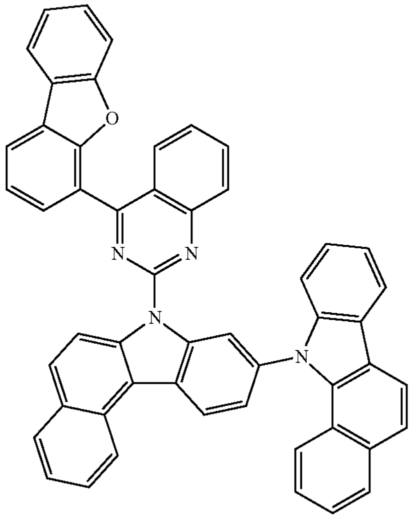
-continued
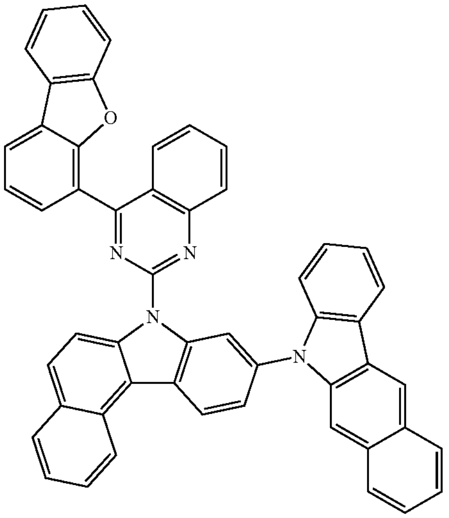
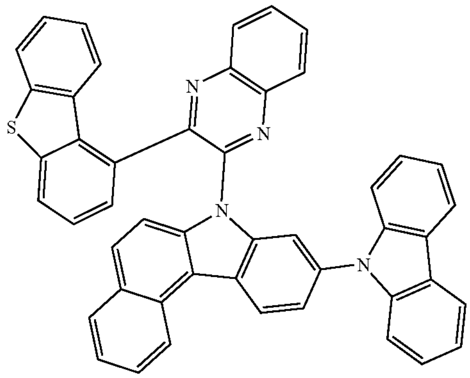
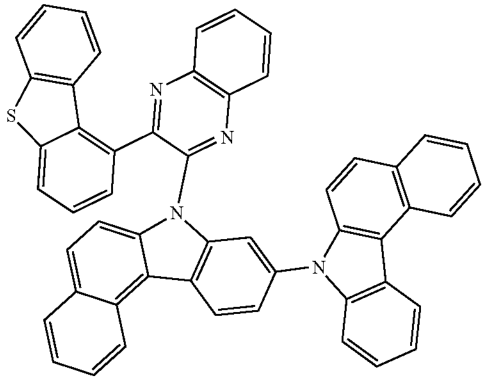
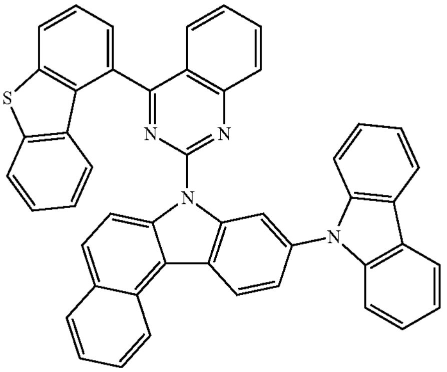

-continued
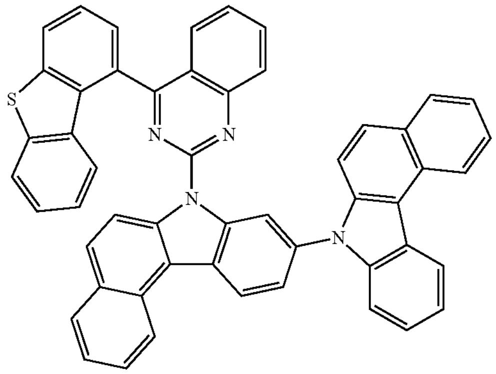
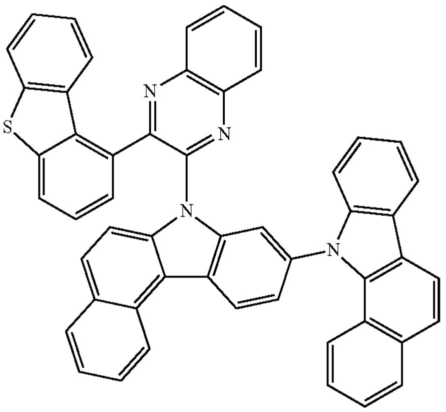
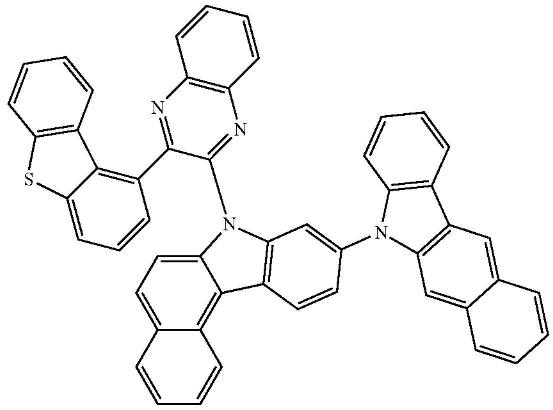
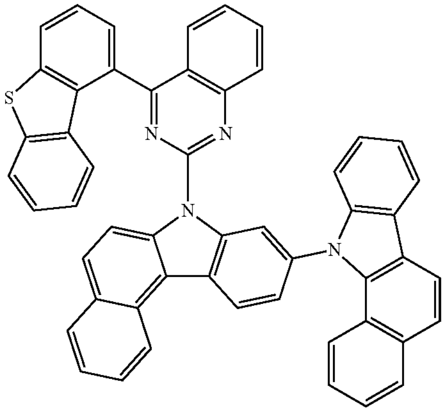
-continued
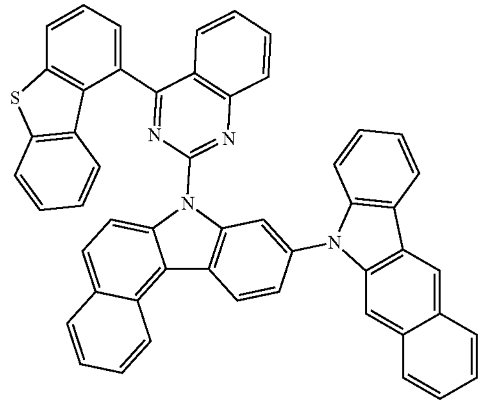
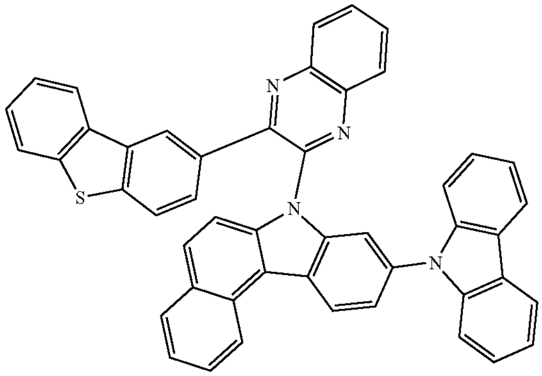
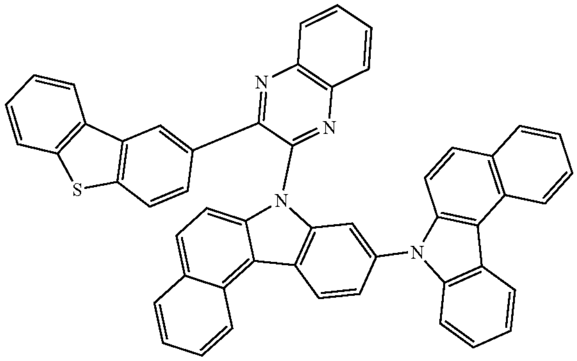
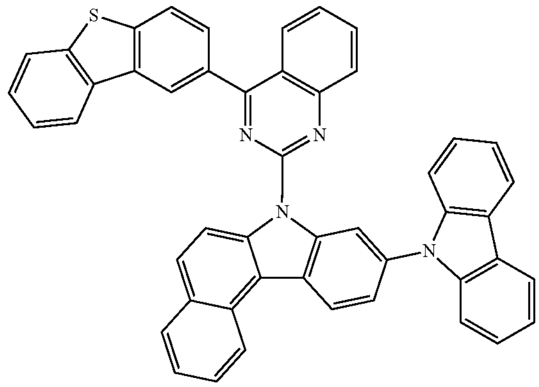

-continued
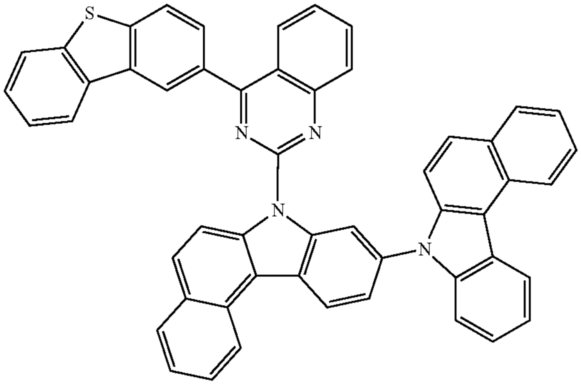
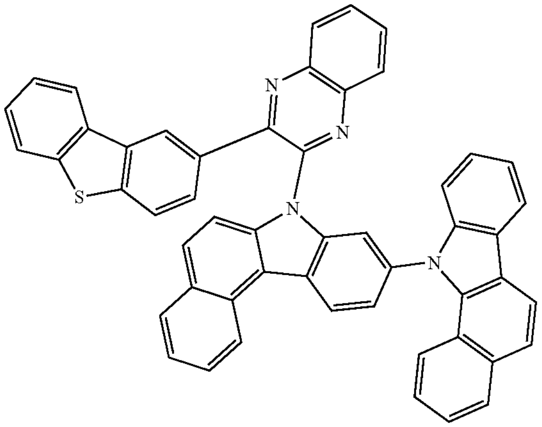
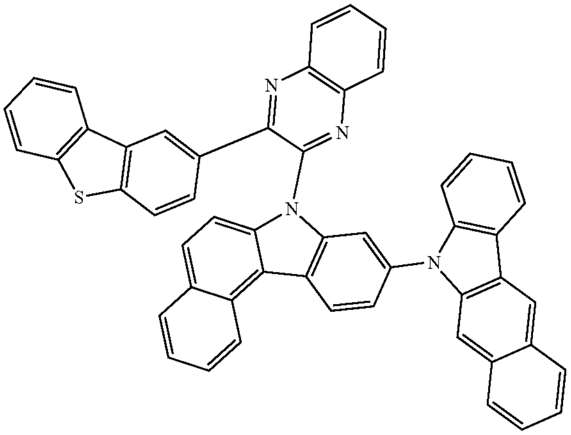
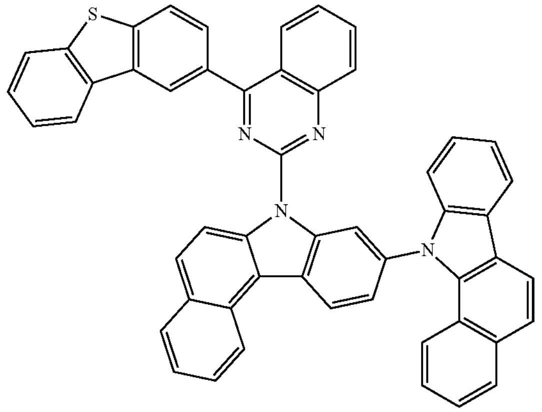
-continued
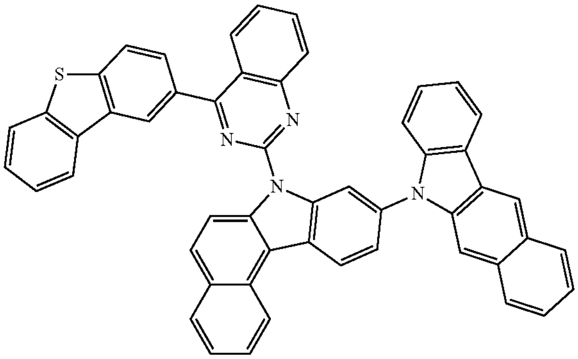
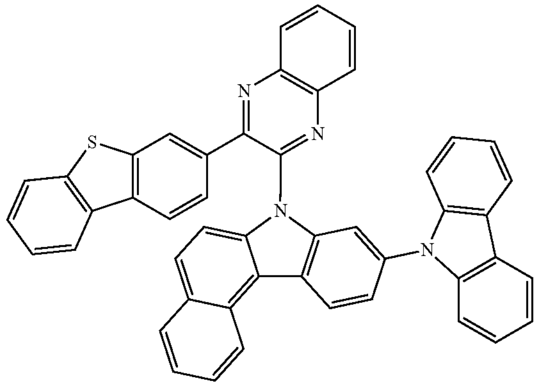
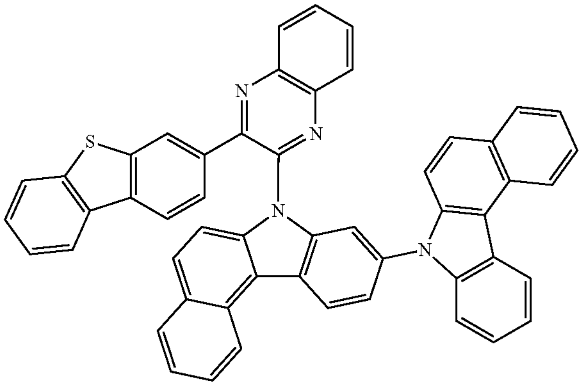
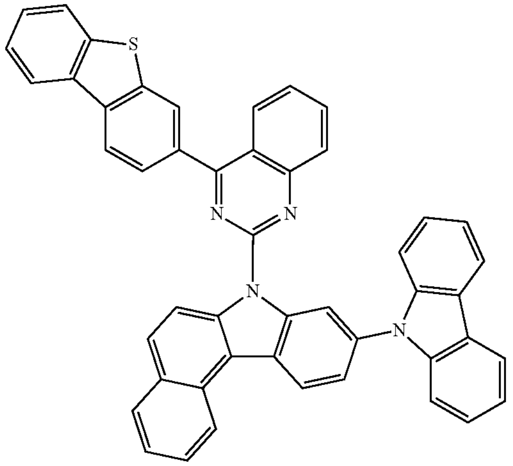

-continued
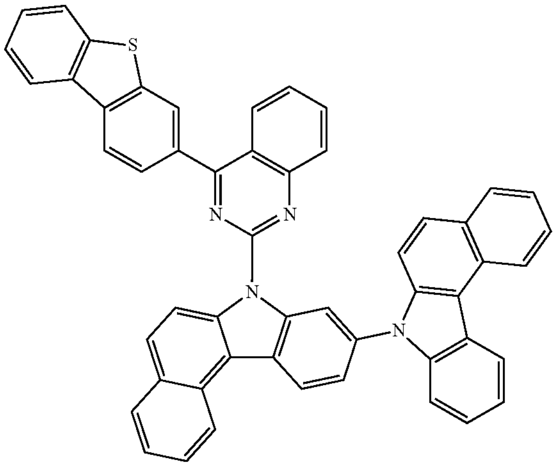
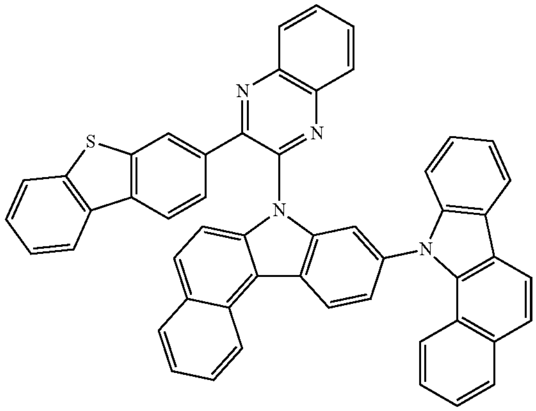
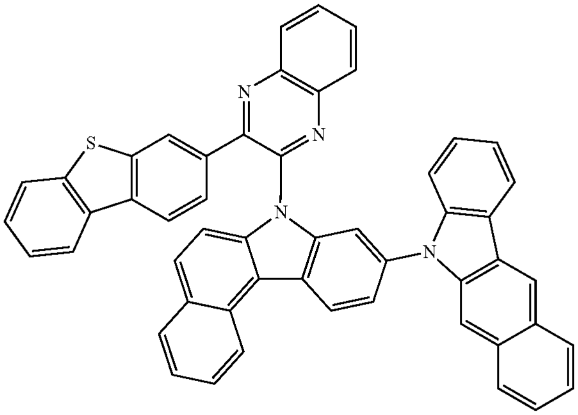
-continued
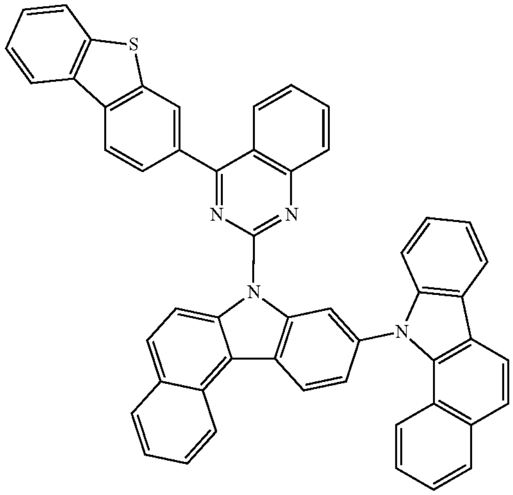
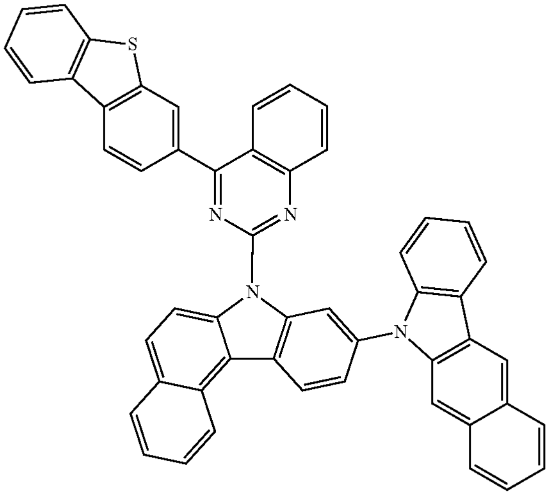
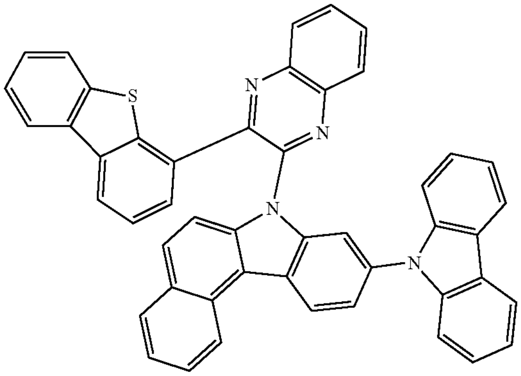

-continued
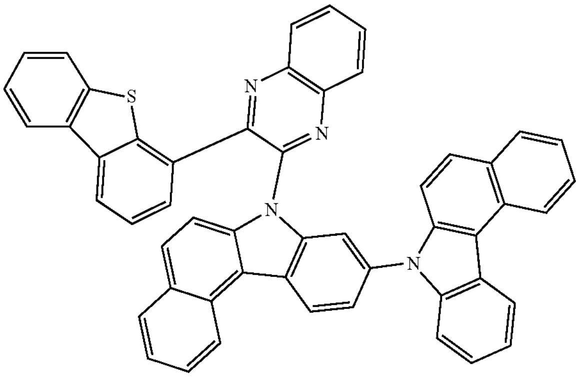
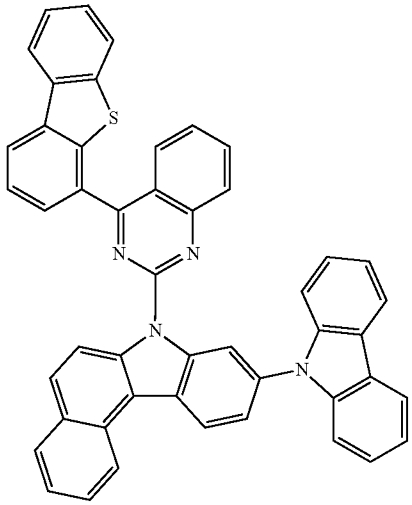
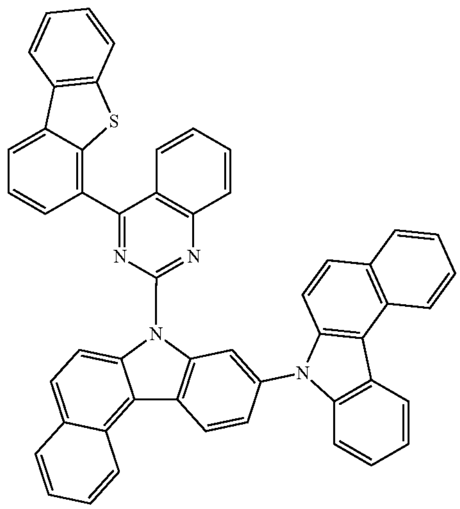
-continued
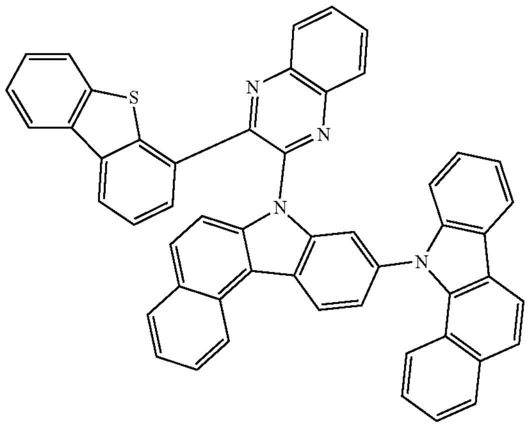
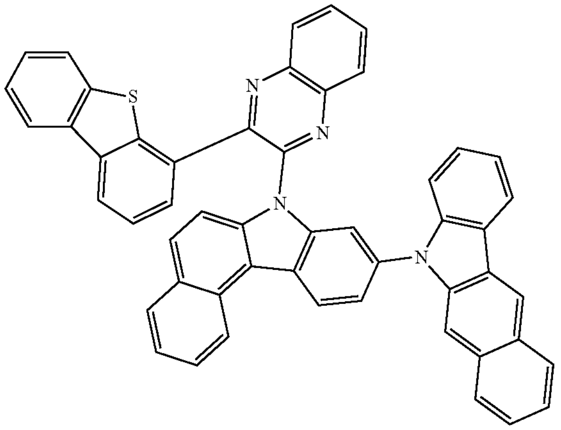
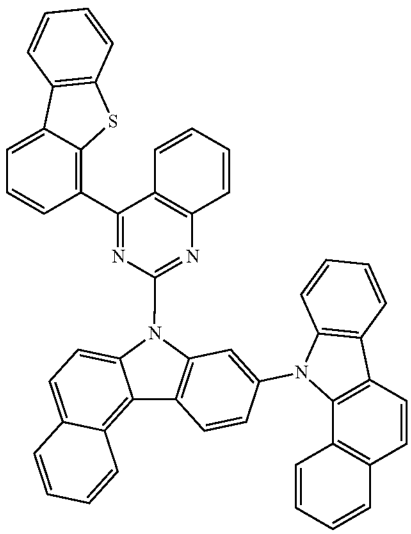

-continued
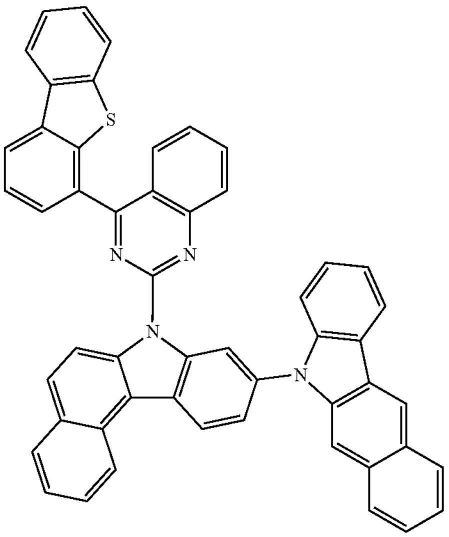
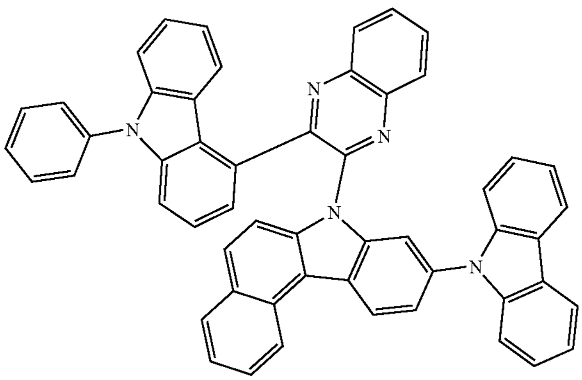
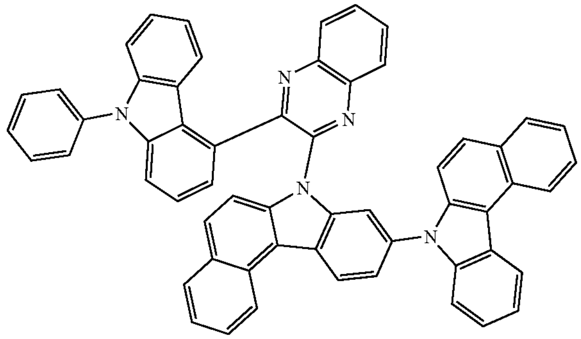
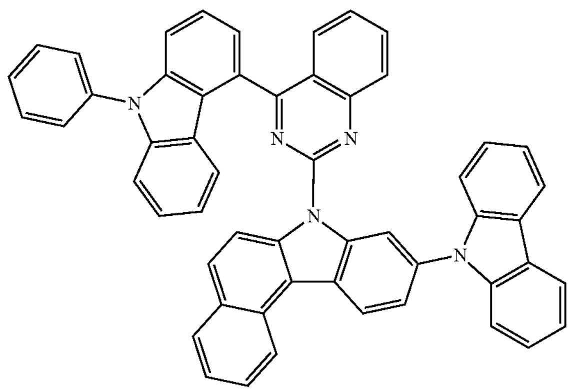
-continued
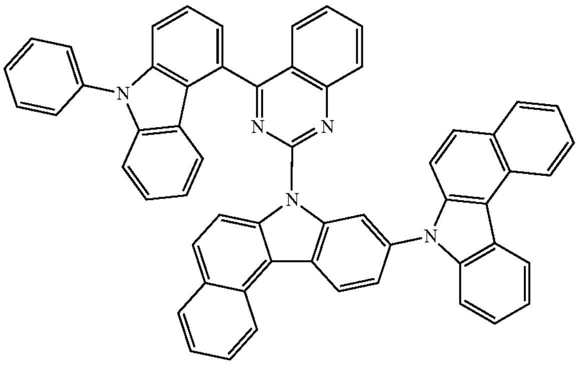
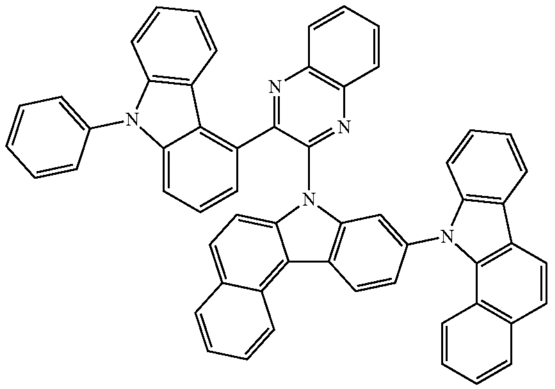
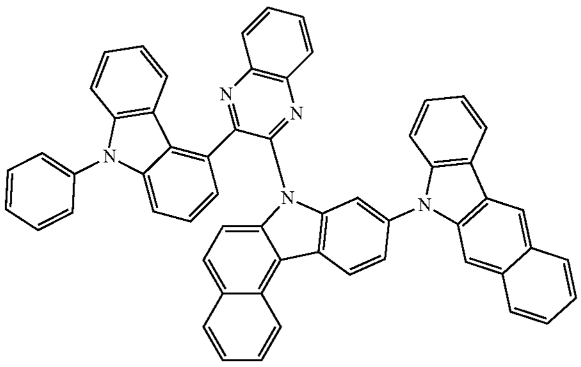
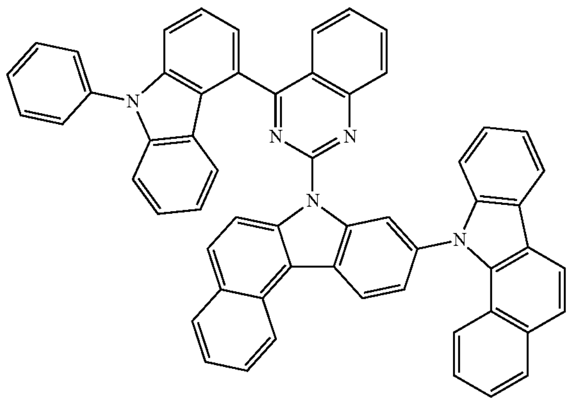

-continued
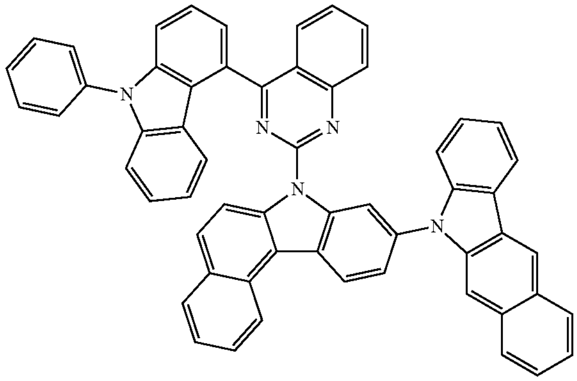
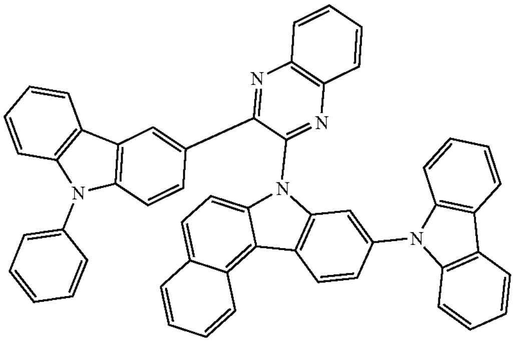
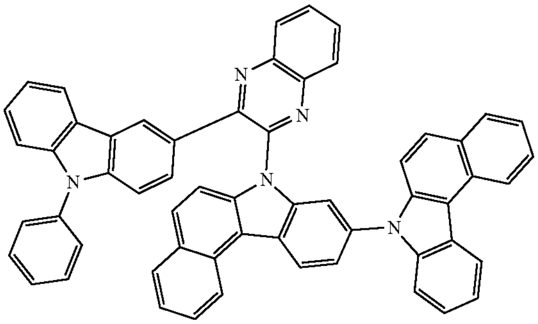
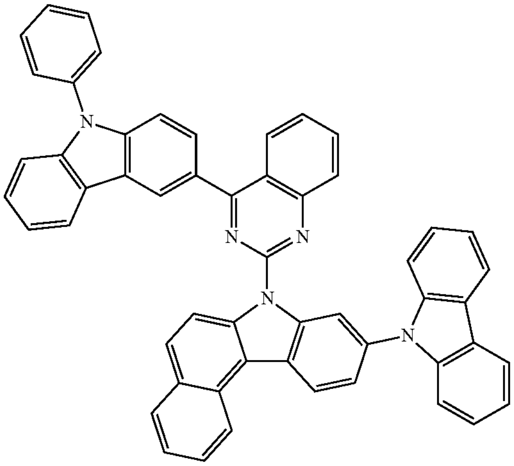
-continued
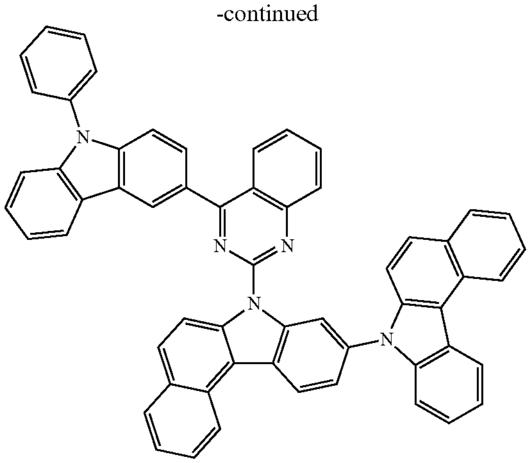
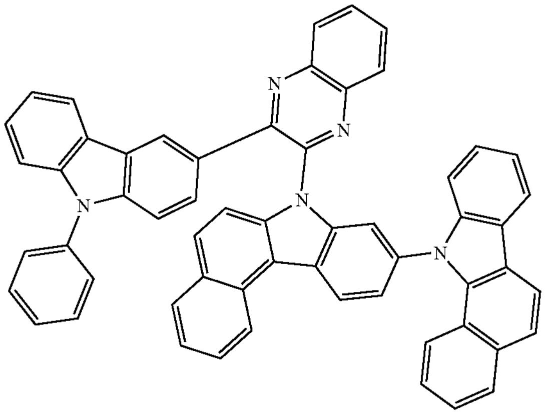
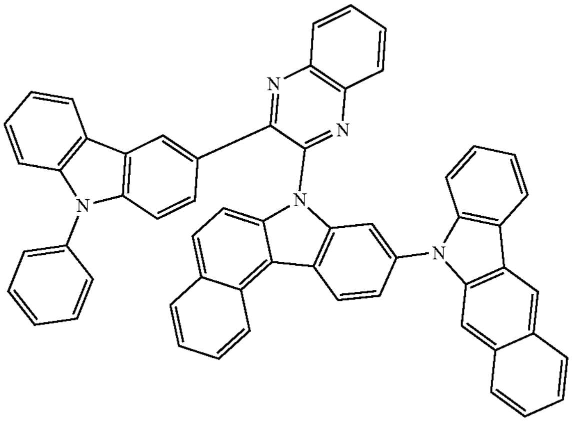

-continued
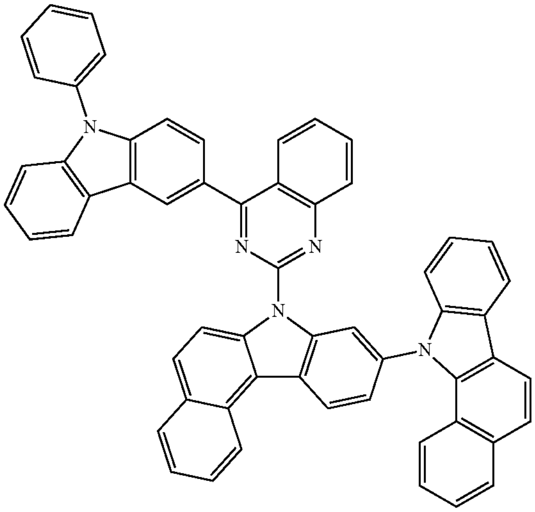
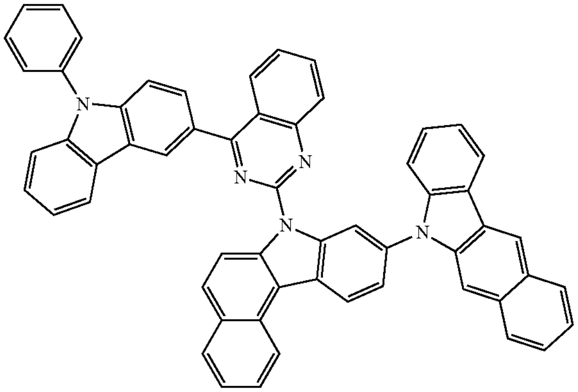
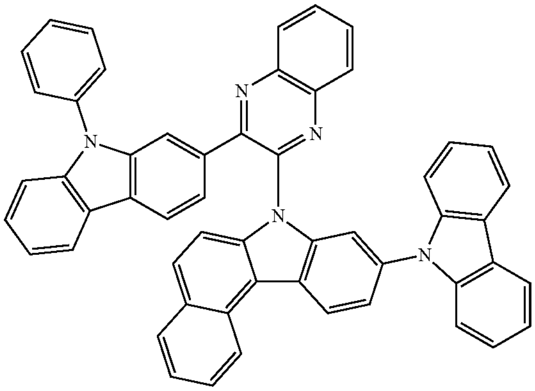
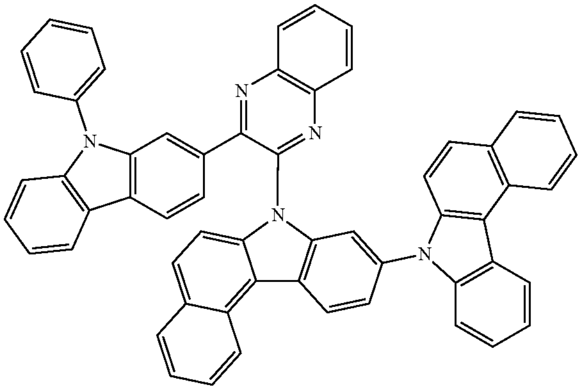
-continued
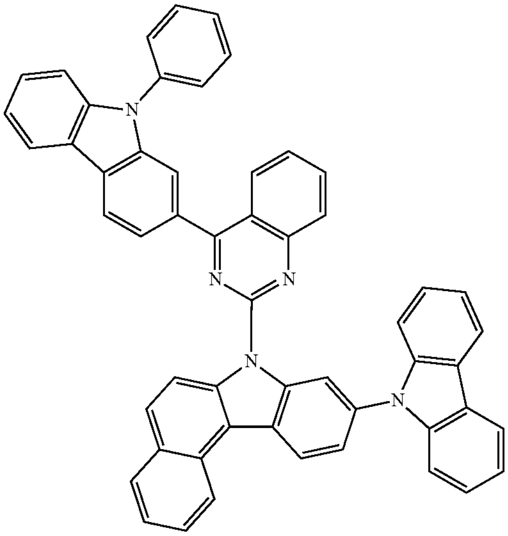
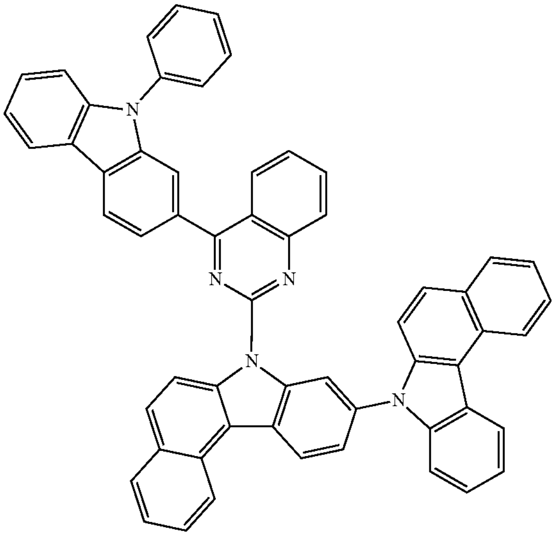
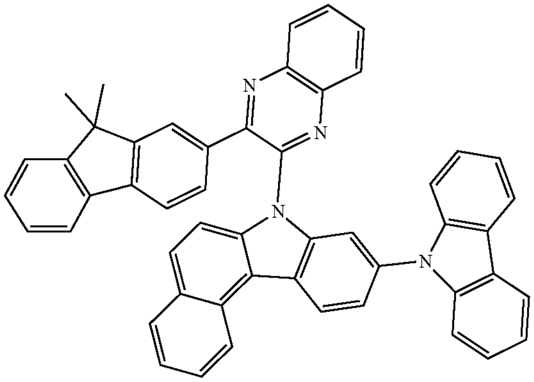

-continued
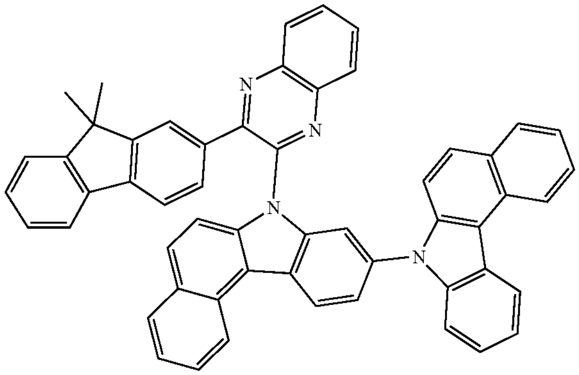
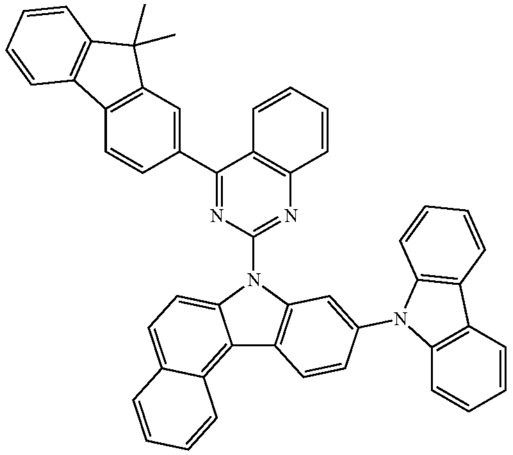
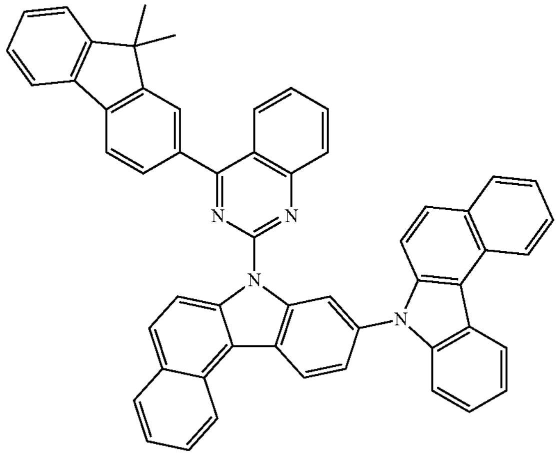
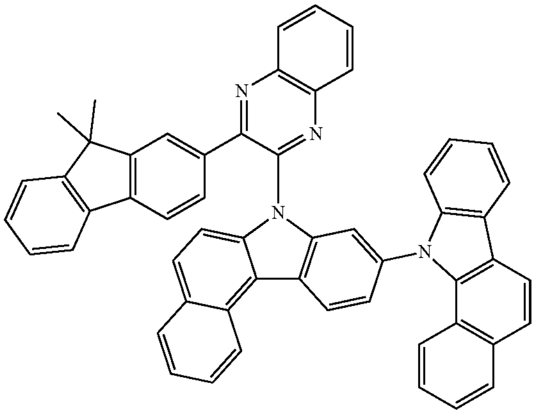
-continued
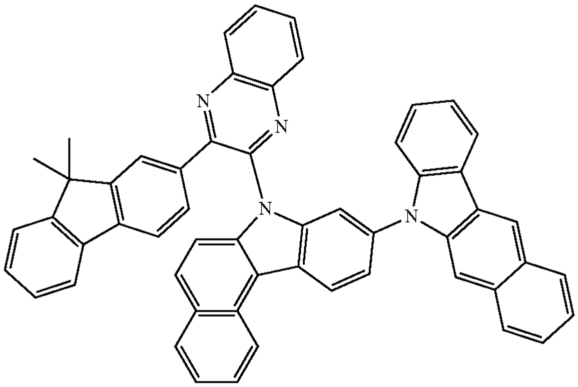
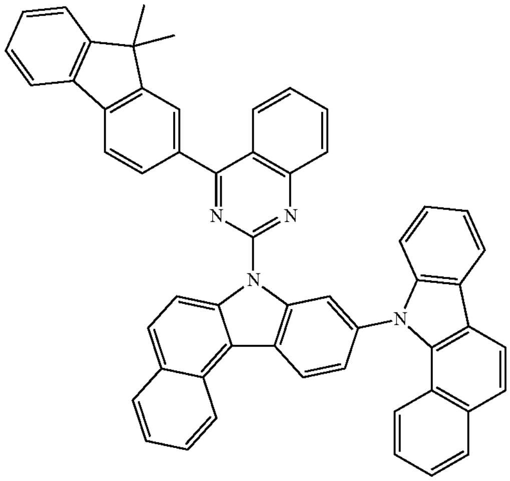
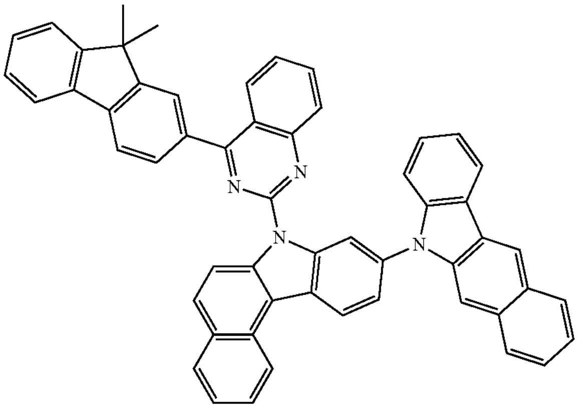
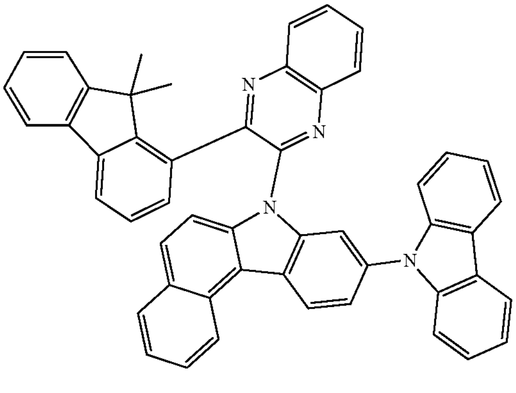

-continued
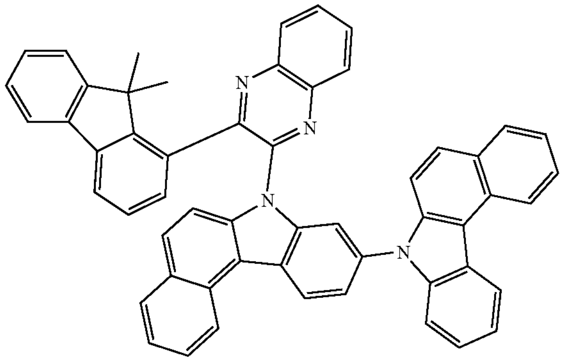
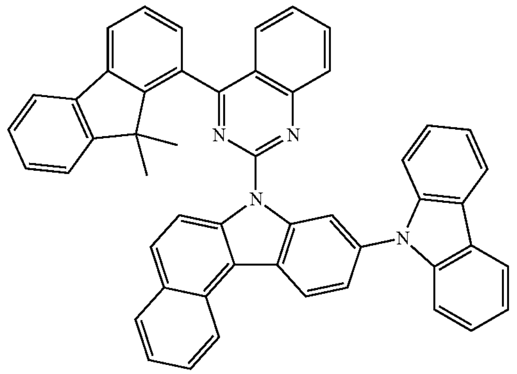
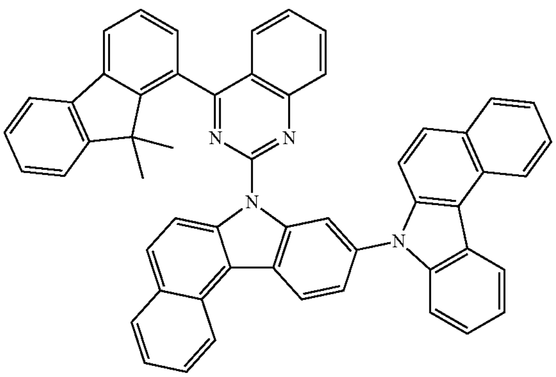
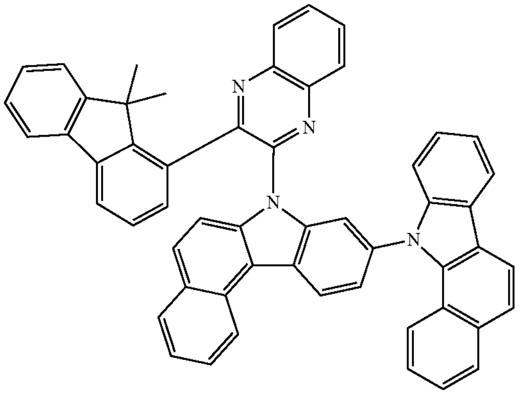
-continued
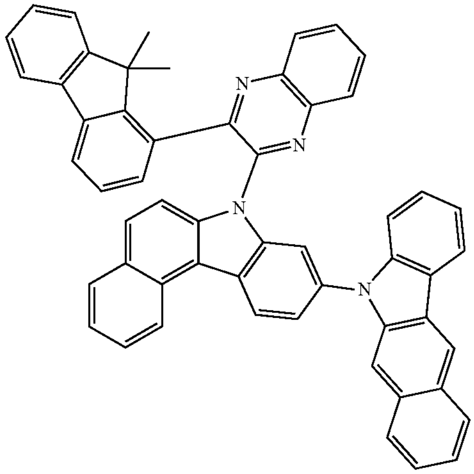
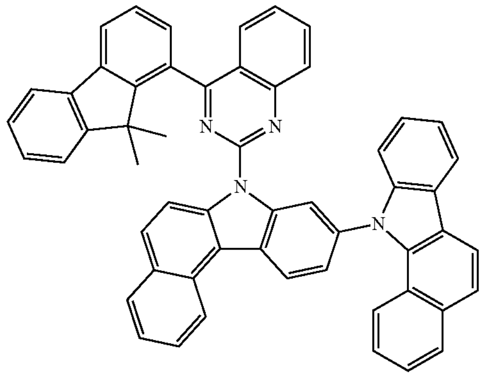
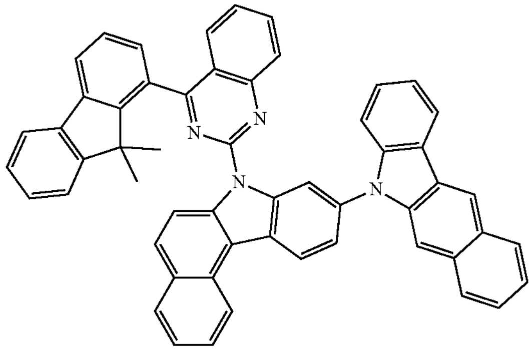
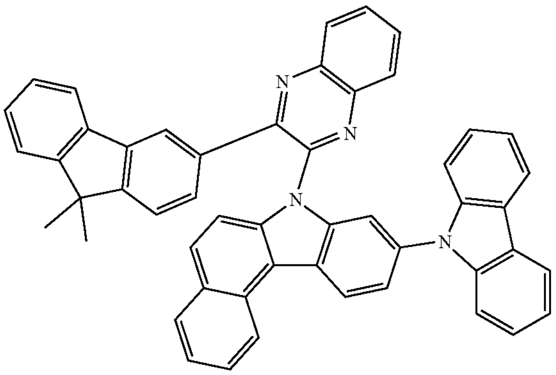

-continued
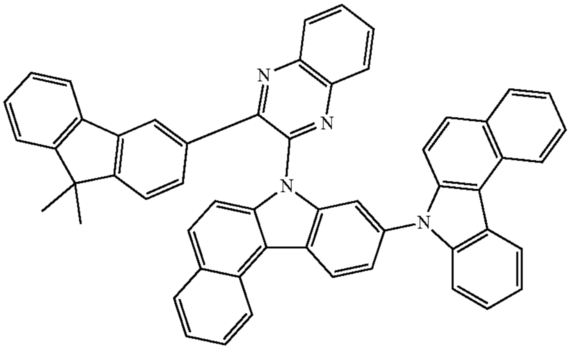
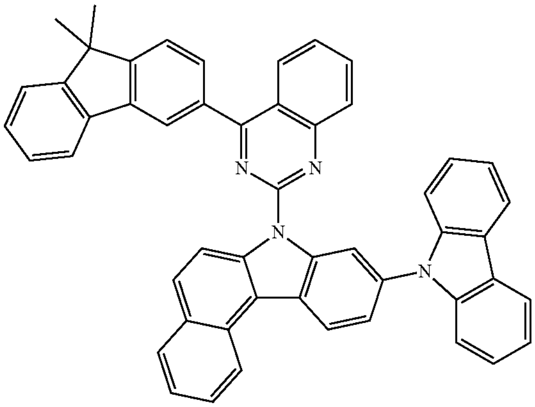
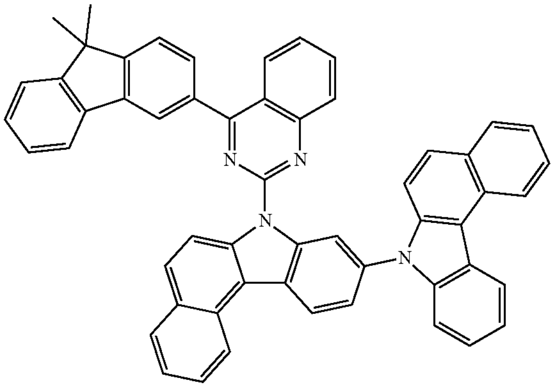
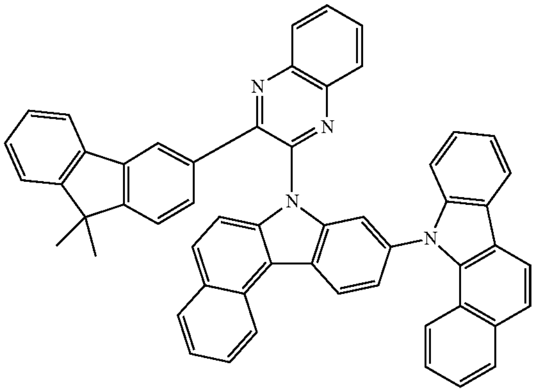
-continued
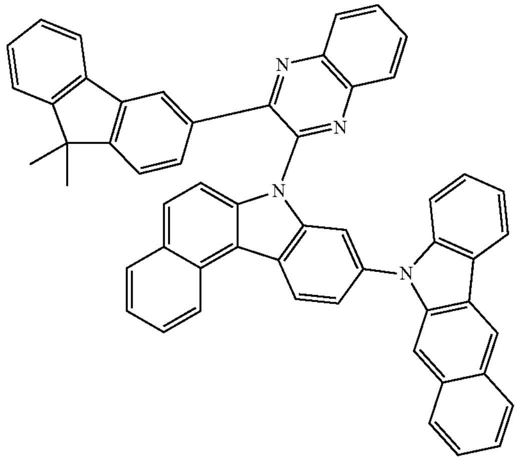
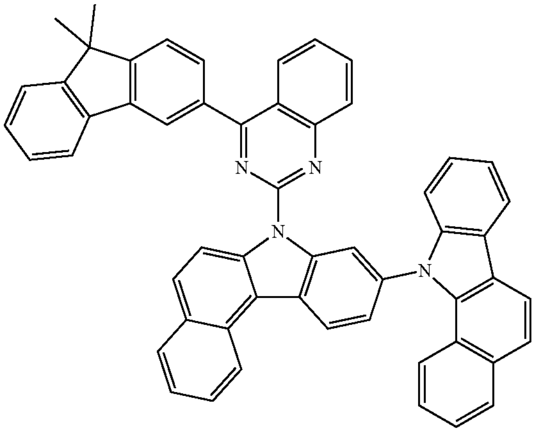
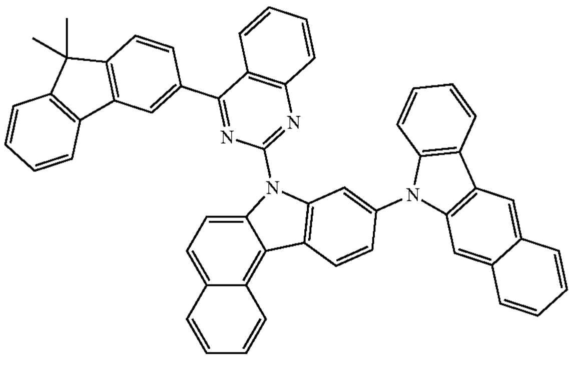

-continued
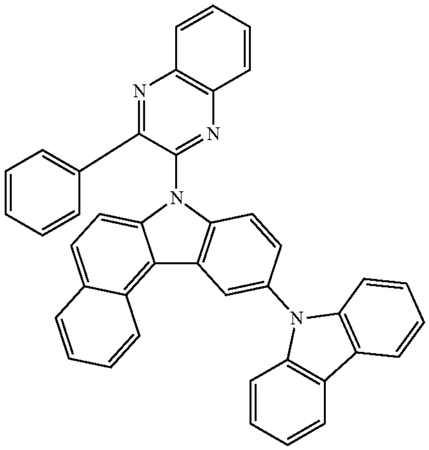
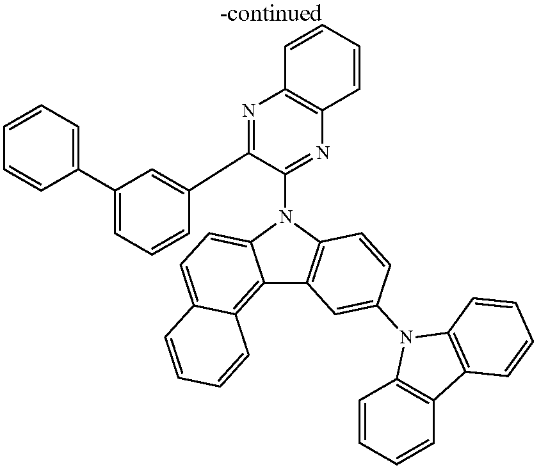
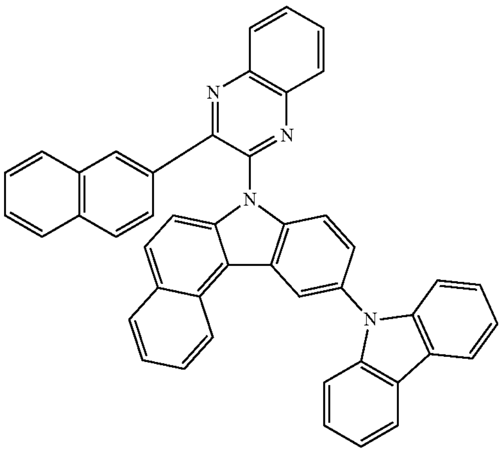
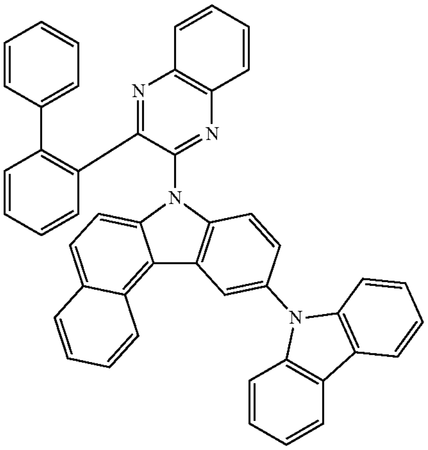 [SMILES: c1ccc(-c2ccccc2-c2nc3ccccc3nc2-n2c3ccc(-n4c5ccccc5c5ccccc54)cc3c3c4ccccc4ccc32)cc1]
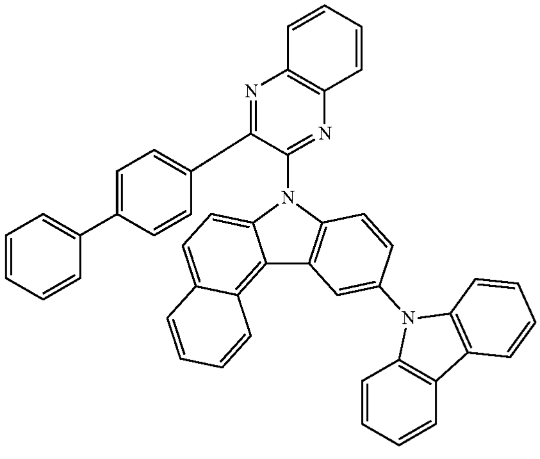
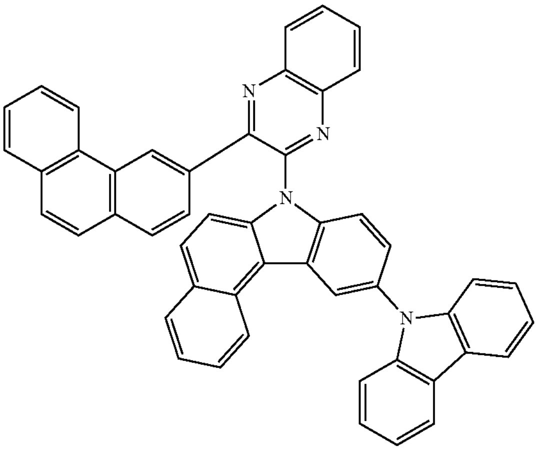

-continued
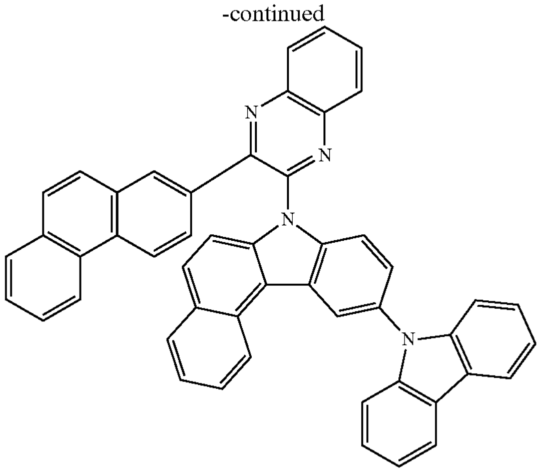
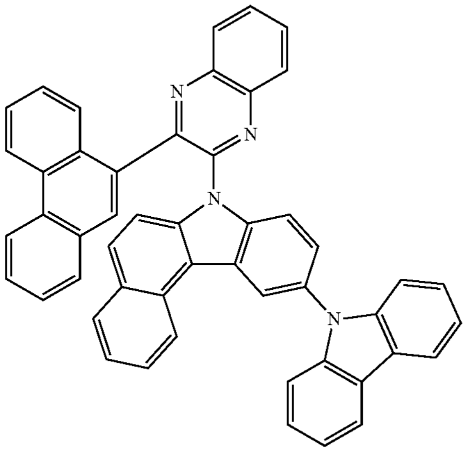
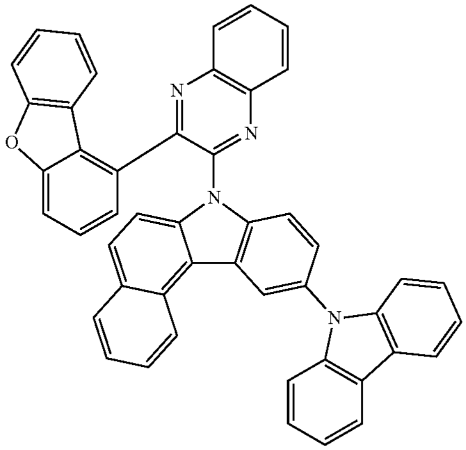
-continued
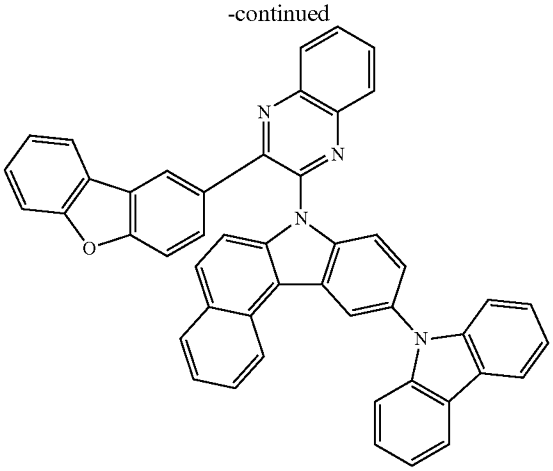
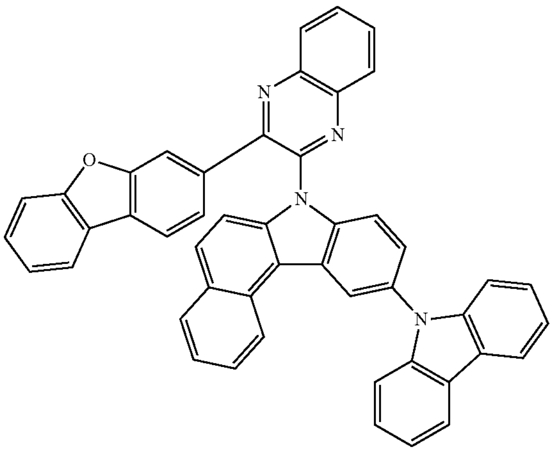
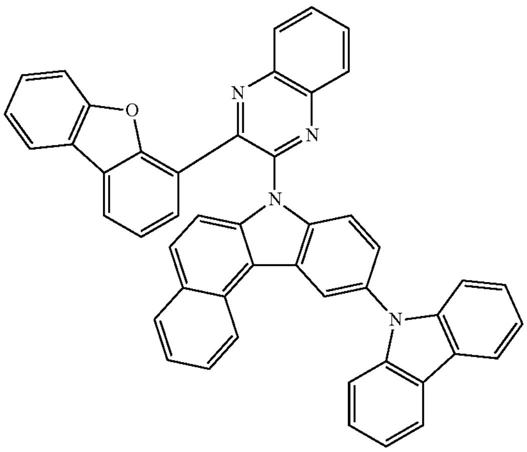

-continued
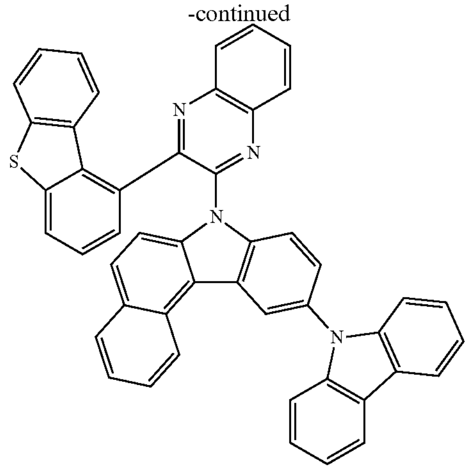
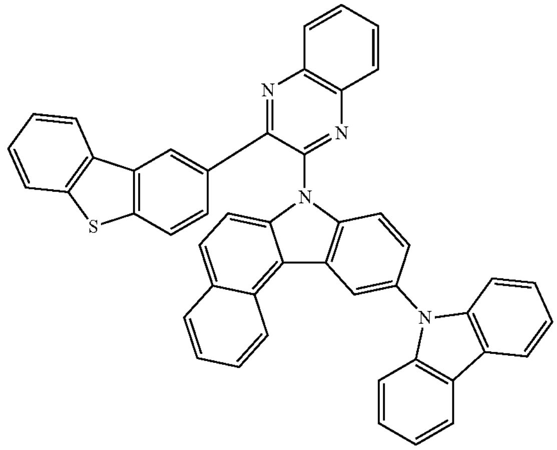 [SMILES: c1ccc2c(c1)ccc1c2c2cc(-n3c4ccccc4c4ccccc43)ccc2n1-c1nc2ccccc2nc1-c1ccc2oc3ccccc3c2c1]
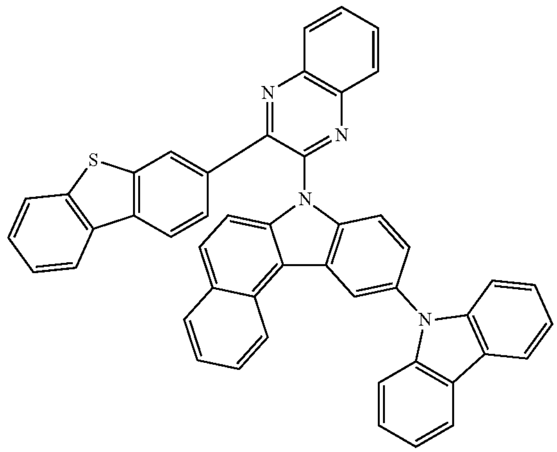 [SMILES: c1ccc2c(c1)ccc1c2c2cc(-n3c4ccccc4c4ccccc43)ccc2n1-c1nc2ccccc2nc1-c1ccc2c(c1)sc1ccccc12]
-continued
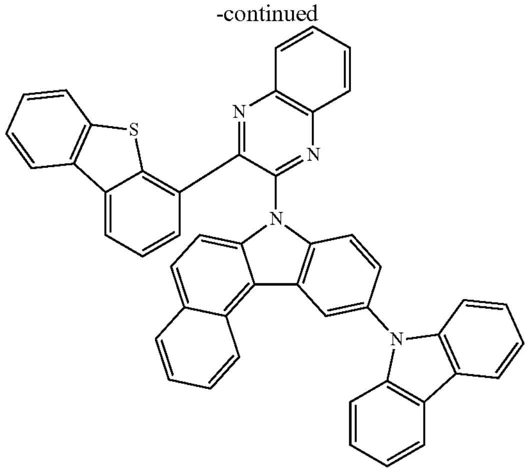
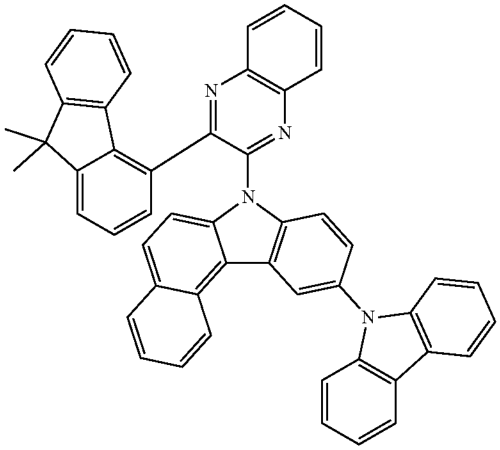
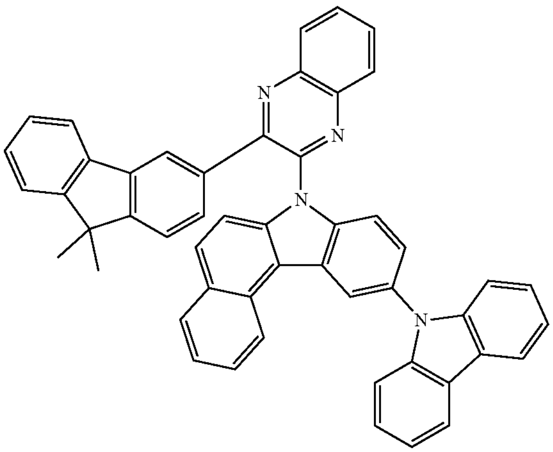

-continued
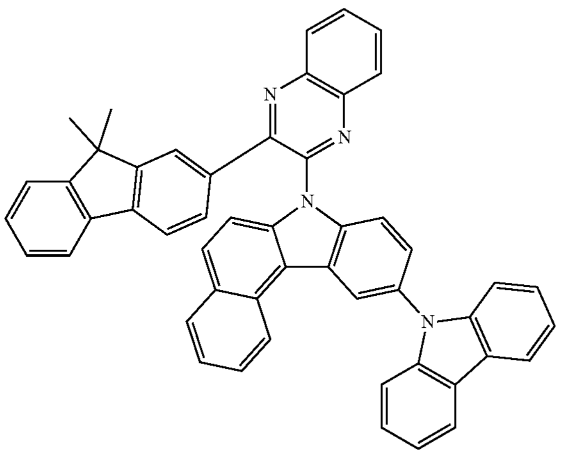
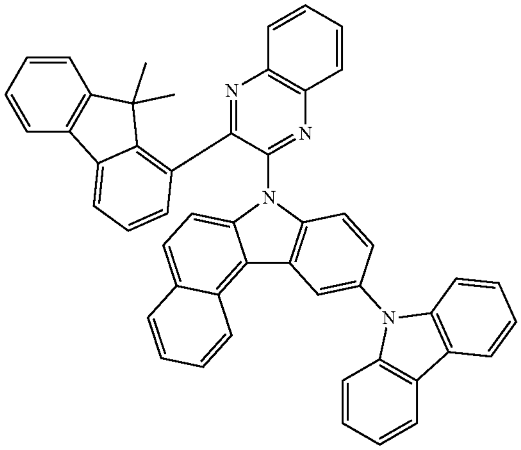 [SMILES: CC1(C)c2ccccc2-c2cccc(-c3nc4ccccc4nc3-n3c4ccc(-n5c6ccccc6c6ccccc65)cc4c4c5ccccc5ccc43)c21]
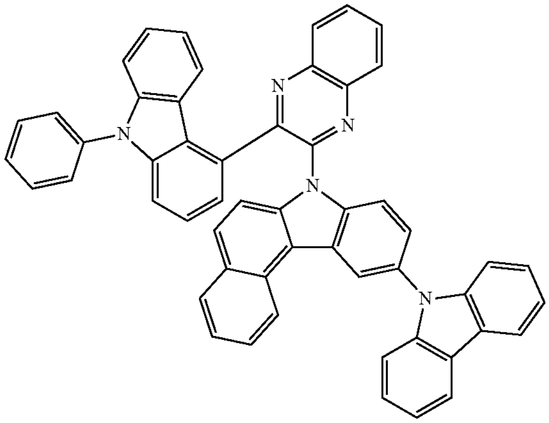
-continued
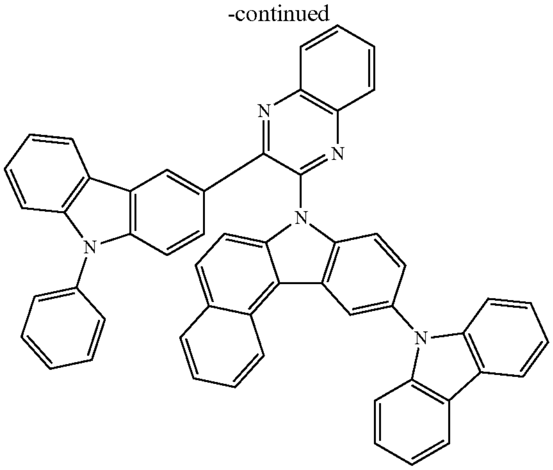
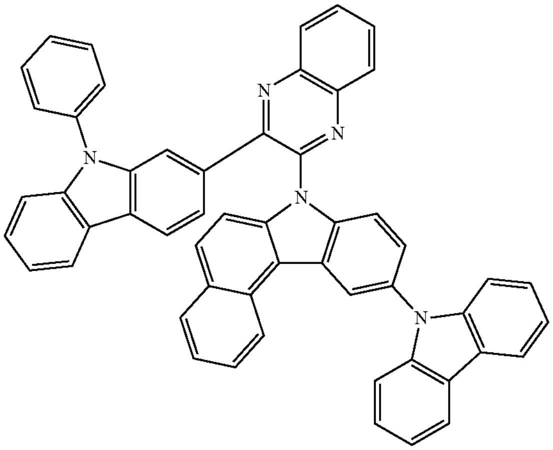
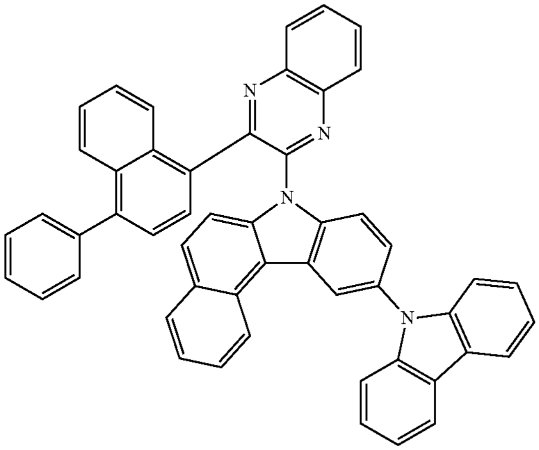

-continued
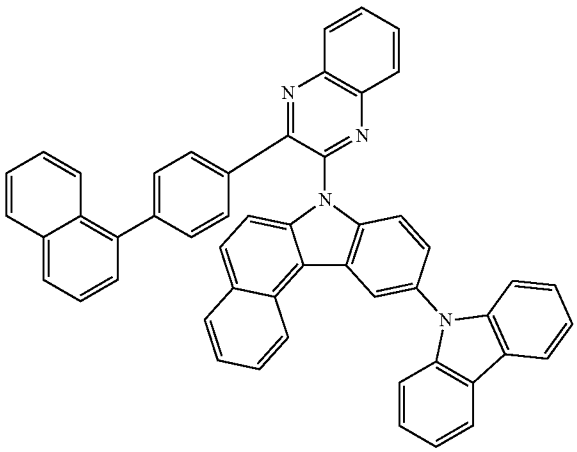 [SMILES: c1ccc2c(-c3ccc(-c4nc5ccccc5nc4-n4c5ccc(-n6c7ccccc7c7ccccc76)cc5c5c6ccccc6ccc54)cc3)cccc2c1]
-continued
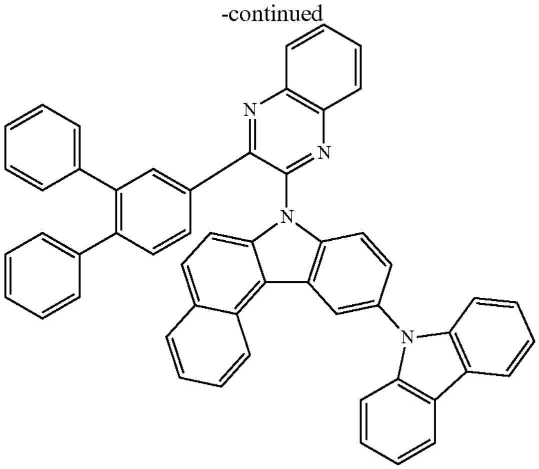
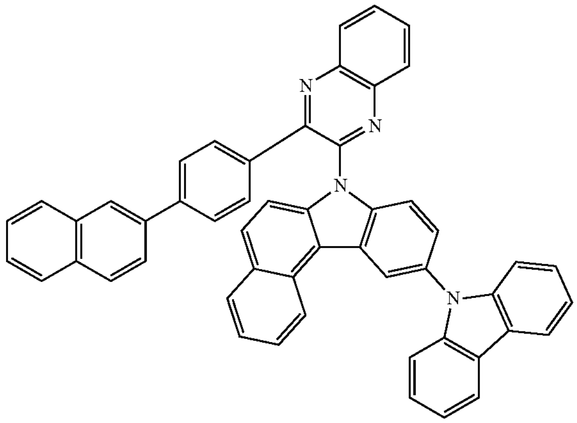
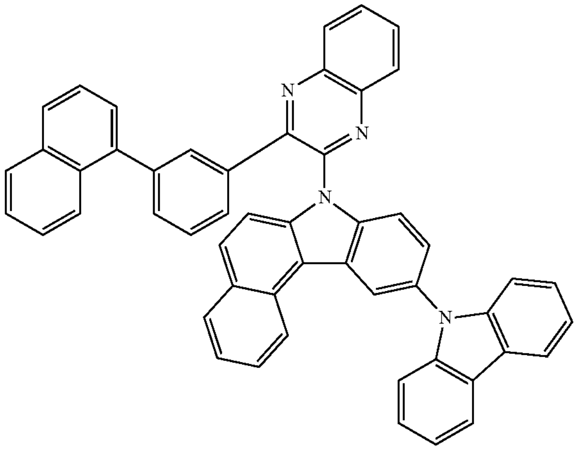
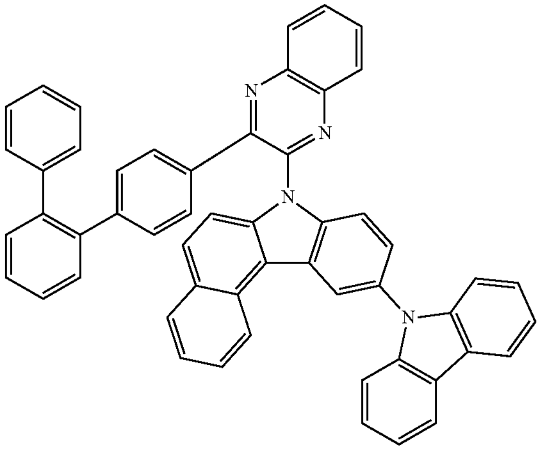
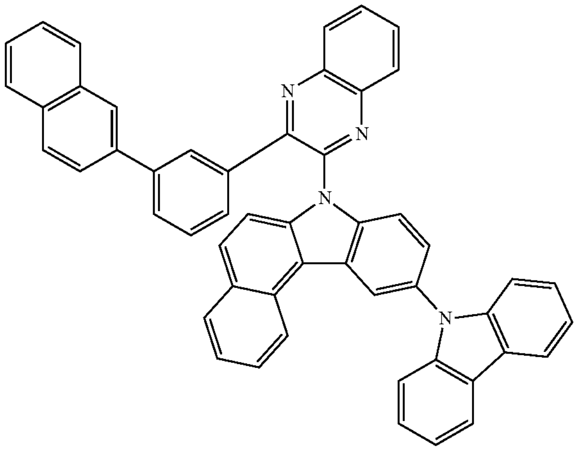 [SMILES: c1cc(-c2ccc3ccccc3c2)cc(-c2nc3ccccc3nc2-n2c3ccc(-n4c5ccccc5c5ccccc54)cc3c3c4ccccc4ccc32)c1]

-continued
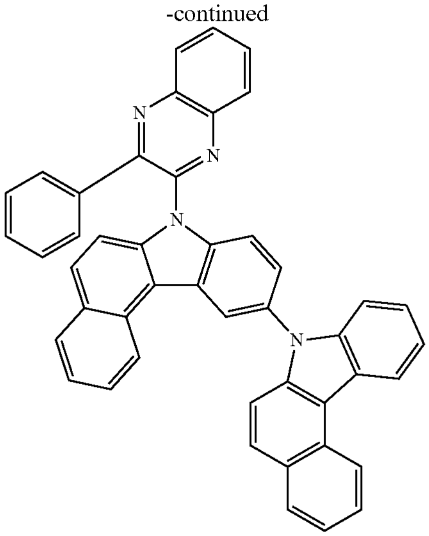
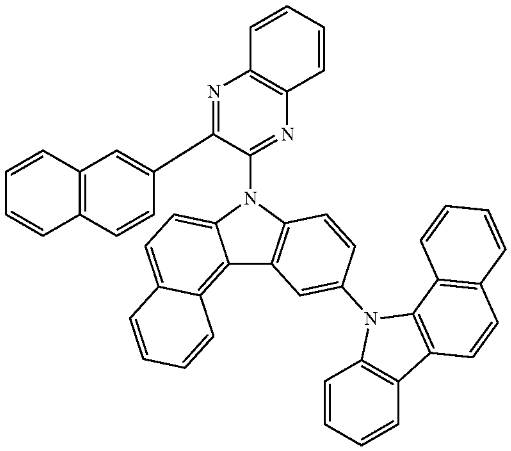
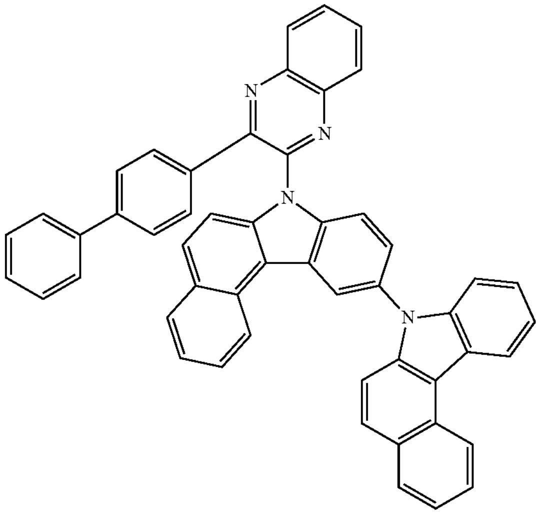
-continued
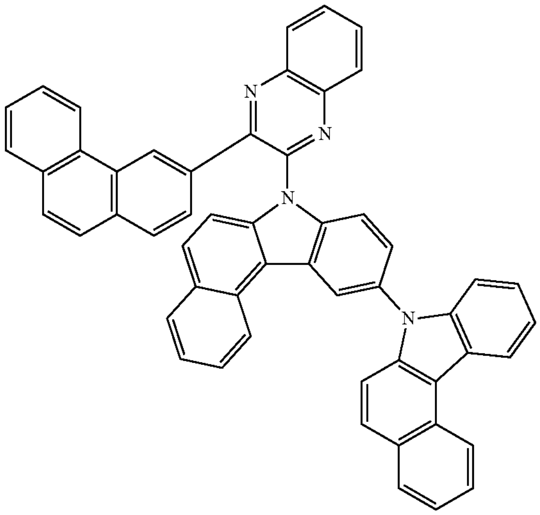
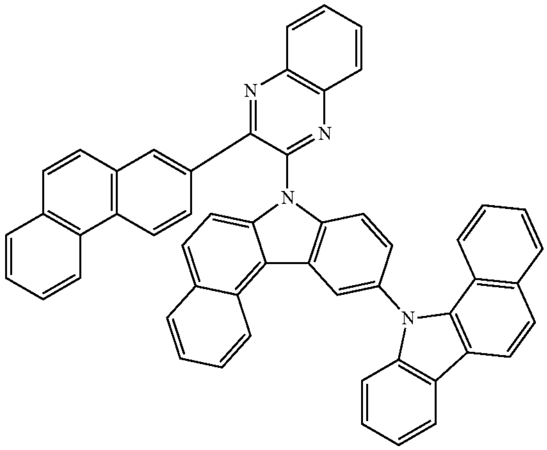
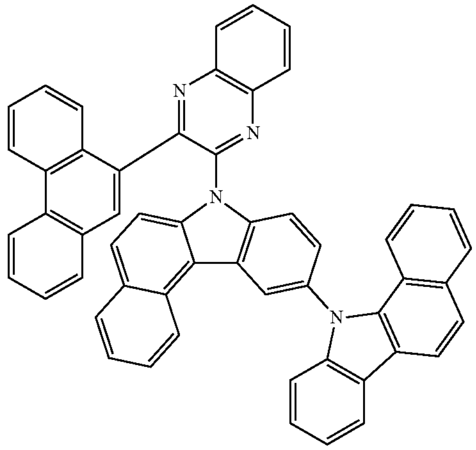

-continued
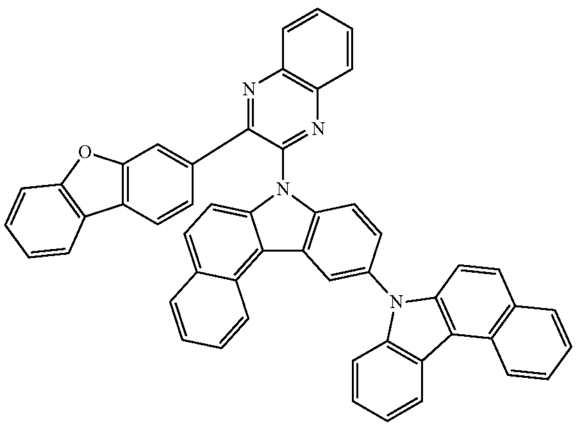
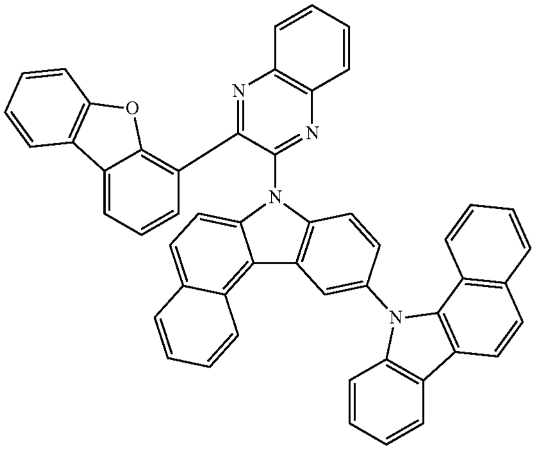
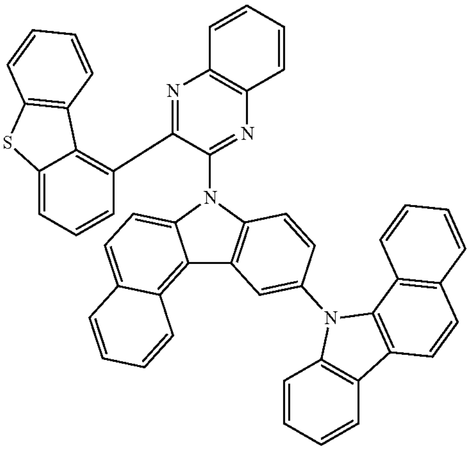
-continued
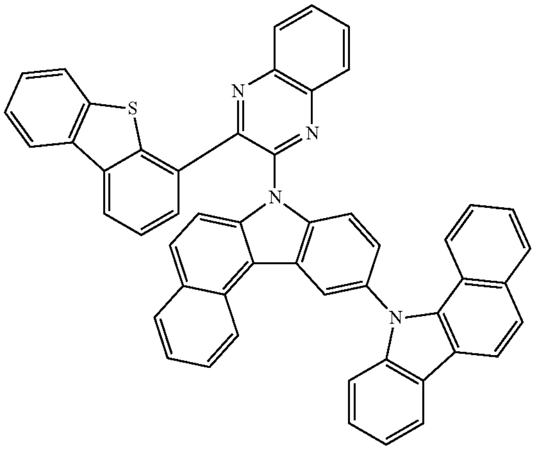
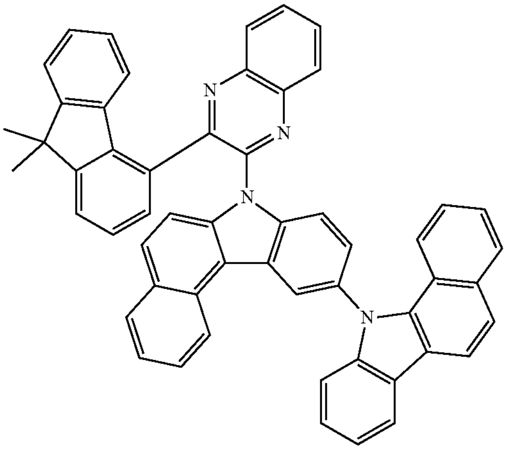
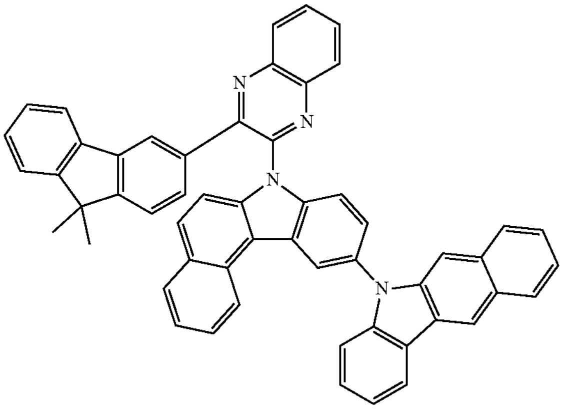

-continued
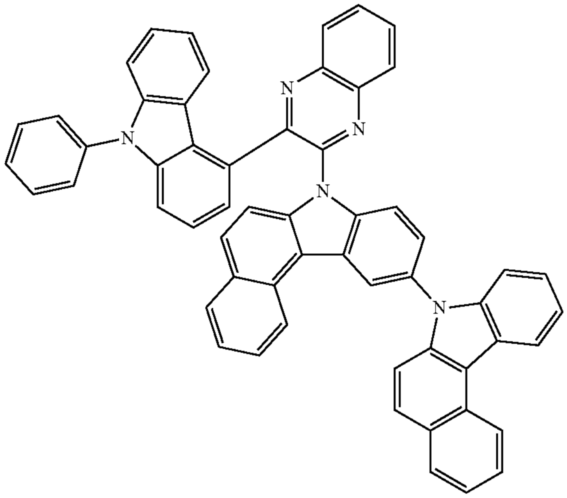
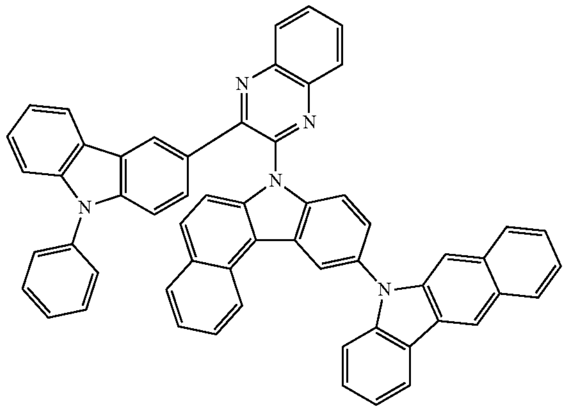
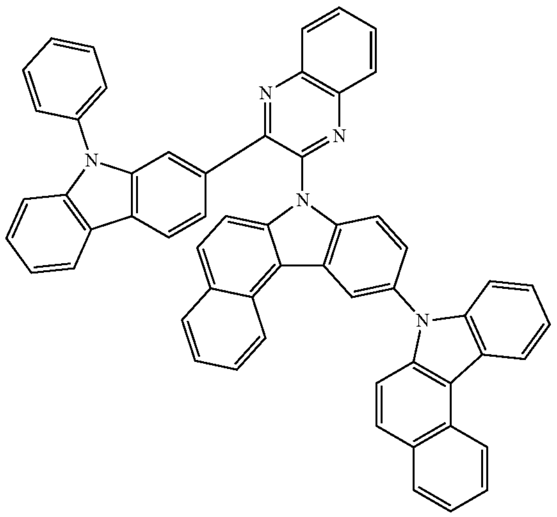
-continued
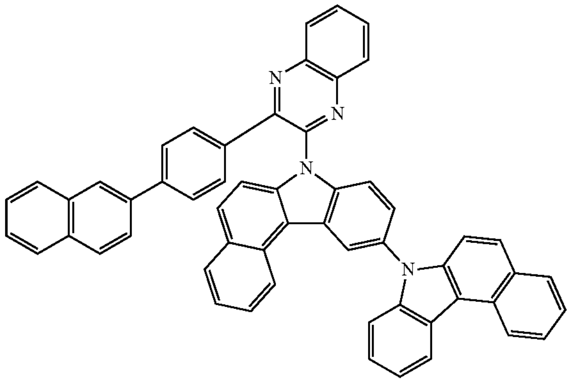
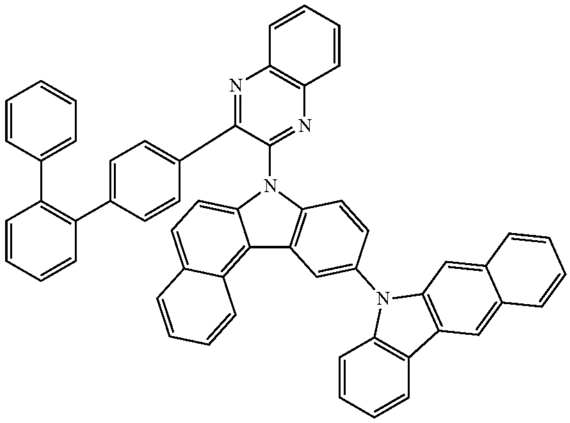
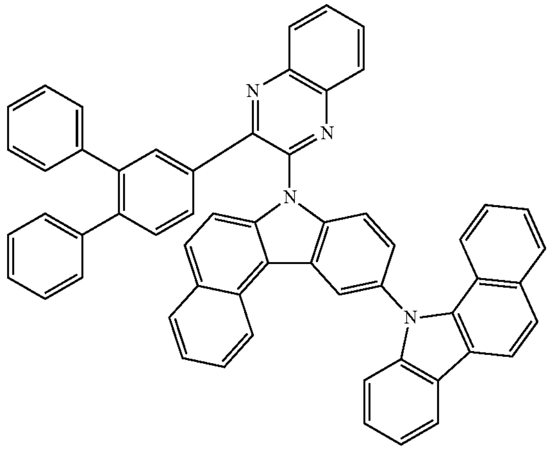
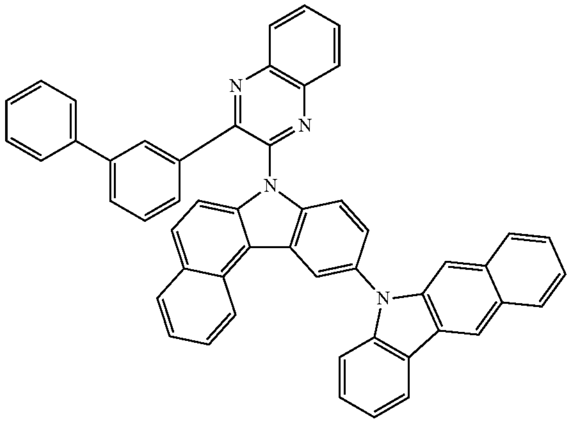

-continued
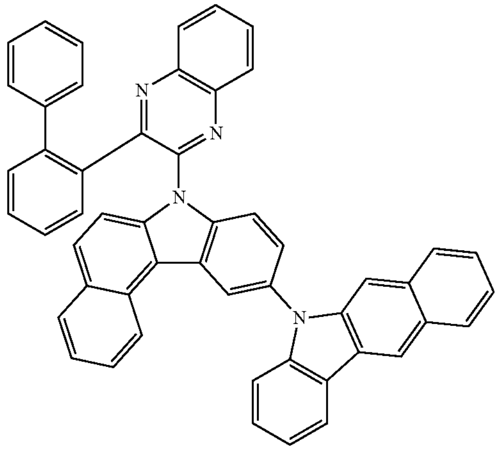
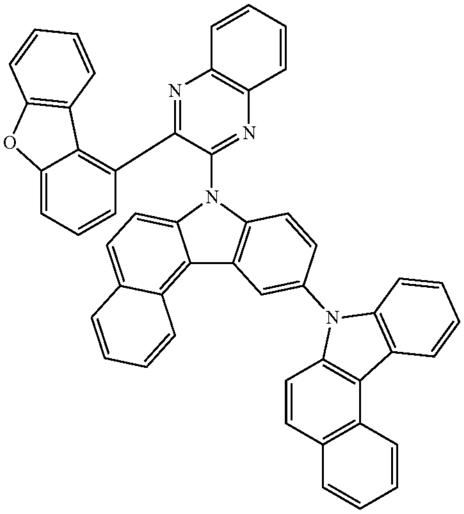
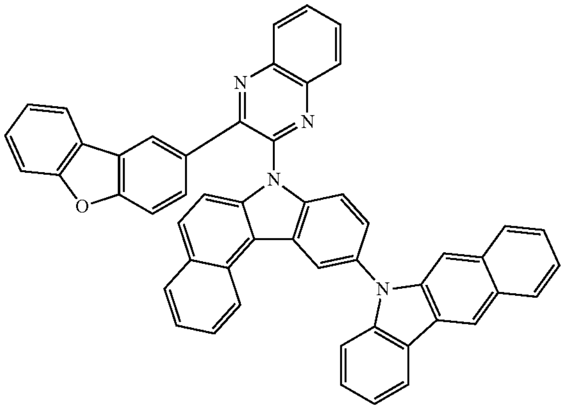
-continued
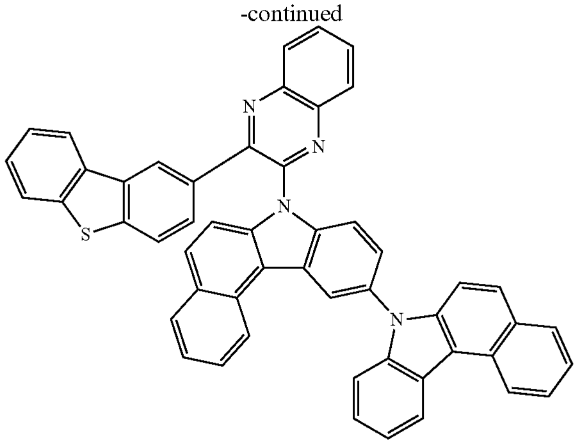
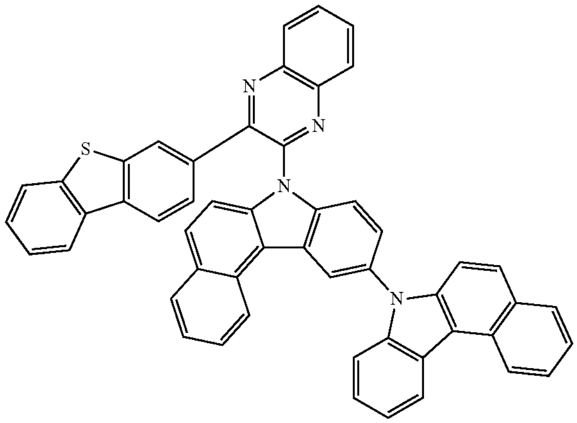
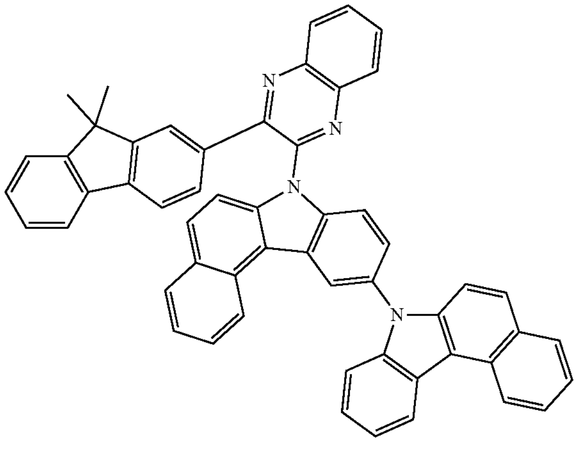

-continued

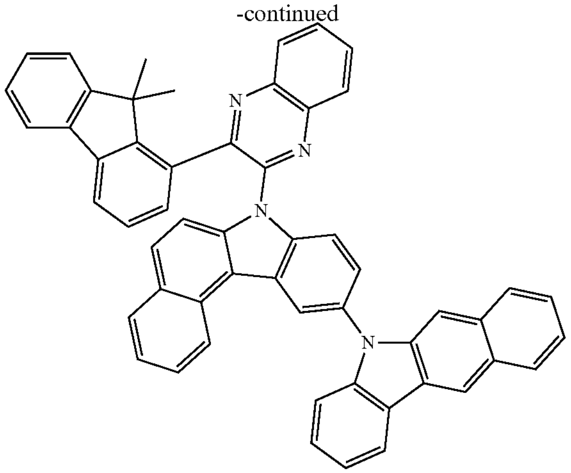

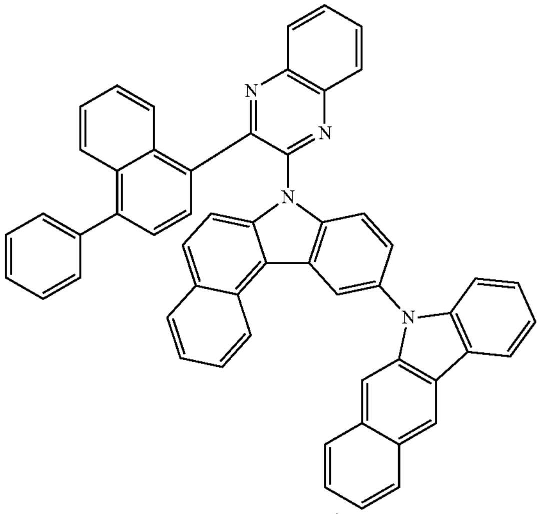

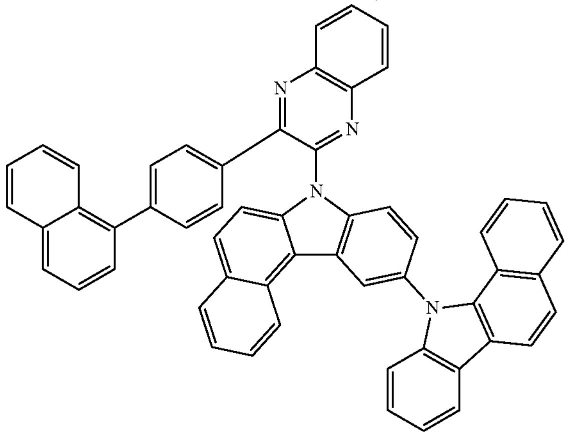

-continued

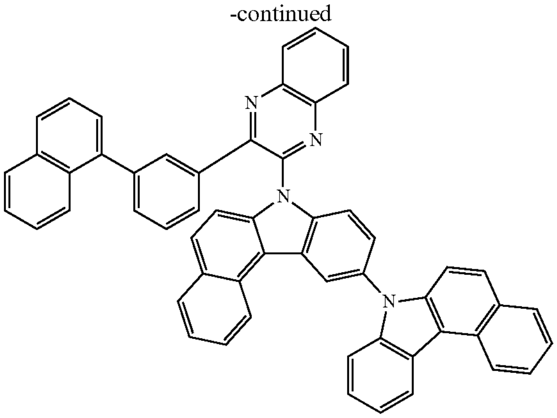

and

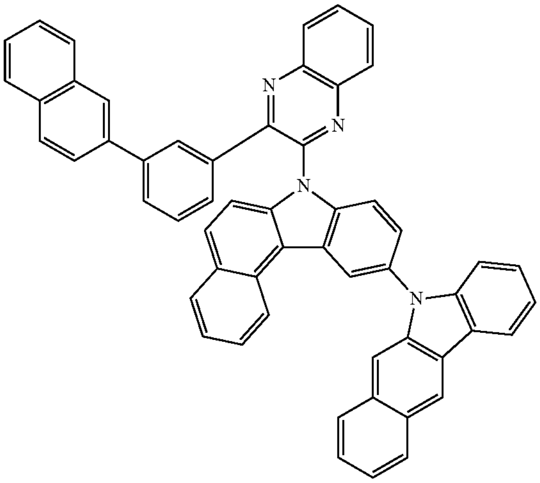

.

3. An organic light emitting device comprising:

a first electrode;

a second electrode; and one or more organic material layers provided between the first electrode and the second electrode, wherein at least one of the one or more organic material layers is a red light emitting layer, and the red light emitting layer includes the compound of Chemical Formula 1 of claim 1.

4. The compound of claim 1, wherein R is a phenyl group; a phenyl group substituted with a naphthyl group; a naphthyl group; a naphthyl group substituted a phenyl group; a biphenyl group; a terphenyl group; a phenanthrene group; a fluorene group substituted with a methyl group; a dibenzofuran group; a dibenzothiophene group; or a carbazole group that is unsubstituted or substituted with a phenyl group.

* * * * *